US012230369B2

(12) United States Patent
Shriberg et al.

(10) Patent No.: US 12,230,369 B2
(45) Date of Patent: *Feb. 18, 2025

(54) SYSTEMS AND METHODS FOR MENTAL HEALTH ASSESSMENT

(71) Applicant: Ellipsis Health, Inc., San Francisco, CA (US)

(72) Inventors: Elizabeth Shriberg, Berkeley, CA (US); Michael Aratow, Mountain View, CA (US); Mainul Islam, San Francisco, CA (US); Amir Hossein Harati Nejad Torbati, Toronto (CA); Tomasz Rutowski, Gdansk (PL); David Lin, Foster City, CA (US); Yang Lu, Waterloo, CA (US); Farshid Haque, San Francisco, CA (US); Robert D. Rogers, Pleasanton, CA (US)

(73) Assignee: Ellipsis Health, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/430,067

(22) Filed: Feb. 1, 2024

(65) Prior Publication Data

US 2024/0170109 A1    May 23, 2024

Related U.S. Application Data

(63) Continuation of application No. 17/671,337, filed on Feb. 14, 2022, now Pat. No. 11,942,194, which is a
(Continued)

(51) Int. Cl.
*G16H 10/20*    (2018.01)
*A61B 5/00*    (2006.01)
(Continued)

(52) U.S. Cl.
CPC .............. *G16H 10/20* (2018.01); *A61B 5/164* (2013.01); *A61B 5/165* (2013.01); *A61B 5/4803* (2013.01);
(Continued)

(58) Field of Classification Search
CPC ........ G16H 10/20; G16H 50/30; G16H 50/20; A61B 5/164; A61B 5/165; A61B 5/4803;
(Continued)

(56) References Cited

U.S. PATENT DOCUMENTS 5,769,074 A    6/1998    Barnhill et al.
5,961,332 A    10/1999    Joao
(Continued)

FOREIGN PATENT DOCUMENTS

AU    2007292359 A1    3/2008
AU    2009244709 A1    11/2009
(Continued)

OTHER PUBLICATIONS

Japanese Patent Office, Office Action issued for Japanese Patent Application No. 2020-571611, dated Mar. 24, 2024, 9 pages with English language translation.
(Continued)

*Primary Examiner* — Eddy Saint-Vil
(74) *Attorney, Agent, or Firm* — Norton Rose Fulbright US LLP

(57) ABSTRACT

The present disclosure provides systems and methods for assessing a mental state of a subject in a single session or over multiple different sessions, using for example an automated module to present and/or formulate at least one query based in part on one or more target mental states to be assessed. The query may be configured to elicit at least one response from the subject. The query may be transmitted in an audio, visual, and/or textual format to the subject to elicit
(Continued)

the response. Data comprising the response from the subject can be received. The data can be processed using one or more individual, joint, or fused models. One or more assessments of the mental state associated with the subject can be generated for the single session, for each of the multiple different sessions, or upon completion of one or more sessions of the multiple different sessions.

27 Claims, 60 Drawing Sheets

Related U.S. Application Data continuation of application No. 17/400,066, filed on Aug. 11, 2021, now abandoned, which is a continuation of application No. 17/129,859, filed on Dec. 21, 2020, now Pat. No. 11,120,895, which is a continuation of application No. 16/918,624, filed on Jul. 1, 2020, now abandoned, which is a continuation of application No. 16/560,720, filed on Sep. 4, 2019, now Pat. No. 10,748,644, which is a continuation of application No. 16/523,298, filed on Jul. 26, 2019, now abandoned, which is a continuation of application No. PCT/US2019/037953, filed on Jun. 19, 2019.

(60) Provisional application No. 62/755,356, filed on Nov. 2, 2018, provisional application No. 62/755,361, filed on Nov. 2, 2018, provisional application No. 62/754,547, filed on Nov. 1, 2018, provisional application No. 62/754,541, filed on Nov. 1, 2018, provisional application No. 62/754,534, filed on Nov. 1, 2018, provisional application No. 62/749,672, filed on Oct. 24, 2018, provisional application No. 62/749,654, filed on Oct. 23, 2018, provisional application No. 62/749,663, filed on Oct. 23, 2018, provisional application No. 62/749,669, filed on Oct. 23, 2018, provisional application No. 62/749,113, filed on Oct. 22, 2018, provisional application No. 62/733,552, filed on Sep. 19, 2018, provisional application No. 62/733,568, filed on Sep. 19, 2018, provisional application No. 62/687,176, filed on Jun. 19, 2018.

(51) Int. Cl.
| | |
|---|---|
| *A61B 5/16* | (2006.01) |
| *G06F 16/24* | (2019.01) |
| *G09B 19/00* | (2006.01) |
| *G10L 15/18* | (2013.01) |
| *G10L 25/66* | (2013.01) |
| *G16H 50/20* | (2018.01) |
| *G16H 50/30* | (2018.01) |

(52) U.S. Cl.
CPC .............. *G09B 19/00* (2013.01); *G10L 25/66* (2013.01); *G16H 50/20* (2018.01); *G16H 50/30* (2018.01); *A61B 5/4088* (2013.01); *A61B 5/7275* (2013.01); *G06F 16/24* (2019.01); *G10L 15/18* (2013.01)

(58) Field of Classification Search
CPC .... A61B 5/4088; A61B 5/7275; G09B 19/00; G10L 25/66; G10L 15/18; G06F 16/24
See application file for complete search history.

(56) References Cited

U.S. PATENT DOCUMENTS

| | | |
|---|---|---|
| 6,113,540 A | 9/2000 | Iliff |
| 6,256,613 B1 | 7/2001 | Falchuk et al. |
| 6,289,313 B1 | 9/2001 | Heinonen et al. |
| 6,334,778 B1 | 1/2002 | Brown |
| 6,482,156 B2 | 11/2002 | Iliff |
| 6,491,525 B1 | 12/2002 | Hersh |
| 6,523,008 B1 | 2/2003 | Avrunin et al. |
| 6,629,242 B2 | 9/2003 | Kamiya et al. |
| 6,658,388 B1 | 12/2003 | Kleindienst et al. |
| 6,665,644 B1 | 12/2003 | Kanevsky et al. |
| 6,725,209 B1 | 4/2004 | Iliff |
| 6,731,307 B1 | 5/2004 | Strubbe et al. |
| 6,760,717 B2 | 7/2004 | Suda et al. |
| 6,842,877 B2 | 1/2005 | Robarts et al. |
| 6,874,127 B2 | 3/2005 | Newell et al. |
| 6,968,333 B2 | 11/2005 | Abbott et al. |
| 6,993,381 B2 | 1/2006 | Connolly et al. |
| 7,089,497 B2 | 8/2006 | Abbott et al. |
| 7,165,033 B1 | 1/2007 | Liberman |
| 7,222,075 B2 | 5/2007 | Petrushin |
| 7,231,439 B1 | 6/2007 | Abbott et al. |
| 7,272,559 B1 | 9/2007 | Hayre |
| 7,280,968 B2 | 10/2007 | Blass |
| 7,300,402 B2 | 11/2007 | Iliff |
| 7,314,444 B2 | 1/2008 | Buschke |
| 7,315,821 B2 | 1/2008 | Monchi et al. |
| 7,340,393 B2 | 3/2008 | Mitsuyoshi |
| 7,398,213 B1 | 7/2008 | Levanon et al. |
| 7,429,243 B2 | 9/2008 | KenKnight et al. |
| RE40,634 E | 2/2009 | Blair et al. |
| 7,590,550 B2 | 9/2009 | Schoenberg |
| 7,606,701 B2 | 10/2009 | Degani et al. |
| 7,627,475 B2 | 12/2009 | Petrushin |
| 7,665,024 B1 | 2/2010 | Kondziela |
| 7,676,369 B2 | 3/2010 | Fujimoto et al. |
| 7,684,984 B2 | 3/2010 | Kemp |
| 7,689,319 B2 | 3/2010 | Kanda et al. |
| 7,729,914 B2 | 6/2010 | Tato et al. |
| 7,756,721 B1 | 7/2010 | Falchuk et al. |
| 7,761,308 B2 | 7/2010 | Falchuk et al. |
| 7,765,113 B2 | 7/2010 | Ware et al. |
| 7,818,183 B2 | 10/2010 | Schoenberg |
| 7,835,928 B2 | 11/2010 | Schoenberg |
| 7,840,418 B2 | 11/2010 | Schoenberg |
| 7,848,937 B2 | 12/2010 | Schoenberg |
| 7,849,115 B2 | 12/2010 | Reiner |
| 7,865,377 B2 | 1/2011 | Schoenberg |
| 7,874,983 B2 | 1/2011 | Zancho et al. |
| 7,890,345 B2 | 2/2011 | Schoenberg |
| 7,890,351 B2 | 2/2011 | Schoenberg |
| 7,895,061 B2 | 2/2011 | Schoenberg |
| 7,912,737 B2 | 3/2011 | Schoenberg |
| 7,917,366 B1 | 3/2011 | Levanon et al. |
| 7,933,226 B2 | 4/2011 | Woodruff et al. |
| 7,933,783 B2 | 4/2011 | Schoenberg |
| 7,935,307 B2 | 5/2011 | Angelides |
| 7,937,275 B2 | 5/2011 | Schoenberg |
| 7,945,456 B2 | 5/2011 | Schoenberg |
| 7,962,342 B1 | 6/2011 | Coughlan et al. |
| 7,983,920 B2 | 7/2011 | Sinclair, II |
| 8,055,591 B2 | 11/2011 | Jung et al. |
| 8,065,360 B2 | 11/2011 | Jung et al. |
| 8,066,640 B2 | 11/2011 | Angelides |
| 8,078,470 B2 | 12/2011 | Levanon et al. |
| 8,086,563 B2 | 12/2011 | Jung et al. |
| 8,126,712 B2 | 2/2012 | Mukaigaito et al. |
| 8,195,460 B2 | 6/2012 | Degani et al. |
| 8,209,173 B2 | 6/2012 | Bejar et al. |
| 8,209,182 B2 | 6/2012 | Narayanan |
| 8,214,214 B2 | 7/2012 | Bennett |
| 8,219,406 B2 | 7/2012 | Yu et al. |
| 8,249,875 B2 | 8/2012 | Levanon et al. |
| 8,249,898 B2 | 8/2012 | Schoenberg |
| 8,260,729 B2 | 9/2012 | Firminger et al. |
| 8,280,827 B2 | 10/2012 | Muller et al. |

(56) References Cited

U.S. PATENT DOCUMENTS

| | | |
|---|---|---|
| 8,340,956 B2 | 12/2012 | Matsukawa et al. |
| 8,346,680 B2 | 1/2013 | Castleman et al. |
| D676,555 S | 2/2013 | Angelides |
| 8,386,257 B2 | 2/2013 | Irie et al. |
| 8,442,563 B2 | 5/2013 | Chen et al. |
| 8,463,620 B2 | 6/2013 | Schoenberg |
| 8,500,635 B2 | 8/2013 | Zilca et al. |
| 8,504,382 B2 | 8/2013 | Schoenberg |
| 8,510,128 B2 | 8/2013 | Schoenberg |
| 8,510,130 B2 | 8/2013 | Schoenberg |
| 8,515,776 B2 | 8/2013 | Schoenberg |
| 8,521,553 B2 | 8/2013 | Schoenberg |
| 8,538,755 B2 | 9/2013 | Bollano et al. |
| 8,568,309 B2 | 10/2013 | Angelides |
| 8,595,005 B2 | 11/2013 | Krishnan et al. |
| 8,600,773 B2 | 12/2013 | Schoenberg |
| 8,615,529 B2 | 12/2013 | Reiner |
| 8,615,664 B2 | 12/2013 | Jung et al. |
| 8,639,532 B2 | 1/2014 | Schoenberg |
| 8,645,124 B2 | 2/2014 | Karov Zangvil |
| 8,682,666 B2 | 3/2014 | Degani et al. |
| 8,701,003 B2 | 4/2014 | Kondziela |
| 8,719,036 B2 | 5/2014 | Ariu |
| 8,719,047 B2 | 5/2014 | Schoenberg |
| 8,738,370 B2 | 5/2014 | Mitsuyoshi et al. |
| 8,738,727 B2 | 5/2014 | Schoenberg |
| 8,768,708 B2 | 7/2014 | Levanon et al. |
| 8,784,311 B2 | 7/2014 | Shrivastav et al. |
| 8,788,270 B2 | 7/2014 | Patel et al. |
| 8,793,127 B2 | 7/2014 | Printz et al. |
| 8,812,244 B2 | 8/2014 | Angelides |
| 8,825,479 B2 | 9/2014 | Krishnan et al. |
| 8,838,513 B2 | 9/2014 | Sudharsan |
| 8,892,424 B2 | 11/2014 | Harada et al. |
| 8,914,278 B2 | 12/2014 | Zangvil et al. |
| 8,949,170 B2 | 2/2015 | Zadeh |
| 8,949,233 B2 | 2/2015 | Hsiao et al. |
| 8,974,231 B2 | 3/2015 | Duffy |
| 8,979,542 B2 | 3/2015 | Duffy |
| 8,979,543 B2 | 3/2015 | Duffy |
| 8,979,544 B2 | 3/2015 | Duffy |
| 8,979,547 B2 | 3/2015 | Duffy |
| 8,983,846 B2 | 3/2015 | Di Profio et al. |
| 8,996,373 B2 | 3/2015 | Hayakawa et al. |
| D726,205 S | 4/2015 | Angelides |
| D726,206 S | 4/2015 | Angelides |
| D726,207 S | 4/2015 | Angelides |
| D726,209 S | 4/2015 | Angelides |
| D726,210 S | 4/2015 | Angelides |
| D726,751 S | 4/2015 | Angelides |
| D726,752 S | 4/2015 | Angelides |
| D726,753 S | 4/2015 | Angelides |
| D726,754 S | 4/2015 | Angelides |
| D726,755 S | 4/2015 | Angelides |
| D726,756 S | 4/2015 | Angelides |
| D726,757 S | 4/2015 | Angelides |
| D727,941 S | 4/2015 | Angelides |
| D727,942 S | 4/2015 | Angelides |
| 9,014,614 B2 | 4/2015 | Roots et al. |
| 9,015,036 B2 | 4/2015 | Karov Zangvil et al. |
| 9,015,609 B2 | 4/2015 | Schoenberg |
| D728,601 S | 5/2015 | Angelides |
| 9,026,432 B2 | 5/2015 | Zangvil |
| 9,028,257 B2 | 5/2015 | Duffy |
| D733,172 S | 6/2015 | Angelides |
| 9,058,816 B2 | 6/2015 | Lech et al. |
| 9,064,040 B2 | 6/2015 | Sudharsan |
| 9,099,088 B2 | 8/2015 | Washio et al. |
| 9,101,263 B2 | 8/2015 | Jung et al. |
| 9,183,833 B2 | 11/2015 | Runge et al. |
| 9,192,300 B2 | 11/2015 | Jung et al. |
| 9,202,520 B1 | 12/2015 | Tang |
| 9,220,453 B2 | 12/2015 | Roots |
| 9,230,542 B2 | 1/2016 | Velasco |
| 9,239,989 B2 | 1/2016 | Bouqata et al. |
| 9,286,442 B2 | 3/2016 | Csoma et al. |
| 9,298,766 B2 | 3/2016 | Kozloski et al. |
| D754,179 S | 4/2016 | Angelides |
| D754,705 S | 4/2016 | Angelides |
| 9,324,241 B2 | 4/2016 | Roots et al. |
| 9,348,812 B2 | 5/2016 | Kelly et al. |
| 9,357,071 B2 | 5/2016 | Conway et al. |
| 9,361,589 B2 | 6/2016 | Ziolko et al. |
| 9,396,437 B2 | 7/2016 | Ponomarev et al. |
| 9,407,768 B2 | 8/2016 | Conway et al. |
| 9,413,891 B2 | 8/2016 | Dwyer et al. |
| 9,420,970 B2 | 8/2016 | Dagum |
| 9,425,974 B2 | 8/2016 | Tucker et al. |
| 9,443,205 B2 | 9/2016 | Wall |
| 9,445,763 B2 | 9/2016 | Davis et al. |
| 9,456,350 B2 | 9/2016 | Lau et al. |
| 9,471,623 B2 | 10/2016 | Kozloski et al. |
| 9,474,481 B2 | 10/2016 | Dagum |
| 9,508,360 B2 | 11/2016 | Allam et al. |
| 9,513,699 B2 | 12/2016 | Jung et al. |
| 9,530,139 B2 | 12/2016 | Khor et al. |
| 9,536,049 B2 | 1/2017 | Brown et al. |
| 9,536,053 B2 | 1/2017 | Sudharsan |
| 9,538,948 B2 | 1/2017 | Dagum |
| 9,549,068 B2 | 1/2017 | Krishnan et al. |
| 9,570,064 B2 | 2/2017 | Onishi et al. |
| 9,571,650 B2 | 2/2017 | Conway et al. |
| 9,575,962 B2 | 2/2017 | Kelly et al. |
| 9,578,152 B2 | 2/2017 | Schoenberg |
| 9,594,807 B2 | 3/2017 | Rappoport et al. |
| 9,603,564 B2 | 3/2017 | Forbes |
| 9,634,855 B2 | 4/2017 | Poltorak |
| 9,652,593 B1 | 5/2017 | Schoenberg |
| 9,661,130 B2 | 5/2017 | Feast et al. |
| 9,667,788 B2 | 5/2017 | Conway et al. |
| 9,678,636 B2 | 6/2017 | Schoenberg |
| 9,679,553 B2 | 6/2017 | Onishi et al. |
| 9,685,174 B2 | 6/2017 | Karam et al. |
| 9,687,187 B2 | 6/2017 | Dagum |
| 9,693,724 B2 | 7/2017 | Dagum |
| 9,711,056 B1 | 7/2017 | Nguyen |
| 9,750,433 B2 | 9/2017 | Hu et al. |
| 9,754,077 B2 | 9/2017 | Sysko et al. |
| 9,762,719 B2 | 9/2017 | Tartz et al. |
| 9,767,470 B2 | 9/2017 | Forbes |
| 9,769,630 B2 | 9/2017 | Lau et al. |
| 9,786,299 B2 | 10/2017 | Un et al. |
| 9,792,825 B1 | 10/2017 | Fanty et al. |
| 9,807,559 B2 | 10/2017 | Clark et al. |
| 9,817,949 B2 | 11/2017 | Poulin et al. |
| 9,818,406 B1 | 11/2017 | Chan et al. |
| 9,819,711 B2 | 11/2017 | Davey et al. |
| 9,824,190 B2 | 11/2017 | Sudharsan |
| 9,830,423 B2 | 11/2017 | Biswas et al. |
| 9,836,581 B2 | 12/2017 | Madan et al. |
| 9,858,394 B2 | 1/2018 | Sudharsan |
| 9,867,562 B2 | 1/2018 | Roots et al. |
| 9,881,136 B2 | 1/2018 | Sysko et al. |
| 9,886,551 B2 | 2/2018 | Schoenberg |
| 9,892,155 B2 | 2/2018 | Levanon |
| 9,930,102 B1 | 3/2018 | Paulus et al. |
| 9,947,342 B2 | 4/2018 | Feast et al. |
| 9,959,328 B2 | 5/2018 | Jain et al. |
| 9,971,873 B2 | 5/2018 | Schoenberg |
| 9,998,886 B2 | 6/2018 | Lau et al. |
| 10,014,077 B2 | 7/2018 | Moturu et al. |
| 10,025,775 B2 | 7/2018 | Nowson et al. |
| 10,037,767 B1 | 7/2018 | Nichkawde et al. |
| 10,049,664 B1 | 8/2018 | Indyk et al. |
| 10,052,056 B2 | 8/2018 | Levanon |
| 10,056,094 B2 | 8/2018 | Feast et al. |
| 10,068,059 B2 | 9/2018 | Moturu et al. |
| 10,068,060 B2 | 9/2018 | Madan et al. |
| 10,068,670 B2 | 9/2018 | Moturu et al. |
| 10,068,672 B2 | 9/2018 | Madan et al. |
| 10,068,673 B2 | 9/2018 | Madan et al. |
| 10,074,384 B2 | 9/2018 | Hayakawa |
| 10,096,319 B1 | 10/2018 | Jin et al. |
| 10,102,341 B2 | 10/2018 | Moturu et al. |

(56) References Cited

U.S. PATENT DOCUMENTS

| | | |
|---|---|---|
| 10,116,598 B2 | 10/2018 | Tucker et al. |
| 10,127,929 B2 | 11/2018 | Quatieri, Jr. et al. |
| 10,142,483 B2 | 11/2018 | Li et al. |
| 10,149,798 B2 | 12/2018 | Roth |
| 10,152,675 B2 | 12/2018 | Sudharsan |
| 10,152,988 B2 | 12/2018 | Kim et al. |
| 10,169,827 B1 | 1/2019 | Paulus et al. |
| 10,176,299 B2 | 1/2019 | Torres et al. |
| 10,176,893 B2 | 1/2019 | Sysko et al. |
| 10,192,638 B2 | 1/2019 | Sysko et al. |
| 10,204,642 B2 | 2/2019 | Levanon |
| 10,210,867 B1 | 2/2019 | Chan et al. |
| 10,216,723 B2 | 2/2019 | Kelly et al. |
| 10,223,459 B2 | 3/2019 | Liu et al. |
| 10,226,866 B2 | 3/2019 | Thapliya |
| 10,242,754 B2 | 3/2019 | Moturu et al. |
| 10,244,975 B2 | 4/2019 | Wrenn |
| 10,250,741 B2 | 4/2019 | Feast et al. |
| 10,265,012 B2 | 4/2019 | Levanon |
| 10,265,028 B2 | 4/2019 | Moturu et al. |
| 10,268,689 B2 | 4/2019 | Subramanian et al. |
| 10,269,372 B1 | 4/2019 | Fiedler et al. |
| 10,269,448 B2 | 4/2019 | Moturu et al. |
| 10,276,188 B2 | 4/2019 | Feast et al. |
| 10,276,190 B2 | 4/2019 | Ashoori et al. |
| 10,276,260 B2 | 4/2019 | Moturu et al. |
| 10,311,869 B2 | 6/2019 | Weng et al. |
| 10,311,980 B2 | 6/2019 | Kim et al. |
| 10,325,070 B2 | 6/2019 | Beale et al. |
| 10,354,051 B2 | 7/2019 | Hickle et al. |
| 10,478,112 B2 | 11/2019 | Wall |
| 10,748,644 B2 | 8/2020 | Shriberg et al. |
| 10,839,950 B2 | 11/2020 | Vaughan |
| 10,874,355 B2 | 12/2020 | Vaughan et al. |
| 10,902,351 B1 | 1/2021 | Neumann |
| 11,120,895 B2 | 9/2021 | Shriberg et al. |
| 2001/0034615 A1 | 10/2001 | Wilkinson et al. |
| 2001/0049597 A1 | 12/2001 | Klipstein |
| 2002/0019747 A1 | 2/2002 | Ware et al. |
| 2002/0059029 A1 | 5/2002 | Todder et al. |
| 2002/0083025 A1 | 6/2002 | Robarts et al. |
| 2002/0152096 A1 | 10/2002 | Falchuk et al. |
| 2002/0165642 A1 | 11/2002 | Sakaue et al. |
| 2002/0194002 A1 | 12/2002 | Petrushin |
| 2003/0059750 A1 | 3/2003 | Bindler et al. |
| 2003/0144977 A1 | 7/2003 | Suda et al. |
| 2003/0174122 A1 | 9/2003 | Dinges et al. |
| 2003/0180698 A1 | 9/2003 | Salerian |
| 2003/0181793 A1 | 9/2003 | Buschke |
| 2003/0182117 A1 | 9/2003 | Monchi et al. |
| 2003/0182123 A1 | 9/2003 | Mitsuyoshi |
| 2003/0187660 A1 | 10/2003 | Gong |
| 2003/0199000 A1 | 10/2003 | Valkirs et al. |
| 2003/0216917 A1 | 11/2003 | Sakunaga et al. |
| 2004/0138582 A1 | 7/2004 | Connolly et al. |
| 2004/0147814 A1 | 7/2004 | Zancho et al. |
| 2004/0193421 A1 | 9/2004 | Blass |
| 2004/0210159 A1 | 10/2004 | Kibar |
| 2004/0243443 A1 | 12/2004 | Asano et al. |
| 2004/0249650 A1 | 12/2004 | Freedman et al. |
| 2005/0005266 A1 | 1/2005 | Datig |
| 2005/0019734 A1 | 1/2005 | Peled |
| 2005/0058276 A1 | 3/2005 | Oh |
| 2005/0144013 A1 | 6/2005 | Fujimoto et al. |
| 2005/0171411 A1 | 8/2005 | KenKnight et al. |
| 2005/0187436 A1 | 8/2005 | Doniger et al. |
| 2005/0192513 A1 | 9/2005 | Darby et al. |
| 2005/0209181 A1 | 9/2005 | Akil et al. |
| 2005/0228236 A1 | 10/2005 | Diederich et al. |
| 2005/0238207 A1 | 10/2005 | Tavares |
| 2005/0246165 A1 | 11/2005 | Pettinelli et al. |
| 2006/0052674 A1 | 3/2006 | Eisenstein |
| 2006/0122834 A1 | 6/2006 | Bennett |
| 2006/0240393 A1 | 10/2006 | Reeves et al. |
| 2006/0277474 A1 | 12/2006 | Robarts et al. |
| 2006/0293787 A1 | 12/2006 | Kanda et al. |
| 2007/0055524 A1 | 3/2007 | Cao et al. |
| 2007/0156891 A1 | 7/2007 | Abbott et al. |
| 2007/0162283 A1 | 7/2007 | Petrushin |
| 2007/0191704 A1 | 8/2007 | DeCharms |
| 2007/0192108 A1 | 8/2007 | Konchitsky |
| 2007/0282912 A1 | 12/2007 | Reiner |
| 2007/0288266 A1 | 12/2007 | Sysko et al. |
| 2008/0040110 A1 | 2/2008 | Pereg et al. |
| 2008/0045805 A1 | 2/2008 | Sarel et al. |
| 2008/0052080 A1 | 2/2008 | Narayanan |
| 2008/0065414 A1 | 3/2008 | Schoenberg |
| 2008/0065726 A1 | 3/2008 | Schoenberg |
| 2008/0103761 A1 | 5/2008 | Printz et al. |
| 2008/0133511 A1 | 6/2008 | Schoenberg |
| 2008/0155472 A1 | 6/2008 | Runge et al. |
| 2008/0167878 A1 | 7/2008 | Hause et al. |
| 2008/0208015 A1 | 8/2008 | Morris et al. |
| 2008/0214944 A1 | 9/2008 | Morris et al. |
| 2008/0221401 A1 | 9/2008 | Derchak et al. |
| 2008/0234558 A1 | 9/2008 | Kumar et al. |
| 2008/0242950 A1 | 10/2008 | Jung et al. |
| 2008/0243005 A1 | 10/2008 | Jung et al. |
| 2008/0270123 A1 | 10/2008 | Levanon et al. |
| 2008/0294014 A1 | 11/2008 | Goodfield |
| 2008/0299009 A1 | 12/2008 | Angelides |
| 2008/0306770 A1 | 12/2008 | Sysko et al. |
| 2008/0319276 A1 | 12/2008 | Jung et al. |
| 2008/0320080 A1 | 12/2008 | Lee et al. |
| 2009/0005654 A1 | 1/2009 | Jung et al. |
| 2009/0018407 A1 | 1/2009 | Jung et al. |
| 2009/0018832 A1 | 1/2009 | Mukaigaito et al. |
| 2009/0024050 A1 | 1/2009 | Jung et al. |
| 2009/0063188 A1 | 3/2009 | Schoenberg |
| 2009/0089074 A1 | 4/2009 | Schoenberg |
| 2009/0089084 A1 | 4/2009 | Schoenberg |
| 2009/0089085 A1 | 4/2009 | Schoenberg |
| 2009/0089086 A1 | 4/2009 | Schoenberg |
| 2009/0089090 A1 | 4/2009 | Schoenberg |
| 2009/0089096 A1 | 4/2009 | Schoenberg |
| 2009/0089097 A1 | 4/2009 | Schoenberg |
| 2009/0089098 A1 | 4/2009 | Schoenberg |
| 2009/0089147 A1 | 4/2009 | Schoenberg |
| 2009/0099848 A1 | 4/2009 | Lerner et al. |
| 2009/0112623 A1 | 4/2009 | Schoenberg |
| 2009/0113298 A1 | 4/2009 | Jung et al. |
| 2009/0113312 A1 | 4/2009 | Schoenberg |
| 2009/0132441 A1 | 5/2009 | Muller et al. |
| 2009/0138317 A1 | 5/2009 | Schoenberg |
| 2009/0150252 A1 | 6/2009 | Schoenberg |
| 2009/0210220 A1 | 8/2009 | Mitsuyoshi et al. |
| 2009/0248594 A1 | 10/2009 | Castleman et al. |
| 2009/0254361 A1 | 10/2009 | Schoenberg |
| 2009/0262919 A1 | 10/2009 | Schoenberg |
| 2009/0264337 A1 | 10/2009 | Angelides |
| 2009/0265170 A1 | 10/2009 | Irie et al. |
| 2009/0271010 A1 | 10/2009 | Hyde et al. |
| 2009/0287469 A1 | 11/2009 | Matsukawa et al. |
| 2009/0292657 A1 | 11/2009 | Jung et al. |
| 2009/0292702 A1 | 11/2009 | Jung et al. |
| 2009/0292713 A1 | 11/2009 | Jung et al. |
| 2009/0292724 A1 | 11/2009 | Jung et al. |
| 2009/0292733 A1 | 11/2009 | Jung et al. |
| 2009/0292928 A1 | 11/2009 | Jung et al. |
| 2009/0313018 A1 | 12/2009 | Degani et al. |
| 2009/0313043 A1 | 12/2009 | Schoenberg |
| 2009/0313076 A1 | 12/2009 | Schoenberg |
| 2009/0318794 A1 | 12/2009 | DeCharms |
| 2009/0319296 A1 | 12/2009 | Schoenberg |
| 2010/0036660 A1 | 2/2010 | Bennett |
| 2010/0088088 A1 | 4/2010 | Bollano et al. |
| 2010/0131436 A1 | 5/2010 | Firminger et al. |
| 2010/0151889 A1 | 6/2010 | Chen et al. |
| 2010/0191075 A1 | 7/2010 | Angelides |
| 2010/0205006 A1 | 8/2010 | Bergh |
| 2010/0223341 A1 | 9/2010 | Manolescu et al. |
| 2010/0286979 A1 | 11/2010 | Zangvil et al. |
| 2010/0292545 A1 | 11/2010 | Berka et al. |
| 2010/0293487 A1 | 11/2010 | Schoenberg |

(56) References Cited

U.S. PATENT DOCUMENTS

| | | |
|---|---|---|
| 2010/0298649 A1 | 11/2010 | Warkentin et al. |
| 2010/0299154 A1 | 11/2010 | Benja-Athon |
| 2010/0324909 A1 | 12/2010 | Runge et al. |
| 2010/0332261 A1 | 12/2010 | Schoenberg |
| 2011/0004487 A1 | 1/2011 | Schoenberg |
| 2011/0010190 A1 | 1/2011 | Falchuk et al. |
| 2011/0010197 A1 | 1/2011 | Schoenberg |
| 2011/0040569 A1 | 2/2011 | Schoenberg |
| 2011/0041077 A1 | 2/2011 | Reiner |
| 2011/0054985 A1 | 3/2011 | Ricci et al. |
| 2011/0066036 A1 | 3/2011 | Zilca et al. |
| 2011/0066436 A1 | 3/2011 | Bezar |
| 2011/0086331 A1 | 4/2011 | Karov Zangvil |
| 2011/0112852 A1 | 5/2011 | Ware et al. |
| 2011/0118555 A1 | 5/2011 | Dhumne et al. |
| 2011/0119079 A1 | 5/2011 | Schoenberg |
| 2011/0119212 A1 | 5/2011 | De Bruin et al. |
| 2011/0137683 A1 | 6/2011 | Schoenberg |
| 2011/0137756 A1 | 6/2011 | Schoenberg |
| 2011/0173003 A1 | 7/2011 | Levanon et al. |
| 2011/0184720 A1 | 7/2011 | Zangvil |
| 2011/0184763 A1 | 7/2011 | Schoenberg |
| 2011/0191119 A1 | 8/2011 | Schoenberg |
| 2011/0196699 A1 | 8/2011 | Schoenberg |
| 2011/0263946 A1 | 10/2011 | el Kaliouby et al. |
| 2011/0267196 A1 | 11/2011 | Hu et al. |
| 2011/0283190 A1 | 11/2011 | Poltorak |
| 2012/0029327 A1 | 2/2012 | Angelides |
| 2012/0078062 A1 | 3/2012 | Bagchi et al. |
| 2012/0078634 A1 | 3/2012 | Ariu |
| 2012/0089396 A1 | 4/2012 | Patel et al. |
| 2012/0116186 A1 | 5/2012 | Shrivastav et al. |
| 2012/0166195 A1 | 6/2012 | Hayakawa et al. |
| 2012/0221336 A1 | 8/2012 | Degani et al. |
| 2012/0231431 A1 | 9/2012 | Angelides |
| 2012/0246102 A1 | 9/2012 | Sudharsan |
| 2012/0265024 A1 | 10/2012 | Shrivastav et al. |
| 2012/0284362 A1 | 11/2012 | Schoenberg |
| 2012/0296667 A1 | 11/2012 | Schoenberg |
| 2012/0316883 A1 | 12/2012 | Levanon et al. |
| 2013/0006613 A1 | 1/2013 | Karov Zangvil et al. |
| 2013/0018663 A1 | 1/2013 | Schoenberg |
| 2013/0030843 A1 | 1/2013 | Schoenberg |
| 2013/0035563 A1 | 2/2013 | Angelides |
| 2013/0035953 A1 | 2/2013 | Schoenberg |
| 2013/0036153 A1 | 2/2013 | Schoenberg |
| 2013/0046550 A1 | 2/2013 | Schoenberg |
| 2013/0054288 A1 | 2/2013 | Schoenberg |
| 2013/0080169 A1 | 3/2013 | Harada et al. |
| 2013/0085758 A1 | 4/2013 | Csoma et al. |
| 2013/0101976 A1 | 4/2013 | Roots et al. |
| 2013/0110408 A1 | 5/2013 | Cook et al. |
| 2013/0110551 A1 | 5/2013 | Bingol |
| 2013/0115582 A1 | 5/2013 | el Kaliouby et al. |
| 2013/0116540 A1 | 5/2013 | Li et al. |
| 2013/0117040 A1 | 5/2013 | James et al. |
| 2013/0123583 A1 | 5/2013 | Hill |
| 2013/0124631 A1 | 5/2013 | Rosansky et al. |
| 2013/0130789 A1 | 5/2013 | Brigham et al. |
| 2013/0159228 A1 | 6/2013 | Meijer et al. |
| 2013/0166291 A1 | 6/2013 | Lech et al. |
| 2013/0179472 A1 | 7/2013 | Junqua et al. |
| 2013/0204643 A1 | 8/2013 | Falchuk et al. |
| 2013/0241719 A1 | 9/2013 | Biswas et al. |
| 2013/0245424 A1 | 9/2013 | deCharms |
| 2013/0262349 A1 | 10/2013 | Bougata et al. |
| 2013/0275146 A1 | 10/2013 | Schoenberg |
| 2013/0297536 A1 | 11/2013 | Almosni et al. |
| 2013/0317838 A1 | 11/2013 | Schoenberg |
| 2013/0317842 A1 | 11/2013 | Schoenberg |
| 2013/0317843 A1 | 11/2013 | Schoenberg |
| 2013/0325500 A1 | 12/2013 | Schoenberg |
| 2013/0331737 A1 | 12/2013 | Roots |
| 2014/0006058 A1 | 1/2014 | Schoenberg |
| 2014/0052448 A1 | 2/2014 | Krishnan et al. |
| 2014/0052465 A1 | 2/2014 | Madan et al. |
| 2014/0052474 A1 | 2/2014 | Madan et al. |
| 2014/0052475 A1 | 2/2014 | Madan et al. |
| 2014/0057244 A1 | 2/2014 | Roots et al. |
| 2014/0074454 A1 | 3/2014 | Brown et al. |
| 2014/0095189 A1 | 4/2014 | Holmes |
| 2014/0099614 A1 | 4/2014 | Hu et al. |
| 2014/0112556 A1 | 4/2014 | Kalinli-Akbacak |
| 2014/0114889 A1 | 4/2014 | Dagum |
| 2014/0121540 A1 | 5/2014 | Raskin |
| 2014/0122062 A1 | 5/2014 | Zangvil |
| 2014/0122109 A1 | 5/2014 | Ghanbari et al. |
| 2014/0140489 A1 | 5/2014 | Schoenberg |
| 2014/0181229 A1 | 6/2014 | Tucker et al. |
| 2014/0195255 A1 | 7/2014 | Ghosh et al. |
| 2014/0200463 A1 | 7/2014 | el Kaliouby et al. |
| 2014/0200910 A1 | 7/2014 | Schoenberg |
| 2014/0200911 A1 | 7/2014 | Schoenberg |
| 2014/0201649 A1 | 7/2014 | Schoenberg |
| 2014/0201665 A1 | 7/2014 | Schoenberg |
| 2014/0207811 A1 | 7/2014 | Kim et al. |
| 2014/0214442 A1 | 7/2014 | Duffy et al. |
| 2014/0214443 A1 | 7/2014 | Duffy et al. |
| 2014/0222454 A1 | 8/2014 | Duffy et al. |
| 2014/0222719 A1 | 8/2014 | Poulin et al. |
| 2014/0244305 A1 | 8/2014 | Schoenberg |
| 2014/0247989 A1 | 9/2014 | Deaver |
| 2014/0249823 A1 | 9/2014 | Hayakawa |
| 2014/0257830 A1 | 9/2014 | Schoenberg |
| 2014/0257836 A1 | 9/2014 | Walker et al. |
| 2014/0257837 A1 | 9/2014 | Walker et al. |
| 2014/0258037 A1 | 9/2014 | Schoenberg |
| 2014/0272897 A1 | 9/2014 | Cummings et al. |
| 2014/0288959 A1 | 9/2014 | Schoenberg |
| 2014/0316248 A1 | 10/2014 | deCharms |
| 2014/0358581 A1 | 12/2014 | Sudharsan |
| 2014/0363797 A1 | 12/2014 | Hu et al. |
| 2014/0377727 A1 | 12/2014 | Yom-Tov et al. |
| 2015/0006186 A1 | 1/2015 | Davis et al. |
| 2015/0006192 A1 | 1/2015 | Sudharsan et al. |
| 2015/0006456 A1 | 1/2015 | Sudharsan |
| 2015/0006462 A1 | 1/2015 | Sudharsan |
| 2015/0099257 A1 | 4/2015 | Kozloski et al. |
| 2015/0100521 A1 | 4/2015 | Kozloski et al. |
| 2015/0112232 A1 | 4/2015 | Quatieri et al. |
| 2015/0112703 A1 | 4/2015 | Sysko et al. |
| 2015/0112899 A1 | 4/2015 | Dagum |
| 2015/0127594 A1 | 5/2015 | Parada San Martin et al. |
| 2015/0142422 A1 | 5/2015 | Zangvil et al. |
| 2015/0154492 A1 | 6/2015 | Ponomarev et al. |
| 2015/0154721 A1 | 6/2015 | Thompson |
| 2015/0164430 A1 | 6/2015 | Hu et al. |
| 2015/0170531 A1 | 6/2015 | Hu et al. |
| 2015/0186336 A1 | 7/2015 | Zangvil |
| 2015/0193507 A1 | 7/2015 | Rappoport et al. |
| 2015/0195406 A1 | 7/2015 | Dwyer et al. |
| 2015/0196243 A1 | 7/2015 | Duffy |
| 2015/0199488 A1 | 7/2015 | Falchuk et al. |
| 2015/0213800 A1 | 7/2015 | Krishnan et al. |
| 2015/0220509 A1 | 8/2015 | Karov Zangvil et al. |
| 2015/0234886 A1 | 8/2015 | Levanon |
| 2015/0235009 A1 | 8/2015 | Kashtan |
| 2015/0242593 A1 | 8/2015 | Levenson et al. |
| 2015/0248533 A1 | 9/2015 | Sudharsan |
| 2015/0262572 A1 | 9/2015 | Kelly et al. |
| 2015/0264177 A1 | 9/2015 | Feast et al. |
| 2015/0265205 A1 | 9/2015 | Rosenbek et al. |
| 2015/0279350 A1 | 10/2015 | Onishi et al. |
| 2015/0279359 A1 | 10/2015 | Velasco |
| 2015/0282752 A1 | 10/2015 | Roots et al. |
| 2015/0294595 A1 | 10/2015 | Hu et al. |
| 2015/0304381 A1 | 10/2015 | Rosansky et al. |
| 2015/0305662 A1 | 10/2015 | Kilmer et al. |
| 2015/0305663 A1 | 10/2015 | Roots et al. |
| 2015/0310849 A1 | 10/2015 | Onishi et al. |
| 2015/0310877 A1 | 10/2015 | Onishi et al. |
| 2015/0318002 A1 | 11/2015 | Karam et al. |
| 2015/0327802 A1 | 11/2015 | Miyake |
| 2015/0332021 A1 | 11/2015 | Godla |

(56) References Cited

U.S. PATENT DOCUMENTS

| | | |
|---|---|---|
| 2015/0334214 A9 | 11/2015 | Schoenberg |
| 2015/0334236 A1 | 11/2015 | Conway et al. |
| 2015/0348569 A1 | 12/2015 | Allam et al. |
| 2015/0348570 A1 | 12/2015 | Feast et al. |
| 2015/0356251 A1 | 12/2015 | Junqua et al. |
| 2015/0370993 A1 | 12/2015 | Moturu et al. |
| 2015/0370994 A1 | 12/2015 | Madan et al. |
| 2015/0371663 A1 | 12/2015 | Gustafson et al. |
| 2015/0379477 A1 | 12/2015 | Junqua et al. |
| 2016/0004299 A1 | 1/2016 | Meyer et al. |
| 2016/0005421 A1 | 1/2016 | Gratzel et al. |
| 2016/0007912 A1 | 1/2016 | Hu et al. |
| 2016/0022193 A1 | 1/2016 | Rau et al. |
| 2016/0063205 A1 | 3/2016 | Moturu et al. |
| 2016/0063874 A1 | 3/2016 | Czerwinski et al. |
| 2016/0086088 A1 | 3/2016 | Yehezkel et al. |
| 2016/0095545 A1 | 4/2016 | Levanon |
| 2016/0117684 A1 | 4/2016 | Khor et al. |
| 2016/0140320 A1 | 5/2016 | Moturu et al. |
| 2016/0162569 A1 | 6/2016 | Erle et al. |
| 2016/0164813 A1 | 6/2016 | Anderson et al. |
| 2016/0166191 A1 | 6/2016 | Al-Garni et al. |
| 2016/0174889 A1 | 6/2016 | Yekutieli |
| 2016/0179786 A1 | 6/2016 | Clark et al. |
| 2016/0180038 A1 | 6/2016 | Clark et al. |
| 2016/0188792 A1 | 6/2016 | Zwir et al. |
| 2016/0188822 A1 | 6/2016 | Ryan et al. |
| 2016/0196389 A1 | 7/2016 | Moturu et al. |
| 2016/0196837 A1 | 7/2016 | Levanon |
| 2016/0203729 A1 | 7/2016 | Zilca |
| 2016/0210005 A9 | 7/2016 | Schoenberg |
| 2016/0210636 A9 | 7/2016 | Schoenberg |
| 2016/0210985 A1 | 7/2016 | Deleeuw |
| 2016/0212182 A9 | 7/2016 | Schoenberg |
| 2016/0225368 A1 | 8/2016 | Velasco |
| 2016/0232244 A1 | 8/2016 | Liu et al. |
| 2016/0253316 A1 | 9/2016 | Kelly et al. |
| 2016/0260189 A9 | 9/2016 | Schoenberg |
| 2016/0275247 A9 | 9/2016 | Schoenberg |
| 2016/0322065 A1 | 11/2016 | Shimoji |
| 2016/0324457 A1 | 11/2016 | Dagum |
| 2016/0337519 A1 | 11/2016 | Conway et al. |
| 2016/0342756 A1 | 11/2016 | Wall |
| 2016/0350801 A1 | 12/2016 | Vincent et al. |
| 2016/0357744 A1 | 12/2016 | Kozloski et al. |
| 2016/0359777 A1 | 12/2016 | Tucker et al. |
| 2017/0000422 A1 | 1/2017 | Moturu et al. |
| 2017/0004184 A1 | 1/2017 | Jain et al. |
| 2017/0004260 A1 | 1/2017 | Moturu et al. |
| 2017/0004269 A1 | 1/2017 | Potter |
| 2017/0025125 A1 | 1/2017 | Alvarez Guevara |
| 2017/0053089 A1 | 2/2017 | Kenedy et al. |
| 2017/0053665 A1 | 2/2017 | Quatieri, Jr. et al. |
| 2017/0063737 A1 | 3/2017 | Torii et al. |
| 2017/0069216 A1 | 3/2017 | Vaughan et al. |
| 2017/0076053 A1 | 3/2017 | Sysko et al. |
| 2017/0076064 A1 | 3/2017 | Sudharsan |
| 2017/0076630 A1 | 3/2017 | Angelides et al. |
| 2017/0076740 A1 | 3/2017 | Feast et al. |
| 2017/0078479 A1 | 3/2017 | Feast et al. |
| 2017/0086727 A1 | 3/2017 | Dagum |
| 2017/0095192 A1 | 4/2017 | Sadowsky et al. |
| 2017/0098051 A1 | 4/2017 | Balram |
| 2017/0112446 A1 | 4/2017 | Dagum |
| 2017/0116183 A1 | 4/2017 | Kelly et al. |
| 2017/0119302 A1 | 5/2017 | Rosenbek et al. |
| 2017/0139802 A1 | 5/2017 | Hajiyev et al. |
| 2017/0143246 A1 | 5/2017 | Flickinger |
| 2017/0154637 A1 | 6/2017 | Chu et al. |
| 2017/0169177 A1 | 6/2017 | Beale et al. |
| 2017/0180558 A1 | 6/2017 | Li et al. |
| 2017/0188976 A1 | 7/2017 | Kalra et al. |
| 2017/0189641 A1 | 7/2017 | Moturu et al. |
| 2017/0193171 A1 | 7/2017 | Perlroth et al. |
| 2017/0213003 A9 | 7/2017 | Schoenberg |
| 2017/0213007 A1 | 7/2017 | Moturu et al. |
| 2017/0213190 A1 | 7/2017 | Hazan |
| 2017/0215782 A1 | 8/2017 | Ishimaru et al. |
| 2017/0221336 A1 | 8/2017 | Ogaz |
| 2017/0221484 A1 | 8/2017 | Poltorak |
| 2017/0228515 A1 | 8/2017 | Schoenberg |
| 2017/0228520 A1 | 8/2017 | Kidd et al. |
| 2017/0235912 A1 | 8/2017 | Moturu et al. |
| 2017/0249434 A1 | 8/2017 | Brunner |
| 2017/0251985 A1 | 9/2017 | Howard |
| 2017/0257481 A1 | 9/2017 | Feast et al. |
| 2017/0258382 A1 | 9/2017 | Dagum |
| 2017/0258383 A1 | 9/2017 | Dagum |
| 2017/0262604 A1 | 9/2017 | Francois |
| 2017/0262609 A1 | 9/2017 | Perlroth et al. |
| 2017/0287473 A1 | 10/2017 | Levanon |
| 2017/0289085 A1 | 10/2017 | Kim |
| 2017/0316172 A1 | 11/2017 | Schoenberg |
| 2017/0316330 A1 | 11/2017 | Cohen et al. |
| 2017/0323011 A1 | 11/2017 | Byron et al. |
| 2017/0329917 A1 | 11/2017 | McRaith et al. |
| 2017/0337180 A1 | 11/2017 | Wang |
| 2017/0344706 A1 | 11/2017 | Torres et al. |
| 2017/0344726 A1 | 11/2017 | Duffy et al. |
| 2017/0351830 A1 | 12/2017 | Burger et al. |
| 2017/0353841 A1 | 12/2017 | Lau et al. |
| 2017/0357769 A1 | 12/2017 | Schoenberg |
| 2017/0364641 A1 | 12/2017 | Sysko et al. |
| 2017/0365277 A1 | 12/2017 | Park |
| 2018/0005646 A1 | 1/2018 | Un et al. |
| 2018/0018634 A1 | 1/2018 | Satagopan et al. |
| 2018/0039757 A1 | 2/2018 | Sudharsan |
| 2018/0052974 A1 | 2/2018 | Madan et al. |
| 2018/0055434 A1 | 3/2018 | Cheung et al. |
| 2018/0060302 A1 | 3/2018 | Liang et al. |
| 2018/0061421 A1 | 3/2018 | Sarikaya |
| 2018/0068085 A1 | 3/2018 | Madan et al. |
| 2018/0075205 A1 | 3/2018 | Moturu et al. |
| 2018/0077095 A1 | 3/2018 | Deyle et al. |
| 2018/0096738 A1 | 4/2018 | Moturu et al. |
| 2018/0096740 A1 | 4/2018 | Moturu et al. |
| 2018/0101650 A1 | 4/2018 | Moturu et al. |
| 2018/0103885 A1 | 4/2018 | Wrenn |
| 2018/0108353 A1 | 4/2018 | Gustafson et al. |
| 2018/0114125 A1 | 4/2018 | Ichiboshi et al. |
| 2018/0121619 A1 | 5/2018 | Perlroth et al. |
| 2018/0131733 A1 | 5/2018 | Davey et al. |
| 2018/0132776 A1 | 5/2018 | Flickinger |
| 2018/0150751 A1 | 5/2018 | Lee |
| 2018/0158538 A1 | 6/2018 | Moturu et al. |
| 2018/0166163 A1 | 6/2018 | Sudharsan |
| 2018/0166164 A1 | 6/2018 | Sysko et al. |
| 2018/0174055 A1 | 6/2018 | Tirumale et al. |
| 2018/0184963 A1 | 7/2018 | Levanon |
| 2018/0190284 A1 | 7/2018 | Singh |
| 2018/0197565 A1 | 7/2018 | Feast et al. |
| 2018/0204107 A1 | 7/2018 | Tucker |
| 2018/0204634 A1 | 7/2018 | Sysko et al. |
| 2018/0214061 A1 | 8/2018 | Knoth et al. |
| 2018/0218750 A1 | 8/2018 | Nichkawde et al. |
| 2018/0218783 A1 | 8/2018 | Sysko et al. |
| 2018/0218784 A1 | 8/2018 | Sysko et al. |
| 2018/0228447 A1 | 8/2018 | Arai et al. |
| 2018/0233164 A1 | 8/2018 | Levanon |
| 2018/0240454 A1 | 8/2018 | Raj et al. |
| 2018/0240459 A1 | 8/2018 | Weng et al. |
| 2018/0240535 A1 | 8/2018 | Harper et al. |
| 2018/0254041 A1 | 9/2018 | Harper |
| 2018/0262539 A1 | 9/2018 | Feast et al. |
| 2018/0268821 A1 | 9/2018 | Levanon |
| 2018/0277146 A1 | 9/2018 | Chen et al. |
| 2018/0286383 A1 | 10/2018 | Barari et al. |
| 2018/0296151 A1 | 10/2018 | Kosikowski et al. |
| 2018/0310866 A1 | 11/2018 | Wrenn |
| 2018/0315442 A1 | 11/2018 | Shimoji |
| 2018/0316631 A1 | 11/2018 | Koukoumidis et al. |
| 2018/0322961 A1 | 11/2018 | Kim et al. |
| 2018/0325439 A1 | 11/2018 | Wrenn |
| 2018/0329984 A1 | 11/2018 | Aviles |

(56) References Cited

U.S. PATENT DOCUMENTS

| | | | |
|---|---|---|---|
| 2018/0331839 A1 | 11/2018 | Gao et al. |
| 2018/0332062 A1 | 11/2018 | Ford |
| 2018/0342325 A1 | 11/2018 | Madan et al. |
| 2018/0342326 A1 | 11/2018 | Moturu et al. |
| 2018/0342327 A1 | 11/2018 | Madan et al. |
| 2018/0349560 A1 | 12/2018 | McCloskey et al. |
| 2018/0357286 A1 | 12/2018 | Wang et al. |
| 2018/0357917 A1 | 12/2018 | Ekambaram et al. |
| 2018/0365551 A1 | 12/2018 | Bostick et al. |
| 2018/0365552 A1 | 12/2018 | Bostick et al. |
| 2018/0366143 A1 | 12/2018 | Ashoori et al. |
| 2018/0366144 A1 | 12/2018 | Ashoori et al. |
| 2019/0012599 A1 | 1/2019 | el Kaliouby et al. |
| 2019/0013088 A1 | 1/2019 | Moturu et al. |
| 2019/0013092 A1 | 1/2019 | Van Halteren et al. |
| 2019/0015033 A1 | 1/2019 | Sahin |
| 2019/0019581 A1 | 1/2019 | Vaughan et al. |
| 2019/0029582 A1 | 1/2019 | Chen |
| 2019/0038202 A1 | 2/2019 | Wall |
| 2019/0043606 A1 | 2/2019 | Roots et al. |
| 2019/0043610 A1 | 2/2019 | Vaughan |
| 2019/0052724 A1 | 2/2019 | Dancel |
| 2019/0057186 A1 | 2/2019 | Zwir et al. |
| 2019/0058740 A1 | 2/2019 | Singman et al. |
| 2019/0066840 A1 | 2/2019 | Schoenberg |
| 2019/0074028 A1 | 3/2019 | Howard |
| 2019/0074089 A1 | 3/2019 | Kochura et al. |
| 2019/0079916 A1 | 3/2019 | Eyigoz |
| 2019/0080804 A1 | 3/2019 | Kim et al. |
| 2019/0088270 A1 | 3/2019 | Malur Srinivasan et al. |
| 2019/0094980 A1 | 3/2019 | Reddy et al. |
| 2019/0102511 A1 | 4/2019 | Murray et al. |
| 2019/0109878 A1 | 4/2019 | Boyadjiev et al. |
| 2019/0110754 A1 | 4/2019 | Rao et al. |
| 2019/0114321 A1 | 4/2019 | Lam et al. |
| 2019/0122661 A1 | 4/2019 | Hansen et al. |
| 2019/0130077 A1 | 5/2019 | De et al. |
| 2019/0147995 A1 | 5/2019 | Sudharsan et al. |
| 2019/0151603 A1 | 5/2019 | Horoshutin |
| 2019/0155862 A1 | 5/2019 | Yi et al. |
| 2019/0156222 A1 | 5/2019 | Emma et al. |
| 2019/0167105 A1 | 6/2019 | Shrubsole et al. |
| 2019/0172363 A1 | 6/2019 | Arun |
| 2019/0172458 A1 | 6/2019 | Mishra et al. |
| 2019/0180871 A1 | 6/2019 | Doerflinger |
| 2019/0197073 A1 | 6/2019 | Liu et al. |
| 2019/0205329 A1 | 7/2019 | Subramanian et al. |
| 2019/0206228 A1 | 7/2019 | Bhattacharya et al. |
| 2019/0206393 A1 | 7/2019 | Fang et al. |
| 2019/0206401 A1 | 7/2019 | Liu et al. |
| 2019/0206402 A1 | 7/2019 | Shukla et al. |
| 2019/0206407 A1 | 7/2019 | Shukla |
| 2019/0206424 A1 | 7/2019 | Feast et al. |
| 2019/0313903 A1 | 10/2019 | McKinnon |
| 2019/0341152 A1 | 11/2019 | Mellem et al. |
| 2019/0385711 A1 | 12/2019 | Shriberg et al. |
| 2020/0118458 A1 | 4/2020 | Shriberg et al. |
| 2020/0321082 A1 | 10/2020 | Shriberg et al. |
| 2021/0110895 A1 | 4/2021 | Shriberg et al. |

FOREIGN PATENT DOCUMENTS

| | | |
|---|---|---|
| AU | 2012216577 A1 | 9/2012 |
| AU | 2017263835 A1 | 1/2019 |
| CA | 2283976 A1 | 9/1998 |
| CA | 2456625 A1 | 2/2003 |
| CA | 2662786 A1 | 3/2008 |
| CA | 2694327 A1 | 2/2009 |
| CA | 2701257 A1 | 4/2009 |
| CA | 2701259 A1 | 4/2009 |
| CA | 2701267 A1 | 4/2009 |
| CA | 2707496 A1 | 6/2009 |
| CA | 2721157 A1 | 12/2009 |
| CA | 2727649 A1 | 12/2009 |
| CA | 2731899 A1 | 2/2010 |
| CA | 2787390 A1 | 8/2011 |
| CA | 3024111 A1 | 11/2017 |
| CN | 101802812 A | 8/2010 |
| CN | 102016955 A | 4/2011 |
| CN | 102124515 A | 7/2011 |
| CN | 102165435 A | 8/2011 |
| CN | 102884518 A | 1/2013 |
| CN | 104584017 A | 4/2015 |
| CN | 109785972 A | 5/2019 |
| DE | 60210295 T2 | 12/2006 |
| EP | 1298645 A1 | 4/2003 |
| EP | 1423846 A1 | 6/2004 |
| EP | 1969589 A1 | 9/2008 |
| EP | 2062215 A1 | 5/2009 |
| EP | 2124223 A1 | 11/2009 |
| EP | 2183685 A2 | 5/2010 |
| EP | 2212835 A1 | 8/2010 |
| EP | 2212836 A2 | 8/2010 |
| EP | 2212837 A1 | 8/2010 |
| EP | 2220603 A1 | 8/2010 |
| EP | 2277157 A1 | 1/2011 |
| EP | 2304718 A2 | 4/2011 |
| EP | 2313835 A1 | 4/2011 |
| EP | 2531930 A1 | 12/2012 |
| EP | 2884888 A2 | 6/2015 |
| EP | 3117431 A1 | 1/2017 |
| EP | 3350806 A1 | 7/2018 |
| EP | 3350980 A1 | 7/2018 |
| EP | 3396668 A1 | 10/2018 |
| EP | 3455755 A1 | 3/2019 |
| ES | 2261706 T3 | 11/2006 |
| IL | 192013 A | 10/2015 |
| JP | 2007052774 A | 3/2007 |
| JP | 2008116826 A | 5/2008 |
| JP | 2009103721 A | 5/2009 |
| JP | 2010503122 A | 1/2010 |
| JP | 2011255106 A | 12/2011 |
| JP | 2015529359 A | 10/2015 |
| JP | 2016502422 A | 1/2016 |
| JP | 6185066 B2 | 8/2017 |
| JP | 2017532082 A | 11/2017 |
| WO | WO-9841943 A1 | 9/1998 |
| WO | WO-2007143083 A2 | 12/2007 |
| WO | WO-2008030850 A1 | 3/2008 |
| WO | WO-2008030855 A1 | 3/2008 |
| WO | WO-2008103827 A1 | 8/2008 |
| WO | WO-2008115927 A2 | 9/2008 |
| WO | WO-2009016631 A2 | 2/2009 |
| WO | WO-2009046099 A2 | 4/2009 |
| WO | WO-2009046106 A1 | 4/2009 |
| WO | WO-2009046111 A1 | 4/2009 |
| WO | WO-2009076419 A1 | 6/2009 |
| WO | WO-2009137164 A2 | 11/2009 |
| WO | WO-2009153788 A2 | 12/2009 |
| WO | WO-2009155336 A1 | 12/2009 |
| WO | WO-2011140113 A1 | 11/2011 |
| WO | WO-2012129507 A1 | 9/2012 |
| WO | WO-2012151570 A2 | 11/2012 |
| WO | WO-2013022820 A2 | 2/2013 |
| WO | WO-2014028888 A2 | 2/2014 |
| WO | WO-2014037937 A2 | 3/2014 |
| WO | WO-2014058894 A1 | 4/2014 |
| WO | WO-2014066273 A2 | 5/2014 |
| WO | WO-2014110120 A1 | 7/2014 |
| WO | WO-2014131763 A2 | 9/2014 |
| WO | WO-2014181524 A1 | 11/2014 |
| WO | WO-2014210210 A1 | 12/2014 |
| WO | WO-2015023952 A1 | 2/2015 |
| WO | WO-2015026797 A1 | 2/2015 |
| WO | WO-2015102733 A1 | 7/2015 |
| WO | WO-2015105994 A1 | 7/2015 |
| WO | WO-2015116678 A1 | 8/2015 |
| WO | WO-2015123058 A1 | 8/2015 |
| WO | WO-2015130457 A1 | 9/2015 |
| WO | WO-2015143897 A1 | 10/2015 |
| WO | WO-2015145403 A1 | 10/2015 |
| WO | WO-2015153127 A1 | 10/2015 |
| WO | WO-2015154382 A1 | 10/2015 |
| WO | WO-2015167652 A1 | 11/2015 |

(56) References Cited

FOREIGN PATENT DOCUMENTS

| | | |
|---|---|---|
| WO | WO-2015168606 A1 | 11/2015 |
| WO | WO-2016001257 A1 | 1/2016 |
| WO | WO-2016004425 A1 | 1/2016 |
| WO | WO-2016028495 A1 | 2/2016 |
| WO | WO-2016031650 A1 | 3/2016 |
| WO | WO-2016035069 A1 | 3/2016 |
| WO | WO-2016035070 A2 | 3/2016 |
| WO | WO-2016048502 A1 | 3/2016 |
| WO | WO-2016065020 A2 | 4/2016 |
| WO | WO-2016065020 A3 | 6/2016 |
| WO | WO-2016156867 A1 | 10/2016 |
| WO | WO-2016179428 A2 | 11/2016 |
| WO | WO-2016179432 A2 | 11/2016 |
| WO | WO-2016179434 A1 | 11/2016 |
| WO | WO-2016193839 A1 | 12/2016 |
| WO | WO-2016209888 A1 | 12/2016 |
| WO | WO-2017024553 A1 | 2/2017 |
| WO | WO-2017027709 A1 | 2/2017 |
| WO | WO-2017031350 A1 | 2/2017 |
| WO | WO-2017048730 A1 | 3/2017 |
| WO | WO-2017057022 A1 | 4/2017 |
| WO | WO-2017065318 A1 | 4/2017 |
| WO | WO-2017068816 A1 | 4/2017 |
| WO | WO-2017085714 A2 | 5/2017 |
| WO | WO-2017086811 A1 | 5/2017 |
| WO | WO-2017106770 A1 | 6/2017 |
| WO | WO-2017112240 A1 | 6/2017 |
| WO | WO-2017112496 A1 | 6/2017 |
| WO | WO-2017113974 A1 | 7/2017 |
| WO | WO-2017141261 A2 | 8/2017 |
| WO | WO-2017147552 A1 | 8/2017 |
| WO | WO-2017147552 A9 | 9/2017 |
| WO | WO-2017141261 A3 | 10/2017 |
| WO | WO-2017187712 A1 | 11/2017 |
| WO | WO-2017197333 A1 | 11/2017 |
| WO | WO-2017199433 A1 | 11/2017 |
| WO | WO-2017206861 A1 | 12/2017 |
| WO | WO-2017212783 A1 | 12/2017 |
| WO | WO-2018016459 A1 | 1/2018 |
| WO | WO-2018025267 A1 | 2/2018 |
| WO | WO-2018033498 A1 | 2/2018 |
| WO | WO-2018074996 A1 | 4/2018 |
| WO | WO-2018102867 A1 | 6/2018 |
| WO | WO-2018106481 A1 | 6/2018 |
| WO | WO-2018110544 A1 | 6/2018 |
| WO | WO-2018121624 A1 | 7/2018 |
| WO | WO-2018132483 A1 | 7/2018 |
| WO | WO-2018153359 A1 | 8/2018 |
| WO | WO-2018172410 A1 | 9/2018 |
| WO | WO-2018174290 A1 | 9/2018 |
| WO | WO-2018180134 A1 | 10/2018 |
| WO | WO-2018192567 A1 | 10/2018 |
| WO | WO-2018204935 A1 | 11/2018 |
| WO | WO-2018205224 A1 | 11/2018 |
| WO | WO-2018212134 A1 | 11/2018 |
| WO | WO-2018220499 A1 | 12/2018 |
| WO | WO-2018223172 A1 | 12/2018 |
| WO | WO-2019011356 A1 | 1/2019 |
| WO | WO-2019032128 A1 | 2/2019 |
| WO | WO-2019035007 A1 | 2/2019 |
| WO | WO-2019036013 A1 | 2/2019 |
| WO | WO-2019037700 A1 | 2/2019 |
| WO | WO-2019044485 A1 | 3/2019 |
| WO | WO-2019054894 A1 | 3/2019 |
| WO | WO-2019064299 A1 | 4/2019 |
| WO | WO-2019068203 A1 | 4/2019 |
| WO | WO-2019069955 A1 | 4/2019 |
| WO | WO-2019075432 A1 | 4/2019 |
| WO | WO-2019079475 A1 | 4/2019 |
| WO | WO-2019081915 A1 | 5/2019 |
| WO | WO-2019094155 A1 | 5/2019 |
| WO | WO-2019098423 A1 | 5/2019 |
| WO | WO-2019103484 A1 | 5/2019 |
| WO | WO-2019132772 A1 | 7/2019 |
| WO | WO-2019133694 A1 | 7/2019 |
| WO | WO-2019133698 A1 | 7/2019 |
| WO | WO-2019133710 A1 | 7/2019 |
| WO | WO-2019133715 A1 | 7/2019 |
| WO | WO-2019246239 A1 | 12/2019 |
| WO | WO-2020206178 A1 | 10/2020 |
| WO | WO-2021081418 A1 | 4/2021 |

OTHER PUBLICATIONS

Chan, J. et al. "Contactless Cardiac Arrest Detection Using Smart Devices," npj Digit. Med., vol. 2, No. 52 (2019) doi: 10.1038/s41746-019-0128-7, 8 pages.

Co-pending U.S. Appl. No. 16/918,624, inventor Shriberg, Elizabeth E. et al., filed Jul. 1, 2020, 187 pages.

Co-pending U.S. Appl. No. 17/400,066, inventor Shriberg, Elizabeth E. et al., filed Aug. 11, 2021, 183 pages.

Correia, J. et al. "In-The-Wild End-To-End Detection of Speech Affecting Diseases," 2019 IEEE Automatic Speech Recognition and Understanding Workshop (ASRU), Dec. 2019, pp. 734-741, 8 pages.

EP19823035.1, Extended European Search Report dated Feb. 9, 2022, 11 pages.

PCT/US19/37953, International Search Report dated Oct. 28, 2019, 14 pages.

PCT/US2020/026472, International Search Report dated Jun. 30, 2020, 15 pages.

U.S. Appl. No. 17/129,859, Notice of Allowance dated Jun. 3, 2021, 7 pages.

U.S. Appl. No. 17/129,859, Office Action dated Feb. 1, 2021, 14 pages.

U.S. Appl. No. 17/129,859, Office Action dated Feb. 16, 2021, 16 pages.

U.S. Appl. No. 17/130,649, Office Action dated Feb. 9, 2021, 23 pages.

U.S. Appl. No. 17/130,649, Office Action dated Jan. 28, 2021, 18 pages.

U.S. Appl. No. 17/130,649, Office Action dated May 14, 2021, 28 pages.

U.S. Appl. No. 16/523,298, Office Action dated May 1, 2020, 48 pages.

U.S. Appl. No. 16/523,298, Office Action dated Sep. 24, 2019, 37 pages.

U.S. Appl. No. 16/560,720, Notice of Allowance dated May 12, 2020, 12 pages.

U.S. Appl. No. 16/560,720, Office Action dated Dec. 30, 2019, 32 pages.

Anonymous. "Machine Translation versus Multilingual Approaches for Speech-Based Depression Prediction in a New Language," 6 pages.

Co-pending U.S. Appl. No. 17/726,999, inventor Shriberg, Elizabeth E. et al., filed Apr. 22, 2022, 113 pages.

Cummins, N. et al. "A Review of Depression and Suicide Risk Assessment Using Speech Analysis," Speech Communication vol. 71, Jul. 2015, pp. 10-49, Available online Apr. 6, 2015, 40 pages.

Dai, Andrew, M. et al. "Semi-supervised Sequence Learning," Advances in Neural Information Processing Systems 28 (NIPS 2015); Edited by: C. Cortes and N. Lawrence and D. Lee and M. Sugiyama and R. Garnett, submitted on Nov. 4, 2015, 9 pages.

World Health Organization, "Depression and Other Common Mental Disorders: Global Health Estimates," Geneva, 2017, 24 pages.

Devlin, J. et al. "Bert: Pre-training of Deep Bidirectional Transformers for Language Understanding," Proceedings of NAACL-HLT 2019, pp. 4171-4186, Minneapolis, Minnesota, Jun. 2-Jun. 7, 2019. First Submitted Oct. 11, 2018, 16 pages.

Google Inc. https://cloud.google.com/translate, 2021. (website), 11 pages.

Howard, J. et al. "Universal Language Model Fine-Tuning for Text Classification," Proceedings of the 56th Annual Meeting of the Association for Computational Linguistics (Long Papers), pp. 328-339, Melbourne, Australia, Jul. 15-20, 2018, 12 pages.

(56) References Cited

OTHER PUBLICATIONS

Kroenke, K. et al. "The PHQ-8 as a Measure of Current Depression in the General Population," J Affect Disord. 114:1-3 (2009): 163-73, 11 pages.

Lan, Z. et al. "Albert: A Lite Bert for Self-Supervised Learning of Language Representations," International Conference on Learning Representations, 2020, 17 pages.

Liu, Y et al. "RoBERTa: A Robustly Optimized Bert Pretraining Approach," arXiv:1907.11692 [cs.CL], submitted Jul. 26, 2019, 13 pages.

Mikolov, T. et al. "Efficient Estimation of Word Representations in Vector Space," Published at ICLR 2013, arXiv:1301.3781v3, 13 pages.

Manea, L. et al. "Optimal Cut-off Score for Diagnosing Depression with the Patient Health Questionnaire (PHQ-9): A Meta-analysis," CMAJ, Feb. 21, 2012, vol. 184, No. 3, E191-E196, 6 pages.

Mitchell, A. J. et al. "Clinical Diagnosis of Depression in Primary Care: A Meta-analysis," The Lancet, vol. 374, No. 9690 (2009): 609-619, 13 pages.

Morency et al. Tutorial on Multimodal Machine Learning. ACL 2017 Tutorials. Retrieved on Dec. 22, 2020. Retrieved from URL: https://www.cs.cmu.edu/-morency/MMML-Tutorial-ACL2017.pdf, 49 pages.

Nease, Jr. et al. "Depression Screening: A Practical Strategy," J Fam Pract. Feb. 2003;52(2):118-124. 8 pages.

Pampouchidou, A. et al. "Depression Assessment by Fusing High and Low Level Features from Audio, Video, and Text," In Proceedings of the 6th International Workshop on Audio/Visual Emotion Challenge, Association for Computing Machinery, New York, NY, USA. (2016): 27-34, 8 pages.

PCT/US2020/057182, International Search Report and Written Opinion dated Mar. 10, 2021, 24 pages.

Pennebaker, J. W. et al. "Psychological Aspects of Natural Language Use: Our Words, Our Selves," Annu. Rev. Psychol. 2003. 54:547-577; first published online Aug. 14, 2002, 32 pages.

Peters, M. E. et al. "Semi-supervised Sequence Tagging with Bidirectional Language Models," Proceedings of the 55th Annual Meeting of the Association for Computational Linguistics, pp. 1756-1765 Vancouver, Canada, Jul. 30-Aug. 4, 2017, 10 pages.

Raffel, C. et al. "Exploring the Limits of Transfer Learning with a Unified Text-to-Text Transformer," Journal of Machine Learning Research 21 (2020) 1-67, 67 pages.

Resnik, P. et al. "Using Topic Modeling to Improve Prediction of Neuroticism and Depression in College Students," Proceedings of the 2013 Conference on Empirical Methods in Natural Language Processing, pp. 1348-1353, Seattle, Washington, USA, Oct. 18-21, 2013, 6 pages.

Ringeval, F. et al. "AVEC 2019 Workshop and Challenge: State-of-Mind, Detecting Depression with AI, and Cross-Cultural Affect Recognition," AVEC '19: Proceedings of the 9th International on Audio/Visual Emotion Challenge and WorkshopOct. 2019, pp. 3-12, Published: Oct. 15, 2019, 11 pages.

Rutowski, T. et al. "Optimizing Speech-Input Length for Speaker-Independent Depression Classification," Interspeech 2019, Sep. 15-19, 2019, Graz, Austria, 5 pages.

Shannon, C. E. "Prediction and Entropy of Printed English," The Bell System Technical Journal, 30(1):50-64, Jan. 1951, 12 pages.

Vaswani, A. et al. "Attention is All You Need," Advances in Neural Information Processing Systems, NIPS'17: Proceedings of the 31st International Conference on Neural Information Processing Systems, Dec. 2017, pp. 6000-6010; Published: Dec. 4, 2017, 11 pages.

Wenzek, G. et al. "CCNet: Extracting High Quality Monolingual Datasets from Web Crawl Data," Proceedings of the 12th Conference on Language Resources and Evaluation. (2020): 4003-4012, May 11-16, 2020, 10 pages.

Williamson, J. R. et al. "Detecting Depression Using Vocal, Facial and Semantic Communication Cues," Proceedings of the 6th International Workshop on Audio/Visual Emotion Challenge, pp. 11-18, New York, NY, USA, Oct. 16, 2016, 8 pages.

Xue, L. et al. "mT5: A Massively Multilingual Pre-trained Text-to-Text Transformer," Proceedings of the 2021 Conference of the North American Chapter of the Association for Computational Linguistics: Human Language Technologies, pp. 483-498, Jun. 6-11, 2021, 16 pages.

Yang, L. et al. "Hybrid Depression Classification and Estimation from Audio Video and Text Information," AVEC '17: Proceedings of the 7th Annual Workshop on Audio/Visual Emotion Challenge, Oct. 2017, pp. 45-51, Published: Oct. 23, 2017, 7 pages.

Yang, Z. et al. "XLNet: Generalized Autoregressive Pretraining for Language Understanding," 33rd Conference on Neural Information Processing Systems (NeurIPS 2019), Vancouver, Canada, 11 pages.

Bengio, Y. "Deep Learning of Representations for Unsupervised and Transfer Learning," JMLR: Workshop and Conference Proceedings, vol. 27, pp. 17-37, Jul. 2, 2011, 21 pages.

U.S. Appl. No. 17/671,337 Office Action dated Apr. 29, 2022.

Co-pending U.S. Appl. No. 17/671,337, inventor Shriberg, Elizabeth E. et al., filed Feb. 14, 2022.

Co-pending U.S. Appl. No. 17/130,649, inventor Shriberg, Elizabeth E. et al., filed Dec. 22, 2020, 189 pages.

Co-pending U.S. Appl. No. 16/377,090, filed Apr. 5, 2019, 88 pages.

Co-pending U.S. Appl. No. 16/523,298, filed Jul. 26, 2019, 213 pages.

Co-pending U.S. Appl. No. 16/560,720, filed Sep. 4, 2019.

Co-pending U.S. Appl. No. 17/129,859, filed Dec. 21, 2020.

Japanese Office Action issued for Japanese Patent Application No. 2020-571611, dated Sep. 5, 2023, 8 pages with English language translation.

SYSTEMS AND METHODS FOR MENTAL HEALTH ASSESSMENT

CROSS-REFERENCE

This application is a continuation application of U.S. patent application Ser. No. 17/671,337, filed Feb. 14, 2022, which is a continuation of U.S. patent application Ser. No. 17/400,066, filed Aug. 11, 2021, which is a continuation application of U.S. patent application Ser. No. 17/129,859, filed Dec. 21, 2020, issued as U.S. Pat. No. 11,120,895, which is a continuation of U.S. patent application Ser. No. 16/918,624, filed Jul. 1, 2020, which is a continuation of U.S. patent application Ser. No. 16/560,720, filed Sep. 4, 2019, now U.S. Pat. No. 10,748,644, which is a continuation of U.S. application Ser. No. 16/523,298, filed on Jul. 26, 2019, which is a continuation of U.S. International Application No. PCT/US2019/037953, filed on Jun. 19, 2019, which claims priority to U.S. Provisional Application No. 62/687,176, filed Jun. 19, 2018, U.S. Provisional Application No. 62/749,113, filed Oct. 22, 2018, U.S. Provisional Application No. 62/749,654, filed Oct. 23, 2018, U.S. Provisional Application No. 62/749,663, filed Oct. 23, 2018, U.S. Provisional Application No. 62/749,669, filed Oct. 23, 2018, U.S. Provisional Application No. 62/749,672, filed Oct. 24, 2018, U.S. Provisional Application No. 62/754,534, filed Nov. 1, 2018, U.S. Provisional Application No. 62/754,541, filed Nov. 1, 2018, U.S. Provisional Application No. 62/754,547, filed Nov. 1, 2018, U.S. Provisional Application No. 62/755,356, filed Nov. 2, 2018, U.S. Provisional Application No. 62/755,361, filed Nov. 2, 2018, U.S. Provisional Application No. 62/733,568, filed Sep. 19, 2018, U.S. Provisional Application No. 62/733,552, filed Sep. 19, 2018, each of which is incorporated herein by reference in their entirety for all purposes.

BACKGROUND

Behavioral health is a serious problem. In the United States, suicide ranks in the top causes of death as reported by the Center for Disease Control (CDC). Depression is the leading cause of disability worldwide, according to the World Health Organization (WHO). Screening for depression and other mental health disorders by doctors and health service providers is widely recommended. The current "gold standard" for screening or monitoring for depression in patients is the PHQ-9 (Patient Health Questionnaire 9), a written depression screening or monitoring test with nine (9) multiple-choice questions. Other similar assessment tests include the PHQ-2 and the Generalized Anxiety Disorder 7 (GAD-7).

Many believe the PHQ-9 and other, similar screening or monitoring tools for detecting behavioral health diagnoses such as depression are inadequate. While the PHQ-9 is purported to successfully detect depression in 85-95% of patients, it is also purported that 54% of all suicides are committed by people with no diagnosis of depression. These two assertions appear entirely inconsistent with each other, screening or monitoring but, the reality is that not enough people are being screened.

Part of the problem is that, traditional screening or monitoring surveys are not engaging due to their repetitive nature and lack of personalization. Another problem is that patients can be dishonest in their responses to the assessment tool, and the PHQ-9 and similar tools provide no mechanism by which dishonesty in the patient's responses can be assessed. Finally, it takes effort on the part of the clinician and the patient for these surveys, as some patients need assistance for their completion, and this disrupts both the clinician and patient workflows.

SUMMARY

The present disclosure provides systems and methods that can more accurately and effectively assess, screen, estimate, and/or monitor the mental state of human subjects, when compared to conventional mental health assessment tools. In one aspect, a method for assessing a mental state of a subject in a single session or over multiple different sessions is provided. The method can comprise using an automated module to present and/or formulate at least one query based in part on one or more target mental states to be assessed. The at least one query can be configured to elicit at least one response from the subject. The method may also comprise transmitting the at least one query in an audio, visual, and/or textual format to the subject to elicit the at least one response. The method may also comprise receiving data comprising the at least one response from the subject in response to transmitting the at least one query. The data can comprise speech data. The method may further comprise processing the data using one or more individual, joint, or fused models comprising a natural language processing (NLP) model, an acoustic model, and/or a visual model. The method may further comprise generating, for the single session, for each of the multiple different sessions, or upon completion of one or more sessions of the multiple different sessions, one or more assessments of the mental state associated with the subject.

In some embodiments, the one or more individual, joint, or fused models may comprise a metadata model. The metadata model can be configured to use demographic information and/or a medical history of the subject to generate the one or more assessments of the mental state associated with the subject.

In some embodiments, the at least one query can comprise a plurality of queries and the at least one response can comprise a plurality of responses. The plurality of queries can be transmitted in a sequential manner to the subject and configured to systematically elicit the plurality of responses from the subject. In some embodiments, the plurality of queries can be structured in a hierarchical manner such that each subsequent query of the plurality of queries is structured as a logical follow on to the subject's response to a preceding query, and can be designed to assess or draw inferences on a plurality of aspects of the mental state of the subject.

In some embodiments, the automated module can be further configured to present and/or formulate the at least one query based in part on a profile of the subject.

In some embodiments, the one or more target mental states can be selected from the group consisting of depression, anxiety, post-traumatic stress disorder (PTSD), schizophrenia, suicidality, and bipolar disorder.

In some embodiments, the one or more target mental states can comprise one or more conditions or disorders associated or comorbid with a list of predefined mental disorders. The list of predefined mental disorders may include mental disorders as defined or provided in the Diagnostic and Statistical Manual of Mental Disorders. In some embodiments, the one or more associated or comorbid conditions or disorders can comprise fatigue, loneliness, low motivation, or stress.

In some embodiments, the assessment can comprise a score that indicates whether the subject is (i) more likely than others to experience at least one of the target mental states or (ii) more likely than others to experience at least one of the target mental states at a future point in time. In some embodiments, the future point in time can be within a clinically actionable future.

In some embodiments, the method can further comprise: transmitting the assessment to a healthcare provider to be used in evaluating the mental state of the subject. The transmitting can be performed in real-time during the assessment, just-in-time, or after the assessment has been completed.

In some embodiments, the plurality of queries can be designed to test for or detect a plurality of aspects of the mental state of the subject.

In some embodiments, the assessment can comprise a score that indicates whether the subject is (i) more likely than others to experience at least one of the target mental states or (ii) more likely than others to experience at least one of the target mental states at a future point in time. The score can be calculated based on processed data obtained from the subject's plurality of responses to the plurality of queries. In some embodiments, the score can be continuously updated with processed data obtained from each of the subject's follow-on response to a preceding query.

In some embodiments, the method can further comprise based on the at least one response, identifying additional information to be elicited from the subject. The method can further comprise transmitting a subsequent query to the subject. The subsequent query relates to the additional information and can be configured to elicit a subsequent response from the subject. The method can further comprise receiving data comprising the subsequent response from the subject in response to transmitting the subsequent query. The method can further comprise processing the subsequent response to update the assessment of the mental state of the subject. In some embodiments, identifying additional information to be elicited from the subject can comprise: identifying (i) one or more elements of substantive content or (ii) one or more patterns in the data that are material to the mental state of the subject. The method can further comprise: for each of the one or more elements of substantive content or the one or more patterns: identifying one or more items of follow-up information that are related to the one or more elements or the one or more patterns to be asked of the subject, and generating a subsequent query. The subsequent query can relate to the one or more items of follow-up information.

In some embodiments, the NLP model can be selected from the group consisting of a sentiment model, a statistical language model, a topic model, a syntactic model, an embedding model, a dialog or discourse model, an emotion or affect model, and a speaker personality model.

In some embodiments, the data can further comprise images or video of the subject. The data can be further processed using the visual model to generate the assessment of the mental state of the subject. In some embodiments, the visual model can be selected from the group consisting of a facial cue model, a body movement/motion model, and an eye activity model.

In some embodiments, the at least one query can be transmitted in a conversational context in a form of a question, statement, or comment that is configured to elicit the at least one response from the subject. In some embodiments, the conversational context can be designed to promote elicitation of truthful, reflective, thoughtful, or candid responses from the subject. In some embodiments, the conversational context can be designed to affect an amount of time that the subject takes to compose the at least one response. In some embodiments, the method can further comprise: transmitting one or more prompts in the audio and/or visual format to the subject when a time latency threshold is exceeded. In some embodiments, the conversational context can be designed to enhance one or more performance metrics of the assessment of the mental state of the subject. In some embodiments, the one or more performance metrics can be selected from the group consisting of an F1 score, an area under the curve (AUC), a sensitivity, a specificity, a positive predictive value (PPV), and an equal error rate.

In some embodiments, the at least one query is not or need not be transmitted or provided in a format of a standardized test or questionnaire. In some embodiments, the at least one query can comprise subject matter that has been adapted or modified from a standardized test or questionnaire. In some embodiments, the standardized test or questionnaire can be selected from the group consisting of PHQ-9, GAD-7, HAM-D, and BDI. The standardized test or questionnaire can be another similar test or questionnaire for assessing a patient's mental health state.

In some embodiments, the one or more individual, joint, or fused models can comprise a regression model.

In some embodiments, the at least one query can be designed to be open-ended without limiting the at least one response from the subject to be a binary yes-or-no response.

In some embodiments, the score can be used to calculate one or more scores with a clinical value.

In some embodiments, the assessment can comprise a quantized score estimate of the mental state of the subject. In some embodiments, the quantized score estimate can comprise a calibrated score estimate. In some embodiments, the quantized score estimate can comprise a binary score estimate.

In some embodiments, the plurality of queries can be represented as a series of edges and the plurality of responses can be represented as a series of nodes in a nodal network.

In some embodiments, the mental state can comprise one or more medical, psychological, or psychiatric conditions or symptoms.

In some embodiments, the method can be configured to further assess a physical state of the subject as manifested based on the speech data of the subject. The method can further comprise: processing the data using the one or more individual, joint, or fused models to generate an assessment of the physical state of the subject. The assessment of the physical state can comprise a score that indicates whether the subject is (i) more likely than others to experience at least one of a plurality of physiological conditions or (ii) more likely than others to experience at least one of the physiological conditions at a future point in time.

In some embodiments, the physical state of the subject is manifested due to one or more physical conditions that affect a characteristic or a quality of voice of the subject.

In some embodiments, the automated module can be a mental health screening module that can be configured to dynamically formulate the at least one query based in part on the one or more target mental states to be assessed.

In some embodiments, the one or more individual, joint, or fused models can comprise a composite model that can be an aggregate of two or more different models.

Another aspect of the present disclosure provides a non-transitory computer readable-medium comprising machine-executable instructions that, upon execution by one or more computer processors, implements any of the foregoing methods described in the above or elsewhere herein.

Another aspect of the present disclosure provides a system comprising one or more computer processors and memory comprising machine-executable instructions that, upon execution by the one or more computer processors, implements any of the methods foregoing described in the above or elsewhere herein.

Another aspect of the present disclosure provides a method for screening or monitoring a subject for, or diagnosing the subject with a mental health disorder. The method can comprise: transmitting at least one query to the subject. The at least one query can be configured to elicit at least one response from the subject. The method can further comprise receiving data comprising the at least one response from the subject in response to transmitting the at least one query. The data can comprise speech data. The method can further comprise processing the data using one or more individual, joint, or fused models comprising a natural language processing (NLP) model, an acoustic model, and/or a visual model to generate an output. The method can further comprise using at least the output to generate a score and a confidence level of the score. The score can comprise an estimate that the subject has the mental health disorder. The confidence level can be based at least in part on a quality of the speech data and represents a degree to which the estimate can be trusted.

In some embodiments, the one or more individual, joint, or fused models can comprise a metadata model. The metadata model can be configured to use demographic information and/or a medical history of the subject to generate the one or more assessments of the mental state associated with the subject.

In some embodiments, the output can comprise an NLP output, an acoustic output, and a visual output. In some embodiments, the NLP output, the acoustic output, and the visual output can each comprise a plurality of outputs corresponding to different time ranges of the data. In some embodiments, generating the score can comprise: (i) segmenting the NLP output, the acoustic output, and the visual output into discrete time segments, (ii) assigning a weight to each discrete time segment, and (iii) computing a weighted average of the NLP output, the acoustic output, and the visual output using the assigned weights. In some embodiments, the weights can be based at least on (i) base weights of the one or more individual, joint, or fused models (ii) a confidence level of each discrete time segment of the NLP output, the acoustic output, and the visual output.

In some embodiments, the one or more individual, joint, or fused models can be interdependent such that each of the one or more individual, joint, or fused models is conditioned on an output of at least one other of the one or more individual, joint, or fused models.

In some embodiments, generating the score can comprise fusing the NLP output, the acoustic output, and the visual output.

In some embodiments, generating the confidence level of the score can comprise fusing (i) a confidence level of the NLP output with (ii) a confidence level of the acoustic output.

In some embodiments, the method can further comprise converting the score into one or more scores with a clinical value.

In some embodiments, the method can further comprise transmitting the one or more scores with a clinical value to the subject and/or a contact for the subject. In some embodiments, the method can further comprise transmitting the one or more scores with a clinical value to a healthcare provider for use in evaluating and/or providing care for a mental health of the subject. In some embodiments, the transmitting can comprise transmitting the one or more scores with a clinical value to the healthcare provider during the screening, monitoring, or diagnosing. In some embodiments, the transmitting can comprise transmitting the one or more scores with a clinical value to the healthcare provider or a payer after the screening, monitoring, or diagnosing has been completed.

In some embodiments, the at least one query can comprise a plurality of queries, the at least one response can comprise a plurality of responses. Generating the score can comprise updating the score after receiving each of the plurality of responses, and the method can further comprise: converting the score to one or more scores with a clinical value after each of the updates. The method can further comprise transmitting the one or more scores with a clinical value to a healthcare provider after the converting.

In some embodiments, the method can further comprise: determining that the confidence level does not satisfy a predetermined criterion, in real time and based at least in part on the at least one response, generating at least one additional query, and using the at least one additional query, repeating steps (a)-(d) until the confidence level satisfies the predetermined criterion.

In some embodiments, the confidence level can be based on a length of the at least one response. In some embodiments, the confidence level can be based on an evaluated truthfulness of the one or more responses of the subject.

In some embodiments, the one or more individual, joint, or fused models can be trained on speech data from a plurality of test subjects, wherein each of the plurality of test subjects has completed a survey or questionnaire that indicates whether the test subject has the mental health disorder. The confidence level can be based on an evaluated truthfulness of responses in the survey or questionnaire.

In some embodiments, the method can further comprise extracting from the speech data one or more topics of concern of the subject using a topic model.

In some embodiments, the method can further comprise generating a word cloud from the one or more topics of concern. The word cloud reflects changes in the one or more topics of concern of the subject over time. In some embodiments, the method can further comprise transmitting the one or more topics of concern to a healthcare provider, the subject, or both.

In some embodiments, the video output can be assigned a higher weight than the NLP output and the acoustic output in generating the score when the subject is not speaking. In some embodiments, a weight of the video output in generating the score can be increased when the NLP output and the acoustic output indicate that a truthfulness level of the subject is below a threshold.

In some embodiments, the video model can comprise one or more of a facial cue model, a body movement/motion model, and a gaze model.

In some embodiments, the at least one query can comprise a plurality of queries and the at least one response can comprise a plurality of responses. The plurality of queries can be configured to sequentially and systematically elicit the plurality of responses from the subject. The plurality of queries can be structured in a hierarchical manner such that each subsequent query of the plurality of queries can be a logical follow on to the subject's response to a preceding query and can be designed to assess or draw inferences about different aspects of the mental state of the subject.

In some embodiments, the at least one query can include subject matter that has been adapted or modified from a clinically-validated survey, test or questionnaire.

In some embodiments, the acoustic model can comprise one or more of an acoustic embedding model, a spectral-temporal model, a supervector model, an acoustic affect model, a speaker personality model, an intonation model, a speaking rate model, a pronunciation model, a non-verbal model, or a fluency model.

In some embodiments, the NLP model can comprise one or more of a sentiment model, a statistical language model, a topic model, a syntactic model, an embedding model, a dialog or discourse model, an emotion or affect model, or a speaker personality model.

In some embodiments, the mental health disorder can comprise depression, anxiety, post-traumatic stress disorder, bipolar disorder, suicidality or schizophrenia.

In some embodiments, the mental health disorder can comprise one or more medical, psychological, or psychiatric conditions or symptoms.

In some embodiments, the score can comprise a score selected from a range. The range can be normalized with respect to a general population or to a specific population of interest.

In some embodiments, the one or more scores with a clinical value can comprise one or more descriptors associated with the mental health disorder.

In some embodiments, steps (a)-(d) as described above can be repeated at a plurality of different times to generate a plurality of scores. The method can further comprise: transmitting the plurality of scores and confidences to a computing device and graphically displaying, on the computing device, the plurality of scores and confidences as a function of time on a dashboard or other representation for one or more end users.

In some embodiments, the quality of the speech data can comprise a quality of an audio signal of the speech data.

In some embodiments, the quality of the speech data can comprise a measure of confidence of a speech recognition process performed on an audio signal of the speech data.

In some embodiments, the method can be implemented for a single session. The score and the confidence level of the score can be generated for the single session.

In some embodiments, the method can be implemented for and over multiple different sessions, and the score and the confidence level of the score can be generated for each of the multiple different sessions, or upon completion of one or more sessions of the multiple different sessions.

Another aspect of the present disclosure provides a non-transitory computer readable-medium comprising machine-executable instructions that, upon execution by one or more computer processors, implements any of the methods described in the above or elsewhere herein.

Another aspect of the present disclosure provides a system comprising one or more computer processors and memory comprising machine-executable instructions that, upon execution by the one or more computer processors, implements any of the methods described above or elsewhere herein.

Another aspect of the present disclosure provides a method for processing speech and/or video data of a subject to identify a mental state of the subject. The method can comprise: receiving the speech and/or video data of the subject and using at least one processing technique to process the speech and/or video data to identify the mental state at (i) a reduced error rate of at least 10% lower or (ii) an accuracy of at least 10% higher, than a standardized mental health questionnaire or testing tool usable for identifying the mental state. The reduced error rate or the accuracy can be established relative to at least one or more benchmark standards usable by an entity for identifying or assessing one or more medical conditions comprising the mental state.

In some embodiments, the entity can comprise one or more of the following: clinicians, healthcare providers, insurance companies, and government-regulated bodies. In some embodiments, the at least one or more benchmark standards can comprise at least one clinical diagnosis that has been independently verified to be accurate in identifying the mental state. In some embodiments, the speech data can be received substantially in real-time as the subject is speaking. In some embodiments, the speech data can be produced in an offline mode from a stored recording of the subject's speech.

Another aspect of the present disclosure provides a method for processing speech data of a subject to identify a mental state of the subject. The method can comprise: receiving the speech data of the subject and using at least one processing technique to process the speech data to identify the mental state. The identification of the mental state is better according to one or more performance metrics as compared to a standardized mental health questionnaire or testing tool usable for identifying the mental state.

In some embodiments, the one or more performance metrics can comprise a sensitivity or specificity, and the speech data can be processed according to a desired level of sensitivity or a desired level of specificity. In some embodiments, the desired level of sensitivity or the desired level of specificity can be defined based on criteria established by an entity. In some embodiments, the entity can comprise one or more of the following: clinicians, healthcare providers, personal caregivers, insurance companies, and government-regulated bodies.

Another aspect of the present disclosure provides a method for processing speech data of a subject to identify or assess a mental state of the subject. The method can comprise: receiving the speech data of the subject, using one or more processing technique to process the speech data to generate one or more descriptors indicative of the mental state, and generating a plurality of visual elements of the one or more descriptors. The plurality of visual elements can be configured to be displayed on a graphical user interface of an electronic device of a user and usable by the user to identify or assess the mental state.

In some embodiments, the user can be the subject. In some embodiments, the user can be a clinician or healthcare provider. In some embodiments, the one or more descriptors can comprise a calibrated or normalized score indicative of the mental state. In some embodiments, the one or more descriptors further can comprise a confidence associated with the calibrated or normalized score.

Another aspect of the present disclosure provides a method for identifying, assessing, or monitoring a mental state of a subject. The method can comprise using a natural language processing algorithm, an acoustic processing algorithm, or a video processing algorithm to process data of the subject to identify or assess the mental state of a subject, the data comprising speech or video data of the subject, and outputting a report indicative of the mental state of the subject. The report can be transmitted to a user to be used for identifying, assessing, or monitoring the mental state.

In some embodiments, the user can be the subject. In some embodiments, the user can be a clinician or healthcare provider. In some embodiments, the report can comprise a plurality of graphical visual elements. In some embodiments, the report can be configured to be displayed on a graphical user interface of an electronic device of the user. In some embodiments, the method can further comprise: updating the report in response to one or more detected changes in the mental state of the subject. In some embodiments, the report can be updated substantially in real time as the one or more detected changes in the mental state are occurring in the subject.

Another aspect of the present disclosure provides a method for identifying whether a subject is at risk of a mental or physiological condition. The method can comprise: obtaining speech data from the subject and storing the speech data in computer memory, processing the speech data using in part natural language processing to identify one or more features indicative of the mental or physiological condition, and outputting an electronic report identifying whether the subject is at a risk of the mental or physiological condition, and the risk can be quantified in a form of a normalized score with a confidence level. The normalized score with the confidence level can be usable by a user to identify whether the subject is at a risk of the mental or physiological condition.

In some embodiments, the user can be the subject. In some embodiments, the user can be a clinician or healthcare provider. In some embodiments, the report can comprise a plurality of graphical visual elements. In some embodiments, the report can be configured to be displayed on a graphical user interface of an electronic device of the user.

Another aspect of the present disclosure provides a method for identifying, assessing, or monitoring a mental state or disorder of a subject. The method can comprise: receiving audio or audio-visual data comprising speech of the subject in computer memory and processing the audio or audio-visual data to identify, assess, monitor, or diagnose the mental state or disorder of the subject, which processing can comprise performing natural language processing on the speech of the subject.

In some embodiments, the audio or audio-visual data can be received in response to a query directed to the subject. In some embodiments, the audio or audio-visual data can be from a prerecording of a conversation to which the subject can be a party. In some embodiments, the audio or audio-visual data can be from a prerecording of a clinical session involving the subject and a healthcare provider. In some embodiments, the mental state or disorder can be identified at a higher performance level compared to a standardized mental health questionnaire or testing tool. In some embodiments, the processing further can comprise using a trained algorithm to perform acoustic analysis on the speech of the subject.

Another aspect of the present disclosure provides a method for estimating whether a subject has a mental condition and providing the estimate to a stakeholder. The method can comprise: obtaining speech data from the subject and storing the speech data in computer memory. The speech data can comprise responses to a plurality of queries transmitted in an audio and/or visual format to the subject. The method can further comprise selecting (1) a first model optimized for sensitivity in estimating whether the subject has the mental condition or (2) a second model optimized for specificity in estimating whether the subject has the mental condition. The method can further comprise processing the speech data using the selected first model or the second model to generate the estimate. The method can further comprise transmitting the estimate to the stakeholder.

In some embodiments, the first model can be selected and the stakeholder can be a healthcare payer. In some embodiments, the second model can be selected and the stakeholder can be a healthcare provider.

Another aspect of the present disclosure provides a system for determining whether a subject can be at risk of having a mental condition. The system can be configured to (i) receive the speech data from the memory and (ii) process the speech data using at least one model to determine that the subject is at risk of having the mental condition. The at least one model can be trained on speech data from a plurality of other test subjects who have a clinical determination of the mental condition. The clinical determinations may serve as labels for the speech data. The system can be configured to generate the estimate of the mental condition that is better according to one or more performance metrics as compared to a clinically-validated survey, test or questionnaire.

In some embodiments, the system can be configured to generate the estimate of the mental condition with a higher specificity compared to the clinically-validated survey, test or questionnaire. In some embodiments, the system can be configured to generate the estimate of the mental condition with a higher sensitivity compared to the clinically-validated survey, test, or questionnaire. In some embodiments, the identification can be output while the subject is speaking. In some embodiments, the identification can be output via streaming or a periodically updated signal.

Another aspect of the present disclosure provides a method for assessing a mental state of a subject. The method can comprise using an automated screening module to dynamically formulate at least one query based in part on one or more target mental states to be assessed. The at least one query can be configured to elicit at least one response from the subject. The method can further comprise transmitting the at least one query in an audio and/or visual format to the subject to elicit the at least one response. The method can further comprise receiving data comprising the at least one response from the subject in response to transmitting the at least one query. The data can comprise speech data. The method can further comprise processing the data using a composite model comprising at least one or more semantic models to generate an assessment of the mental state of the subject.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1A:
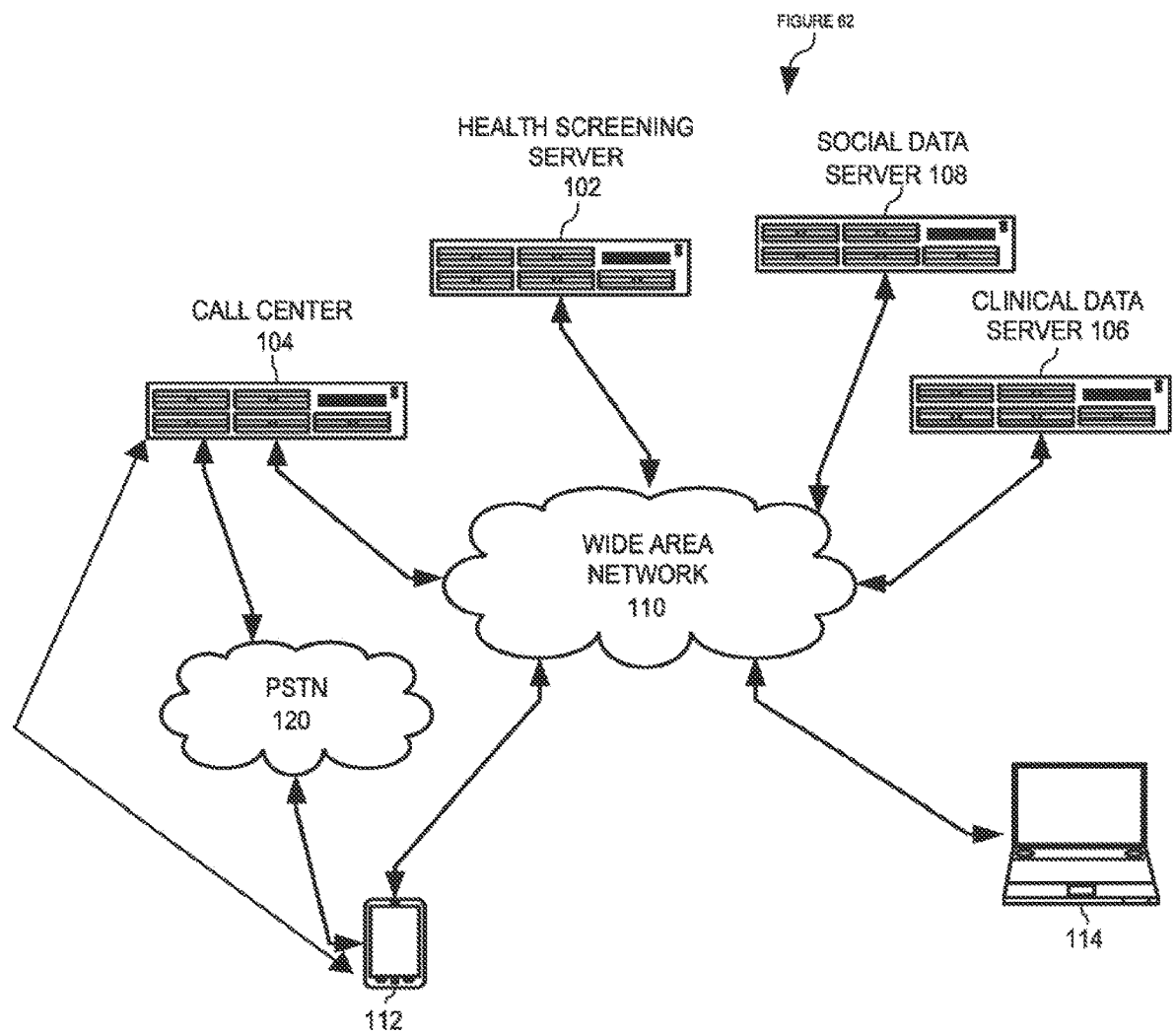
FIG. 1A shows a health screening or monitoring system in which a health screening or monitoring server and a clinical data server computer system and a social data server cooperate to estimate a health state of a patient in accordance with the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto.

Henceforth, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary. The present invention relates to health screening or monitoring systems, and, more particularly, to a computer-implemented mental health screening or monitoring tool with significantly improved accuracy and efficacy by leveraging language analysis, visual cues and acoustic analysis. In this application, the specifics of improved acoustic, visual and speech analysis techniques are described as they pertain to the classification of a respondent as being depressed, or other mental state of interest. While much of the following disclosure will focus largely on assessing depression in a patient, the systems and methods described herein may be equally adept at screening or monitoring a user for a myriad of mental and physical ailments. For example, bipolar disorder, anxiety, and schizophrenia are examples of mental ailments that such a system may be adept at screening or monitoring for. It is also possible that physical ailments may be assessed utilizing such systems. It should be understood that while this disclosure may focus heavily upon depression screening or monitoring, this is not limiting. Any suitable mental or physical ailment may be screened using the disclosed systems and methods.

The systems and methods disclosed herein may use natural language processing (NLP) to perform semantic analysis on patient speech utterances. Semantic analysis, as disclosed herein, may refer to analysis of spoken language from patient responses to assessment questions or captured conversations, in order to determine the meaning of the spoken language for the purpose of conducting a mental health screening or monitoring of the patient. The analysis may be of words or phrases, and may be configured to account for primary queries or follow-up queries. In the case of captured human-human conversations, the analysis may also apply to the speech of the other party. As used herein, the terms "semantic analysis" and "natural language processing (NLP)" may be used interchangeably. Semantic analysis may be used to determine the meanings of utterances by patients, in context. It may also be used to determine topics patients are speaking about.

A mental state, as described herein, may be distinguished from an emotion or feeling, such as happiness, sadness, or anger. A mental state may include one or more feelings in combination with a philosophy of mind, including how a person perceives objects of his or her environment and the actions of other people toward him or her. While feelings may be transient, a mental state may describe a person's overarching disposition or mood, even in situations where the person's feelings may change. For example, a depressed person may variously feel, at different times, happy, sad, or angry.

In accordance with one or more embodiments of the present invention, a server computer system (health screening or monitoring server 102—FIG. 1A) may apply a health state screening or monitoring test to a human patient using a client device (patient device 112), by engaging the patient in an interactive spoken conversation and applying a composite model, that may combine language, acoustic, metadata, and visual models, to a captured audiovisual signal of the patient engaged in the dialogue. While the general subject matter of the screening or monitoring test may be similar to subject matter of standardized depression screening or monitoring tests such as the PHQ-9, the composite model may analyze, in real time, the audiovisual signal of the patient (i) to make the conversation more engaging for the patient and (ii) estimate the patient's health. Appendix A illustrates an exemplary implementation that includes Calendaring, SMS, Dialog, Calling and User Management Services. While the latter goal is primary, the former goal is a significant factor in achieving the latter. Truthfulness of the patient in answering questions posed by the screening or monitoring test is critical in assessing the patient's mood. Health screening or monitoring server 102 encourages patient honesty.

Figure 18:
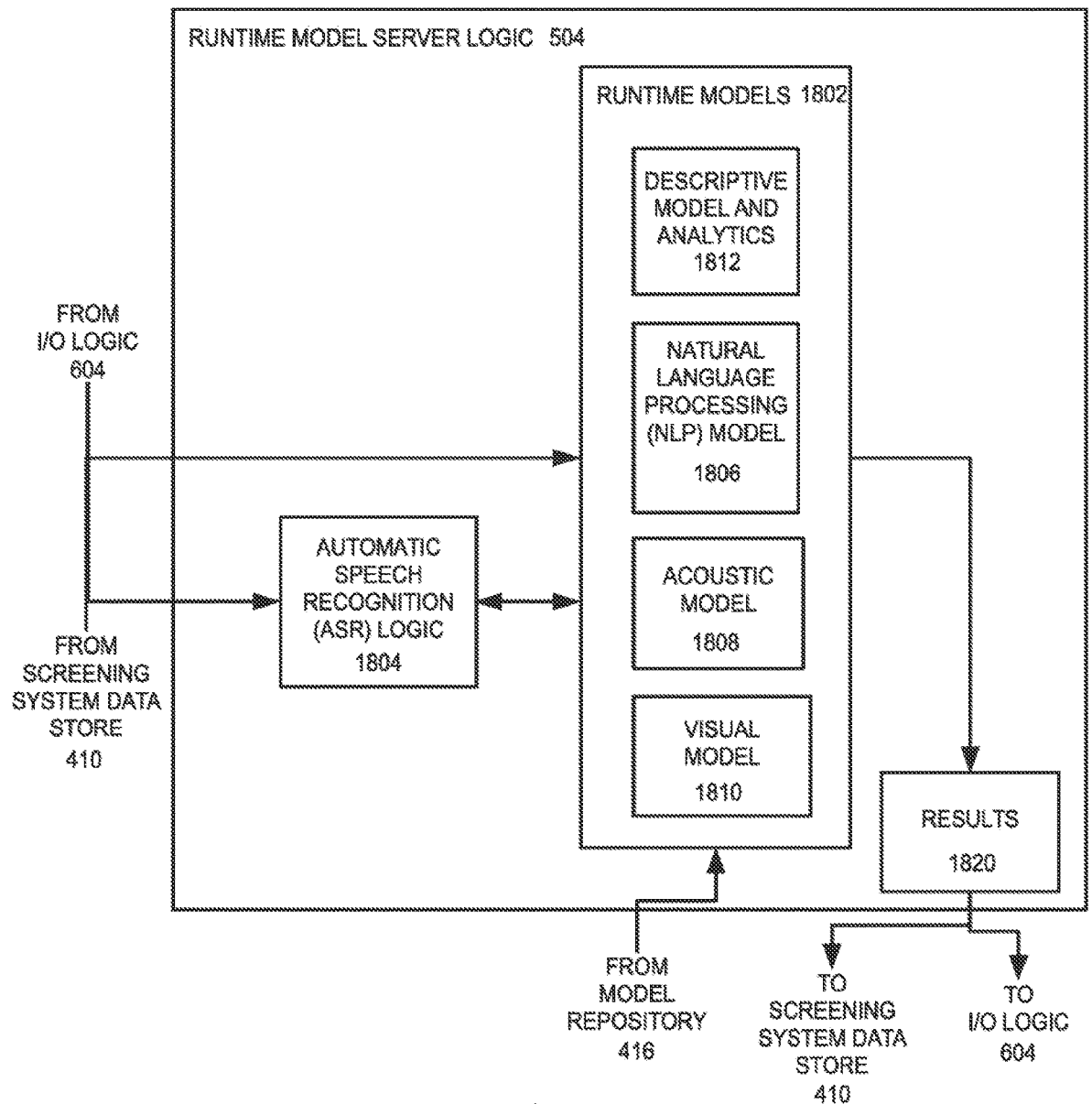
FIG. 18 is a block diagram of runtime model server logic of the interactive health screening or monitoring logic of FIG. 3 in greater detail.

First, the spoken conversation may provide the patient with less time to compose a disingenuous response to a question rather than simply responding honestly to the question. Second, the conversation may feel, to the patient, more spontaneous and personal and may be less annoying to the patient than a generic questionnaire, as would be provided by, for example, simply administering the PHQ-9. Accordingly, the spoken conversation may not induce or exacerbate resentment in the patient for having to answer a questionnaire for the benefit of a doctor or other clinician. Third, the spoken conversation may be adapted in progress to be responsive to the patient, reducing the patient's annoyance with the screening or monitoring test and, in some situations, shortening the screening or monitoring test. Fourth, the screening or monitoring test as administered by health screening or monitoring server 102 additionally may rely on non-verbal aspects of the conversation in addition to the verbal content of the conversation to assess depression in the patient. As shown in FIG. 1A, health screening or monitoring system 100 may include health screening or monitoring server 102, a call center system 104, a clinical data server 106, a social data server 108, a patient device 112, and a clinician device 114 that are connected to one another though a wide area network (WAN) 110, that is the Internet in this illustrative embodiment. In this illustrative embodiment, patient device 112 may also reachable by call center system 104 through a public-switched telephone network (PSTN) 120 or directly. Health screening or monitoring server 102 may be a server computer system that administers the health screening or monitoring test with the patient through patient device 112 and combines a number of language, acoustic, and visual models to produce results 1820 (FIG. 18), using clinical data retrieved from clinical data server 106, social data retrieved from social data server 108, and patient data collected from past screenings or monitoring to train the models of runtime model server 304 (FIG. 18). Clinical data server 106 (FIG. 1A) may be a server computer system that makes available clinical or demographic data of the patient, including diagnoses, medication information, etc., available, e.g., to health screening or monitoring server 102, in a manner that is compliant with HIPAA (Health Insurance Portability and Accountability Act of 1996) and/or any other privacy and security policies and regulations such as GDPR and SOC 2. Social data server 106 may be a server computer system that makes social data of the patient, including social media posts, online purchases, searches, etc., available, e.g., to health screening or monitoring server 102. Clinician device 114 may be a client device that receives data representing results of the screening or monitoring regarding the patient's health from health screening or monitoring server 102.

The system may be used to assess the mental state of the subject in a single session or over multiple sessions. Subsequent sessions may be informed by assessment results from prior assessments. This may be done by providing assessment data as inputs to machine learning algorithms or other analysis methods for the subsequent assessments. Each session may generate one or more assessments. Individual assessments may also compile data from multiple sessions.

Figure 1B:
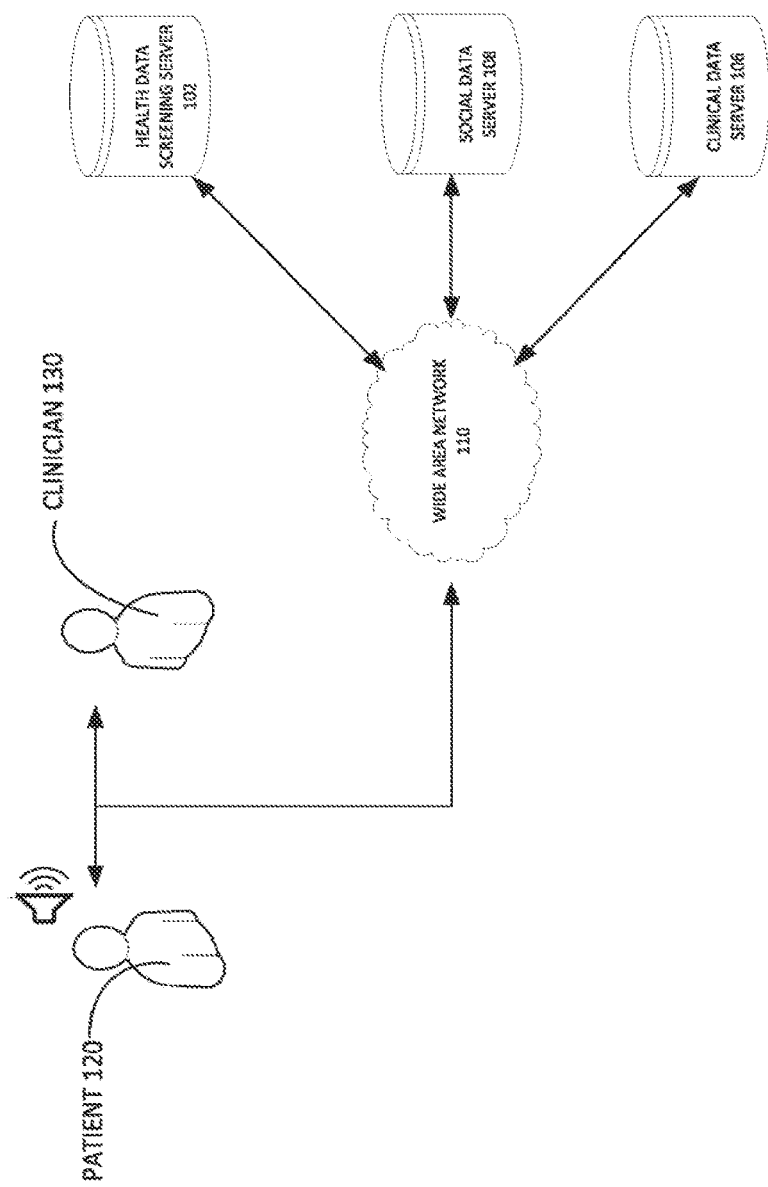
FIG. 1B shows an additional embodiment of the health screening or monitoring system from FIG. 1A.

FIG. 1B shows an additional embodiment of the health screening or monitoring system from FIG. 1A. FIG. 1B illustrates a conversation between patient 120 and clinician 130. The clinician 130 may record one or more speech samples from the patient 120 and upload them to the wide area network 110, with the consent of the patient 120. The speech samples may be analyzed by one or more machine learning algorithms, described elsewhere herein.

Figure 2:
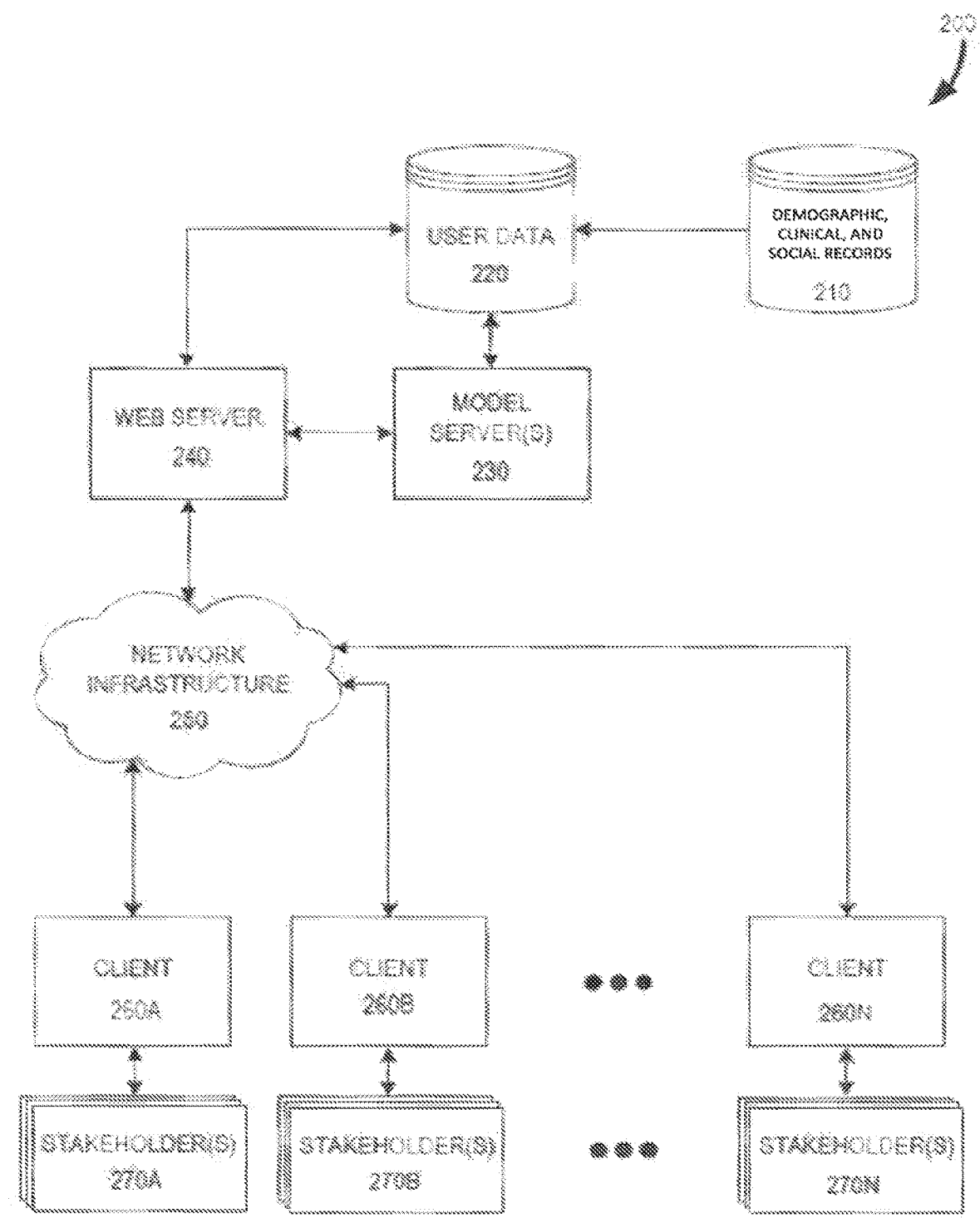
FIG. 2 shows a patient screening or monitoring system in which a web server and modeling server(s) cooperate to assess a state of a patient through a wide area network, in accordance with some embodiments.

FIG. 2 provides an additional embodiment of a health screening or monitoring system. Health screening or monitoring system 200 may apply a health state screening or monitoring test to a human patient using a client device (clients 260a-n), by engaging the patient in an interaction and applying a composite model that combines language, acoustic, and visual models, to a captured audiovisual signal of the patient engaged in the dialogue.

While the general subject matter of the screening or monitoring test may be similar to the subject matter of standardized depression screening or monitoring tests such as the PHQ-9, the composite model can be configured to analyze, in real time, the audiovisual signal of the patient (i) to make the conversation more engaging for the patient, (ii) estimate the patient's mental health, and (iii) provide a judgment free and less embarrassing experience for the patient, who may already be suffering from anxiety and other mental barriers to receiving proper screening or monitoring from a clinician.

It should be noted that throughout this disclosure a series of terms may be used interchangeably, and this usage is not intended to limit the scope of the disclosure in any manner. For example, the terms "patient", "client", "subject", "respondent" and "user" may all be employed interchangeably to refer to the individual being screened for the mental health conditions and/or the device being utilized by this individual to collect and transmit the audio and visual data that is used to screen them. Likewise, "semantic analysis" and "NLP" may be used interchangeably to reference natural language processing models and elements. In a similar manner, "stakeholders" is employed to refer to a wide variety of interested third parties who are not the patient being screened. These stakeholders may include physicians, health care providers, care team members, insurance companies, research organizations, and family/relatives of the patient, hospitals, crisis centers and the like. It should thus be understood that when another label is employed, such as "physician", the intention in this disclosure is to reference any number of stakeholders.

The health screening or monitoring system 200 includes a backend infrastructure designed to administer the screening or monitoring interaction and analyze the results. This includes one or more model servers 230 coupled to a web server 240. The web server 240 and model server(s) 230 leverage user data 220 which is additionally populated by clinical and social data 210. The clinical data portion may be compiled from the healthcare providers, and may include diagnoses, vital information (age, weight, height, blood chemistry, etc.), diseases, medications, lists of clinical encounters (hospitalizations, clinic visits, Emergency Department visits), clinician records, and the like. This clinical data may be compiled from one or more electronic health record (EHR) systems or Health Information Exchanges (HIE) by way of a secure application protocol, extension or socket. Social data may include information collected from a patient's social networks, including social media postings, from databases detailing patient's purchases, and from databases containing patient's economic, educational, residential, legal and other social determinants. This information may be compiled together with additional preference data, metadata, annotations, and voluntarily supplied information, to populate the user database 220. The model server 230 and web server 240 are additionally capable of populating and/or augmenting the user data 220 with preferences, extracted features and the like.

The backend infrastructure communicates with the clients 260a-n via a network infrastructure 250. Commonly this network may include the internet, a corporate local area network, private intranet, cellular network, or some combination of these. The clients 260a-n include a client device of a person being screened, which accesses the backend screening or monitoring system and includes a microphone and camera for audio and video capture, respectively. The client device may be a cellular phone, tablet, laptop or desktop equipped with a microphone and optional camera, smart speaker in the home or other location, smart watch with a microphone and optional camera, or a similar device.

A client device may collect additional data, such as biometric data. For example, smart watches and fitness trackers already have the capability of measuring motion, heart rate and sometimes respiratory rate and blood oxygenation levels and other physiologic parameters. Future smart devices may record conductivity measurements for tracking perspiration, pH changes in the skin, and other chemical or hormonal changes. Client devices may operate in concert to collect data. For example, a phone may capture the audio and visual data while a Bluetooth paired fitness tracker may provide body temperature, pulse rate, respiratory rate and movement data simultaneously.

All of the collected data for each client 260a-n is provided back to the web server 240 via the network infrastructure 250. After processing, results are provided back to the client 260a-n for consumption, and when desired for sharing with one or more stakeholders 270a-n associated with the given client 260a-n, respectively. In this example figure, the stakeholders 270a-n are illustrated as being in direct communication with their respective clients 260a-n. While in practice this may indeed be possible, often the stakeholder 270a-n will be capable of direct access to the backend screening or monitoring system via the network infrastructure 250 and web server 240, without the need to use the client 260a-n as an intermediary. FIG. 2 provides the present arrangement, however, to more clearly illustrate that each client 260a-n may be associated with one or more stakeholders 270a-n, which may differ from any other client's 260a-n stakeholders 270a-n.

In another embodiment of the screening or monitoring system, a server computer system (real-time system 302—FIGS. 3 and 22) applies a depression assessment test to a human patient using a client device (portable device 312), by engaging the patient in an interactive spoken conversation and applying a composite model, that combines language, acoustic, and visual models, to a captured audiovisual signal of the patient engaged in the dialogue. While the general subject matter of the assessment test may incorporate queries including subject matter similar to questions asked in standardized depression assessment tests such as the PHQ-9, the assessment does not merely include analysis of answers to survey questions. In fact, the screening or monitoring system's composite model analyzes, in real time, the audiovisual signal of the patient (i) to make the conversation more engaging for the patient and (ii) assess the patient's mental health.

While the latter goal is the primary goal, the former goal is a significant factor in achieving the latter. Truthfulness of the patient in answering questions posed by the assessment test is critical in assessing the patient's mood. Real-time system 302 encourages honesty of the patient in a number of ways. First, the spoken conversation provides the patient with less time to compose a response to a question rather than it would take to simply respond honestly to the question.

Second, the conversation feels, to the patient, more spontaneous and personal and is less annoying to the patient than an obviously generic questionnaire. Accordingly, the spoken conversation does not induce or exacerbate resentment in the patient for having to answer a questionnaire before seeing a doctor or other clinician. Third, the spoken conversation is adapted in progress to be responsive to the patient, reducing the patient's annoyance with the assessment test and, in some situations, shortening the assessment test. Fourth, the assessment test as administered by real-time system 302 may rely more on non-verbal aspects of the conversation and the patient than on the verbal content of the conversation to assess depression in the patient.

As shown in (FIG. 3), patient assessment system 300 includes real-time system 302, a modeling system 304, a clinical data server 306, a patient device 312, and a clinician device 314 that are connected to one another though a wide area network (WAN) 310, that is the Internet in this illustrative embodiment. Real-time system 302 is a server computer system that administers the depression assessment test with the patient through patient device 312. Modeling system 304 is a server computer system that combines a number of language, acoustic, and visual models to produce a composite model 2204 (FIG. 22), using clinical data retrieved from clinical data server 306 and patient data collected from past assessments to train composite model 2204. Clinical data server 306 (FIG. 3) is a server computer system that makes clinical data of the patient, including diagnoses, medication information, etc., available, e.g., to modeling system 304, in a manner that is compliant with HIPAA (Health Insurance Portability and Accountability Act of 1996) and/or any other privacy and security policies and regulations such as GDPR and SOC 2. Clinician device 314 is a client device that receives data representing a resulting assessment regarding depression from real-time system 302.

End-to-End Nature of the Systems

The systems disclosed herein may provide medical care professionals with a prediction of a mental state of a patient. The mental state may be depression, anxiety, or another mental condition. The systems may provide the medical care professionals with additional information, outside of the mental state prediction. The system may provide demographic information, such as age, weight, occupation, height, ethnicity, medical history, psychological history, and gender to medical care professionals via client devices, such as the client devices 260a-n of FIG. 2. The system may provide information from online systems or social networks to which the patient may be registered. The patient may opt in, by setting permissions on his or her client device to provide this information before the screening or monitoring process begins. The patient may also be prompted to enter demographic information during the screening or monitoring process. Patients may also choose to provide information from their electronic health records to medical care professionals. In addition, medical care professionals may interview patients during or after a screening or monitoring event to obtain the demographic information. During registration for screening or monitoring, patients may also enter information that specifies or constraints their interests. For example, they may enter topics that they do and/or do not wish to speak about. In this disclosure, the terms "medical care provider" and "clinician" are used interchangeably. Medical care providers may be doctors, nurses, physician assistants, nursing assistants, clinical psychologists, social workers, technicians, or other health care providers.

A clinician may set up the mental health assessment with the patient. This may include choosing a list of questions for the system to ask the patient, including follow-up questions. The clinician may add or remove specific questions from the assessment, or change an order in which the questions are administered to the patient. The clinician may be available during the assessment as a proctor, in order to answer any clarifying questions the patient may have.

The system may provide the clinician with the dialogue between itself and the patient. This dialogue may be a recording of the screening or monitoring process, or a text transcript of the dialogue. The system may provide a summary of the dialogue between itself and the patient, using semantic analysis to choose segments of speech that were most important to predicting the mental state of the patient. These segments may be selected because they might be highly weighted in a calculation of a binary or scaled score indicating a mental state prediction, by example. The system may incorporate such a produced score into a summary report for the patient, along with semantic context taken from a transcript of the interview with the patient.

The system may additionally provide the clinician with a "word cloud" or "topic cloud" extracted from a text transcript of the patient's speech. A word cloud may be a visual representation of individual words or phrases, with words and phrases used most frequently designated using larger font sizes, different colors, different fonts, different typefaces, or any combination thereof. Depicting word or phrase frequency in such a way may be helpful as depressed patients commonly say particular words or phrases with larger frequencies than non-depressed patients. For example, depressed patients may use words or phrases that indicate dark, black, or morbid humor. They may talk about feeling worthless or feeling like failures, or use absolutist language, such as "always", "never", or "completely." Depressed patients may also use a higher frequency of first-person singular pronouns (e.g., "I", "me") and a lower frequency of second- or third-person pronouns when compared to the general population. The system may be able to train a machine learning algorithm to perform semantic analysis of word clouds of depressed and non-depressed people, in order to be able to classify people as depressed or not depressed based on their word clouds. Word cloud analysis may also be performed using unsupervised learning. For example, the system may analyze unlabeled word clouds and search for patterns, in order to separate people into groups based on their mental states.

The systems described herein can output an electronic report identifying whether a patient is at risk of a mental or physiological condition. The electronic report can be configured to be displayed on a graphical user interface of a user's electronic device. The electronic report can include a quantification of the risk of the mental or physiological condition, e.g., a normalized score. The score can be normalized with respect the entire population or with respect to a sub-population of interest. The electronic report can also include a confidence level of the normalized score. The confidence level can indicate the reliability of the normalized score (i.e., the degree to which the normalized score can be trusted).

The electronic report can include visual graphical elements. For example, if the patient has multiple scores from multiple screening or monitoring sessions that occurred at several different times, the visual graphical element may be a graph that shows the progression of the patient's scores over time.

The electronic report may be output to the patient or a contact person associated with the patient, a healthcare provider, a healthcare payer, or another third-party. The electronic report can be output substantially in real-time, even while the screening, monitoring, or diagnosis is ongoing. In response to a change in the normalized score or confidence during the course of the screening, monitoring, or diagnosis, the electronic report can be updated substantially in real-time and be re-transmitted to the user.

In some cases, the electronic report may include one or more descriptors about the patient's mental state. The descriptors can be a qualitative measure of the patient's mental state (e.g., "mild depression"). Alternatively or additionally, the descriptors can be topics that the patient mentioned during the screening. The descriptors can be displayed in a graphic, e.g., a word cloud.

The models described herein may be optimized for a particular purpose or based on the entity that may receive the output of the system. For example, the models may be optimized for sensitivity in estimating whether a patient has a mental condition. Healthcare payers such as insurance companies may prefer such models so that they can minimize the number of insurance payments made to patients with false positive diagnoses. In other cases, the models may be optimized for specificity in estimating whether a patient has a mental condition. Healthcare providers may prefer such models. The system may select the appropriate model based on the stakeholder to which the output will be transmitted. After processing, the system can transmit the output to the stakeholder.

The models described herein can alternatively be tuned or configured to process speech and other data according to a desired level of sensitivity or a desired level of specificity determined by a clinician, healthcare provider, insurance company, or government regulated body.

Use Cases

The system may be used to monitor teenagers for depression. The system may perform machine learning analysis on groups of teenagers in order to determine voice-based biomarkers that may uniquely classify teenagers as being at risk for depression. Depression in teenagers may have different causes than in adults. Hormonal changes may also introduce behaviors in teenagers that would be atypical for adults. A system for screening or monitoring teenagers would need to employ a model tuned to recognize these unique behaviors. For example, depressed or upset teenagers may be more prone to anger and irritability than adults, who may withdraw when upset. Thus, questions from assessments may elicit different voice-based biomarkers from teenagers than adults. Different screening or monitoring methods may be employed when testing teenagers for depression, or studying teenagers' mental states, than are employed for screening or monitoring adults. Clinicians may modify assessments to particularly elicit voice-based biomarkers specific to depression in teenagers. The system may be trained using these assessments, and determine a teenager-specific model for predicting mental states. Teenagers may further be segmented by household (foster care, adoptive parent(s), two biological parents, one biological parent, care by guardian/relative, etc.), medical history, gender, age (old vs. young teenager), and socioeconomic status, and these segments may be incorporated into the model's predictions.

The system may also be used to monitor the elderly for depression and dementia. The elderly may also have particular voice-based biomarkers that younger adults may not have. For example, the elderly may have strained or thin voices, owing to aging. Elderly people may exhibit aphasia or dysarthria, have trouble understanding survey questions, follow-ups, or conversational speech, and may use repetitive language. Clinicians may develop, or algorithms may be used to develop, surveys for eliciting particular voice-based biomarkers from elderly patients. Machine learning algorithms may be developed to predict mental states in elderly patients, specifically, by segmenting patients by age. Differences may be present in elderly patients from different generations (e.g., Greatest, Silent, Boomer), who may have different views on gender roles, morality, and cultural norms. Models may be trained to incorporate elder age brackets, gender, race, socioeconomic status, physical medical conditions, and family involvement.

The system may be used to test airline pilots for mental fitness. Airline pilots have taxing jobs, and may experience large amounts of stress and fatigue on long flights. Clinicians or algorithms may be used to develop screening or monitoring methods for these conditions. For example, the system may base an assessment off of queries similar to those tested in the Minnesota Multiphasic Personality Inventory (MMPI) and MMPI-2.

The system may also be used to screen military personnel for mental fitness. For example, the system may implement an assessment that uses queries with similar subject matter to those asked on the Primary Care Post-Traumatic Stress Disorder for Diagnostic and Statistical Manual of Mental Disorders (DSM)-5 (PC-PTSD-5) to test for PTSD. In addition to PTSD, the system may screen military personnel for depression, panic disorder, phobic disorder, anxiety, and hostility. The system may employ different surveys to screen military personnel pre- and post-deployment. The system may segment military personnel by segmenting for occupation, and segment military personnel by branch, officer or enlisted, gender, age, ethnicity, number of tours/deployments, marital status, medical history, and other factors.

The system may be used to evaluate prospective gun buyers, e.g., by implementing background checks. Assessments may be designed, by clinicians or algorithmically, to evaluate prospective buyers for mental fitness for owning a firearm. The survey may have a requirement to determine, using questions and follow-up questions, if a prospective gun buyer would be able to be certified as a danger to him or herself or others, by a court or other authority.

Figure 4:
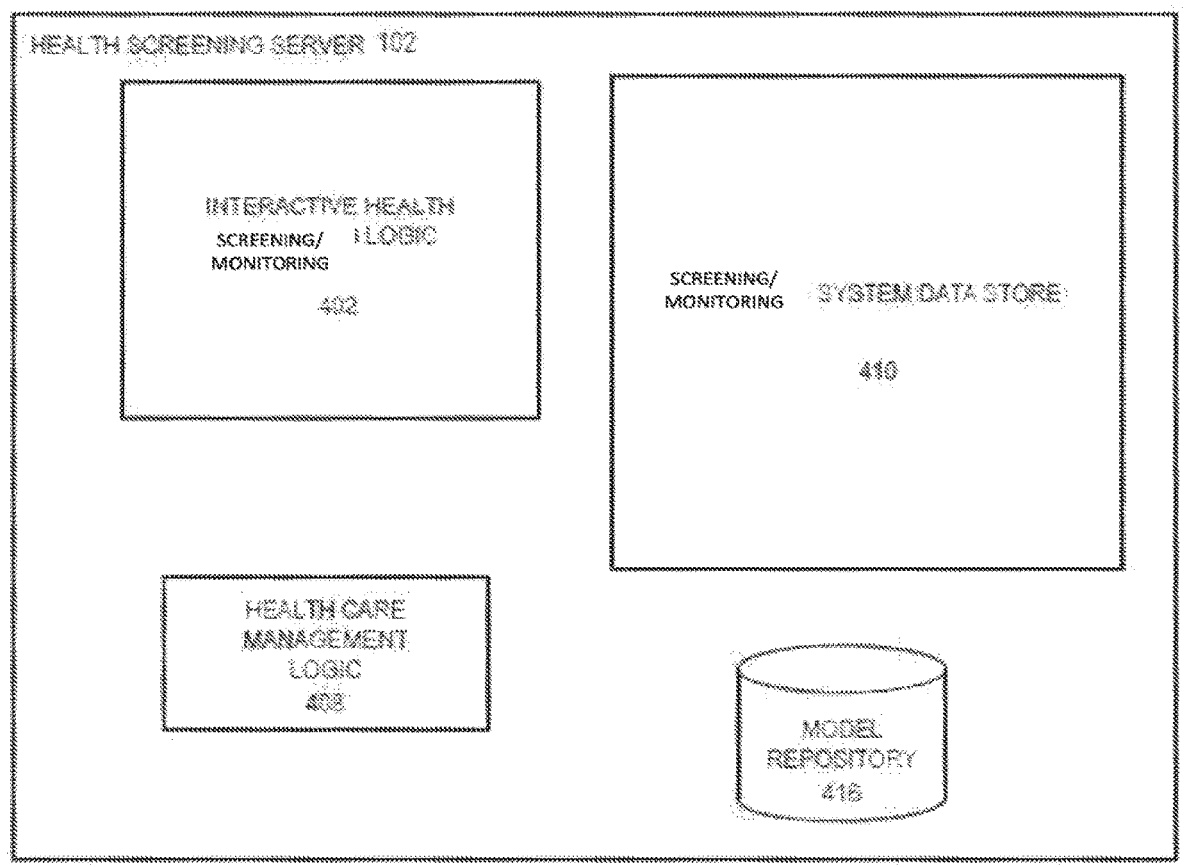
FIG. 4 is a block diagram of the health screening or monitoring server of FIG. 1A in greater detail.
Figure 22:
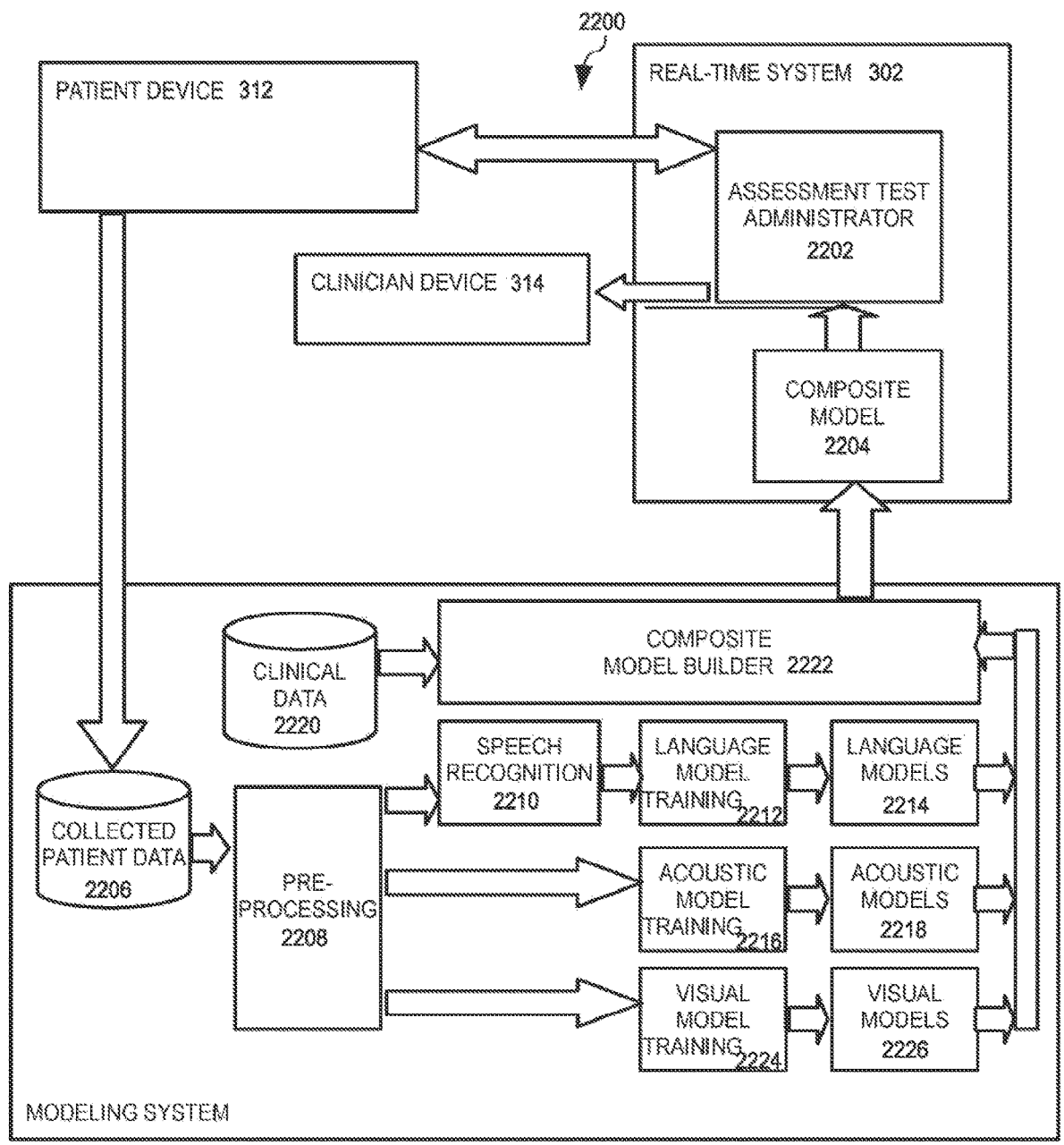
FIG. 22 shows the real-time computer system and the modeling computer system of FIG. 3 in greater detail, including a general flow of data.

Health screening or monitoring server 102 (FIG. 1A) is shown in greater detail in FIG. 4 and in even greater detail in FIG. 22. As shown in FIG. 4, health screening or monitoring server 102 includes interactive health screening or monitoring logic 402 and health care management logic 408. In addition, health screening or monitoring server 102 includes screening or monitoring system data store 410 and model repository 416.

Each of the components of health screening or monitoring server 102 is herein described more completely. Briefly, interactive health screening or monitoring logic 402 conducts an interactive conversation with the subject patient and estimates one or more health states of the patient by application of the models of runtime model server 504 (FIG. 18) to audiovisual signals representing responses by the patient. In this illustrative embodiment, interactive health screening or monitoring logic 402 (FIG. 4) may also operate in a passive listening mode, observing the patient outside the context of an interactive conversation with health screening or monitoring server 102, e.g., during a session with a health care clinician, and estimating a health state of the patient from such observation. Health care management logic 408 makes expert recommendations in response to health state estimations of interactive health screening or monitoring logic 402. Screening system data store 410 stores and maintains all user and patient data needed for, and collected by, screening or monitoring in the manner described herein.

The conversational context of the health screening or monitoring system may improve one or more performance metrics associated with one or more machine learning algorithms used by the system. These metrics may include metrics such as an F1 score, an area under the curve (AUC), a sensitivity, a specificity, a positive predictive value (PPV), and an equal error rate.

It should be appreciated that the behavior of health screening or monitoring server 102 described herein may be distributed across multiple computer systems. For example, in some illustrative embodiments, real-time, interactive behavior of health screening or monitoring server 102 (e.g., interactive screening or monitoring server logic 502 and runtime model server logic 504 described below) is implemented in one or more servers configured to handle large amounts of traffic through WAN 110 (FIG. 1A) and computationally intensive behavior of health screening or monitoring server 102 (e.g., health care management logic 408 and model training logic 506) is implemented in one or more other servers configured to efficiently perform highly complex computation. Distribution of various loads carried by health screening or monitoring server 102 may be distributed among multiple computer systems.

Figure 5:
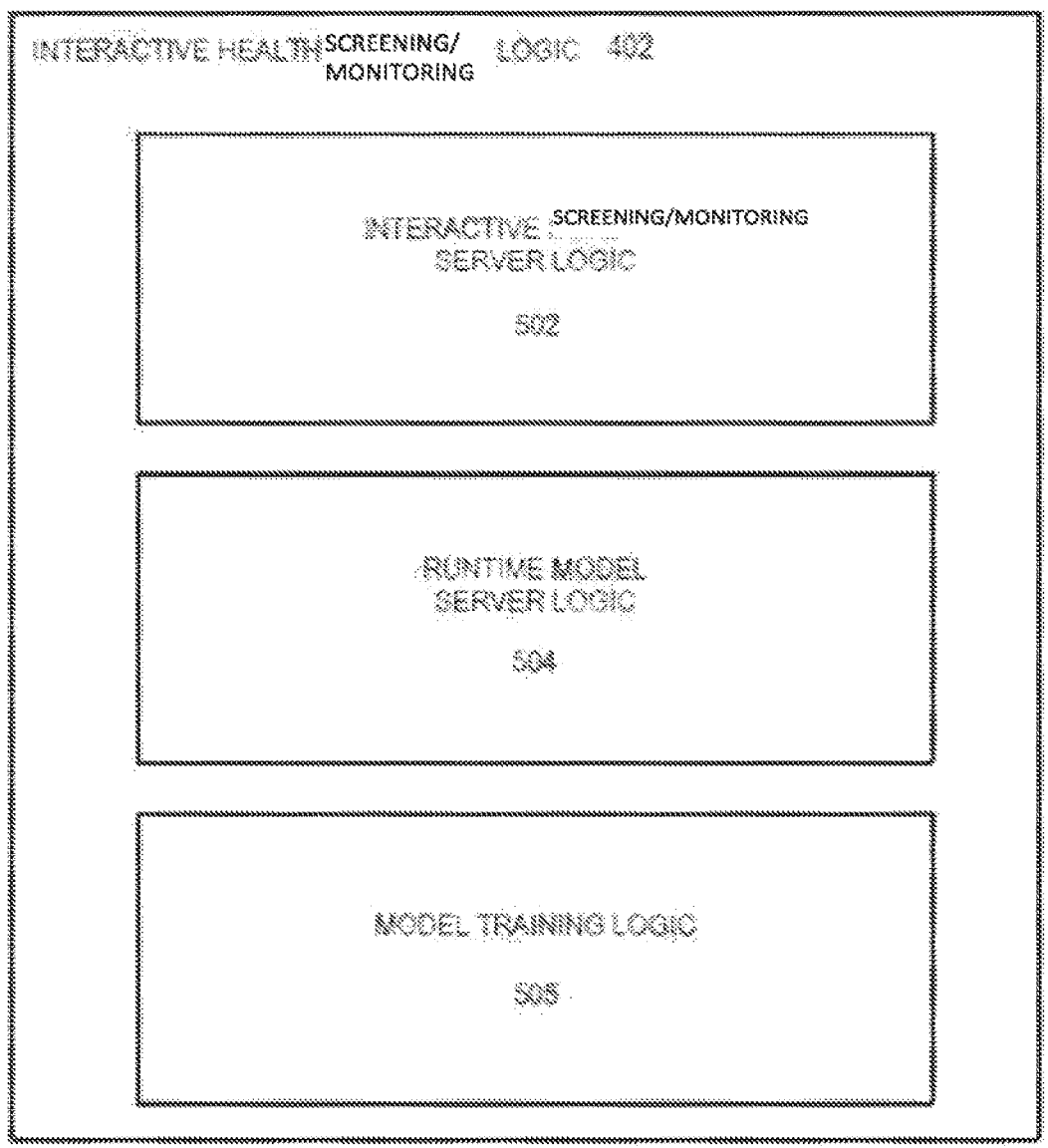
FIG. 5 is a block diagram of interactive health screening or monitoring logic of the health screening or monitoring server of FIG. 4 in greater detail.

Interactive health screening or monitoring logic 402 is shown in greater detail in FIG. 5. Interactive health screening or monitoring logic 402 includes interactive screening or monitoring server logic 502, runtime model server logic 504, and model training logic 506. Interactive screening or monitoring server logic 502 conducts an interactive screening or monitoring conversation with the human patient; runtime model server logic 504 uses and adjusts a number of machine learning models to concurrently evaluate responsive audiovisual signals of the patient; and model training logic 506 trains models of runtime model server logic 504.

Figure 6:
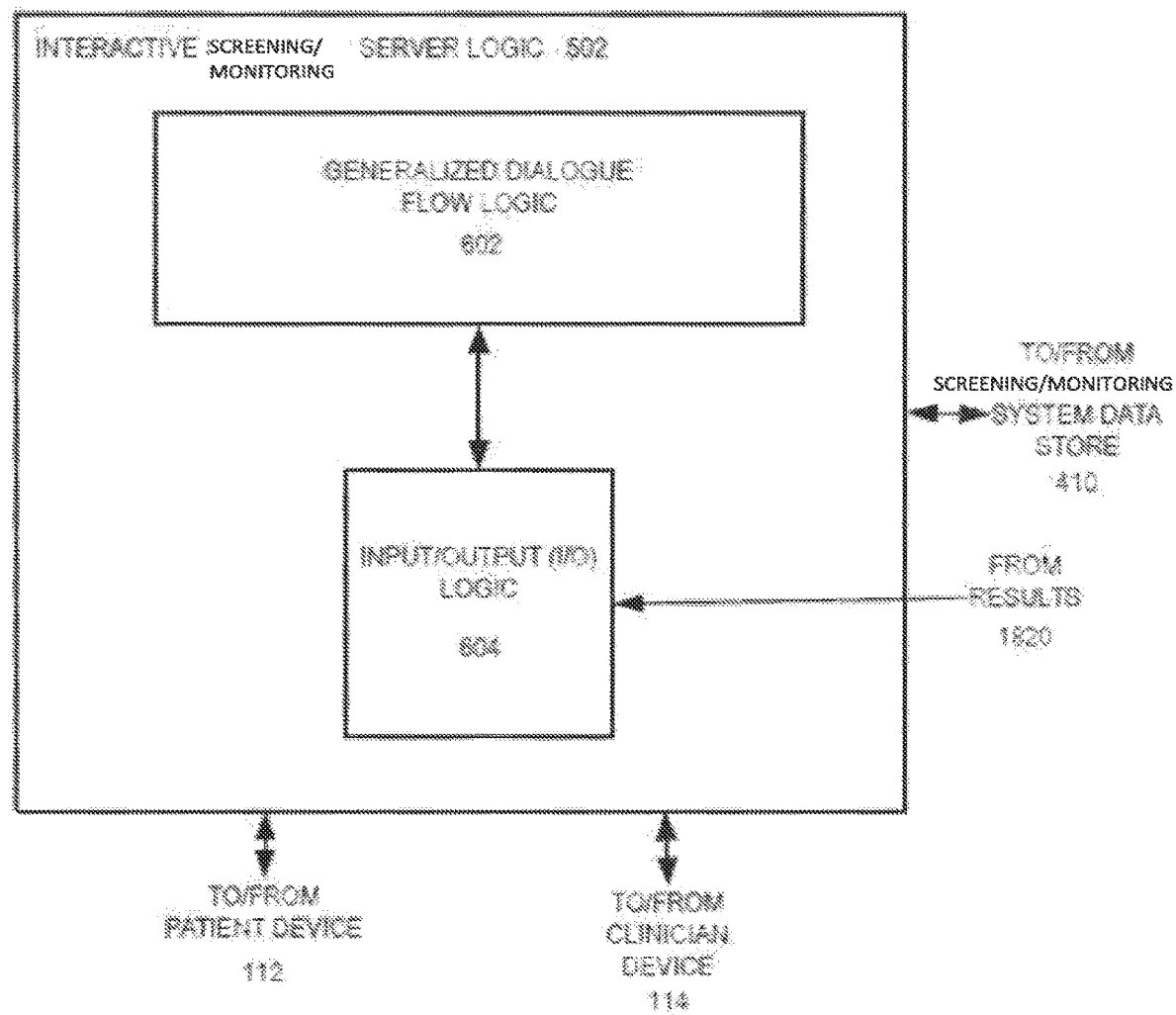
FIG. 6 is a block diagram of interactive screening or monitoring server logic of the interactive health screening or monitoring logic of FIG. 5 in greater detail.
Figure 19:
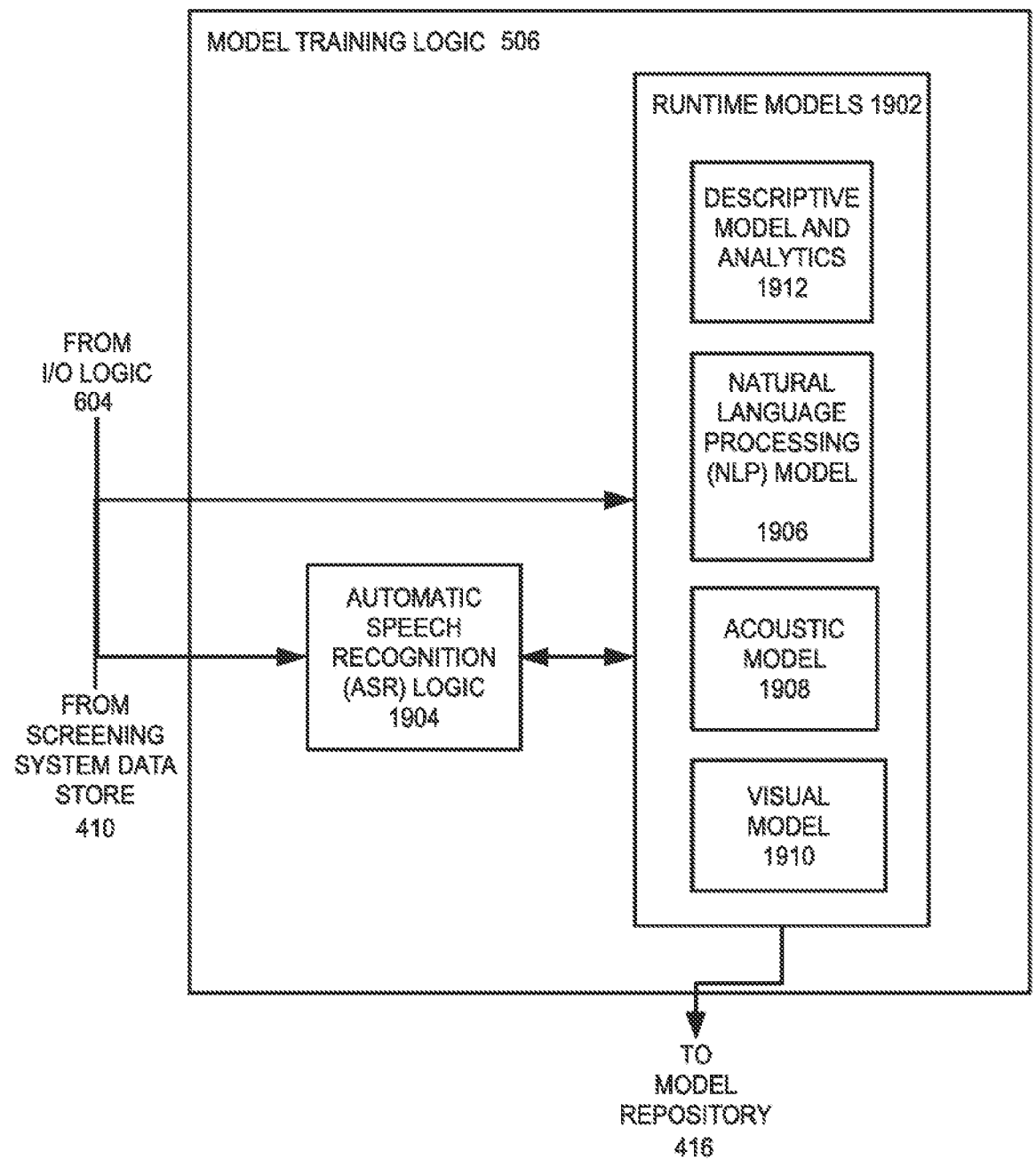
FIG. 19 is a block diagram of model training logic of the interactive health screening or monitoring logic of FIG. 1A in greater detail.

Interactive screening or monitoring server logic 502 is shown in greater detail in FIG. 6 and includes generalized dialogue flow logic 602 and input/output (I/O) logic 604. I/O logic 604 affects the interactive screening or monitoring conversation by sending audiovisual signals to, and receiving audiovisual signals from, patient device 112. I/O logic 604 receives data from generalized dialogue flow logic 602 that specifies questions to be asked of the patient and sends audiovisual data representing those questions to patient device 112. In embodiments in which the interactive screening or monitoring conversation is effected through PSTN 120 (FIG. 1), I/O logic 604 (i) sends an audiovisual signal to patient device 112 by sending data to a human, or automated, operator of call center 104 prompting the operator to ask a question in a telephone call with patient device 112 (or alternatively by sending data to a backend automated dialog system destined for patients) and (ii) receives an audiovisual signal from patient device 112 by receiving an audiovisual signal of the interactive screening or monitoring conversation forwarded by call center 104. I/O logic 604 also sends at least portions of the received audiovisual signal of the interactive screening or monitoring conversation to runtime model server logic 504 (FIG. 18) and model training logic 506 (FIG. 19).

The queries asked to patients, or questions, may be stored as nodes, while patient responses, collected as audiovisual signals, may be stored as edges. A screening or monitoring event, or set of screening or monitoring events, for a particular patient, may be therefore represented as a graph. For example, different answers to different follow-up questions may be represented as multiple spokes connecting a particular node to a plurality of other nodes. Different graph structures for different patients may be used as training examples for a machine learning algorithm as another method of determining a mental state classification for a patient. Classification may be performed by determining similarities between graphs of, for example, depressed patients. Equivalent questions, as discussed herein, may be labeled as such within the graph. Thus, the graphs may also be studied and analyzed to determine idiosyncrasies in interpretations of different versions of questions by patients.

I/O logic 604 also receives results 1820 (FIG. 18) from runtime server logic 504 that represent evaluation of the audiovisual signal. Generalized dialogue flow logic 602 conducts the interactive screening or monitoring conversation with the human patient. Generalized dialogue flow logic 602 determines what questions I/O logic 604 should ask of the patient and monitors the reaction of the patient as represented in results 1820. In addition, generalized dialogue flow logic 602 determines when to politely conclude the interactive screening or monitoring conversation.

Generalized dialogue flow logic 602 is shown in greater detail in FIG. 5. Generalized dialogue flow logic 602 includes interaction control logic generator 702. Interaction control logic generator 702 manages the interactive screening or monitoring conversation with the patient by sending data representing dialogue actions to I/O logic 604 (FIG. 6) that direct the behavior of I/O logic 604 in carrying out the interactive screening or monitoring conversation. Examples of dialogue actions include asking a question of the patient, repeating the question, instructing the patient, politely concluding the conversation, changing aspects of a display of patient device 112, and modifying characteristics of the speech presented by the patient by I/O logic 604, i.e., pace, volume, apparent gender of the voice, etc.

Interaction control logic generator 702 customizes the dialogue actions for the patient. Interaction control logic generator 702 receives data from screening or monitoring data store 210 that represents subjective preferences of the patient and a clinical and social history of the patient. In this illustrative embodiment, the subjective preferences are explicitly specified by the patient, generally prior to any interactive screening or monitoring conversation, and include such things as the particular voice to be presented to the patient through I/O logic 604, default volume and pace of the speech generated by I/O logic 604, and display schemes to be used within patient device 112.

The clinical and social history of the patient, in combination with identified interests of the patient, may indicate that questions related to certain topics should be asked of the patient. Interaction control logic generator 702 uses the patient's preferences and medical history to set attributes of the questions to ask the patient.

Interaction control logic generator 702 receives data from runtime model server logic 504 that represents analytical results of responses of the patient in the current screening or monitoring conversation. In particular, interaction control logic generator 702 receives data representing analytical results of responses, i.e., results 1820 (FIG. 18) of runtime model server logic 504 and patient and results metadata from descriptive model and analytics 1812 that facilitates proper interpretation of the analytical results. Interaction control logic generator 702 interprets the analytical results in the context of the results metadata to determine the patient's current status.

History and state machine 720 tracks the progress of the screening or monitoring conversation, i.e., which questions have been asked and which questions are yet to be asked. Question and dialogue action bank 710 is a data store that stores all dialogue actions that may be taken by interaction control logic generator 702, including all questions that may be asked of the patient. In addition, history and state machine 720 informs question and dialogue action bank 710 as to which question is to be asked next in the screening or monitoring conversation.

Interaction control logic generator 702 receives data representing the current state of the conversation and what questions are queued to be asked from history and state machine 720. Interaction control logic generator 702 processes the received data to determine the next action to be taken by interactive screening or monitoring server logic 302 in furtherance of the screening or monitoring conversation. Once the next action is determined, interaction control logic generator 702 retrieves data representing the action from question and dialogue action bank 710 and sends a request to I/O logic 604 to perform the next action.

Figure 8:
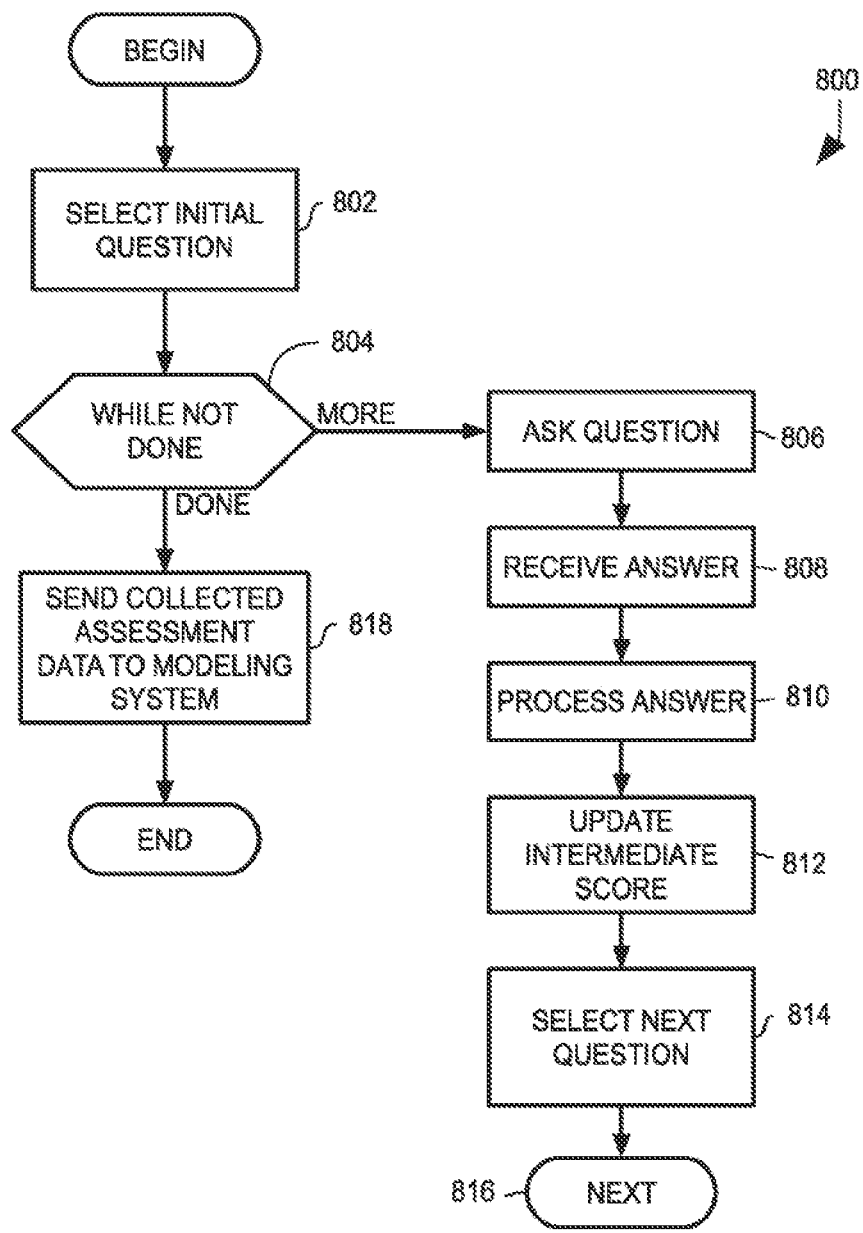
FIG. 8 is a logic flow diagram illustrating the control of an interactive spoken conversation with the patient by the generalized dialogue flow logic in accordance with the present disclosure.

The overall conducting of the screening or monitoring conversation by generalized dialogue flow logic 602 is illustrated in logic flow diagram 800 (FIG. 8). The logic flow diagram of FIG. 8 describes actions taken by components of the interaction engine in the block diagram of FIG. 28. In addition, the logic flow diagram of FIG. 8 is an instantiation of the process described in FIG. 14. In step 802, generalized dialogue flow logic 602 selects a question or other dialogue action to initiate the conversation with the patient. Interaction control logic generator 702 receives data from history and state machine 720 that indicates that the current screening or monitoring conversation is in its initial state. Interaction control logic generator 702 receives data that indicates (i) subjective preferences of the patient and (ii) topics of relatively high pertinence to the patient. Given that information, interaction control logic generator 702 selects an initial dialogue action with which to initiate the screening or monitoring conversation. Examples of the initial dialogue action may include (i) asking a common conversation-starting question such as "can you hear me?" or "are you ready to begin?"; (ii) asking a question from a predetermined script used for all patients; (iii) reminding the patient of a topic discussed in a previous screening or monitoring conversation with the patient and asking the patient a follow-up question on that topic; or (iv) presenting the patient with a number of topics from which to select using a user-interface technique on patient device 112. In step 802, interaction control logic generator 702 causes I/O logic 604 to carry out the initial dialogue action.

Loop step 804 and next step 816 define a loop in which generalized dialogue flow logic 602 conducts the screening or monitoring conversation according to steps 806-814 until generalized dialogue flow logic 602 determines that the screening or monitoring conversation is completed.

In step 806, interaction control logic generator 702 causes I/O logic 604 to carry out the selected dialogue action. In the initial performance of step 806, the dialogue action is selected in step 802. In subsequent performances of step 806, the dialogue action is selected in step 814 as described below. In step 808, generalized dialogue flow logic 602 receives an audiovisual signal of the patient's response to the question. While processing according to logic flow diagram 800 is shown in a manner that suggests synchronous processing, generalized dialogue flow logic 602 performs step 808 effectively continuously during performance of steps 802-816 and processes the conversation asynchronously. The same is true for steps 810-814. In step 810, I/O logic 604 sends the audiovisual signal received in step 808 to runtime model server logic 504, which processes the audiovisual signal in a manner described below. In step 812, I/O logic 604 of generalized dialogue flow logic 602 receives multiplex data from runtime model server logic 504 and produces therefrom an intermediate score for the screening or monitoring conversation so far.

As described above, the results data include analytical results data and results metadata. I/O logic 604 (i) determines to what degree the screening or monitoring conversation has completed screening or monitoring for the target health state(s) of the patient, (ii) identifies any topics in the patient's response that warrant follow-up questions, and (iii) identifies any explicit instructions from the patient for modifying the screening or monitoring conversation. Examples of the last include patient statements such as "can you speak louder?", "can you repeat that?" or "what?", and "please speak more slowly." In step 814, generalized dialogue flow logic 602 selects the next question to ask the subject patient, along with other dialogue actions to be performed by I/O logic 604, in the next performance of step 806. In particular, interaction control logic generator 702 (i) receives dialogue state data from history and state machine 720 regarding the question to be asked next, (ii) receives intermediate results data from I/O logic 604 representing evaluation of the patient's health state so far, and (iii) receives patient preferences and pertinent topics.

Processing transfers through next step 816 to loop step 804. Generalized dialogue flow logic 602 repeats the loop of steps 804-816 until interaction control logic generator 702 determines that the screening or monitoring conversation is complete, at which point generalized dialogue flow logic 602 politely terminates the screening or monitoring conversation. The screening or monitoring conversation is complete when (i) all mandatory questions have been asked and answered by the patient and (ii) the measure of confidence in the score resulting from screening or monitoring determined in step 812 is at least a predetermined threshold. It should be noted that confidence in the screening or monitoring is not symmetrical.

The screening or monitoring conversation seeks to detect specific health states in the patient, e.g., depression and anxiety. If such states are detected quickly, they're detected. However, absence of such states is not assured by failing to detect them immediately. More generally, absence of proof is not proof of absence. Thus, generalized dialogue flow logic 602 finds confidence in early detection but not in early failure to detect. Thus, health screening or monitoring server 102 (FIG. 4) estimates the current health state, e.g., mood, of the patient using a spoken conversation with the patient through patient device 112. Interactive screening or monitoring server logic 502 sends data representing the resulting screening or monitoring of the patient to the patient's doctor or other clinicians by sending the data to clinician device 114. In addition, interactive screening or monitoring server logic 502 records the resulting screening or monitoring in screening or monitoring system data store 410. A top priority of generalized dialogue flow logic 602 is to elicit speech from the patient that is highly informative with respect to the health state attributes for which health screening or monitoring server 102 screens the patient. For example, in this illustrative embodiment, health screening or monitoring server 102 screens most patients for depression and anxiety. The analysis performed by runtime model server logic 504 is most accurate when presented with patient speech of a particular quality. In this context, speech quality refers to the sincerity with which the patient is speaking. Generally speaking, high quality speech is genuine and sincere, while poor quality speech is from a patient not engaged in the conversation or being intentionally dishonest.

For example, if the patient does not care about the accuracy of the screening or monitoring, but instead wants to answer all questions as quickly as possible to end the screening or monitoring as quickly as possible, it is unlikely to reveal much about the patient's true health. Similarly, if the patient intends to control the outcome of the screening or monitoring by giving false responses, not only are the responses linguistically false but the emotional components of the speech may be distorted or missing due to the disingenuous participation by the patient. There are a number of ways in which generalized dialogue flow logic 602 increases the likelihood that the patient's responses are relatively highly informative. For example, generalized dialogue flow logic 602 may invite the patient to engage interactive screening or monitoring server logic 502 as an audio diary whenever the patient is so inclined. Voluntary speech by the patient whenever motivated tends to be genuine and sincere and therefore highly informative.

Generalized dialogue flow logic 602 may also select topics that are pertinent to the patient. These topics may include topics specific to clinical and social records of the patient and topics specific to interests of the patient. Using topics of interest to the patient may have the negative effect of influencing the patient's mood. For example, asking the patient about her favorite sports team may cause the patient's mood to rise or fall with the most recent news of the team. Accordingly, generalized dialogue flow logic 602 distinguishes health-relevant topics of interest to the patient from health-irrelevant topics of interest to the patient. For example, questions related to an estranged relative of the patient may be health-relevant while questions related to the patient's favorite television series are typically not. Adapting any synthetic voice to match the preferences of the patient makes the screening or monitoring conversation more engaging for the patient and therefore elicits more informative speech. In embodiments in which patient device 112 displays a video representation of a speaker, i.e., an avatar, to the patient, patient preferences include, in addition to the preferred voice, physical attributes of the appearance of the avatar.

When a patient has not specified preferences for a synthetic voice or avatar, generalized dialogue flow logic 602 may use a synthetic voice and avatar chosen for the first screening or monitoring conversation and, in subsequent screening or monitoring conversations, change the synthetic voice and avatar and compare the degree of informativeness of the patient's responses to determine which voice and avatar elicit the most informative responses. The voice and avatar chosen for the initial screening or monitoring conversation may be chosen according to which voice and avatar tends to elicit the most informative speech among the general population or among portions of the general population sharing one or more phenotypes with the patient. The manner in which the informativeness of responses elicited by a question is determined is described below.

To make the screening or monitoring conversation more interactive and engaging, generalized dialogue flow logic 602 inserts a synthetic backchannel in the conversation. For example, generalized dialogue flow logic 602 may utter "uh-huh" during short pauses in the patient's speech to indicate that generalized dialogue flow logic 602 is listening and interested in what the patient has to say. Similarly, generalized dialogue flow logic 602 may cause the video avatar to exhibit non-verbal behavior (sometimes referred to as "body language") to indicate attentiveness and interest in the patient.

Generalized dialogue flow logic 602 also selects questions that are of high quality. Question quality is measured in the informativeness of responses elicited by the question. In addition, generalized dialogue flow logic 602 avoids repetition of identical questions in subsequent screening or monitoring conversations, substituting equivalent questions when possible. The manner in which questions are determined to be equivalent to one another is described more completely below. As described above, question and adaptive action bank 710 (FIG. 5) is a data store that stores all dialogue actions that may be taken by interaction control logic generator 702, including all questions that may be asked of the patient.

Figure 9:
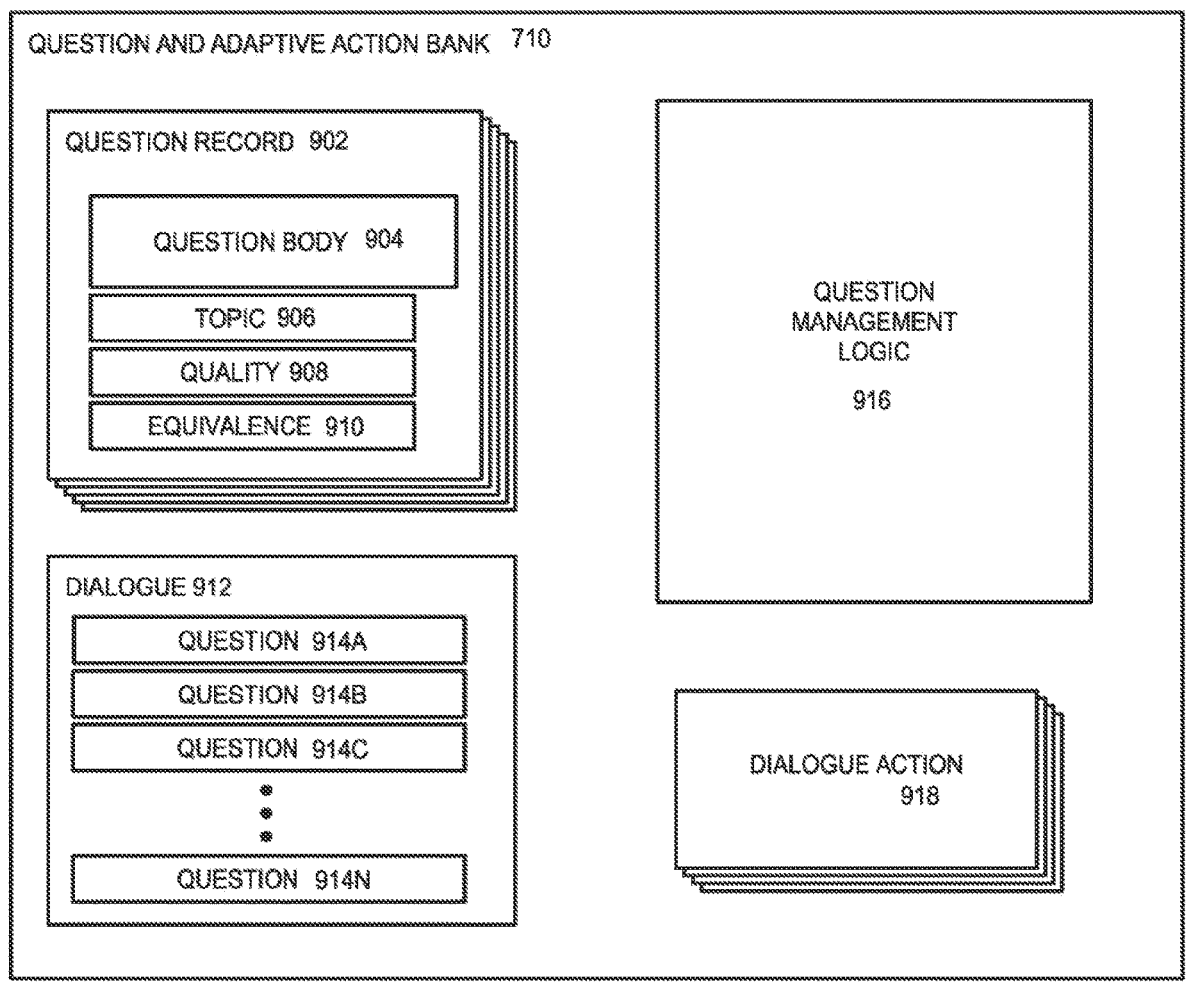
FIG. 9 is a block diagram of a question and adaptive action bank of the generalized dialogue flow logic of FIG. 7 in greater detail.

Question and adaptive action bank 710 is shown in greater detail in FIG. 9. Question and adaptive action bank 710 is shown in greater detail in FIG. 7 and includes a number of question records 902 and a dialogue 912. Each of question records 902 includes data representing a single question that may be asked of a patient. Dialogue 912 is a series of questions to ask a patient in a spoken conversation with the patient. Each of question records 902 includes a question body 904, a classification 906, a quality 908, and an equivalence 910. Question body 904 includes data specifying the substantive content of the question, i.e., the sequence of words to be spoken to the patient to effect asking of the question. Topic 906 includes data specifying a hierarchical topic category to which the question belongs. Categories may correlate to (i) specific health diagnoses such as depression, anxiety, etc.; (ii) specific symptoms such as insomnia, lethargy, general disinterest, etc.; and/or (iii) aspects of a patient's treatment such as medication, exercise, etc. Quality 908 includes data representing the quality of the question. The quality of the question is a measure of informativeness of responses elicited by the question. Equivalence 910 is data identifying one or more other questions in question records 902 that are equivalent to the question represented by this particular one of question records 902. In this illustrative embodiment, only questions of the same topic 906 may be considered equivalent. In an alternative embodiment, any questions may be considered equivalent regardless of classification. Dialogue 912 includes an ordered sequence of questions 914A-N, each of which identifies a respective one of question records 902 to ask in a spoken conversation with the patient. In this illustrative embodiment, the spoken conversation begins with twenty (20) preselected questions and may include additional questions as necessary to produce a threshold degree of confidence to conclude the conversation of logic flow diagram 600 (FIG. 6). The preselected questions include, in order, five (5) open-ended questions of high quality, eight (8) questions of the standard and known PHQ-8 screening or monitoring tool for depression, and the seven (7) questions of the standard and known GAD-7 screening or monitoring tool for anxiety. In other examples, the questions may be generated algorithmically. Dialogue 912 specifies these twenty (20) questions in this illustrative embodiment. As described above with respect to step 814 (FIG. 10), interaction control logic generator 702 determines the next question to ask the patient in step 814. One embodiment of step 814 is shown as logic flow diagram 1014 (FIG. 8). In step 1002, interaction control logic generator 702 dequeues a question from dialogue 912, treating the ordered sequence of questions 914A-N as a queue. History and state machine 720 keeps track of which of questions 914A-N is next. If the screening or monitoring conversation is not complete according to the intermediate score and all of questions 914A-N have been processed in previous performances of step 1002 in the same spoken conversation, i.e., if the question queue is empty, interaction control logic generator 702 selects questions from those of question records 902 with the highest quality 908 and pertaining to topics selected for the patient.

If interaction control logic generator 702 selects multiple questions, interaction control logic generator 702 may select one as the dequeued question randomly with each question weighted by its quality 908 and its closeness to suggested topics.

In step 1004 (FIG. 10), interaction control logic generator 702 collects all equivalent questions identified by equivalence 910 (FIG. 9) for the question dequeued in step 1002. In step 1006, interaction control logic generator 702 selects a question from the collection of equivalent questions collected in step 1004, including the question dequeued in step 1002 itself. Interaction control logic generator 702 may select one of the equivalent questions randomly or using information about prior interactions with the patient, e.g., to select the one of the equivalent questions least recently asked of the patient. Interaction control logic generator 702 processes the selected question as the next question in the next iteration of the loop of steps 804-816 (FIG. 8). The use of equivalent questions is important. The quality of a question, i.e., the degree to which responses the question elicits are informative in runtime model server logic 504, decreases for a given patient over time. In other words, if a given question is asked to a given patient repeatedly, each successive response by the patient becomes less informative than it was in all prior asking's of the question. In a sense, questions become stale over time. To keep questions fresh, i.e., soliciting consistently informative responses over time, a given question is replaced with an equivalent, but different, question in a subsequent conversation. However, the measurement of equivalence may be accurate for comparison of responses to equivalent questions over time to be consistent.

Thus, two important concepts of questions in generalized dialogue flow logic 602 (FIG. 7) are question quality and question equivalence. Question quality and question equivalence are managed by question management logic 916, which is shown in greater detail in FIG. 11. Question management logic 916 includes question quality logic 1102, which measures a question's quality, and question equivalence logic 1104, which determines whether two (2) questions are equivalent in the context of health screening or monitoring server 102. Question quality logic 1102 includes a number of metric records 1106 and metric aggregation logic 1112. To measure the quality of a question, i.e., to measure how informative are the responses elicited by the question, question quality logic 1102 uses a number of metrics to be applied to a question, each of which results in a numeric quality score for the question and each of which is represented by one of metric records 1106. Each of metric records 1106 represents a single metric for measuring question quality and includes metric metadata 1108 and quantification logic 1110. Metric metadata 1108 represents information about the metric of metric record 1106. Quantification logic 1110 defines the behavior of question quality logic 1102 in evaluating a question's quality according to the metric of metric record 1106.

The following are examples of metrics that may be applied by question quality logic 1102 to measure the quality of various questions: (i) the length of elicited responses in terms of a number of words; (ii) the length of elicited responses in terms of duration of the responsive utterance; (iii) a weighted word score; (iv) an amount of acoustic energy in elicited responses; and (v) "voice activation" in the responses elicited by the question. Each is described in turn.

In a metric record 1106 representing a metric of the length of elicited responses in terms of a number of words, quantification logic 1110 retrieves all responses to a given question from screening or monitoring system data store 410 (FIG. 4) and uses associated results data from screening or monitoring system data store 410 to determine the number of words in each of the responses. Quantification logic 1110 quantifies the quality of the question as a statistical measure of the number of words in the responses, e.g., a statistical mean thereof.

With respect to the length of elicited responses in terms of duration of the responsive utterance, the duration of elicited responses may be measured in a number of ways. In one, the duration of the elicited response is simply the elapsed duration, i.e., the entire duration of the response as recorded in screening or monitoring system data store 410. In another, the duration of the elicited response is the elapsed duration less pauses in speech. In yet another, the duration of the elicited response is the elapsed duration less any pause in speech at the end of the response.

In a metric record 1106 (FIG. 11) representing a metric of the duration of elicited responses, quantification logic 1110 retrieves all responses to a given question from screening or monitoring system data store 410 (FIG. 4) and determines the duration of those responses. Quantification logic 1110 (FIG. 11) quantifies the quality of the question as a statistical measure of the duration of the responses, e.g., a statistical mean thereof.

With respect to a weighted word score, semantic models of NLP model 1806 (FIG. 18) estimate a patient's health state from positive and/or negative content of the patient's speech. The semantic models correlate individual words and phrases to specific health states the semantic models are designed to detect. In a metric record 1106 (FIG. 11) representing a metric of a weighted word score, quantification logic 1110 retrieves all responses to a given question from collected patient data 410 (FIG. 5) and uses the semantic models to determine correlation of each word of each response to one or more health states. An individual response's weighted word score is the statistical mean of the correlations of the weighted word scores. Quantification logic 1110 quantifies the quality of the question as a statistical measure of the weighted word scores of the responses, e.g., a statistical mean thereof.

With respect to an amount of acoustic energy in elicited responses, runtime model server logic 504 (FIG. 18) estimates a patient's health state from pitch and energy of the patient's speech as described below. How informative speech is to the various models of runtime model server logic 504 is directly related to how emotional the speech is. In a metric record 1106 (FIG. 11) representing a metric of an amount of acoustic energy, quantification logic 1110 retrieves all responses to a given question from screening or monitoring system data store 410 (FIG. 4) and uses response data from runtime model server logic 504 to determine an amount of energy present in each response. Quantification logic 1110 quantifies the quality of the question as a statistical measure of the measured acoustic energy of the responses, e.g., a statistical mean thereof.

With respect to "voice activation" in the responses elicited by the question, the quality of a question is a measure of how similar responses to the question are to utterances recognized by runtime models 1802 (FIG. 18) as highly indicative of a health state that runtime models 1802 are trained to recognize. In a metric record 1106 (FIG. 11) representing a metric of voice activation, quantification logic 1110 determines how similar deep learning machine features for all responses to a given question are to deep learning machine features for health screening or monitoring server 102 as a whole.

Deep learning machine features are known but are described herein briefly to facilitate understanding and appreciation of the present invention. Deep learning is a sub-science of machine learning in that a deep learning machine is a machine learning machine, i.e., learning machine, that learns for itself how to distinguish one thing represented in data from another thing represented in data. The following is a simple example to illustrate the distinction.

Consider an ordinary (not deep) learning machine that is configured to recognize the representation of a cat in image data. Such a learning machine is typically a computer process with multiple layers of logic. One layer is manually configured to recognize contiguous portions of an image with transitions from one color to another (e.g., light to dark, red to green, etc.). This is commonly referred to as edge detection. A subsequent layer receives data representing the recognized edges and is manually configured to recognize edges that join together to define shapes. A final layer receives data representing shapes and is manually configured to recognize a symmetrical grouping of triangles (cat's ears) and dark regions (eyes and nose). Other layers may be used between those mentioned here.

In machine learning, the data received as input to any step in the computation, including intermediate results from other steps in the computation, are called features. The results of the learning machine are called labels. In this illustrative example, the labels are "cat" and "no cat".

This manually configured learning machine may work reasonably well but may have significant shortcomings. For example, recognizing the symmetrical grouping of shapes might not recognize an image in which a cat is represented in profile. In a deep learning machine, the machine is trained to recognize cats without manually specifying what groups of shapes represent a cat. The deep learning machine may utilize manually configured features to recognize edges, shapes, and groups of shapes, however these are not a required component of a deep learning system. Features in a deep learning system may be learned entirely automatically by the algorithm based on the labeled training data alone.

Training a deep learning machine to recognize cats in image data can, for example, involve presenting the deep learning machine with numerous, preferably many millions of, images and associated knowledge as to whether each image includes a cat, i.e., associated labels of "cat" or "no cat". For each image received in training, the last, automatically configured layer of the deep learning machine receives data representing numerous groupings of shapes and the associated label of "cat" or "no cat". Using statistical analysis and conventional techniques, the deep learning machine determines statistical weights to be given each type of shape grouping, i.e., each feature, in determining whether a previously unseen image includes a cat.

These trained, i.e., automatically generated, features of the deep learning machine will likely include the symmetrical grouping of shapes manually configured into the learning machine as described above. However, these features will also likely include shape groupings and combinations of shape groupings not thought of by human programmers.

In measuring the quality of a question, the features of the constituent models of runtime model server logic 504 (FIG. 18) specify precisely the type of responses that indicate a health state that the constituent models of runtime model server logic 504 are configured to recognize. Thus, in evaluating the quality of a question, these features represent an exemplary feature set. To measure the quality of a question using this metric, quantification logic 1110 (FIG. 11) retrieves all responses to the question from screening or monitoring system data store 410 and data representing the diagnoses associated with those responses and trains runtime models 1802 and model repository 416 using those responses and associated data.

In training runtime models 1802 and model repository 416, the deep learning machine develops a set of features specific to the question being measured and the determinations to be made by the trained models. Quantification logic 1110 measures similarity between the feature set specific to the question and the exemplary feature set in a manner described below with respect to question equivalence logic 1104.

As described above, interaction control logic generator 702 (FIG. 7) uses quality 908 (FIG. 9) of various questions in determining which question(s) to ask a particular patient. To provide a comprehensive measure of quality of a question to store in quality 908 (FIG. 9), metric aggregation logic 1112 (FIG. 11) aggregates the various measures of quality according to metric records 1106. The manner in which aggregation logic 1112 aggregates the measures of quality for a given question is illustrated by logic flow diagram 1200 (FIG. 12).

Loop step 1202 and next step 1210 define a loop in which metric aggregation logic 1112 processes each of metric records 1106 according to steps 1204-1208. The particular one of metric records 1106 processed in an iteration of the loop of steps 1202-1210 is sometimes referred to as "the subject metric record", and the metric represented by the subject metric record is sometimes referred to as "the subject metric." In step 1204, metric aggregation logic 1112 evaluates the subject metric, using quantification logic 1110 of the subject metric record and all responses in screening or monitoring system data store 410 (FIG. 4) to the subject question. In test step 1206 (FIG. 12), metric aggregation logic 1110 determines whether screening or monitoring system data store 410 includes a statistically significant sample of responses to the subject question by the subject patient. If so, metric aggregation logic 1110 evaluates the subject metric using quantification logic 1110 and only data corresponding to the subject patient in screening or monitoring system data store 410 in step 1208. Conversely, if collected patient data 410 does not include a statistically significant sample of responses to the subject question by the subject patient, metric aggregation logic 1112 skips step 1208. Thus, metric aggregation logic 1112 evaluates the quality of a question in the context of the subject patient to the extent screening or monitoring system data store 410 contains sufficient data corresponding to the subject patient.

After steps 1206-1208, processing transfers through next step 1210 to loop step 1202 and metric aggregation logic 1110 processes the next metric according to the loop of steps 1202-1210. Once all metrics have been processed according to the loop of steps 1202-1210, processing transfers to step 1212 in which metric aggregation logic 1110 aggregates the evaluated metrics from all performances of steps 1204 and 1206 into a single measure of quality and stores data representing that measure of quality in quality 908. In this illustrative embodiment, metric metadata 1108 stores data specifying how metric aggregation logic 1112 is to include the associated metric in the aggregate measure in step 1212. For example, metric metadata 1108 may specify a weight to be attributed to the associated metric relative to other metrics.

After step 1212 (FIG. 12), processing according to logic flow diagram 1200 completes.

Figure 13:
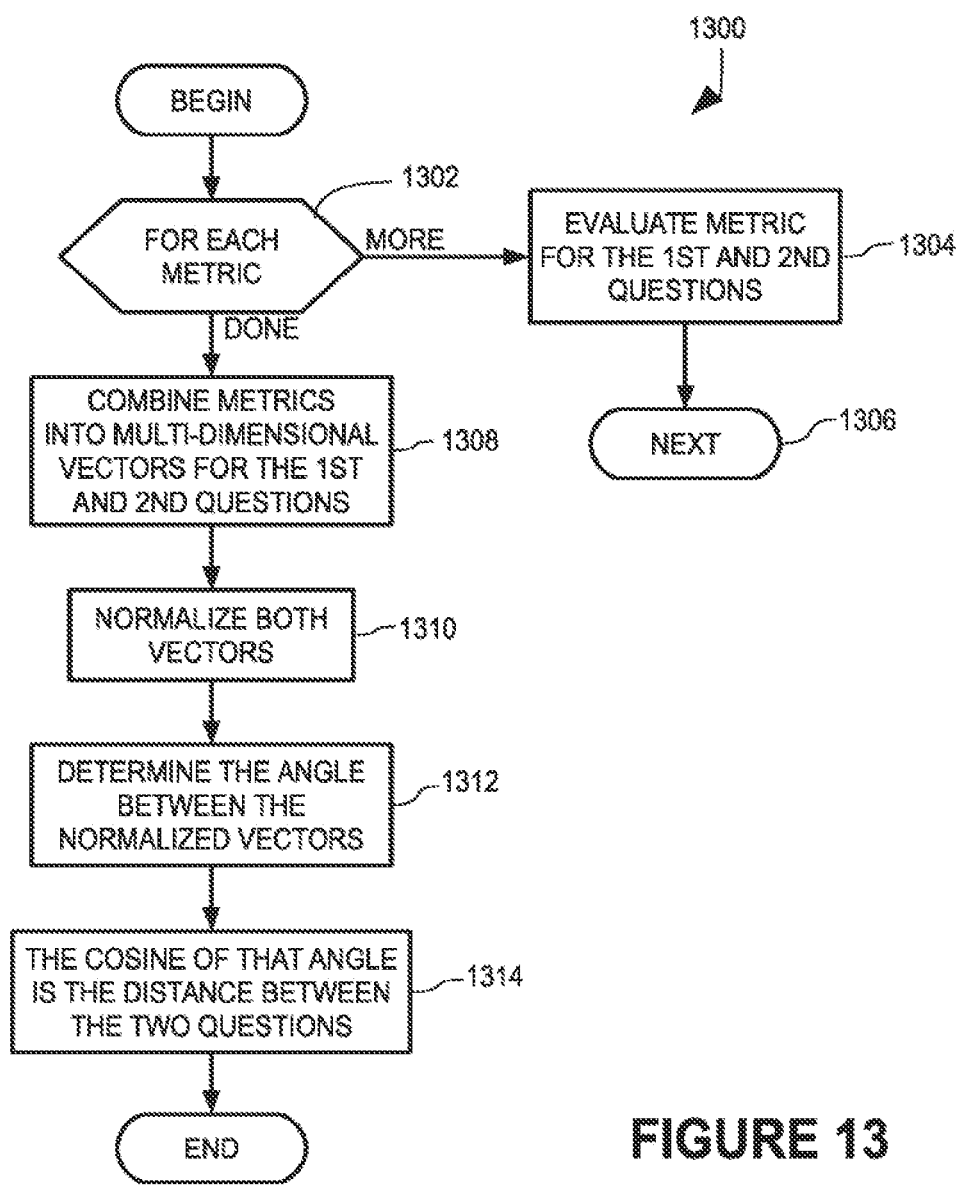
FIG. 13 is a logic flow diagram of determination of the equivalence of two questions in accordance with the present disclosure.

As described above, equivalence 910 for a given question identifies one or more other questions in question records 902 that are equivalent to the given question. Whether two questions are equivalent is determined by question equivalence logic 1104 (FIG. 11) by comparing similarity between the two questions to a predetermined threshold. The similarity here is not how similar the words and phrasing of the sentences are but instead how similarly models of runtime model server 504 and model repository 416 sees them. The predetermined threshold is determined empirically. Question equivalence logic 1104 measures the similarity between two questions in a manner illustrated by logic flow diagram 1300 (FIG. 13).

Loop step 1302 and next step 1306 define a loop in which question equivalence logic 1304 processes each of metric records 1106 according to step 1304. The particular one of metric records 1306 processed in an iteration of the loop of steps 1302-1306 is sometimes referred to as "the subject metric record", and the metric represented by the subject metric record is sometimes referred to as "the subject metric." In step 1304, question equivalence logic 1104 evaluates the subject metric for each of the two questions. Once all metrics have been processed according to the loop of steps 1302-1106, processing by question equivalence logic 1104 transfers to step 1308.

In step 1308, question equivalence logic 1104 combines the evaluated metrics for each question into a respective multi-dimensional vector for each question.

In step 1310, question equivalence logic 1104 normalizes both vectors to have a length of 1.0. In step 1312, question equivalence logic 1104 determines an angle between the two normalized vectors.

In step 1314, the cosine of the angle determined in step 1312 is determined by question equivalence logic 1104 to be the measured similarity between the two questions.

Since the vectors are normalized to a length of 1.0, the similarity between two questions ranges from −1.0 to 1.0, 1.0 being perfectly equivalent. In this illustrative embodiment, the predetermined threshold is 0.98 such that two questions have a measured similarity of at least 0.98 are considered equivalent and are so represented in equivalence 910 (FIG. 9) for both questions.

In addition, since the comparison between questions is not comparison of a single value but instead a comparison of multi-dimensional vectors, two questions are equivalent, not if only similar in general, but if similar in most or every way measured.

Figure 14:
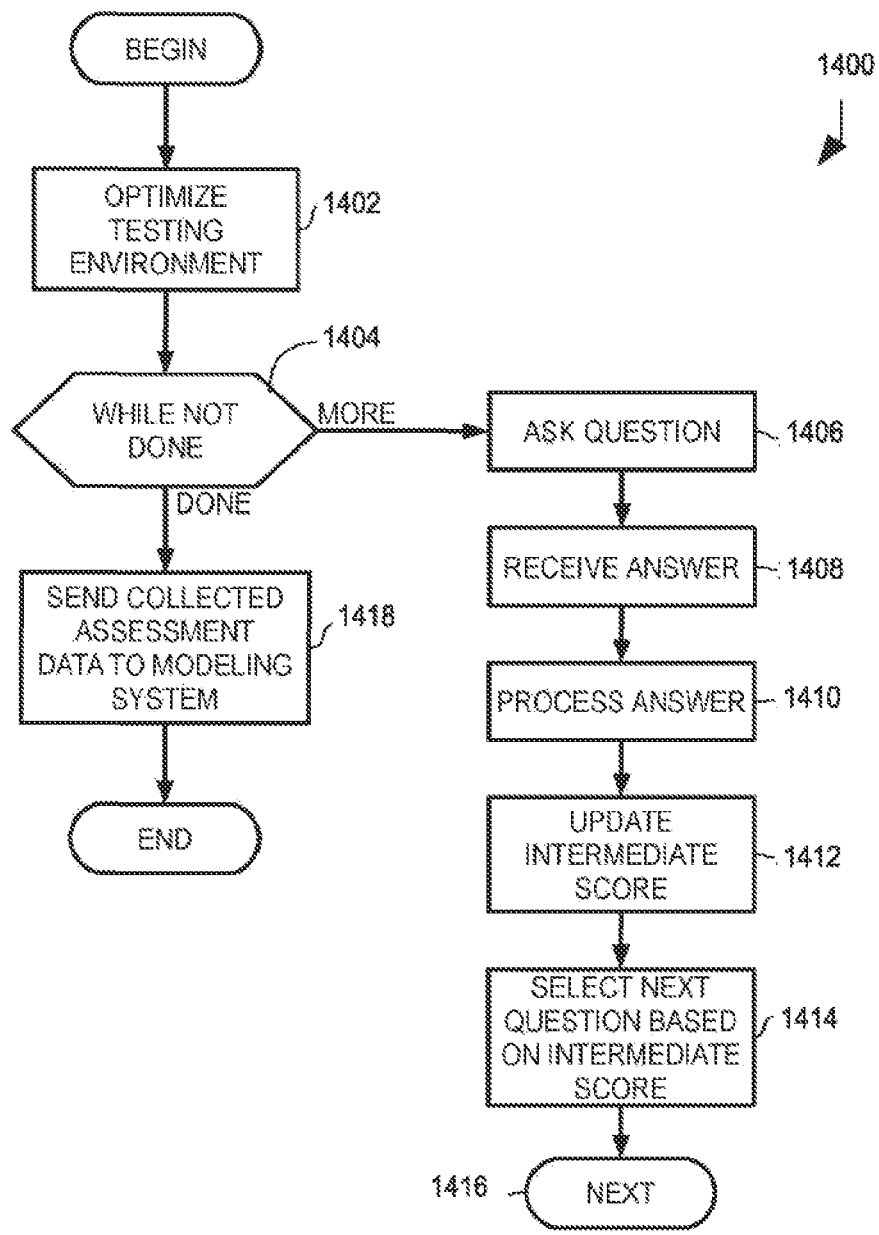
FIG. 14 is a logic flow diagram illustrating the control of an interactive spoken conversation with the patient by the real-time system in accordance with the present disclosure.

In another embodiment (FIG. 3), assessment test administrator 2202 (FIG. 22) administers a depression assessment test to the subject patient by conducting an interactive spoken conversation with the subject patient through patient device 312. The manner in which assessment test administrator 2202 does so is illustrated in logic flow diagram 1400 (FIG. 14). The test administrator 2202 may be a computer program configured to questions to the patient. The questions may be algorithmically generated questions. The questions may be generated by, for example, a natural language processing (NLP) algorithm. Examples of NLP algorithms are semantic parsing, sentiment analysis, vector-space semantics, and relation extraction. In some embodiments, the methods described herein may be able to generate an assessment without requiring the presence or intervention of a human clinician. In other embodiments, the methods described herein may be able to be used to augment or enhance clinician-provided assessments, or aid a clinician in providing an assessment. The assessment may include queries containing subject matter that has been adapted or modified from screening or monitoring methods, such as the PHQ-9 and GAD-7 assessments. The assessment herein may not merely use the questions from such surveys verbatim, but may adaptively modify the queries based at least in part on responses from subject patients.

Figure 15:
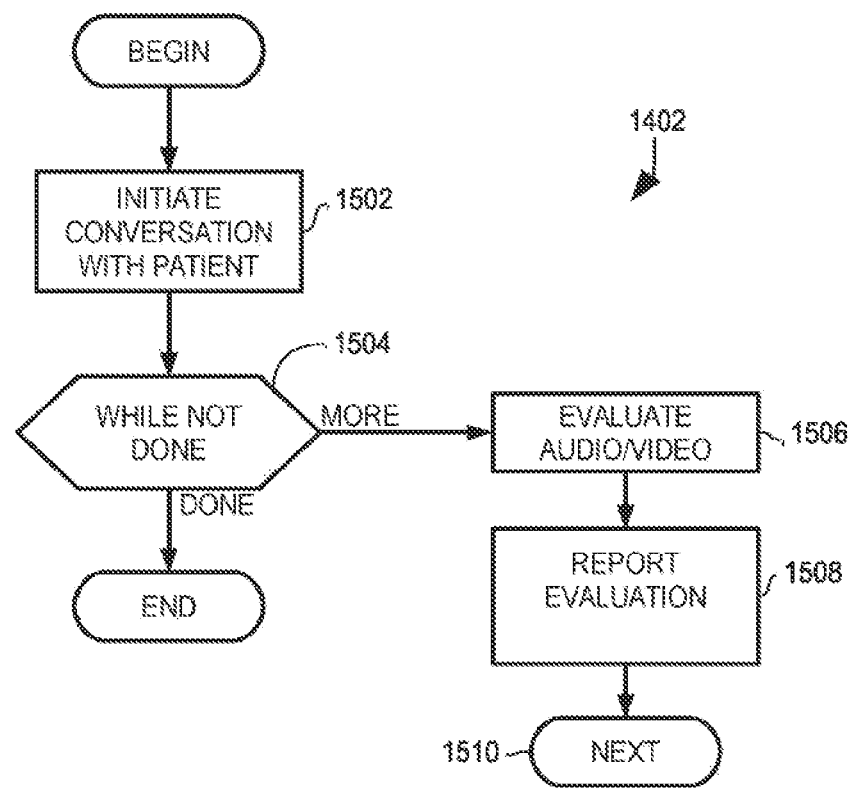
FIGS. 15 and 16 are each a logic flow diagram of a respective step of FIG. 14 in greater detail.

In step 1402, assessment test administrator 2202 optimizes the testing environment. Step 1402 is shown in greater detail in logic flow diagram 1402 (FIG. 15).

In step 1502, assessment test administrator 2202 initiates the spoken conversation with the subject patient. In this illustrative embodiment, assessment test administrator 2202 initiates a conversation by asking the patient the initial question of the assessment test. The initial question is selected in a manner described more completely below. The exact question asked isn't particularly important. What is important is that the patient responds with enough speech that assessment test administrator 2202 may evaluate the quality of the video and audio signal received from patient device 312.

Assessment test administrator 2202 receives and processes audiovisual data from patient device 312 throughout the conversation. Loop step 1504 and next step 1510 define a loop in which assessment test administrator 2202 processes the audiovisual signal according to steps 1506-1508 until assessment test administrator 2202 determines that the audiovisual signal is of high quality or at least of adequate quality to provide accurate assessment.

In step 1506, assessment test administrator 2202 evaluates the quality of the audiovisual signal received from patient device 312. In particular, assessment test administrator 2202 measures the volume of speech, the clarity of the speech, and to what degree the patient's face and, when available, body is visible.

In step 1508, assessment test administrator 2202 reports the evaluation to the patient. In particular, assessment test administrator 2202 generates an audiovisual signal that represents a message to be played to the patient through patient device 312. If the audiovisual signal received from patient device 312 is determined by assessment test administrator 2202 to be of inadequate quality, the message asks the patient to adjust her environment to improve the signal quality. For example, if the audio portion of the signal is poor, the message may be "I'm having trouble hearing you. may you move the microphone closer to you or find a quieter place?" If the patient's face and, when available, body isn't clearly visible, the message may be "I can't see your face (and body). may you reposition your phone so I may see you?" After step 1508, processing by assessment test administrator 2202 transfers through next step 1510 to loop step 1504 and assessment test administrator 2202 continues processing according to the loop of steps 1504-1510 until the received audiovisual is adequate or is determined to be as good as it will get for the current assessment test. It is preferred that subsequent performances of step 1508 are responsive to any speech by the patient. For example, the patient may attempt to comply with a message to improve the environment with the question, "Is this better?" The next message sent in reporting of step 1508 should include an answer to the patient's question. As described herein, composite model 2204 includes a language model component, so assessment test administrator 2202 necessarily performs speech recognition.

When the received audiovisual is adequate or is determined to be as good as it will get for the current assessment test, processing by assessment test administrator 2202 according to the loop of steps 1504-1510 completes. In addition, processing according to logic flow diagram 1402, and therefore step 1402 (FIG. 14), completes.

Loop step 1404 and next step 1416 define a loop in which assessment test administrator 2202 conducts the spoken conversation of the assessment test according to steps 1406-1414 until assessment test administrator 2202 determines that the assessment test is completed.

In step 1406, assessment test administrator 2202 asks a question of the patient in furtherance of the spoken conversation. In this illustrative embodiment, assessment test administrator 2202 uses a queue of questions to ask the patient, and that queue is sometimes referred to herein as the conversation queue. In the first performance of step 1406, the queue may be prepopulated with questions to be covered during the assessment test. In general, these questions cover the same general subject matter covered by currently used written assessment tests such as the PHQ-9 and GAD-7. However, while the questions in those tests are intentionally designed to elicit extremely short and direct answers, assessment test administrator 2202 may require more audio and video than provided by one-word answers. Accordingly, it is preferred that the initially queued questions be more open-ended.

In this illustrative embodiment, the initial questions pertain to the topics of general mood, sleep, and appetite. An example of an initial question pertaining to sleep is question 1702 (FIG. 17): "How have you been sleeping recently?" This question is intended to elicit a sentence or two from the patient to thereby provide more audio and video of the patent than would ordinarily be elicited by a highly directed question.

In step 1408 (FIG. 14), assessment test administrator 2202 receives an audiovisual signal of the patient's response to the question. While processing according to logic flow diagram 1400 is shown in a manner that suggests synchronous processing, assessment test administrator 2202 performs step 1408 effectively continuously during performance of steps 1402-1416 and processes the conversation asynchronously. The same is true for steps 1410-1414.

In step 1410, assessment test administrator 2202 processes the audiovisual signal received in step 1408 using composite model 2204. In step 1412, assessment test administrator 2202 produces an intermediate score for the assessment test according to the audiovisual signal received so far.

Figure 16:
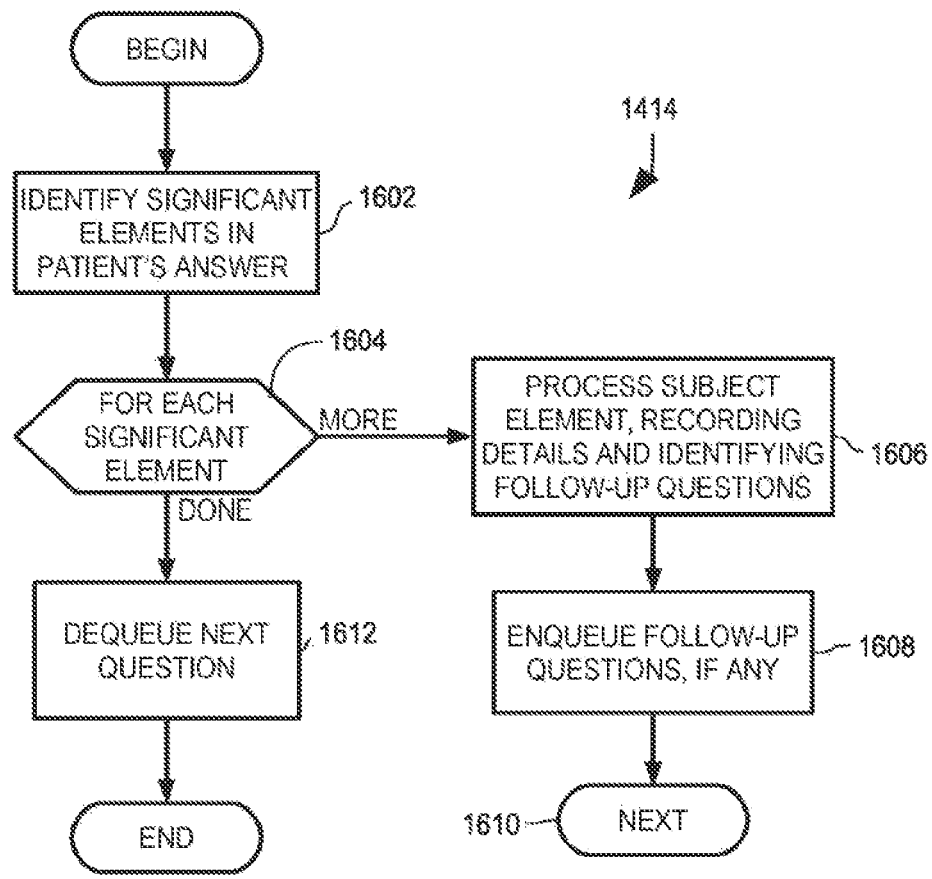

In step 1414, assessment test administrator 2202 selects the next question to ask the subject patient in the next performance of step 1406, and processing transfers through next step 1416 to loop step 1404. Step 1414 is shown in greater detail as logic flow diagram 1414 (FIG. 16). In addition, FIG. 16 may be construed to follow from step 814 from FIG. 8.

In step 1602, assessment test administrator 2202 identifies significant elements in the patient's speech. In particular, assessment test administrator 2202 uses language portions of composite model 2204 to identify distinct assertions in the portion of the audiovisual signal received after the last question asked in step 1406 (FIG. 14). That portion of the audiovisual signal is sometimes referred to herein as "the patient's response" in the context of a particular iteration of the loop of steps 1604-1610.

Figure 17:
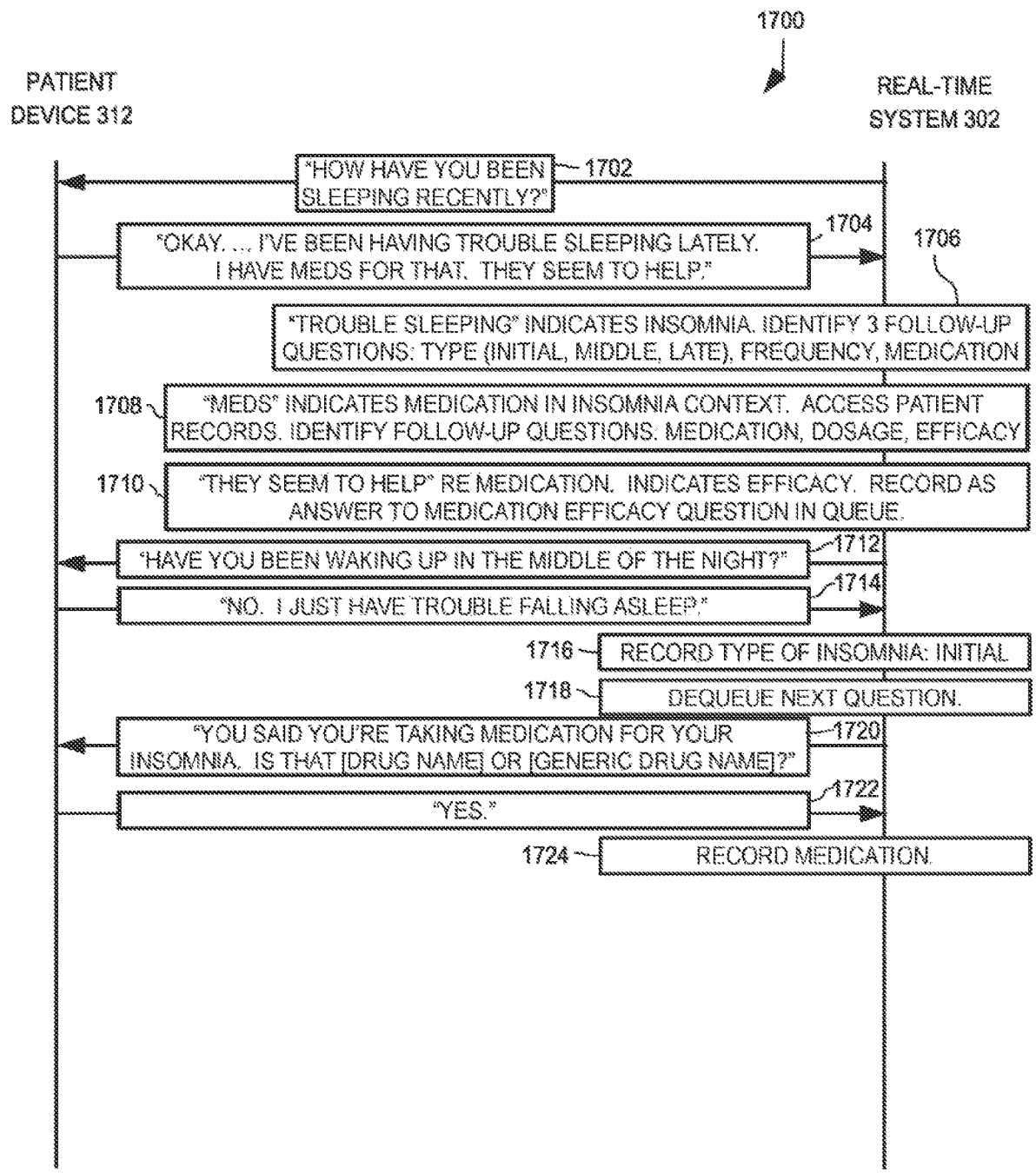
FIG. 17 is a transaction flow diagram showing an illustrative example of a spoken conversation with, and controlled by, the real-time system of FIG. 3.

An example of a conversation conducted by assessment test administrator 2202 of real-time system 302 and patient device 312 is shown in (FIG. 17). It should be appreciated that conversation 1700 is illustrative only. The particular questions to ask, which parts of the patient's response are significant, and the depth to which any topic is followed is determined by the type information to be gathered by assessment test administrator 2202 and is configured therein. In step 1702, assessment test administrator 2202 asks the question, "How have you been sleeping recently?" The patient's response is "Okay . . . I've been having trouble sleeping lately. I have meds for that. They seem to help." In step 1602, assessment test administrator 2202 identifies three (3) significant elements in the patient's response: (i) "trouble sleeping" suggests that the patient has some form of insomnia or at least that sleep is poor; (ii) "I have meds" suggests that the user is taking medication; and (iii) "They seem to help" suggests that the medication taken by the user is effective. In the illustrative example of conversation 1700, each of these significant elements is processed by assessment test administrator 2202 in the loop of steps 1604-1610.

Loop step 1604 and next step 1610 define a loop in which assessment test administrator 2202 processes each significant element of the patient's answer identified in step 1602 according to steps 1606-1608. In the context of a given iteration of the loop of steps 1604-1610, the particular significant element processed is sometimes referred to as "the subject element." In step 1606, assessment test administrator 2202 processes the subject element, recording details included in the element and identifying follow-up questions. For example, in conversation 1700 (FIG. 17), assessment test administrator 2202 identifies three (3) topics for follow-up questions for the element of insomnia: (i) type of insomnia (initial, middle, or late), (ii) the frequency of insomnia experienced by the patient, and (iii) what medication if any the patient is taking for the insomnia.

In step 1608, assessment test administrator 2202 enqueues any follow-up questions identified in step 1606.

After step 1608, processing by assessment test administrator 2202 transfers through next step 1610 to loop step 1604 until assessment test administrator 2202 has processed all significant elements of the patient's response according to the loop of steps 1604-1610. Once assessment test administrator 2202 has processed all significant elements of the patient's response according to the loop of steps 1604-1610, processing transfers from loop step 1604 to step 1612.

In the illustrative context of conversation 1700 (FIG. 17), the state of the conversation queue is as follows. FIG. 17 shows a particular instantiation of a conversation proceeding between the system and a patient. The queries and replies disclosed herein are exemplary and should not be construed as being required to follow the sequence disclosed in FIG. 17. In the processing the response element of insomnia, assessment test administrator 2202 identifies and enqueues follow-up topics regarding the type insomnia and any medication taken for the insomnia.

In processing the response element of medication in the patient's response, assessment test administrator 2202 observes that the patient is taking medication. In step 1606, assessment test administrator 2202 records that fact and, identifying a queued follow-up question regarding medication for insomnia, processes the medication element as responsive to the queued question.

In step 1608 for the medication element, assessment test administrator 2202 enqueues follow-up questions regarding the particular medicine and dosage used by the patient and its efficacy as shown in step 1708.

In this illustrative embodiment, questions in the conversation queue are hierarchical. In the hierarchy, each follow-up question is a child of the question for which the follow-up question follows up. The latter question is the parent of the follow-up question. In dequeuing questions from the conversation queue, assessment test administrator 2202 implements a pre-order depth-first walk of the conversation queue hierarchy. In other words, all child questions of a given question are processed before processing the next sibling question. In conversational terms, all follow-up questions of a given question are processed before processing the next question at the same level, recursively. In the context of conversation 1700, assessment test administrator 2202 processes all follow-up questions of the type of insomnia before processing the questions of frequency and medication and any of their follow-up questions. This is the way conversations happen naturally-staying with the most recently discussed topic until complete before returning to a previously discussed topic.

In addition, the order in which sibling questions are processed by assessment test administrator 2202 may be influenced by the responses of the patient. In this illustrative example, a follow-up question regarding the frequency of insomnia precedes the follow-up question regarding medication. However, when processing the element regarding medication in step 1606, assessment test administrator 2202 changes the sequence of follow-up questions such that the follow-up question regarding medication is processed prior to processing the follow-up question regarding insomnia frequency. Since medication was mentioned by the patient, we'll discuss that before adding new subtopics to the conversation. This is another way in which assessment test administrator 2202 is responsive to the patient.

In processing the response element of medication efficacy (i.e., "They seem to help."), assessment test administrator 2202 records that the medication is moderately effective. Seeing that the conversation queue includes a question regarding the efficacy of medication, assessment test administrator 2202 applies this portion of the patient's response as responsive to the queued follow-up question in step 1710.

In step 1612, assessment test administrator 2202 dequeues the next question from the conversation queue and processing according to logic flow diagram 1414, and therefor step 1414, completes and the conversation continues. Prior to returning to discussion of (FIG. 14), it is helpful to consider additional performances of step 1414, and therefore logic flow diagram 1414, in the context of illustrative conversation 1700. The question dequeued as the next question in this illustrative embodiment asks about the patient's insomnia, trying to discern the type of insomnia. It is appreciated that conventional thinking as reflected in the PHQ-9 and GAD-7 is that the particular type of sleep difficulties experienced by a test subject isn't as strong an indicator of depression as the mere fact that sleep is difficult. However, delving more deeply into a topic of conversation has a number of beneficial consequences. Most significantly is that the user is encouraged to provide more speech for more accurate assessment of the patient's state. In addition, by asking questions about something the patient has just said suggests that assessment test administrator 2202 is interested in the patient personally and, by earning good will from the patient, makes the patient more likely to be honest, both in speech and behavior.

In the illustrative example of conversation 1700, the next question is related to the type of insomnia. The question is intentionally as open-ended as possible while still targeted at specific information: "Have you been waking up in the middle of the night?" See question 1712. While this question may elicit a "Yes" or "No" answer, it may also elicit a longer response, such as response 1714: "No. I just have trouble falling asleep." After step 1612, processing according to logic flow diagram 1414, and therefore step 1414 (FIG. 14), completes. In successive iterations of the loop of steps 1404-1416, assessment test administrator 2202 continues the illustrative example of conversation 1700. In the next performance of step 1406, assessment test administrator 2202 asks question 1712 (FIG. 17). In the next continuing performance of step 1408, assessment test administrator 2202 receives response 1714. Assessment test administrator 2202 processes response 1714 in the next performance of step 1414.

In this illustrative performance of step 1602 (FIG. 16), assessment test administrator 2202 identifies a single significant element, namely, that the patient has trouble falling asleep and doesn't wake in the middle of the night. In step 1606, assessment test administrator 2202 records the type of insomnia (see step 1716) and, in this illustrative embodiment, there are no follow-up questions related to that.

In this illustrative performance of step 1608, assessment test administrator 2202 dequeues the next question from the conversation queue. Since no follow-up questions for the type of insomnia and whether the patient is treating the insomnia with medication have already been answered, the next question is the first child question related to medication, namely, the particular medication taken by the patient.

In the next iterative performance of step 1406 (FIG. 14), assessment test administrator 2202 forms the question, namely, which particular medication the patient is taking for insomnia. In some embodiments, assessment test administrator 2202 asks that question in the most straight-forward way, e.g., "You said you're taking medication for your insomnia. Which drug are you taking?" This has the advantage of being open-ended and eliciting more speech than would a simple yes/no question.

Figure 3:
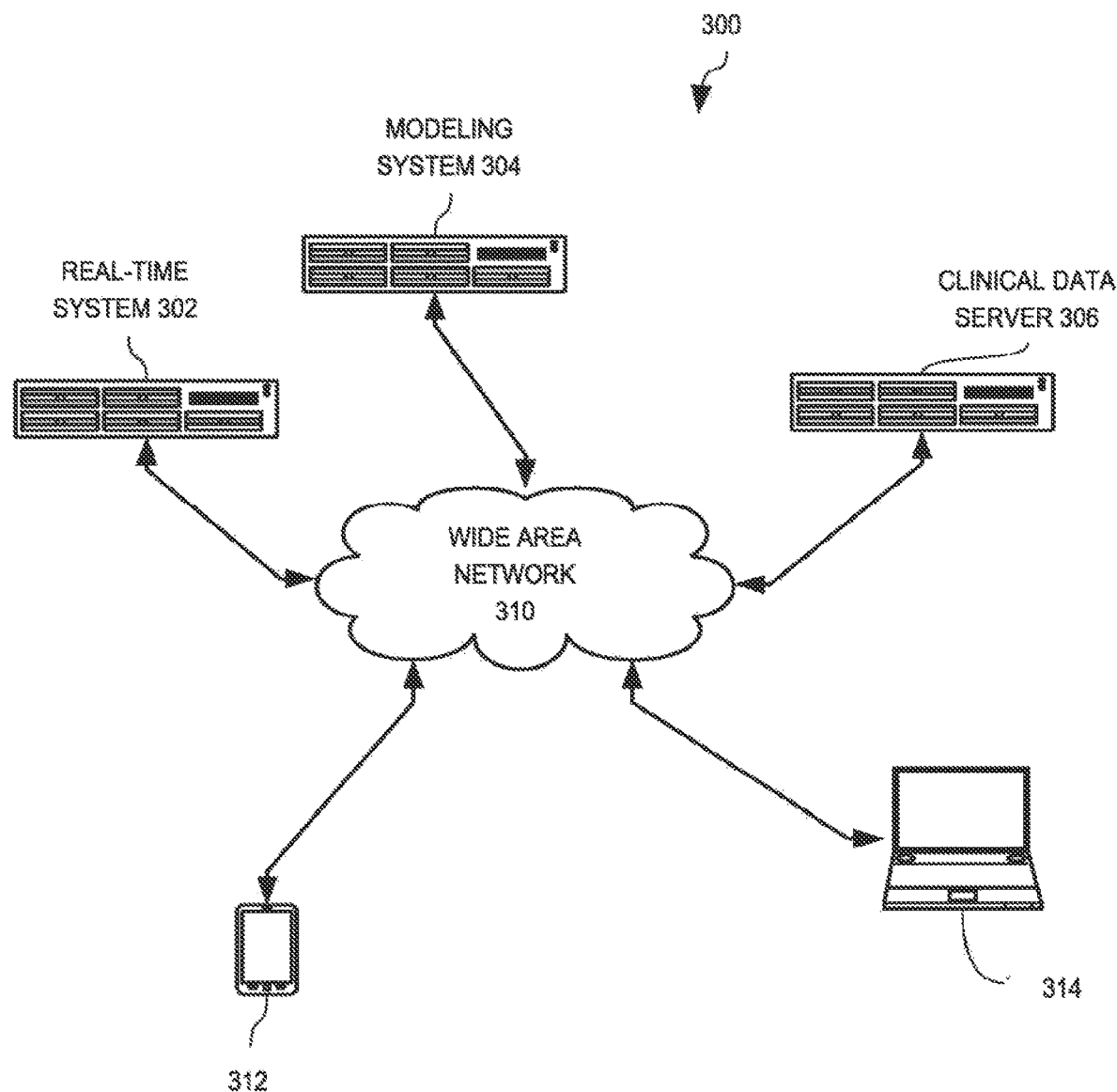
FIG. 3 shows a patient assessment system in which a real-time computer system, a modeling computer system, and a clinical and demographic data server computer system that cooperate to assess a state of a patient and report the assessed state to a clinician using a clinician device through a wide area network in accordance with the present disclosure.

In other embodiments, assessment test administrator 2202 accesses clinical data related to the patient to help identify the particular drug used by the patient. The clinical data may be received from modeling system 302 (FIG. 22), using clinical data 2220, or from clinical data server 306 (FIG. 3). Accordingly, assessment test administrator 2202 may ask a more directed question using the assumed drug's most common name and generic name. For example, if the patient's data indicates that the patient has been prescribed Zolpidem (the generic name of the drug sold under the brand name, Ambien), question 1720 (FIG. 17) may be, "You said you're taking medication for insomnia. Is that Ambien or Zolpidem?" This highly directed question risks eliciting no more than a simple yes/no response (e.g., response 1722). However, this question also shows a knowledge of, and interest in, the patient—further garnering goodwill and increasing the likelihood of honest responses by the patient and a willingness to continue the assessment test longer.

In this illustrative embodiment, assessment test administrator 2202 determines whether to ask a highly directed question rather than a more open-ended question based on whether requisite clinical data for the patient is available and to what degree additional speech is needed to achieve an adequate degree of accuracy in assessing the state of the patient.

The illustrative example of conversation 1700 continues with assessment test administrator 2202 recording the substance of response 1722 in step 1724.

Assessment test administrator 2202 in this illustrative embodiment determines the responsiveness to the patient also in the manner assessment test administrator 2202 determines whether the patient has completed her response to the most recently asked question, e.g., in determining when an answer received in step 1408 is complete and selection of the next question in step 1414 may begin.

To further develop good will in the patient, assessment test administrator 2202 avoids interrupting the patient as much as possible. It helpful to consider response 1704: "Okay . . . . I've been having trouble sleeping lately. I have meds for that. They seem to help." The ellipsis after "Okay." indicates a pause in replying by the patient. To this end, assessment test administrator 2202 waits long enough to permit the patient to pause briefly without interruption but not so long as to cause the patient to believe that assessment test administrator 2202 has become unresponsive, e.g., due to a failure of assessment test administrator 2202 or the communications links therewith. Moreover, pauses in speech are used in assessment as described more completely below and assessment test administrator 2202 should avoid interfering with the patient's speech fluency.

In this illustrative embodiment, assessment test administrator 2202 uses two pause durations, a short one and a long one. After a pause for the short duration, assessment test administrator 2202 indicates that assessment test administrator 2202 continues to listen by playing a very brief sound that acknowledges an understanding and a continuation of listening, e.g., "uh-huh" or "mmm-hmmm". After playing the message, assessment test administrator 2202 waits during any continued pause for the long duration. If the pause continues that long, assessment test administrator 2202 determines that the patient has completed her response.

The particular respective lengths of the short and long durations may be determined empirically. In addition, the optimum lengths may vary from patient to patient. Accordingly, assessment test administrator 2202 continues to adjust these durations for the patient whenever interacting with the patient. Assessment test administrator 2202 recognizes durations that are too short when observing cross-talk, i.e., when speed is being received from the patient while assessment test administrator 2202 concurrently plays any sound. Assessment test administrator 2202 recognizes durations that are too long when (i) the patient explicitly indicates so (e.g., saying "Hello?" or "Are you still there?") and/or (ii) the patient's response indicates increased frustration or agitation relative to the patient's speech earlier in the same conversation.

The conversation is terminated politely by assessment test administrator 2202 when the assessment test is complete. The assessment test is complete when (i) the initial questions in the conversation queue and all of their descendant questions have been answered by the patient or (ii) the measure of confidence in the score resulting from assessment determined in step 1412 is at least a predetermined threshold. It should be noted that confidence in the assessment is not symmetrical. The assessment test seeks depression, or other behavioral health conditions, in the patient. If it's found quickly, it's found. However, its absence is not assured by failing to find it immediately. Thus, assessment test administrator 2202 finds confidence in early detection but not in early failure to detect.

Thus, real-time system 302 (FIG. 22) assesses the current mental state of the patient using an interactive spoken conversation with the patient through patient device 312. Assessment test administrator 2202 sends data representing the resulting assessment of the patient to the patient's doctor or other clinician by sending the data to clinician device 314. In addition, assessment test administrator 2202 records the resulting assessment in clinical data 2220.

While assessment test administrator 2202 is described as conducting an interactive spoken conversation with the patient to assess the mental state of the patient, in other embodiments, assessment test administrator 2202 passively listens to the patient speaking with the clinician and assesses the patient's speech in the manner described herein. The clinician may be a mental health professional, a general practitioner or a specialist such as a dentist, cardiac surgeon, or an ophthalmologist. In one embodiment, assessment test administrator 2202 passively listens to the conversation between the patient and clinician through patient device 312 upon determining that the patient is in conversation with the clinician, e.g., by a "START" control on the clinician's iPad. Upon determining that the conversation between the patient and clinician is completed, e.g., by a "STOP" control on the clinician's iPad, assessment test administrator 2202 ceases passively listening and assessing speech in the manner described above. In addition, since patient device 312 is listening passively and not prompting the patient, assessment test administrator 2202 makes no attempt to optimize the audiovisual signal received through patient device 312 and makes no assumption that faces in any received video signal are that of the patient.

In some embodiments, at the start of the conversation between the patient and the clinician, the clinician asks the patient to initiate listening by assessment test administrator 2202 and the patient does so by issuing a command through patient device 312 that directs assessment test administrator 2202 to begin listening. Similarly, at end of the conversation, the clinician asks the patient to terminate listening by assessment test administrator 2202 and the patient does so by issuing a command through patient device 312 that directs assessment test administrator 2202 to cease listening.

In alternative embodiments, assessment test administrator 2202 listens to the conversation between the patient and the clinician through clinician device 314. The clinician may manually start and stop listening by assessment test administrator 2202 through clinician device 314 using conventional user-interface techniques.

During the conversation passively heard by assessment test administrator 2202, assessment test administrator 2202 assesses the patient's speech and not the clinician's speech. Assessment test administrator 2202 may distinguish the voices in any of a number of ways, e.g., by a "MUTE" control on the clinician's iPad. In embodiments in which assessment test administrator 2202 listens through patient device 312, assessment test administrator 2202 uses acoustic models (e.g., acoustic models 2218) to distinguish the two voices. Assistant test administrator 2202 identifies the louder voice as that of the patient, assuming patient device 312 is closer to the patient than to the clinician. This may also be the case in embodiments in which clinician device 312 is set up to hear the patient more loudly. For example, clinician device 314 may be configured to listen through a highly directional microphone that the clinician directs toward the patient such that any captured audio signal represents the patient's voice much more loudly than other, ambient sounds such as the clinician's voice. Assessment test administrator 2202 may further distinguish the patient's voice from the clinician's voice using language models 2214, particularly, semantic pattern models such as semantic pattern modules 4004, to identify which of the two distinguished voices more frequently asks questions. Assessment test administrator 2202 may further distinguish the patient's voice from the clinician's voice using acoustic models 2016, which may identify and segment out the clinician's voice from an acoustic analysis of the clinician's voice performed prior to the clinical encounter.

Throughout the conversation between the patient and the clinician, assessment test administrator 2202 assesses the mental state of the patient from the patient's speech in the manner described herein and finalizes the assessment upon detecting the conclusion of the conversation.

Runtime model server logic 704, shown in greater detail in FIG. 18, processes audiovisual signals representing the patient's responses in the interactive screening or monitoring conversation and, while the conversation is ongoing, estimates the current health of the patient from the audiovisual signals.

Automatic speech recognition (ASR) logic 1804 is logic that processes speech represented in the audiovisual data from I/O logic 604 (FIG. 6) to identify words spoken in the audiovisual signal. The results of ASR logic 1804 (FIG. 18) are sent to runtime models 1802.

Runtime models 1802 also receive the audiovisual signals directly from I/O logic 604. In a manner described more completely below, runtime models 1802 combine language, acoustic, and visual models to produce results 1820 from the received audiovisual signal. In turn, interactive screening or monitoring server logic 702 uses results 1820 in real time as described above to estimate the current state of the patient and to accordingly make the spoken conversation responsive to the patient as described above.

In addition to identifying words in the audiovisual signal, ASR logic 1804 also identifies where in the audiovisual signal each word appears and a degree of confidence in the accuracy of each identified word in this illustrative embodiment. ASR logic 1804 may also identify non-verbal content of the audiovisual signals, such as laughter and fillers for example, along with location and confidence information. ASR logic 1804 makes such information available to runtime models 1802.

Runtime models 1802 include descriptive model and analytics 1812, natural language processing (NLP) model 1806, acoustic model 1808, and visual model 1810.

NLP model 1806 includes a number of text-based machine learning models to (i) predict depression, anxiety, and perhaps other health states directly from the words spoken by the patient and (ii) model factors that correlate with such health states. Examples of machine learning that models health states directly include sentiment analysis, semantic analysis, language modeling, word/document embeddings and clustering, topic modeling, discourse analysis, syntactic analysis, and dialogue analysis. Models do not need to be constrained to one type of information. A model may contain information for example from both sentiment and topic based features. NLP information includes the score output of specific modules for example the score from a sentiment detector trained for sentiment rather than for mental health state. NLP information includes that obtained via transfer learning based systems.

NLP model 1806 stores text metadata and modeling dynamics and shares that data with acoustic model 1808, visual model 1810, and descriptive model and analytics 1812. Text data may be received directly from ASR logic 1804 as described above or may be received as text data from NLP model 1806. Text metadata may include, for example, data identifying, for each word or phrase, parts of speech (syntactic analysis), sentiment analysis, semantic analysis, topic analysis, etc. Modeling dynamics includes data representing components of constituent models of NLP model 1806. Such components include machine learning features of NLP model 1806 and other components such as long short-term memory (LSTM) units, gated recurrent units (GRUs), hidden Markov model (HMM), and sequence-to-sequence (seq2seq) translation information. NLP metadata allows acoustic model 1808, visual model 1810, and descriptive model and analytics 1812 to correlate syntactic, sentimental, semantic, and topic information to corresponding portions of the audiovisual signal. Accordingly, acoustic model 1808, visual model 1810, and descriptive model and analytics 1812 may more accurately model the audiovisual signal.

Runtime models 1802 include acoustic model 1808, which analyzes the audio portion of the audiovisual signal to find patterns associated with various health states, e.g., depression. Associations between acoustic patterns in speech and health are in some cases applicable to different languages without retraining. They may also be retrained on data from that language. A of the particular language spoken. Accordingly, acoustic model 1808 analyzes the audiovisual signal in a language-agnostic fashion. In this illustrative embodiment, acoustic model 1808 uses machine learning approaches such as convolutional neural networks (CNN), long short-term memory (LSTM) units, hidden Markov models (HMM), etc. for learning high-level representations and for modeling the temporal dynamics of the audiovisual signals.

Acoustic model 1808 stores data representing attributes of the audiovisual signal and machine learning features of acoustic model 1808 as acoustic model metadata and shares that data with NLP model 1806, visual model 1810, and descriptive model and analytics 1812. The acoustic model metadata may include, for example, data representing a spectrogram of the audiovisual signal of the patient's response. In addition, the acoustic model metadata may include both basic features and high-level feature representations of machine learning features. More basic features may include Mel-frequency cepstral coefficients (MFCCs), and various log filter banks, for example, of acoustic model 1808. High-level feature representations may include, for example, convolutional neural networks (CNNs), autoencoders, variational autoencoders, deep neural networks, and support vector machines of acoustic model 1808. The acoustic model metadata allows NLP model 1806 to, for example, use acoustic analysis of the audiovisual signal to improve sentiment analysis of words and phrases. The acoustic model metadata allows visual model 1810 and descriptive model and analytics 1812 to, for example, use acoustic analysis of the audiovisual signal to more accurately model the audiovisual signal.

Runtime model server logic 504 (FIG. 18) includes visual model 1810, which infers various health states of the patient from face, gaze and pose behaviors. Visual model 1810 may include facial cue modeling, eye/gaze modeling, pose tracking and modeling, etc. These are merely examples.

Visual model 1810 stores data representing attributes of the audiovisual signal and machine learning features of visual model 1810 as visual model metadata and shares that data with NLP model 1806, acoustic model 1808, and descriptive model and analytics 1812. For example, the visual model metadata may include data representing face locations, pose tracking information, and gaze tracking information of the audiovisual signal of the patient's response. In addition, the visual model metadata may include both basic features and high-level feature representations of machine learning features. More basic features may include image processing features of visual model 1810. High-level feature representations may include, for example, CNNs, autoencoders, variational autoencoders, deep neural networks, and support vector machines of visual model 1810. The visual model metadata allows descriptive model and analytics 1812 to, for example, use video analysis of the audiovisual signal to improve sentiment analysis of words and phrases. Descriptive model and analytics 1812 may even use the visual model metadata in combination with the acoustic model metadata to estimate the veracity of the patient in speaking words and phrases for more accurate sentiment analysis. The visual model metadata allows acoustic model 1808 to, for example, use video analysis of the audiovisual signal to better interpret acoustic signals associated with various gazes, poses, and gestures represented in the video portion of the audiovisual signal.

Descriptive features or descriptive analytics are interpretable descriptions that may be computed based on features in the speech, language, video, and metadata that convey information about a speaker's speech patterns in a way in which a stakeholder may understand. For example, descriptive features may include a speaker sounding nervous or anxious, having a shrill or deep voice, or speaking quickly or slowly. Humans can interpret "features" of voices, such as pitch, rate of speaking, and semantics, in order to mentally determine emotions. A descriptive analytics module, by applying interpretable labels to speech utterances, based on their features, differs from a machine learning module. Machine learning models also make predictions by analyzing features, but the methods by which machine learning algorithms process the features, and determine representations of those features, differs from how humans interpret them. Thus, labels that machine learning algorithms may "apply" to data, in the context of analyzing features, may not be labels that humans may be able to interpret.

Descriptive model and analytics 1812 (FIG. 18) may generate analytics and labels for numerous health states, not just depression. Examples of such labels include emotion, anxiety, how engaged the patient is, patient energy, sentiment, speech rate, and dialogue topics. In addition, descriptive model and analytics 1812 applies these labels to each word of the patient's response and determines how significant each word is in the patient's response. While the significance of any given word in a spoken response may be inferred from the part of speech, e.g., articles and filler words as relatively insignificant, descriptive model and analytics 1812 infers a word's significance from additional qualities of the word, such as emotion in the manner in which the word is spoken as indicated by acoustic model 1808.

Descriptive model and analytics 1812 also analyzes trends over time and uses such trends, at least in part, to normalize analysis of the patient's responses. For example, a given patient might typically speak with less energy than others. Normalizing analysis for this patient might set a lower level of energy as "normal" than would be used for the general population. In addition, a given patient may use certain words more frequently than the general population and use of such words by this patient might not be as notable as such use would be by a different patient. Descriptive model and analytics 1812 may analyze trends in real-time, i.e., while a screening or monitoring conversation is ongoing, and in non-real-time contexts.

Descriptive model and analytics 1812 stores data representing the speech analysis and trend analysis described above, as well as metadata of constituent models of descriptive model and analytics 1812, as descriptive model metadata and shares that data with NLP model 1806, acoustic model 1808, and visual model 1810. The descriptive model metadata allows NLP model 1806, acoustic model 1808, and visual model 1810 to more accurately model the audiovisual signal.

Through runtime models 1802, runtime model server logic 504 estimates a health state of a patient using what the patient says, how the patient says it, and contemporaneous facial expressions, eye expressions, and poses in combination and stores resulting data representing such estimation as results 1820. Such provides a particularly accurate and effective tool for estimating the patient's health state.

Runtime model server logic 504 sends results 1820 to I/O logic 604 (FIG. 6) to enable interactive screening or monitoring server logic 502 to respond to the patient's responses, thereby making the screening or monitoring dialogue interactive in the manner described above. Runtime model server logic 504 (FIG. 18) also sends results 1820 to screening or monitoring system data store 410 to be included in the history of the subject.

Model training logic 506, shown in greater detail in FIG. 19, trains the models used by runtime model server logic 504 (FIG. 18).

Model training logic 506 (FIG. 19) includes runtime models 1802 and ASR logic 1804 and trains runtime models 1802. Model training logic 506 sends the trained models to model repository 416 to make runtime models 1802, as trained, available to runtime model server logic 504.

Figure 20A:
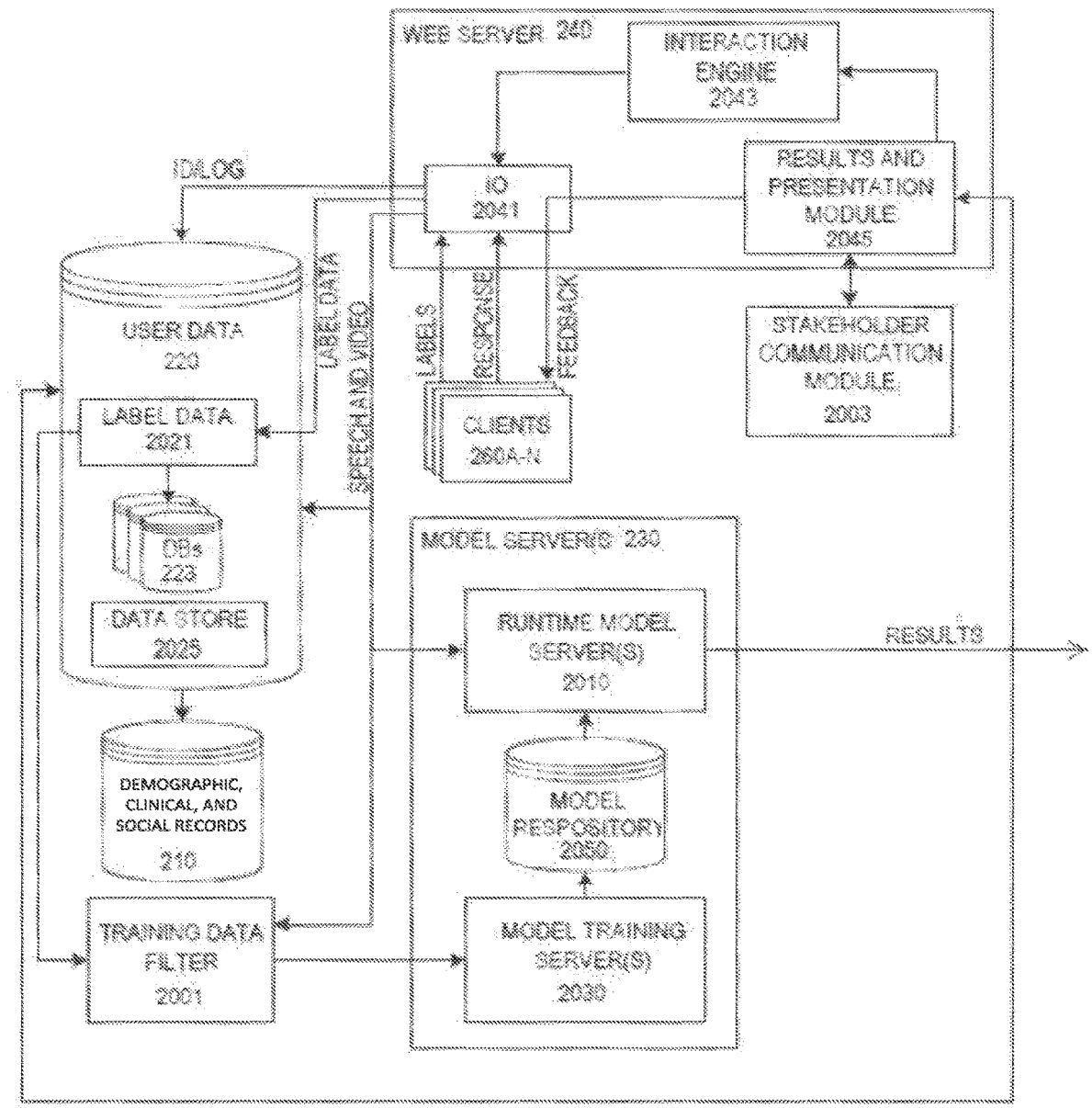
FIG. 20A shows a greater detailed block diagram of the patient screening or monitoring system, in accordance with some embodiments.

FIG. 20A provides a more detailed example illustration of the backend screening or monitoring system of the embodiment of FIG. 2. In this example block diagram, the web server 240 is expanded to illustrate that it includes a collection of functional modules. The primary component of the web server 240 includes an input/output (IO) module 2041 for accessing the system via the network infrastructure 250. This IO 2041 enables the collection of response data (in the form of at least speech and video data) and labels from the clients 260*a-n*, and the presentation of prompting information (such as a question or topic), and feedback to the clients 260*a-n*. The prompting materials is driven by the interaction engine 2043, which is responsive to the needs of the system, user commands and preferences to fashion an interaction that maintains the clients' 260*a-n* engagement and generates meaningful response data. The interaction engine will be discussed in greater detail below.

Truthfulness of the patient in answering questions (or other forms of interaction) posed by the screening or monitoring test is critical in assessing the patient's mental state, as is having a system that is approachable and that will be sought out and used by a prospective patient. The health screening or monitoring system 200 encourages honesty of the patient in a number of ways. First, a spoken conversation provides the patient with less time to compose a response to a question, or discuss a topic, than a written response may take. This truncated time generally results in a more honest and "raw" answer. Second, the conversation feels, to the patient, more spontaneous and personal and is less annoying than an obviously generic questionnaire, especially when user preferences are factored into the interaction, as will be discussed below. Accordingly, the spoken interaction does not induce or exacerbate resentment in the patient for having to answer a questionnaire before seeing a doctor or other clinician. Third, the spoken interaction is adapted in progress to be responsive to the patient, reducing the patient's annoyance with the screening or monitoring test and, in some situations, shortening the screening or monitoring test. Fourth, the screening or monitoring test as administered by health screening or monitoring system 200 relies on more than mere verbal components of the interaction. Non-verbal aspects of the interaction are leveraged synergistically with the verbal content to assess depression in the patient. In effect, 'what is said' is not nearly as reliably accurate in assessing depression as is 'how it's said'.

The final component of the web server 240 is a results and presentation module 2045 which collates the results from the model server(s) 230 and provides then to the clients 260*a-n* via the IO 2041, as well as providing feedback information to the interaction engine 2043 for dynamically adapting the course of the interaction to achieve the system's goals. Additionally, the results and presentation module 2045 additionally supplies filtered results to stakeholders 270*a-n* via a stakeholder communication module 2003. The communication module 2003 encompasses a process engine, routing engine and rules engine. The rules engine embodies conditional logic that determines what, when and who to send communications to, the process engine embodies clinical and operational protocol logic to pass messages through a communications chain that may be based on serial completion of tasks and the routing engine gives the ability to send any messages to the user's platform of choice (e.g., cellphone, computer, landline, tablet, etc.).

The filtering and/or alteration of the results by the results and presentation module 2045 is performed when necessary to maintain HIPAA (Health Insurance Portability and Accountability Act of 1996) and other privacy and security regulations and policies such as GDPR and SOC 2 compliance as needed and to present the relevant stakeholder 270*a-n* with information of the greatest use. For example, a clinician may desire to receive not only the screening or monitoring classification (e.g., depressed or neurotypical) but additional descriptive features, such as suicidal thoughts, anxiety around another topic, etc. In contrast, an insurance provider may not need or desire many of these additional features, and may only be concerned with a diagnosis/screening or monitoring result. Likewise, a researcher may be provided only aggregated data that is not personally identifiable, in order to avoid transgression of privacy laws and regulations.

The IO 2041, in addition to connecting to the clients 260*a-n*, provides connectivity to the user data 220 and the model server(s) 230. The collected speech and video data (raw audio and video files in some embodiments) are provided by the IO 2041 to the user data 220, runtime model server(s) 2010 and a training data filter 2001. Label data from the clients 260a-n is provided to a label data set 2021 in the user data 220. This may be stored in various databases 2023. Label data includes not only verified diagnosed patients, but inferred labels collected from particular user attributes or human annotation. Client ID information and logs may likewise be supplied from the IO 2041 to the user data 220. The user data 220 may be further enriched with clinical and social records 210 sourced from any number of third party feeds. This may include social media information obtained from web crawlers, EHR databases from healthcare providers, public health data sources, and the like.

The training data filter 2001 may consume speech and video data and append label data 2021 to it to generate a training dataset. This training dataset is provided to model training server(s) 2030 for the generation of a set of machine learned models. The models are stored in a model repository 2050 and are utilized by the runtime model server(s) 2010 to make a determination of the screening or monitoring results, in addition to generating other descriptors for the clients 260a-n. The model repository 2050 together with the model training server(s) 2030 and runtime model server(s) 2010 make up the model server(s) 250. The runtime model server(s) 2010 and model training server(s) 2030 are described in greater detail below in relation to FIGS. 20B and 21, respectively.

Figure 20B:
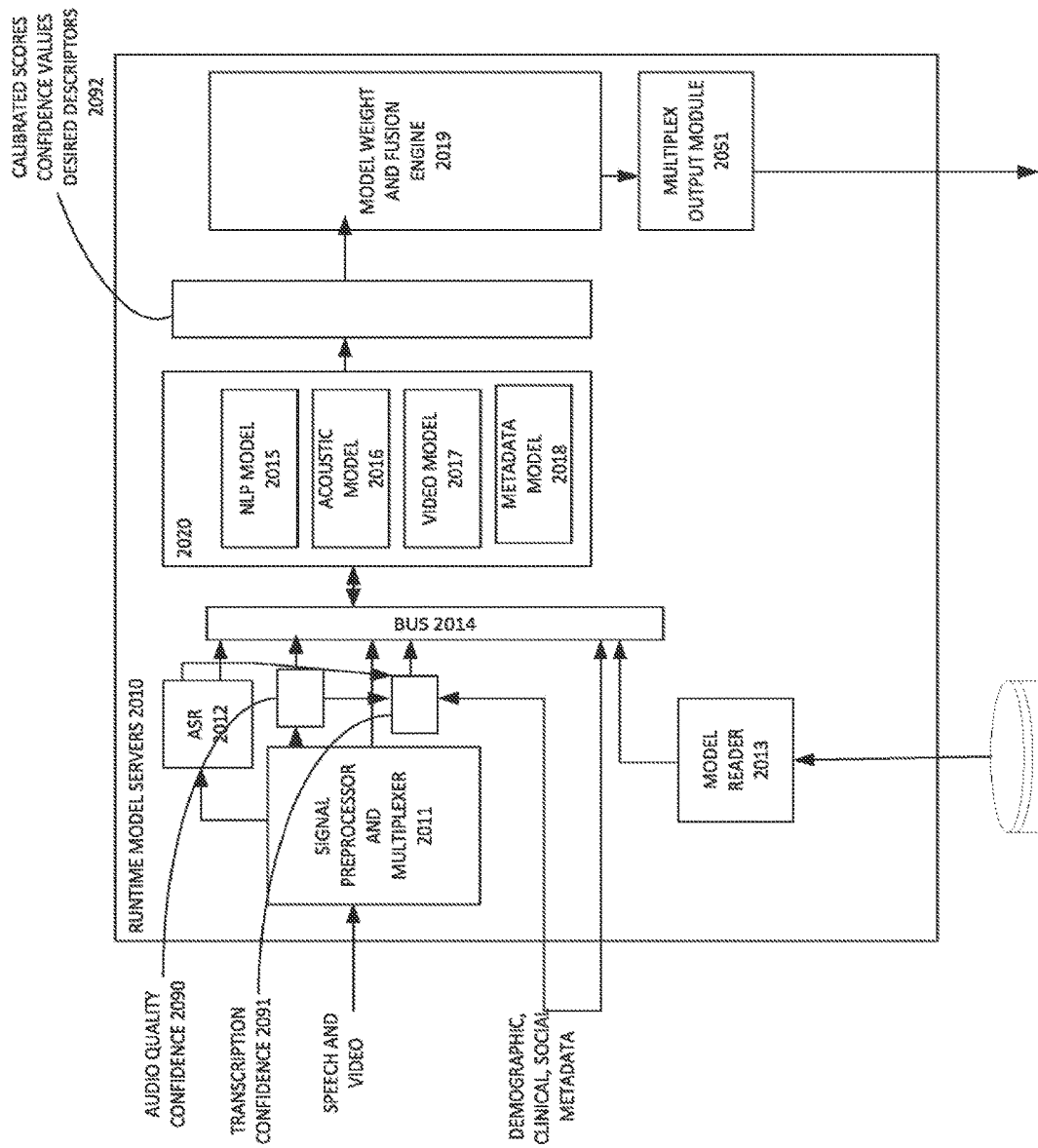
FIG. 20B provides a block diagram of the runtime model server(s), in accordance with some embodiments.

In FIG. 20B the runtime model server(s) 2010 is provided in greater detail. The server received speech and video inputs that originated from the clients 260a-n. A signal preprocessor and multiplexer 2011 performs conditioning on the inputted data, such as removal of noise or other artifacts in the signal that may cause modeling errors. These signal processing and data preparation tasks include diarization, segmentation and noise reduction for both the speech and video signals. Additionally, metadata may be layered into the speech and video data. This data may be supplied in this preprocessed form to a bus 2014 for modelers 2020 consumption and may also be subjected to any number of third parties, off the shelf Automatic Speech Recognition (ASR) systems 2012. The ASR 2012 output includes a machine readable transcription of the speech portion of the audio data. This ASR 2012 output is likewise supplied to the bus 2014 for consumption by later components. The signal preprocessor and multiplexer 2011 may be provided with confidence values, such as audio quality (signal quality, length of sample) and transcription confidence (how accurate the transcription is) values 2090 and 2091.

FIG. 20B also includes a metadata model 2018. The metadata model may analyze patient data, such as demographic data, medical history data, and patient-provided data.

Additionally, clinical data, demographic data, and social data may be presented to the bus 2014 for subsequent usage by the modelers 202. Lastly, a model reader 2013 may access protected models from a model repository 2050 which are likewise provided to the bus 2014. The modelers 2020 consume the models, preprocessed audio and visual data, and ASR 2012 output to analyze the clients' 260a-n responses for the health state in question. Unlike prior systems for modeling a health condition, the present system includes a natural language processing (NLP) model 2015, acoustic model 2016, and video model 2017 that all operate in concert to generate classifications for the clients' 260a-n health state. These modelers not only operate in tandem, but consume outputs from one another to refine the model outputs. Each of the modelers and the manner in which they coordinate to enhance their classification accuracy will be explored in greater detail in conjunction with subsequent figures.

The output for each of these modelers 2020 is provided, individually, to a calibration, confidence, and desired descriptors module 2092. This module calibrates the outputs in order to produce scaled scores, as well as provides confidence measures for the scores. The desired descriptors module may assign human-readable labels to scores. The output of desired description module 2092 is provided to model weight and fusion engine 2019. This model weight and fusion engine 2019 combines the model outputs into a single consolidated classification for the health state of each client 260a-n. Model weighting may be done using static weights, such as weighting the output of the NLP model 2015 more than either the acoustic model 2016 or video model 2017 outputs. However, more robust and dynamic weighting methodologies may likewise be applied. For example, weights for a given model output may, in some embodiments, be modified based upon the confidence level of the classification by the model. For example, if the NLP model 2015 classifies an individual as being not depressed, with a confidence of 0.56 (out of 0.00-1.00), but the acoustic model 2016 renders a depressed classification with a confidence of 0.97, in some cases the weight of a the models' outputs may be weighted such that the acoustic model 2016 is provided a greater weight. In some embodiments, the weight of a given model may be linearly scaled by the confidence level, multiplied by a base weight for the model. In yet other embodiments, model output weights are temporally based. For example, generally the NLP model 2015 may be afforded a greater weight than other models, however, when the user isn't speaking, the video model 2017 may be afforded a greater weight for that time domain. Likewise, if the video model 2017 and acoustic model 2016 are independently suggesting the person is being nervous and untruthful (frequent gaze shifting, perspiration increased, pitch modulation upward, increased speech rate, etc.) then the weight of the NLP model 2015 may be minimized, since it is likely the individual is not answering the question truthfully.

After model output fusion and weighting the resulting classification may be combined with features and other user information in a multiplex output module 2051 in order to generate the final results. As discussed before, these results are provided back to the user data 220 for storage and potentially as future training materials, and also to the results and presentation module 2045 of the webserver 240 for display, at least in part, to the clients 260a-n and the stakeholders 270a-n. These results are likewise used by the interaction engine 2043 to adapt the interaction with the client 260a-n moving forward.

Figure 21:
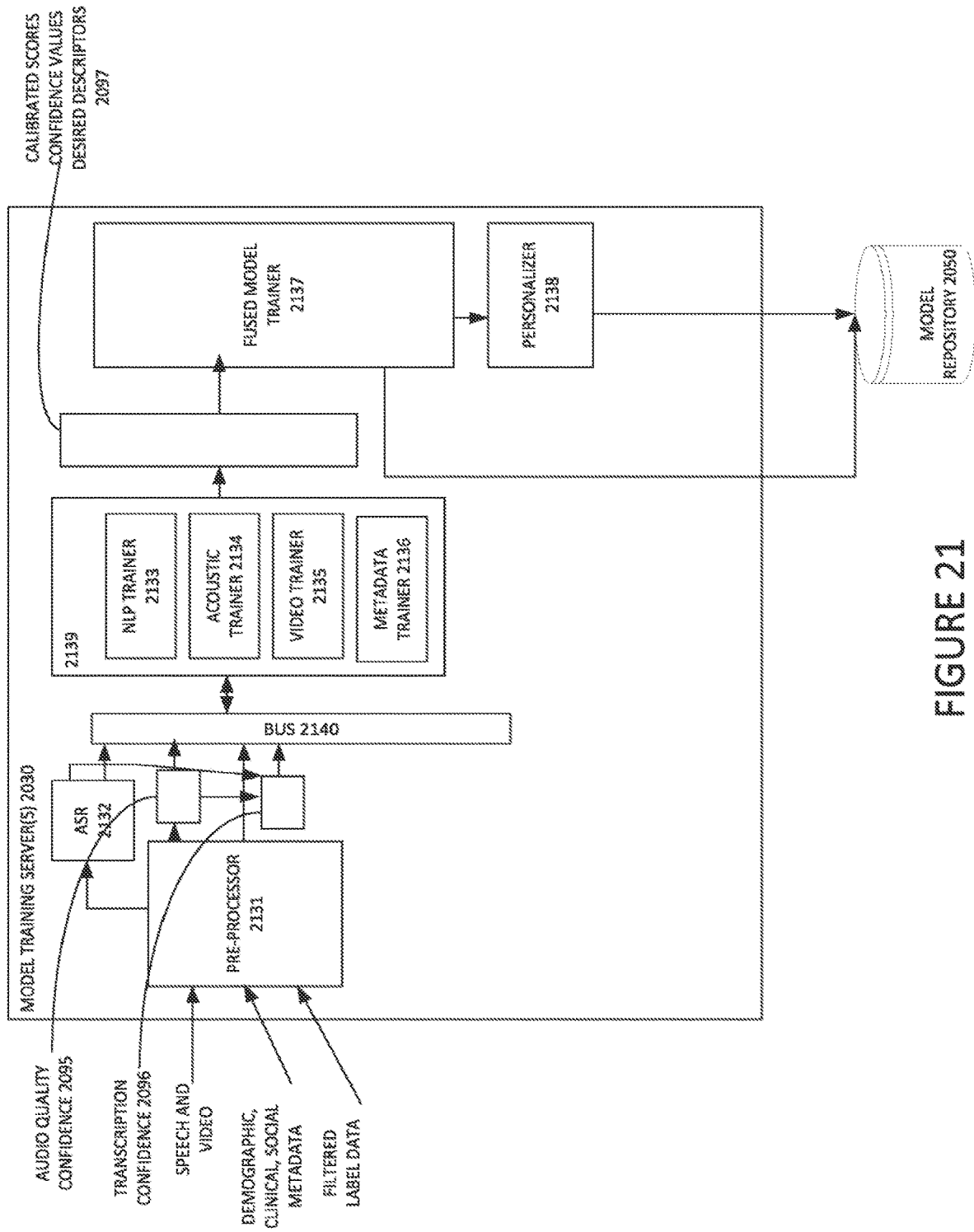
FIG. 21 provides a block diagram of the model training server(s), in accordance with some embodiments.

Turning now to FIG. 21, the model training server(s) 2030 is provided in greater detail. Like the runtime model server(s) 2010, the model training server(s) 2030 consume a collection of data sources. However, these data sources have been filtered by the training data filter 2001 to provide only data for which label information is known or imputable. The model training server additionally takes as inputs audio quality confidence values 2095 (which may include bit rate, noise, and length of the audio signal) and transcription confidence values 2096. These confidence values may include the same types of data as those of FIG. 20B. The filtered social, demographic, and clinical data, speech and video data, and label data are all provided to a preprocessor 2031 for cleaning and normalization of the filtered data sources. The processed data is then provided to a bus 2040 for consumption by various trainers 2039, and also to one or more third party ASR systems 2032 for the generation of ASR outputs, which are likewise supplied to the bus 2040. The signal preprocessor and multiplexer 2011 may be provided with confidence values, such as audio quality (signal quality, length of sample) and transcription confidence (how accurate the transcription is) values 2095 and 2096.

The model trainers 2039 consume the processed audio, visual, metadata, and ASR output data in a NLP trainer 2033, an acoustic trainer 2034, a video trainer 2035, and a metadata trainer 2036. The trained models are provided, individually, to a calibration, confidence, and desired descriptors module 2097. This module calibrates the outputs in order to produce scaled scores, as well as provides confidence measures for the scores. The desired descriptors module may assign human-readable labels to scores. The trained and calibrated models are provided to a fused model trainer 2037 for combining the trained models into a trained combinational model. Each individual model and the combined model may be stored in the model repository 2050. Additionally and optionally, the trained models may be provided to a personalizer 2038, which leverages metadata (such as demographic information and data collated from social media streams) to tailor the models specifically for a given client 260a-n.

For example, a particular model xo may be generated for classifying acoustic signals as either representing someone who is depressed, or not. The tenor, pitch and cadence of an audio input may vary significantly between a younger individual versus and elderly individual. As such, specific models are developed based upon if the patient being screened is younger or elderly (models xy and xe respectively). Likewise, women generally have variances in their acoustic signals as compared to men, suggesting that yet another set of acoustic models are needed (models xf and xm respectively). It is also apparent that combinational models are desired for a young woman versus an elderly woman, and a young man versus an elderly man (models xyf, xef, xym and xem respectively). Clearly, as further personalization groupings are generated the possible number of applicable models will increase exponentially.

In some embodiments, if the metadata for an individual provides insight into that person's age, gender, ethnicity, educational background, accent/region they grew up in, etc. this information may be utilized to select the most appropriate model to use in future interactions with this given patient, and may be likewise used to train models that apply to individuals that share similar attributes.

In addition to personalizing models based upon population segments and attributes, the personalizer 2038 may personalize a model, or set of models, for a particular individual based upon their past history and label data known for the individual. This activity is more computationally expensive than relying upon population wide, or segment wide, modeling, but produces more accurate and granular results. All personalized models are provided from the personalizer 2038 to the model repository 2050 for retention until needed for patient assessment.

During analysis then, a client 260a-n is initially identified, and when able, a personalized model may be employed for their screening or monitoring. If not available, but metadata is known for the individual, the most specific model for the most specific segment is employed in their screening or monitoring. If no metadata is available, then the model selected is the generic, population-wide model. Utilizing such a tiered modeling structure, the more information that is known regarding the client 260a-n allows for more specific and accurate models to be employed. Thus, for each client 260a-n, the 'best' model is leveraged given the data available for them.

The general overall flow of information is shown in (FIG. 22). Assessment test administrator 2202 of real-time system 302 conducts an interactive conversation with the patient through patient device 312. The responsive audiovisual signal of the patient is received by real-time system 302 from patient device 312. The exchange of information between real-time system 302 and patient device 312 may be through a purpose-built app executing in patient device 112 or through a conventional video call between patient device 312 and video call logic of assessment test administrator 2202. While this illustrative embodiment uses an audiovisual signal to assess the state of the patient, it should be appreciated that, in alternative embodiments, an audio-only signal may be used with good results. In such alternative embodiments, an ordinary, audio-only telephone conversation may serve as the vehicle for assessment by assessment test administrator 2202.

In a manner described more completely below, assessment test administrator 2202 uses composite model 2204 to assess the state of the patient in real-time, i.e., as the spoken conversation transpires. Such intermediate assessment is used, in a manner described more completely below, to control the conversation, making the conversation more responsive, and therefore more engaging, to the patient and to help make the conversation as brief as possible while maintaining the accuracy of the final assessment.

Modeling system 304 receives collected patient data 2206 that includes the audiovisual signal of the patient during the assessment test. In embodiments in which the assessment test involves patient device 312 a purpose-built app executing in patient device 312, modeling system 104 may receive collected patient data 2206 from patient device 312. Alternatively, and in embodiments in which the assessment test involves a video or voice call with patient device 312, modeling system 304 receives collected patient data 2206 from real-time system 302.

Modeling system 304 retrieves clinical data 2220 from clinical data server 306. Clinical data 2220 includes generally any available clinical data related to the patient, other patients assessed by assessment test administrator 2202, and the general public that may be helpful in training any of the various models described herein.

Preprocessing 2208 conditions any audiovisual data for optimum analysis. Having a high-quality signal to start is very helpful in providing accurate analysis. Preprocessing 2208 is shown within modeling system 304. In alternative embodiments, preprocessing is included in real-time system 302 to improve accuracy in application of composite model 204.

Speech recognition 2210 processes speech represented in the audiovisual data after preprocessing 2208, including automatic speech recognition (ASR). ASR may be conventional. Language model training 2212 uses the results of speech recognition 2210 to train language models 214.

Acoustic model training 2216 uses the audiovisual data after preprocessing 2208 to train acoustic models 2218. Visual model training 2224 uses the audiovisual data after preprocessing 2208 to train visual models 2226. To the extent sufficient data (both collected patient data 2206 and clinical data 2222) is available for the subject patient, language model training 2212, acoustic model training 2216, and visual model training 2224 train language models 2214, acoustic models 2218, and visual models 2226, respectively, specifically for the subject patient. Training may also use clinical data 2222 for patients that share one or more phenotypes with the subject patient.

In a manner described more completely below, composite model builder 2222 uses language models 2214, acoustic models 2218, and visual models 2226, in combination with clinical data 2220, to combine language, acoustic, and visual models into composite model 2204. In turn, assessment test administrator 2202 uses composite model 2204 in real time to assess the current state of the subject patient and to accordingly make the spoken conversation responsive to the subject patient as described more completely below.

As mentioned above, assessment test administrator 2202 administers a depression assessment test to the subject patient by conducting an interactive spoken conversation with the subject patient through patient device 312.

Attention will now be focused upon the specific models used by the runtime model server(s) 2010. Moving on to FIG. 23A, a general block diagram for one example substantiation of the acoustic model 2016 is provided. The speech and video data is provided to a high level feature representor 2320 that operates in concert with a temporal dynamics modeler 2330. Influencing the operation of these components is a model conditioner 2340 that consumed features from the descriptive features 2018, results generated from the speech and video models 2015 and 2017, respectively, and clinical and social data.

Returning to the acoustic model 2016, the high level feature representor 2320 and temporal dynamics modeler 2330 also receive raw and higher level feature extractor 2310 outputs, that identify features within the incoming acoustic signals, and feeds them to the models. The high level feature representor 2320 and temporal dynamics modeler 2330 generate the acoustic model results, which may be fused into a final result that classifies the health state of the individual, and may also be consumed by the other models for conditioning purposes.

The high level feature representor 2320 includes leveraging existing models for frequency, pitch, amplitude and other acoustic features that provide valuable insights into feature classification. A number of off-the-shelf "black box" algorithms accept acoustic signal inputs and provide a classification of an emotional state with an accompanying degree of accuracy. For example, emotions such as sadness, happiness, anger and surprise are already able to be identified in acoustic samples using existing solutions. Additional emotions such as envy, nervousness, excited-ness, mirth, fear, disgust, trust and anticipation will also be leveraged as they are developed. However, the present systems and methods go further by matching these emotions, strength of the emotion, and confidence in the emotion, to patterns of emotional profiles that signify a particular mental health state. For example, pattern recognition may be trained, based upon patients that are known to be suffering from depression, to identify the emotional state of a respondent that is indicative of depression.

Figure 23A:
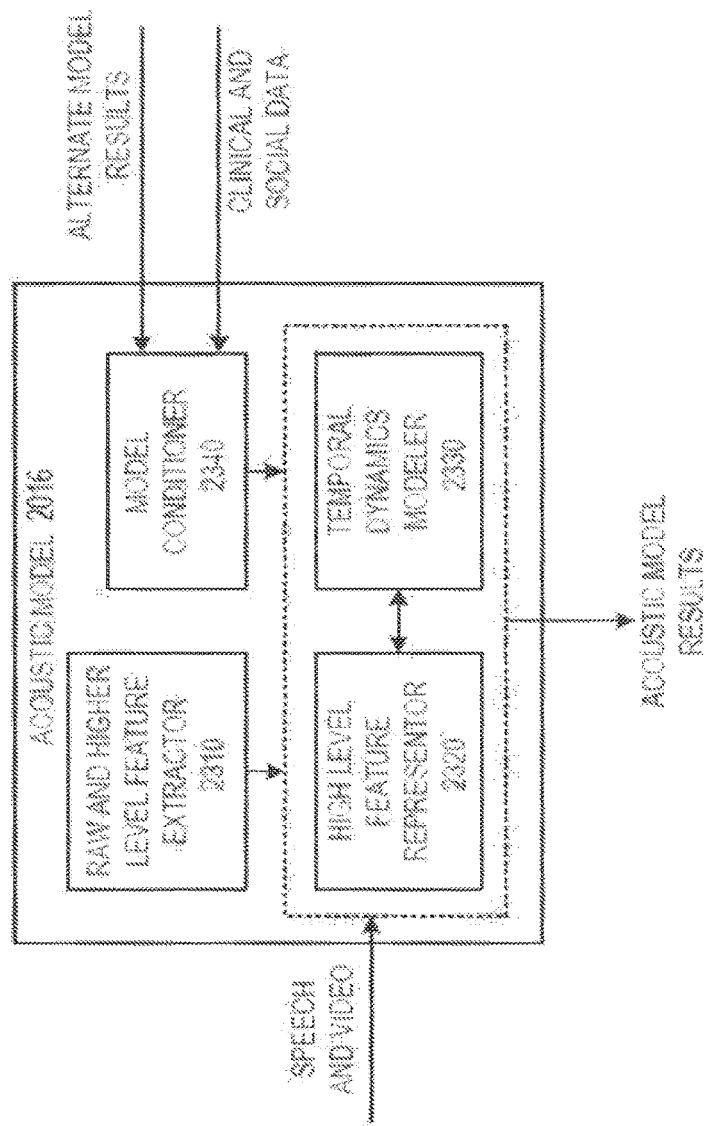
FIG. 23A provides a block diagram of the acoustic model, in accordance with some embodiments.
Figure 23B:
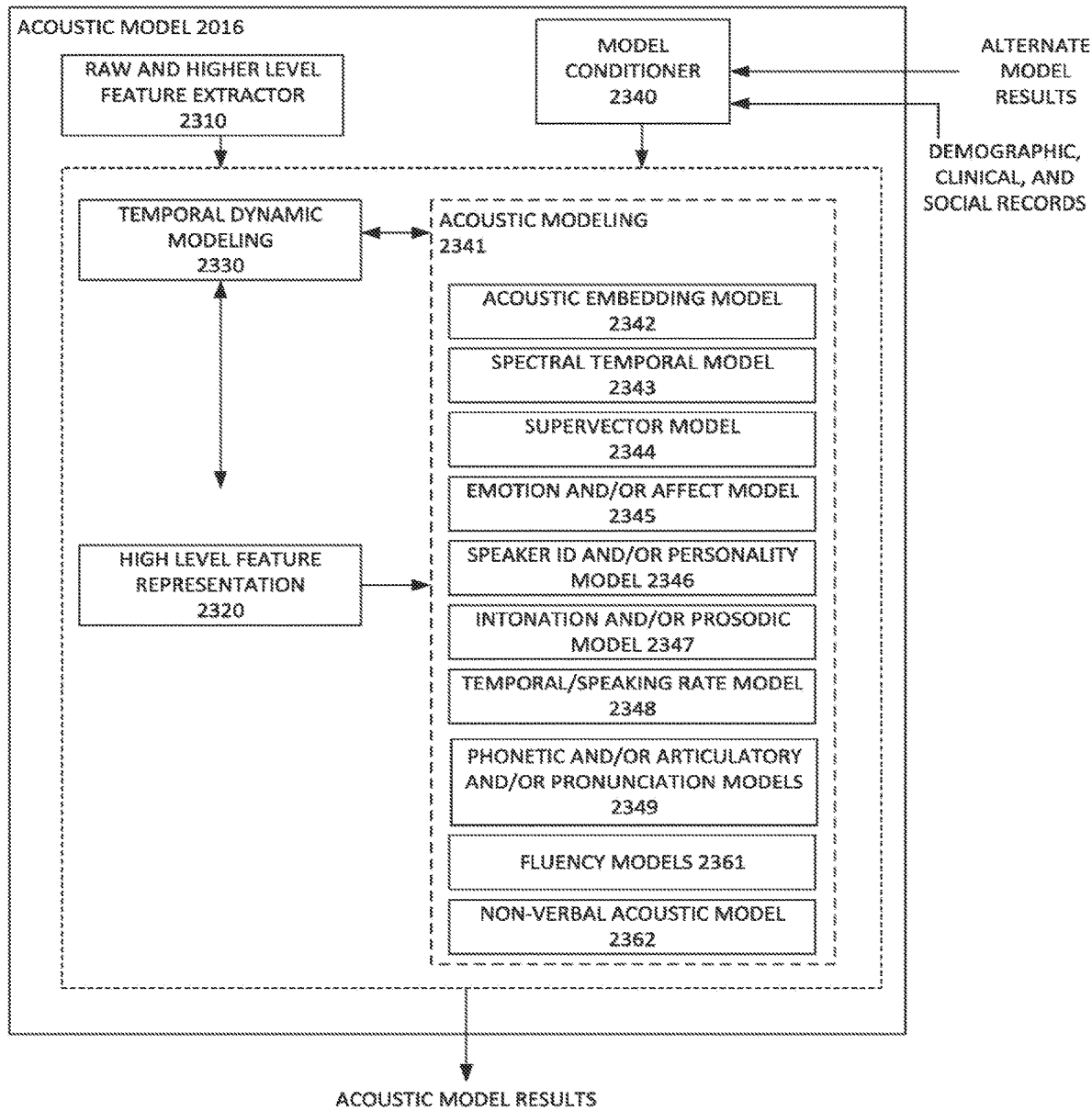
FIG. 23B shows an embodiment of FIG. 23A including an acoustic modeling block.

FIG. 23B shows an embodiment of FIG. 23A including an acoustic modeling block 2341. The acoustic modeling block 2341 includes a number of acoustic models. The acoustic models may be separate models that use machine learning algorithms. The illustrated listing of models shown in FIG. 23B is not necessarily an exhaustive listing of possible models. These models may include a combination of existing third party models and internally derived models. FIG. 23B includes acoustic embedding model 2342, spectral temporal model 2343, acoustic effect model 2345, speaker personality model 2346, intonation model 2347, temporal/speaking rate model 2348, pronunciation models 2349, and fluency models 2361. The machine learning algorithms used by these models may include neural networks, deep neural networks, support vector machines, decision trees, hidden Markov models, and Gaussian mixture models.

Figure 23C:
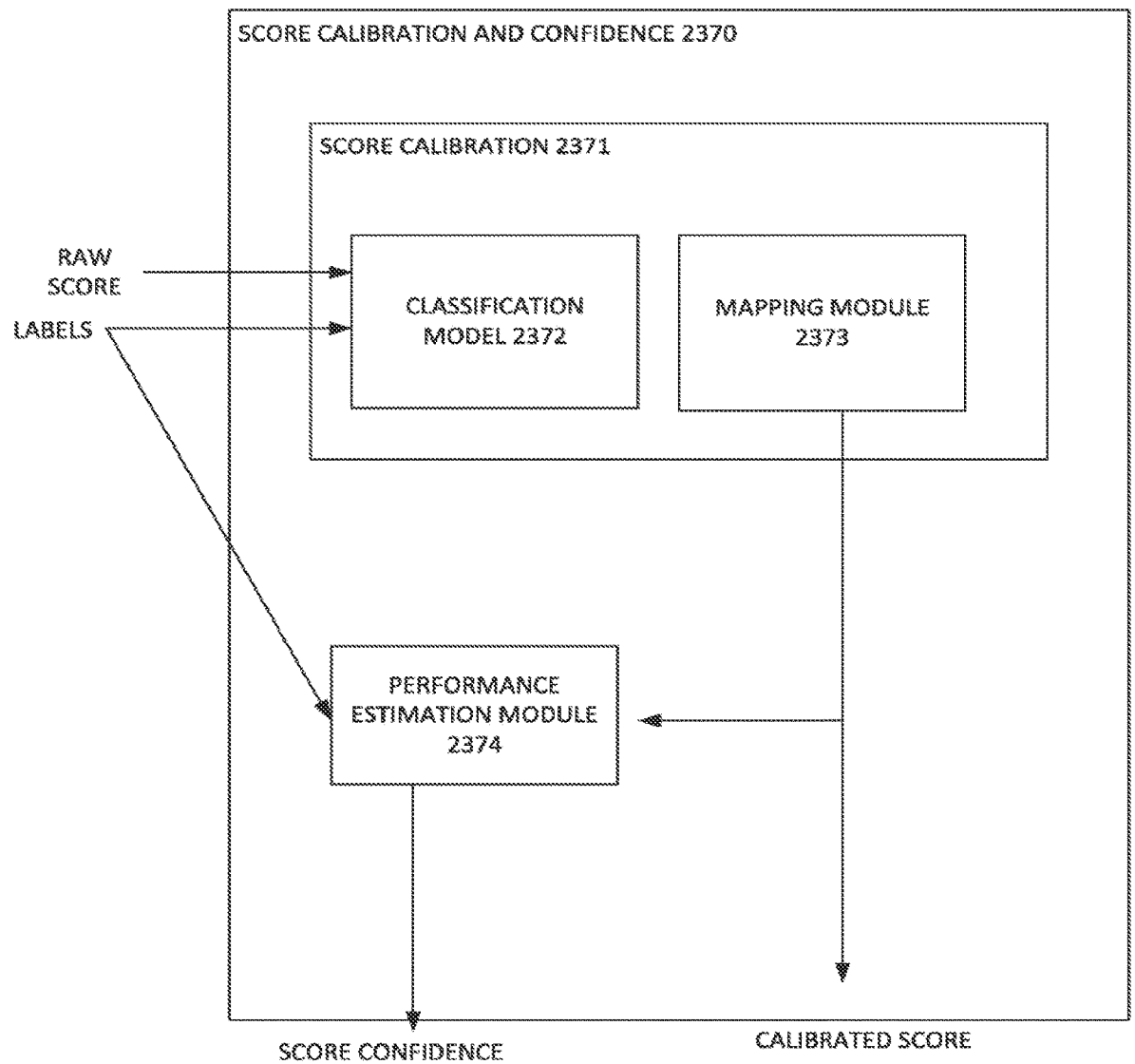
FIG. 23C shows a score calibration and confidence module.

FIG. 23C shows a score calibration and confidence module 2370. The score calibration and confidence module 2370 includes a score calibration module 2371 and a performance estimation module 2374. The score calibration module 2371 includes a classification module 2372 and a mapping module 2373.

The score calibration and confidence module 2370 may accept as inputs a raw score, produced by a machine learning algorithm, such as a neural network or deep learning network, that may be analyzing audiovisual data. The score calibration and confidence module 2370 may also accept a set of labels, with which to classify data. The labels may be provided by clinicians. The classification module 2371 may apply one or more labels to the raw score, based on the value of the score. For example, if the score is a probability near 1, the classification module 2371 may apply a "severe" label to the score. The classification module 2371 may apply labels based on criteria set by clinicians, or may algorithmically determine labels for scores, e.g., using a machine learning algorithm. The mapping module 2372 may scale the raw score to fit within a range of numbers, such as 120-180 or 0-700. The classification module 2371 may operate before or after the mapping module 2372.

After calibrating the data, the score calibration and confidence module 2370 may determine a confidence measure 2376 by estimating a performance for the labeled, scaled score. The performance may be estimated by analyzing features of the collected data, such as duration, sound quality, accent, and other features. The estimated performance may be a weighted parameter that is applied to the score. This weighted parameter may comprise the score confidence.

Figure 24:
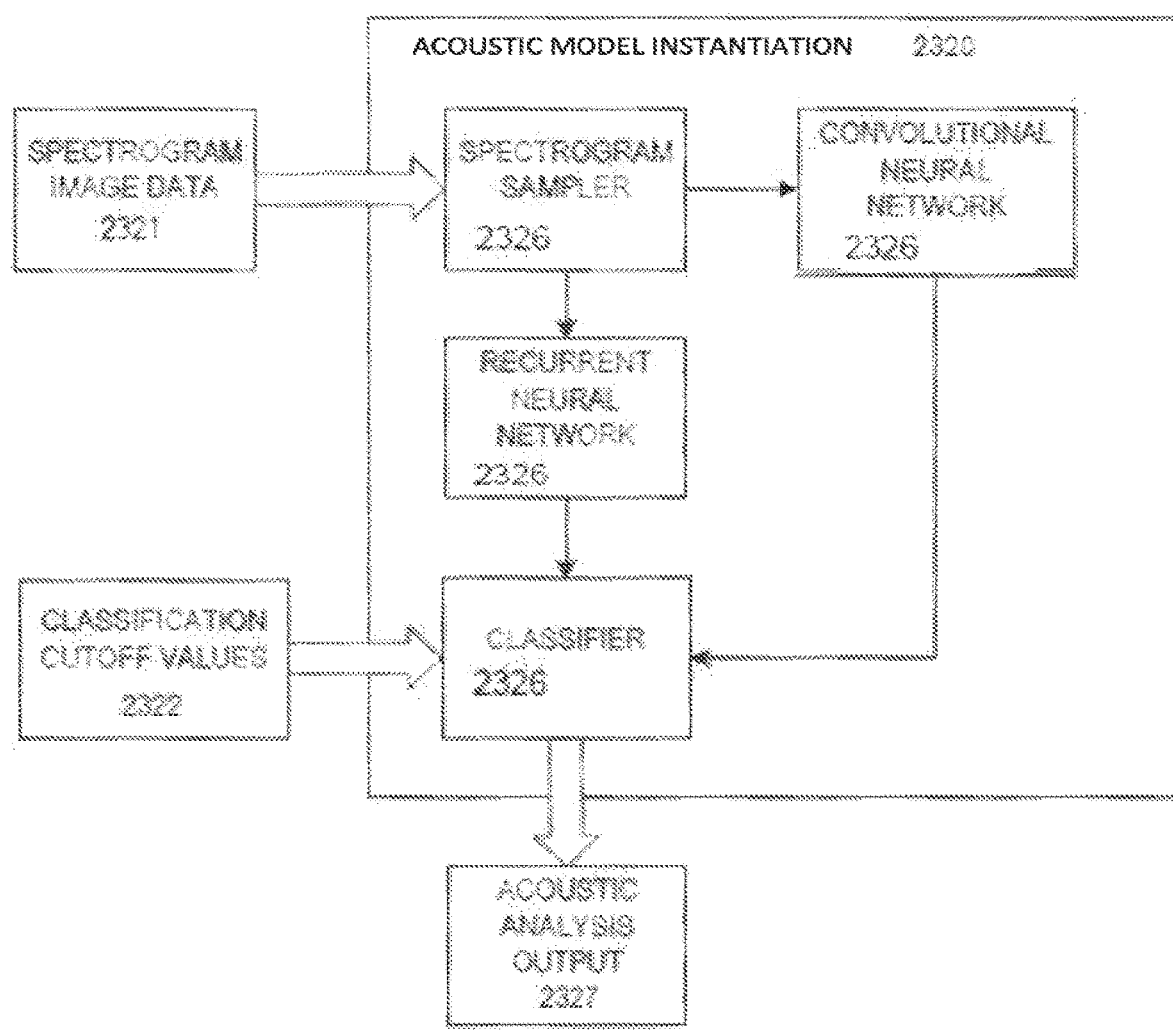
FIG. 24 provides a simplified example of the high level feature representor of the acoustic model, for illustrative purposes.

To provide greater context, and clarification around the acoustic model's 2016 operation, a highly simplified and single substantiation of one possible version of the high level feature representor 2320 is provided in relation to FIG. 24. It should be noted that this example is provided for illustrative purposes only, and is not intended to limit the embodiments of the high level feature representor 2320 in any way.

Figure 55:
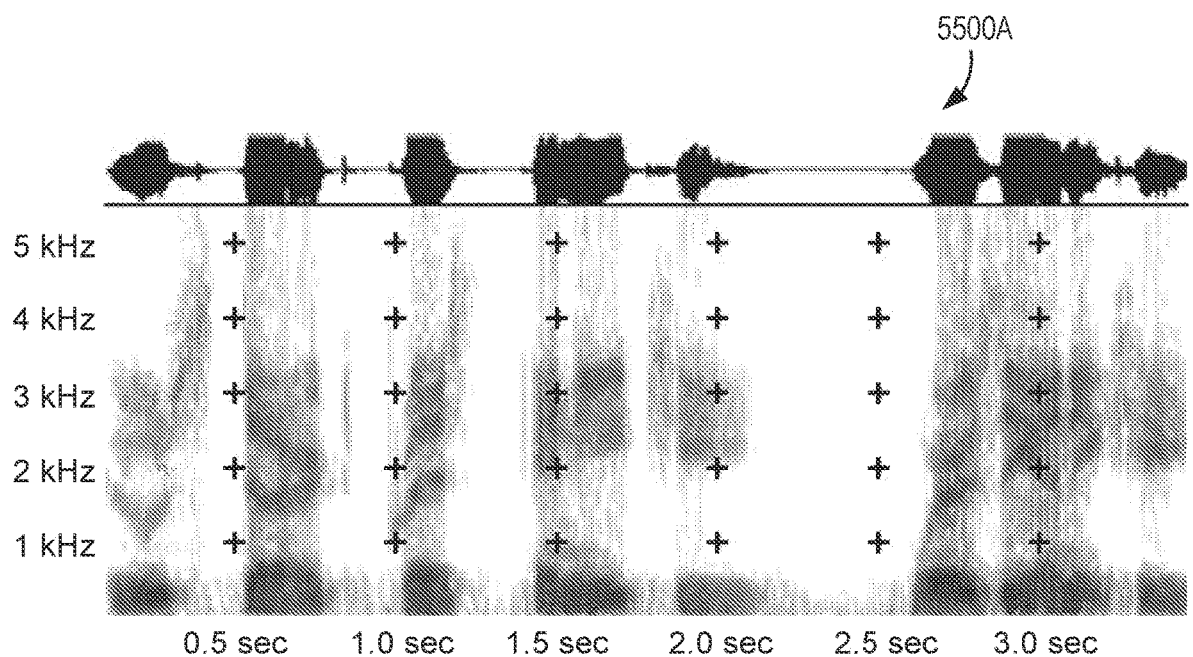
FIGS. 55 and 56 provide example illustrations of spectrograms of an acoustic signal used for analysis, in accordance with some embodiments.

In this example embodiment, the raw and high level feature extractor 2310 takes the acoustic data signal and converts it into a spectrogram image 2321. FIG. 55 provides an example image of such a spectrogram 5500 of a human speaking. A spectrogram of this sort provides information along one axis regarding the audio signal frequency, amplitude of the signal (here presented in terms of intensity/how dark the frequency is labeled), and time. Such a spectrogram 5500 is considered a raw feature of the acoustic signal, as would pitch, cadence, energy level, etc.

Figure 56:
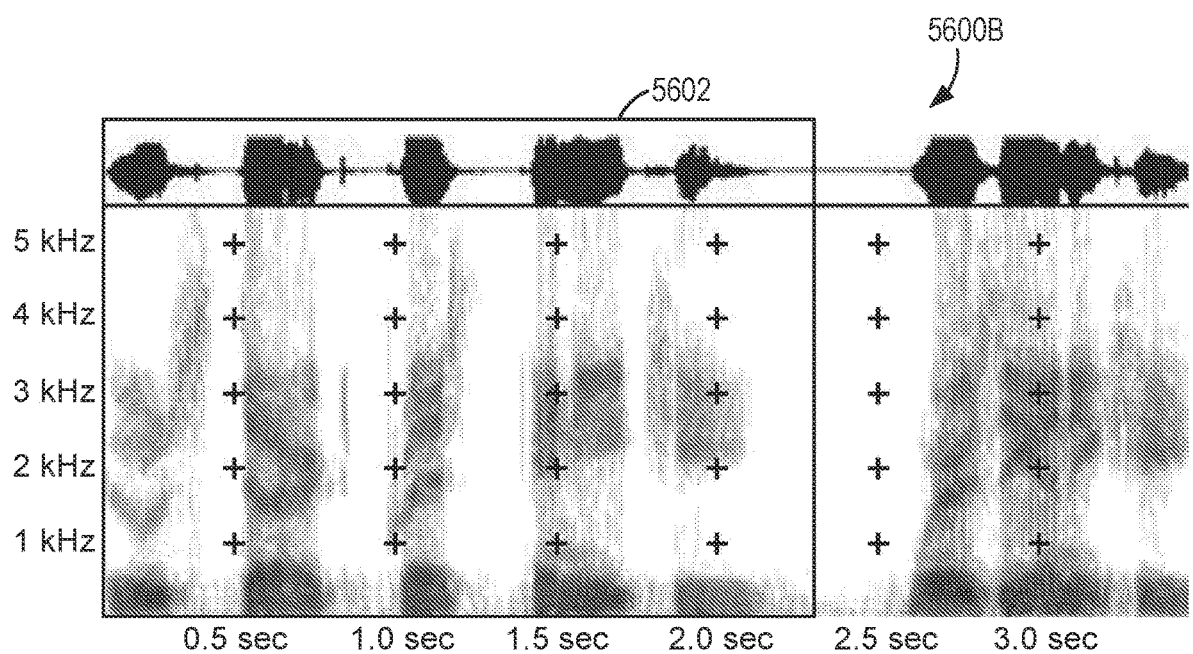

A spectrogram sampler 2323 then selects a portion of the image at a constant timeframe, for example between time zero and 10 seconds is one standard sample size, but other sample time lengths are possible. FIG. 56 provides an example of a sampled portion 5502 of the spectrogram 5600. This image data the then represented as an M×N matrix (x), in this particular non-limiting example. An equation that includes x as a variable, and for which the solution is known, is then processed to determine estimates of the unknown variables (matrices and vectors) within the equation. For example, a linear equation such as: $\hat{y}=w^T x+b$ may be utilized. As noted, the solution y is known.

This includes determining a set of randomized guesses for the unknown variables ($w^T$ and b in this example equation). The equation is solved for, using these guessed variables, and the error of this solved solution is computed using the known solution value. The error may be computed as:

$$\hat{E} = \frac{(y-\hat{y})^2}{N}.$$

By repeating this process iteratively, thousands if not millions of times, values for the variables that are approximates to the actual variable values may be determined. This is a brute force regression, where the error value ($\hat{E}$) is minimized for.

This approximate value is an abstraction of the mental state being tested, dependent upon the input equation. The system may have previously determined threshold, or cutoff values 2322, for the variables which indicate if the response is indicative of the mental state or not. These cutoff values are trained for by analyzing responses from individuals for which the mental state is already known.

Equation determination may leverage deep learning techniques, as previously discussed. This may include recurrent neural networks 2324 and/or convolutional neural networks 2325. In some cases, long short-term memory (LSTM) or gated recurrent unit (GRU) may be employed, for example. In this manner, depression, or alternate mental states may be directly analyzed for in the acoustic portion of the response. This, in combination with using off-the-shelf emotion detection 'black box' systems, with pattern recognition, may provide a robust classification by a classifier 2326 of the mental state based upon the acoustic signal which, in this example, is provided as acoustic analysis output 2327.

As noted above, this example of using a spectrogram as a feature for analysis is but one of many possible substantiations of the high level feature representor's 2320 activity. Other features and mechanisms for processing these features may likewise be analyzed. For example pitch levels, isolated breathing patterns, total energy of the acoustic signal, or the like may all be subject to similar temporally based analysis to classify the feature as indicative of a health condition.

Figure 25:
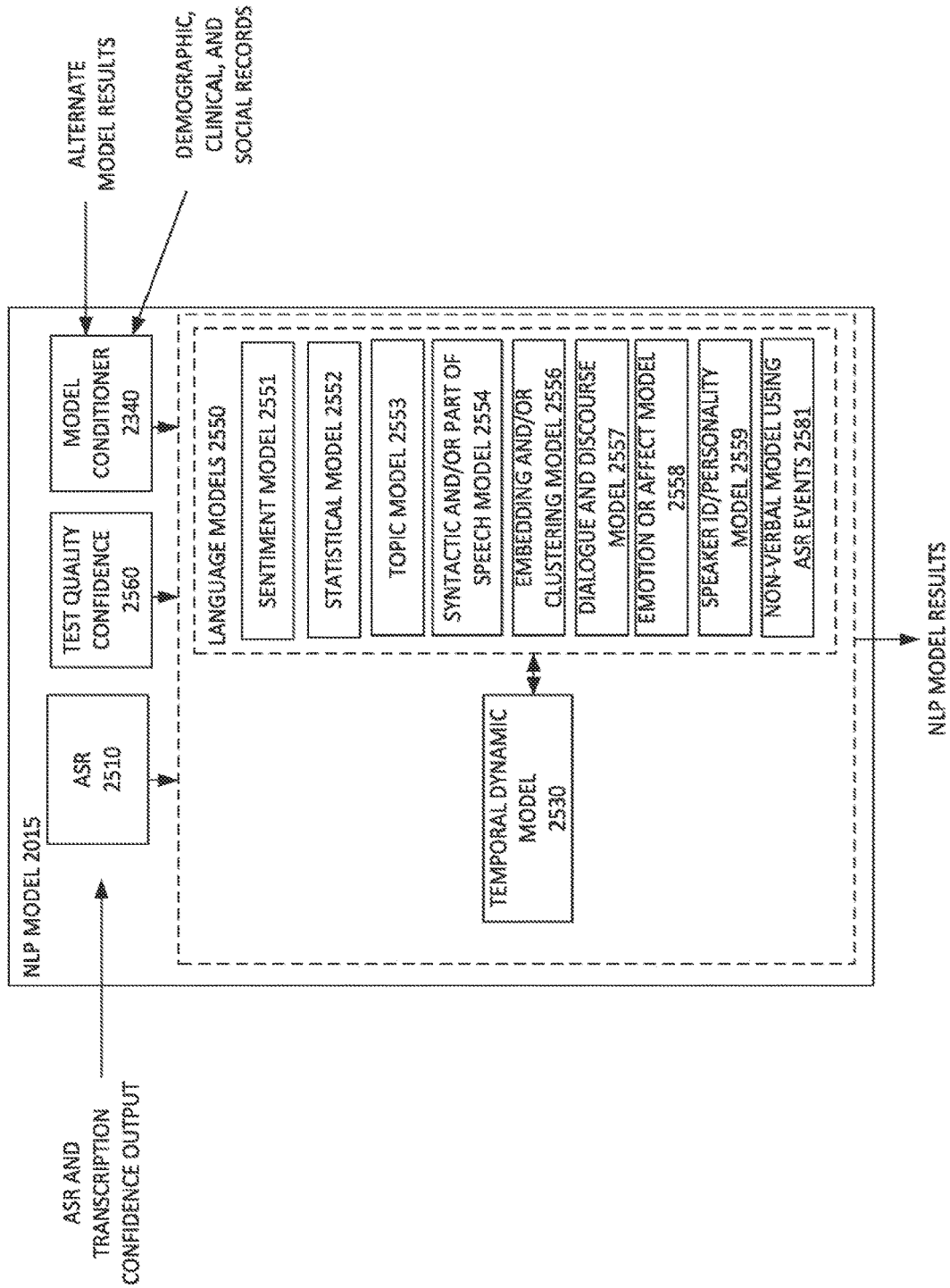
FIG. 25 provides a block diagram of the Natural Language Processing (NLP) model, in accordance with some embodiments.

Turning now to FIG. 25, the NLP model 2015 is provided in greater detail. This system consumes the output from the ASR system 2012 and performs post-processing on it via an ASR output post processor 2510. This post processing includes reconciling the ASR outputs (when multiple outputs are present). Post processing may likewise include n-gram generation, parsing activities and the like.

Likewise, the results from the video and acoustic models 2016 and 2017 respectively, as well as clinical and social data are consumed by a model conditioner 2540 for altering the functioning of the language models 2550. The language models 2550 operate in concert with a temporal dynamics modeler 2520 to generate the NLP model results.

The language models 2550 include a number of separate models. The illustrated listing of models shown in FIG. 25 is not necessarily an exhaustive listing of possible models. These models may include a combination of existing third party models and internally derived models. Language models may use standard machine learning or deep learning algorithms, as well as language modeling algorithms such as n-grams. For example, sentiment model 2551 is a readily available third party model that uses either original text samples or spoken samples that have been transcribed by a human or machine speech recognizer, to output to determine if the sentiment of the discussion is generally positive or negative. In general, a positive sentiment is inversely correlated with depression, whereas a negative sentiment is correlated with a depression classification.

Statistical language model 2552 utilizes n-grams and pattern recognition within the ASR output to statistically match patterns and n-gram frequency to known indicators of depression. For example, particular sequences of words may be statistically indicative of depression. Likewise, particular vocabulary and word types used by a speaker may indicate depression or not having depression.

A topic model 2553 identifies types of topics within the ASR output. Particular topics, such as death, suicide, hopelessness and worth (or lack thereof) may all be positively correlated with a classification of depression. Additionally, there is a latent negative correlation between activity (signified by verb usage) and depression. Thus, ASR outputs that are high in verb usage may indicate that the client 260a-n is not depressed. Furthermore, topic modeling based on the known question or prompt given the subject, can produce better performance via using pre-trained topic-specific models for processing the answer for mental health state.

Syntactic model 2554 identifies situations where the focus of the ASR output is internal versus external. The usage of terms like 'I' and 'me' are indicative of internal focus, while terms such as 'you' and 'they' are indicative of a less internalized focus. More internal focus has been identified as generally correlated with an increased chance of depression. Syntactic model 2554 may additionally look at speech complexity. Depressed individuals tend to have a reduction in sentence complexity. Additionally, energy levels, indicated by language that is strong or polarized, is negatively correlated with depression. Thus, someone with very simple, sentences focused internally, and with low energy descriptive language would indicate a depressed classification.

Embedding and clustering model 2556 maps words to prototypical words or word categories. For example, the terms "kitten", "feline" and "kitty" may all be mapped to the term "cat". Unlike the other models, the embedding and clustering model 2556 does not generate a direct indication of whether the patient is depressed or not, rather this model's output is consumed by the other language models 2550.

A dialogue and discourse model 2557 identifies latency and usage of spacer words ("like", "umm", etc.) Additionally the dialogue and discourse model 2557 identifies dialogue acts such as questions versus statements.

An emotion or affect model 2558 provides a score, typically a posterior probability over a set of predetermined emotions (for example happy, sad) that describes how well the sample matches pre-trained models for each of the said emotions. These probabilities can then be used in various forms as input to the mental health state models, and/or in a transfer learning set up. A speaker personality model 2559 provides a score, typically a posterior probability over a set of predetermined speaker personality traits (for example agreeableness, openness) that describes how well the sample matches pre-trained models for each of the said traits. These probabilities can then be used in various forms as input to the mental health state models, and/or in a transfer learning set up.

The non-verbal model 2561 using ASR events may provide a score based on non-lexical speech utterances of patients, which may regardless be indicative of mental state. These utterances may be laughter, sighs, or deep breaths, which may be picked up and transcribed by an ASR.

The text quality confidence module 2560 determines a confidence measure for the output of the ASR output post processor 2510. The confidence measure may be determined based on text metadata (demographic information about the patient, environmental conditions, method of recording, etc.) as well as context (e.g., length of speech sample, question asked).

It should be noted that each of these models may impact one another and influence the results and/or how these results are classified. For example, a low energy language response typically is indicative of depression, whereas high energy verbiage would negatively correlate with depression.

Figure 26:
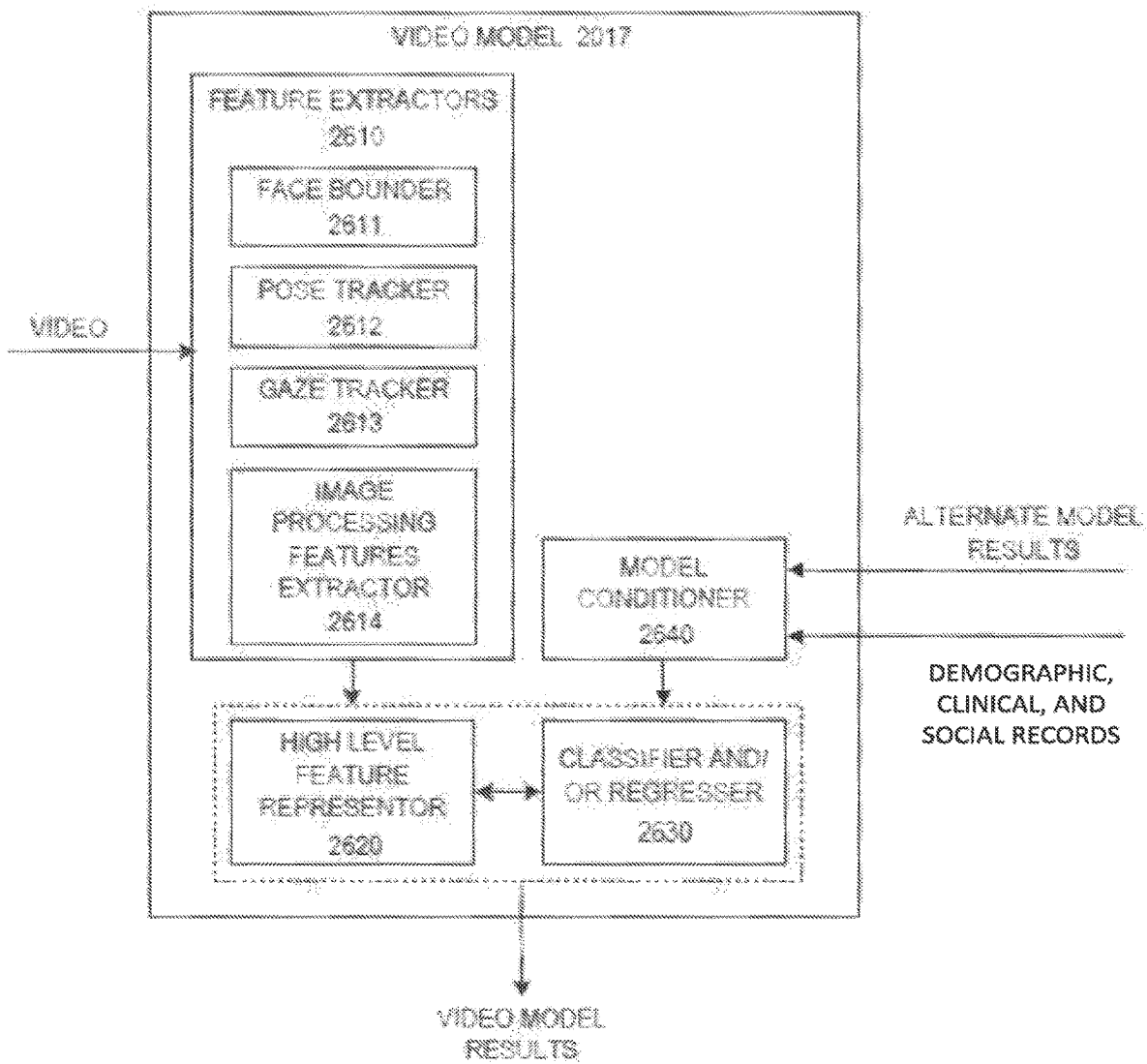
FIG. 26 provides a block diagram of the visual model, in accordance with some embodiments.

Turning now to the video model 2017 of FIG. 26, again we see a collection of feature extractors 2610 that consume the video data. Within the feature extractors 2610 there is a face bounder 2611 which recognizes the edges of a person's face, and extract this region of the image for processing. Obviously, facial features provide significant input on how an individual is feeling. Sadness, exhaustion, worry, and the like, are all associated with a depressive state, whereas jubilation, excitation, and mirth are all negatively correlated with depression.

Additionally, more specific bounders are contemplated, for example the region around the eyes may be analyzed separately from regions around the mouth. This allows greater emphasis to be placed upon differing image regions based upon context. In this set of examples, the region around the mouth generally provides a large amount of information regarding an individual's mood, however when a person is speaking, this data is more likely to be inaccurate due to movements associated with the speech formation. The acoustic and language models may provide insight as to when the user is speaking in order to reduce reliance on the analysis of a mouth region extraction. In contrast, the region around the eyes is generally very expressive when someone is speaking, so the reliance upon this feature is relied upon more during times when the individual is speaking.

A pose tracker 2612 is capable or looking at larger body movements or positions. A slouched position indicates unease, sadness, and other features that indicate depression. The presence of excessing fidgeting, or conversely unusual stillness likewise are indicative of depression. Moderate movement and fidgeting, however, is not associated with depression. Upright posture and relaxed movement likewise are inversely related to a depressive classification. Lastly, even the direction that the individual sits or stands is an indicator of depression. A user who directly faces the camera is less likely to be depressed. In contrast, an individual that positions their body oblique to the camera, or otherwise covers themselves (by crossing their arms for example) is more likely to be depressed.

A gaze tracker 2613 is particularly useful in determining where the user is looking, and when (in response to what stimulus) the person's gaze shifts. Looking at the screen or camera of the client device 260a-n indicates engagement, confidence and honesty—all hallmarks of a non-depressed state. Looking down constantly, on the other hand, is suggestive of depression. Constantly shifting gaze indicates nervousness and dishonesty. Such feedback may be used by the NLP model 2015 to reduce the value of analysis based on semantics during this time period as the individual is more likely to be hedging their answers and/or outright lying. This is particularly true if the gaze pattern alters dramatically in response to a stimulus. For example, if the system asks if the individual has had thoughts of self-harm, and suddenly the user looks away from the camera and has a shifting gaze, a denial of such thought (which traditionally would be counted strongly as an indication of a non-depressed state) is discounted. Rather, emphasis is placed on outputs of the acoustic model 2016, and the video model 2017 from analysis of the other extracted features.

The image processing features extractor 2614 may take the form of any number of specific feature extractions, such as emotion identifiers, speaking identifiers (from the video as opposed to the auditory data), and the above disclosed specific bounder extractors (region around the eyes for example). All of the extracted features are provided to a high-level feature representor 2620 and classifier and/or regressor 2630 that operate in tandem to generate the video model results. As with the other models, the video model 2017 is influenced by the outputs of the NLP model 2015 and the acoustic model 2016, as well as clinical and social data. The model conditioner 2640 utilizes this information to modify what analysis is performed, or the weight afforded to any specific findings.

Figure 27:
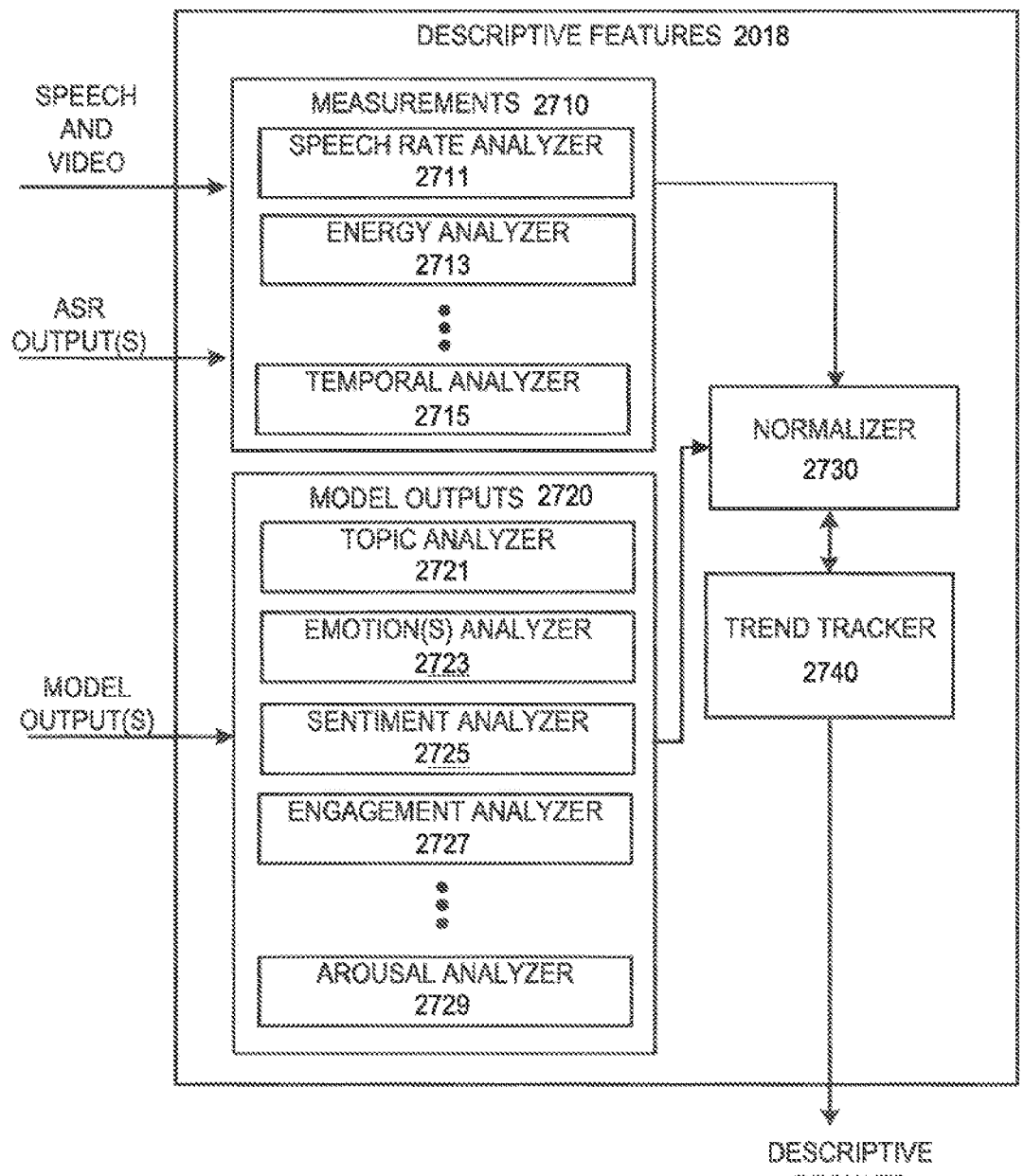
FIG. 27 provides a block diagram of the descriptive features, in accordance with some embodiments.

The descriptive features module 2018 of FIG. 27 includes direct measurements 2710 and model outputs 2720 that result from the analysis of the speech and video data. The descriptive features module may not be included in either the runtime model servers 2010 or model training servers 2030. Instead, descriptive features may be incorporated in the acoustic and NLP models. Disclosed in the description of FIG. 27 are examples of descriptive features. Many different measurements 2710 and model outputs 2720 are collected by the descriptive features 2018 module. For example, measurements include at least speech rate analyzer 2711 which tracks a speaker's words per minute. Faster speech generally indicates excitement, energy and/or nervousness.

Slow speech rates on the other hand are indicative of hesitancy, lethargy, or the presence of a difficult topic. Alone, this measurement has little value, but when used as an input for other models, the speech rate provides context that allows for more accurate classification by these other models. Likewise energy analyzer 2713 measures the total acoustic energy in an audio component. Increased energy may indicate emphasis on particular portions of the interaction, general excitement or lethargy levels, and the like. Again, such information alone provides very little in determining if a person has depression, but when combined with the other models is useful for ensuring that the appropriate classification is being made. For example, if the energy level increases when a person is speaking about their pet dog, the system determines that this topic is of interest to the individual, and if a longer interaction is needed to collect additional user data for analysis, the interaction may be guided to this topic. A temporal analyzer 2715 determines the time of the day, week and year, in order to provide context around the interaction. For example, people are generally more depressed in the winter months, around particular holidays, and at certain days of the week and times of the day. All this timing information is usable to alter the interaction (by providing topicality) or by enabling classification thresholds to be marginally altered to reflect these trends.

The model outputs 2720 may include a topic analyzer 2721, various emotion analyzers 2723 (anxiety, joy, sadness, etc.), sentiment analyzer 2725, engagement analyzer 2727, and arousal analyzer 2729. Some of these analyzers may function similarly in the other models; for example the NLP model 2015 already includes a sentiment model 2551, however the sentiment analyzer 2725 in the descriptive features 2018 module operates independently from the other models, and includes different input variables, even if the output is similar.

The engagement analyzer 2727 operates to determine how engaged a client 260a-n is in the interaction. High levels of engagement tend to indicate honesty and eagerness. Arousal analyzer 2729 provides insights into how energetic or lethargic the user is. A key feature of the descriptive features 2018 module is that each of these features, whether measured or the result of model outputs, is normalized by the individual by a normalizer 2730. For example, some people just speak faster than others, and a higher word per minute measurement for this individual versus another person may not indicate anything unusual. The degree of any of these features is adjusted for the baseline level of the particular individual by the normalizer 2730. Obviously, the normalizer 2730 operates more accurately the more data that is collected for any given individual. A first time interaction with a client 260*a-n* cannot be effectively normalized immediately, however as the interaction progresses, the ability to determine a baseline for this person's speech rate, energy levels, engagement, general sentiment/demeanor, etc. may be more readily ascertained using standard statistical analysis of variation of these features over time. This becomes especially true after more than one interaction with any given individual.

After normalization, the system may identify trends in these features for the individual by analysis by a trend tracker 2740. The trend tracker splits the interaction by time domains and looks for changes in values between the various time periods. Statistically significant changes, and especially changes that continue over multiple time periods, are identified as trends for the feature for this individual. The features, both in raw and normalized form, and any trends are all output as the descriptive results.

Although not addressed in any of the Figures, it is entirely within the scope of embodiments of this disclosure that additional models are employed to provide classification regarding the client's 260*a-n* health state using alternate data sources. For example, it has been discussed that the client devices may be capable of collecting biometric data (temperature, skin chemistry data, pulse rate, movement data, etc.) from the individual during the interaction. Models focused upon these inputs may be leveraged by the runtime model server(s) 2010 to arrive at determinations based upon this data. The disclosed systems may identify chemical markers in the skin (cortisol for example), perspiration, temperature shifts (e.g. flushing), and changes in heart rate, etc. for diagnostic purposes.

Figure 28:
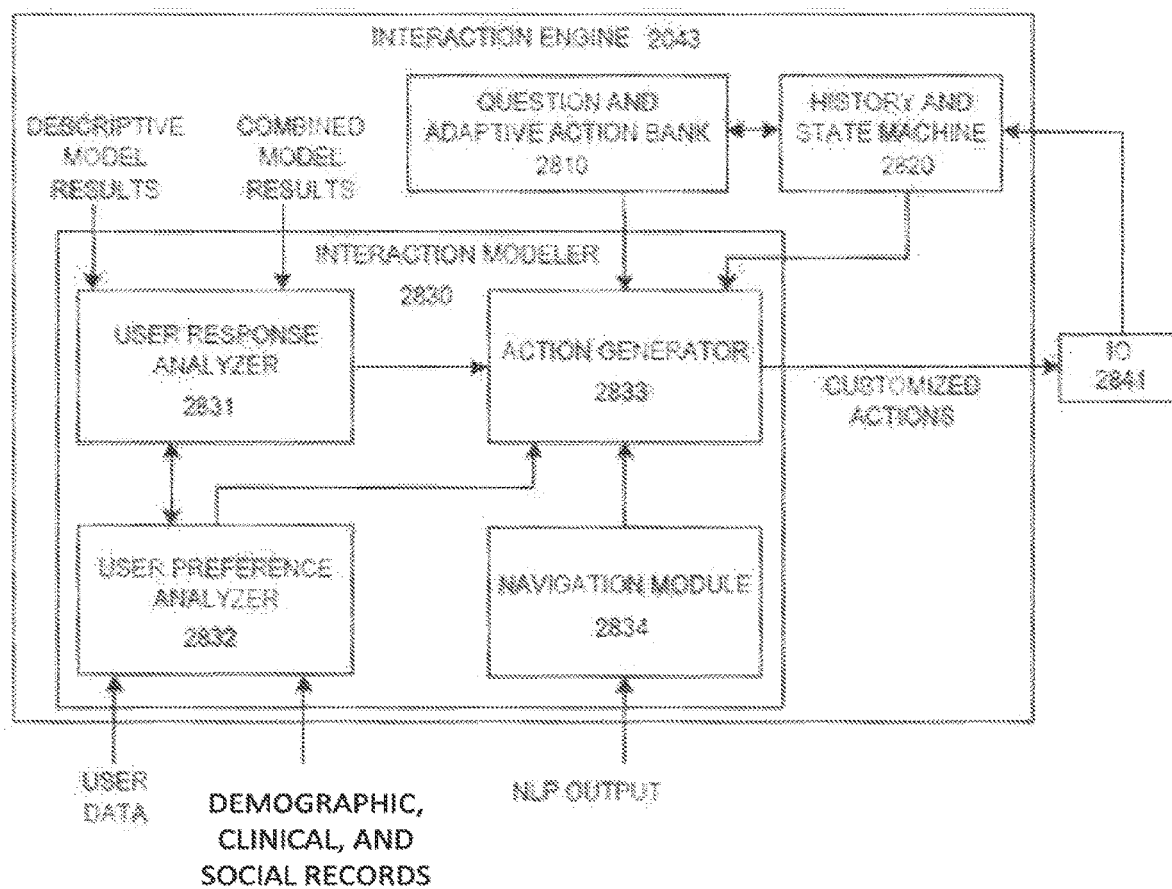
FIG. 28 provides a block diagram of the interaction engine, in accordance with some embodiments.

Now that the specifics of the runtime model server(s) 2010 has been discussed in considerable depth, attention will be turned to the interaction engine 2043, as seen in greater detail in relation to FIG. 28. A process flow diagram featuring the components of the interaction engine 2043 is featured in FIG. 8. The interaction engine 2043 dictates the interactions between the web server(s) 240 and the clients 260*a-n*. These interactions, as noted previously may consist of a question and answer session, with a set number and order or questions. In such embodiments, this type of assessment is virtually an automated version of what has previously been leveraged for depression diagnosis, except with audio and video capture for improved screening or monitoring accuracy. Such question and answer may be done with text questions displayed on the client device, or through a verbal recording of a question. However, such systems are generally not particularly engaging to a client 260*a-n*, and may cause the interaction to not be completed honestly, or terminated early. As such, it is desirable to have a dynamic interaction which necessitates a more advanced interaction engine 2043, such as the one seen in the present Figure.

This interaction engine 2043 includes the ability to take a number of actions, including different prompts, questions, and other interactions. These are stored in a question and action bank 2810. The interaction engine 2043 also includes a history and state machine 2820 which tracks what has already occurred in the interaction, and the current state of the interaction.

The state and history information, database of possible questions and actions, and additional data is consumed by an interaction modeler 2830 for determining next steps in the interaction. The other information consumed consists of user data, clinical data and social data for the client being interacted with, as well as model results, NLP outputs and descriptive feature results. The user data, clinical data and social media data are all consumed by a user preference analyzer 2832 for uncovering the preferences of a user. As noted before, appealing to the user is one of the large hurdles to successful screening or monitoring. If a user doesn't want to use the system they will not engage it in the first place, or may terminate the interaction prematurely. Alternatively, an unpleasant interaction may cause the user to be less honest and open with the system. Not being able to properly screen individuals for depression, or health states generally, is a serious problem, as these individuals are likely to continue struggling with their disease without assistance, or even worse die prematurely. Thus, having a high degree of engagement with a user may literally save lives.

By determining preference information, the interactions are tailored in a manner that appeals to the user's interests and desires. Topics identified within social media feeds are incorporated into the interaction to pique interest of the user. Collected preference data from the user modulates the interaction to be more user friendly, and particular needs or limitations of the user revealed in clinical data are likewise leveraged to make the interaction experience user-friendly. For example, if the clinical data includes information that the user experiences hearing loss, the volume of the interaction may be proportionally increased to make the interaction easier. Likewise, if the user indicates their preferred language is Spanish, the system may automatically administer the interaction in this language.

The descriptive features and model results, in contrast, are used by a user response analyzer 2831 to determine if the user has answered the question (when the interaction is in a question-answer format), or when sufficient data has been collected to generate an appropriate classification if the interaction is more of a 'free-form' conversation, or even a monologue by the client about a topic of interest.

Additionally, a navigation module 2834 receives NLP outputs and semantically analyzes the NLP results for command language in near real time. Such commands may include statements such as "Can you repeat that?", "Please speak up", "I don't want to talk about that", etc. These types of 'command' phrases indicate to the system that an immediate action is being requested by the user.

Output from each of the navigation module 2834, user response analyzer 2831 and user preference analyzer 2832 are provided to an action generator 2833, in addition to access to the question and adaptive action bank 2810 and history and state machine 2820. The action generator 2833 applies a rule based model to determine which action within the question and adaptive action bank 2810 is appropriate. Alternatively, a machine learned model is applied in lieu of a rule based decision model. This results in the output of a customized action that is supplied to the IO 2041 for communication to the client 260*a-n*. The customized action is likewise passed back to the history and state machine 2820 so that the current state, and past actions may be properly logged. Customized actions may include, for example, asking a specific question, prompting a topic, switching to another voice or language, ending the interaction, altering the loudness of the interaction, altering speech rates, font sizes and colors, and the like.

Now that the structures and systems of the health screening or monitoring system 2000 have been described in considerable detail, attention will now be turned to one example process 2900 of health screening or monitoring of a client. In this example process the clinical and social data for the clients are collated and stored within the data store (at step 2910). This information may be gathered from social media platforms utilizing crawlers or similar vehicles. Clinical data may be collected from health networks, physicians, insurance companies or the like. In some embodiments, the health screening or monitoring system 2000 may be deployed as an extension of the care provider, which allows the sharing of such clinical data with reduced concerns with violation of privacy laws (such as HIPAA). However, when the health screening or monitoring system 2000 is operated as a separate entity, outside a healthcare network, additional consents, encryption protocols, and removal of personally identifiable information may be required to enable open sharing of the clinical data while staying in compliance with applicable regulations. Clinical data may include electronic health records, physician notes, medications, diagnoses and the like.

Next, the process may require that models are available to analyze a client's interaction. Initial datasets that include labeling data (confirmed or imputed diagnoses of depression) are fed to a series of trainers that train individual models, and subsequently fuse them into a combined model (at 2920). Such training may also include personalization of models when additional metadata is available.

Figure 30:
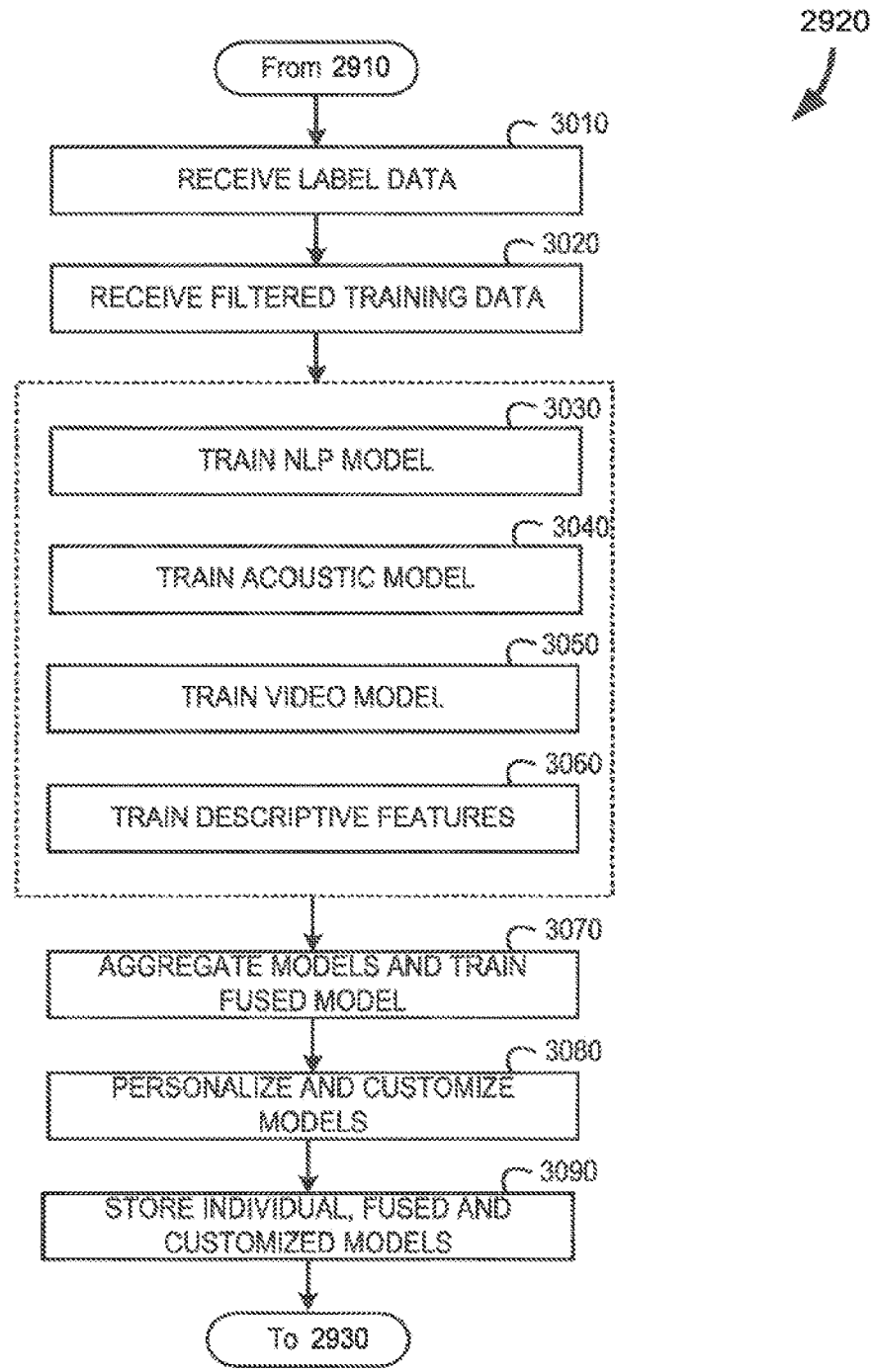
FIG. 30 is a logic flow diagram of the example process of model training, in accordance with some embodiments.

FIG. 30 provides a greater detailed illustration of an example process for such model training. As mentioned, label data is received (at 3010). Labels include a confirmed diagnosis of depression (or other health condition being screened for). Likewise, situations where the label may be imputed or otherwise estimated are used to augment the training data sets.

Imputed label data is received by a manual review of a medical record and/or interaction record with a given client. For example, in prediction mode, when the label is unknown, it is possible to decide whether it is possible to estimate a label for a data point given other information such as patient records, system predictions, clinically-validated surveys and questionnaires, and other clinical data. Due to the relative rarity of label data sets, and the need for large numbers of training samples to generate accurate models, it is often important that the label data includes not just confirmed cases of depression, but also these estimated labels.

Additionally, the process includes receiving filtered data (at 3020). This data is filtered so that only data for which labels are known (or estimated) is used. Next each of the models is trained. Such training includes training of the NLP model (at 3030), the acoustic model (at 3040) the video model (at 3050) and the descriptive features (at 3060). It should be noted that these training processes occur in any order, or are trained in parallel. In some embodiments the parallel training includes generating cross dependencies between the various models. These cross dependencies are one of the critical features that render the presently disclosed systems and methods uniquely capable of rendering improved and highly accurate classifications for a health condition.

The resulting trained models are fused, or aggregated, and the final fused trained model may be stored (at 3070). The models (both individual and fused models) are stored in a model repository. However, it is also desirable to generate model variants that are customized to different population groups or even specific individuals (at 3080).

Figure 31:
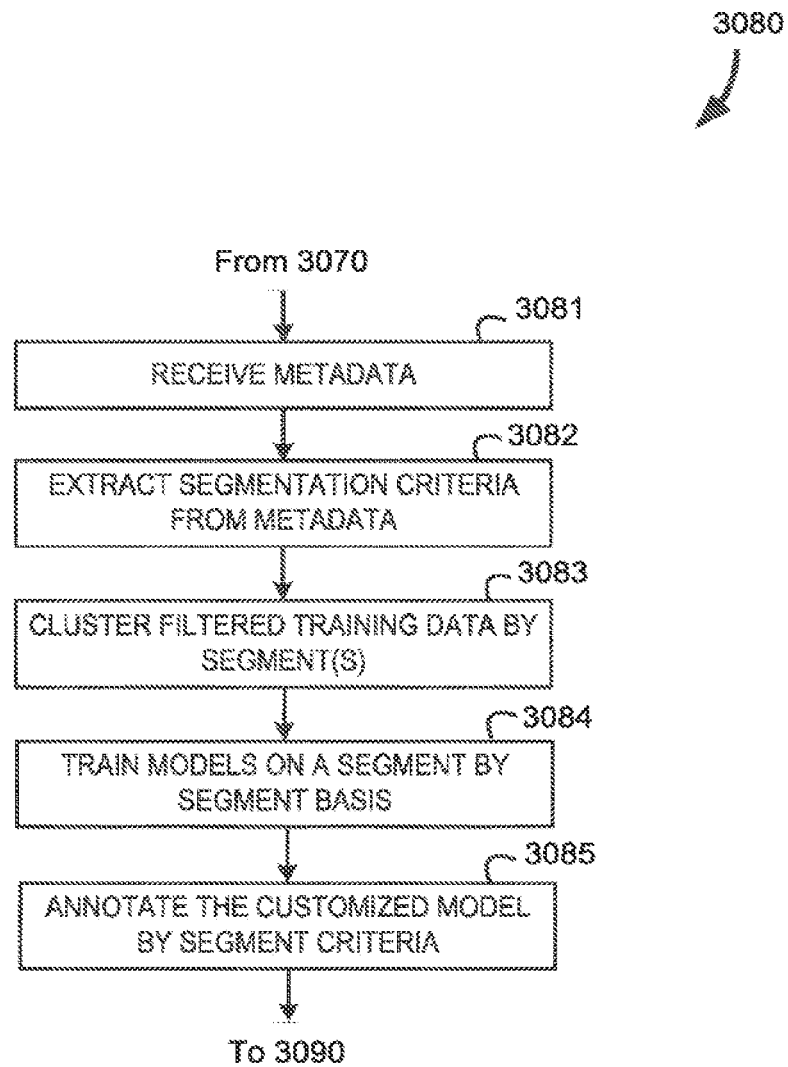
FIG. 31 is a logic flow diagram of the example process of model personalization, in accordance with some embodiments.

The process for model customization and personalization is explored in further depth in relation to FIG. 31. Personalization relies upon metadata stored with the filtered training data. This metadata is received (at 3081). Particular population segment features are identified in the metadata and extracted out (at 3082). These segment features are used to train models that are specific to that segment. This is accomplished by clustering the filtered training data by these segmentation features (at 3083). A given training piece may be included in a number of possible segments, each non-overlapping, or of continually increasing granularity.

For example, assume labeled training data is received from a known individual. This individual is identified as a black woman in her seventies, in this example. This training data is then used to train for models specific to African American individuals, African American women, women, elderly people, elderly women, elderly African American people, and elderly African American women. Thus, this single piece of training data is used to generate seven different models, each with slightly different scope and level of granularity. In situations where age is further divided out, this number of models being trained off of this data is increased even further (e.g., adult women, women over 50, women over 70, individuals over 70, etc.). The models are then trained on this segment-by-segment basis (at 3084). The customized models are annotated by which segment(s) they are applicable to (at 3085), allowing for easy retrieval when a new response is received for classification where information about the individual is known, and may be utilized to select the most appropriate/tailored model for this person.

This is important because, often, the model for one identifying a health condition in one individual may be wholly inadequate for classifying another individual. For example, a Caucasian person may require different video models compared to an individual of African descent. Likewise, men and women often have divergent acoustic characteristics that necessitate the leveraging of different acoustic models to accurately classify them. Even a woman in her early twenties sounds different than a woman in her fifties, which again differs from a woman in her eighties. NLP models for a native speaker, versus a second language speaker, may likewise be significantly different. Even between generations, NLP models differ significantly to address differences in slang and other speech nuances. By making models available for individuals at different levels of granularity, the most appropriate model may be applied, thereby greatly increasing classification accuracy by these models.

Returning to FIG. 30, after this personalization is completed, the customized models are also stored in the model repository, along with the original models and fused models (at 3090). It should be noted that while model customization generally increases classification accuracy, any such accuracy gains are jeopardized if a low number of training datasets are available for the models. The system tracks the number of training data sets that are used to train any given customized model, and only models with sufficiently large enough training sets are labeled as 'active' within the model repository. Active models are capable of being used by the runtime model server(s) 2010 for processing newly received response data. Inactive models are merely stored until sufficient data has been collected to properly train these models, at which time they are updated as being active.

Figure 29:
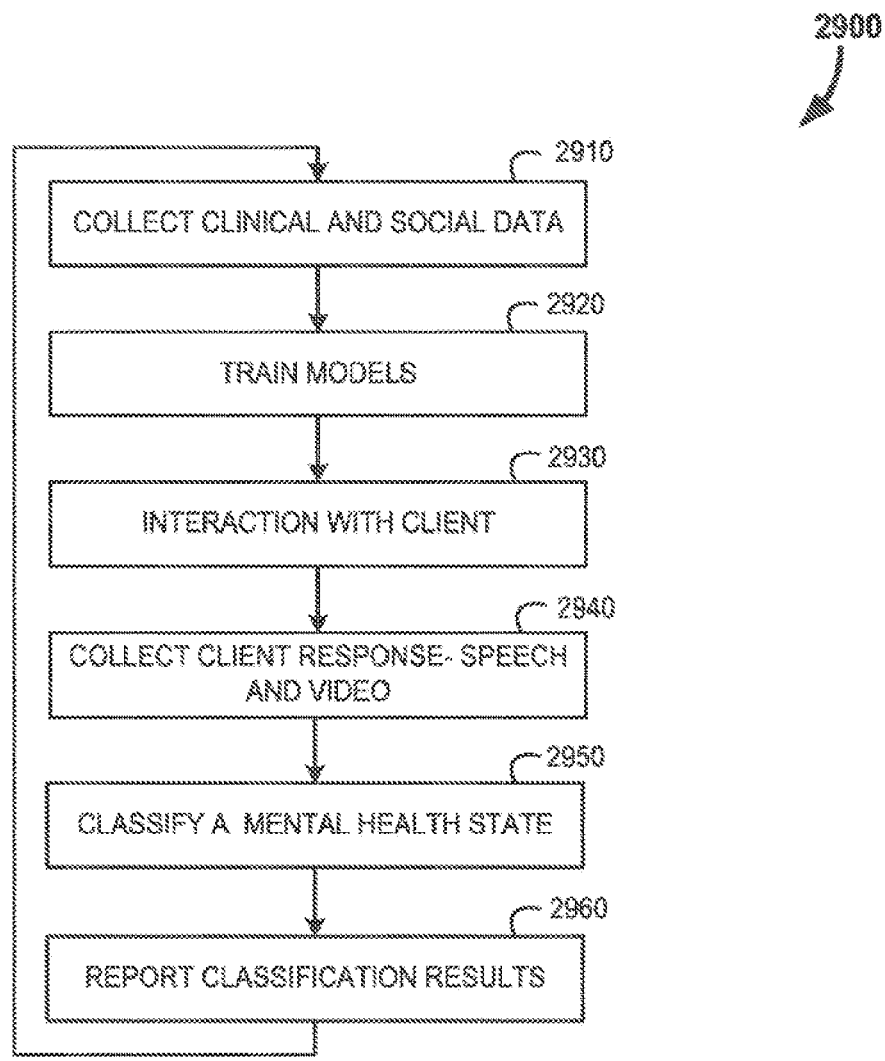
FIG. 29 is a logic flow diagram of the example process of testing a patient for a mental health condition, in accordance with some embodiments.

Returning to FIG. 29, after model training, the process may engage with an interaction with a client (at 2930). This interaction may consist of a question and answer style format, a free-flowing conversation, or even a topic prompt and the client providing a monologue style input.

Figure 32:
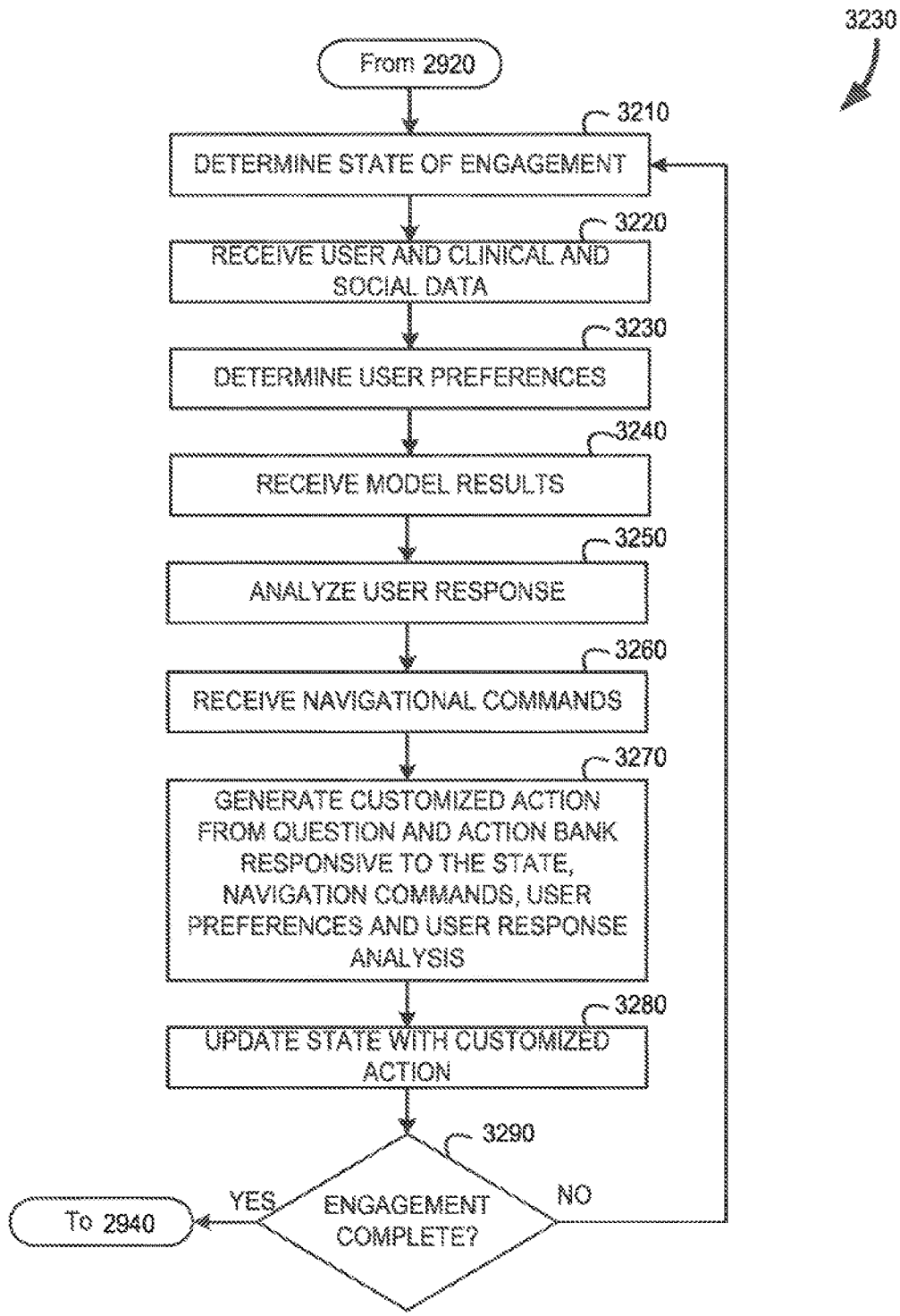
FIG. 32 is a logic flow diagram of the example process of client interaction, in accordance with some embodiments.

FIG. 32 provides an example of this interaction process. Initially the system needs to be aware of the current state of the interaction (at 3210) as well as the historical action that have been taken in the interaction. A state machine and log of prior actions provides this context. The process also receives user, clinical and social data (at 3220). This data is used to extract user preference information (at 3230). For example, preferences may be explicitly directed in the user data, such as language preferences, topic of interest, or the like. Alternatively, these preferences are distilled from the clinical and social data. For example the social data provides a wealth of information regarding the topics of interest for the user, and clinical data provides insight into any accessibility issues, or the like.

Additionally, the model results are received (at 3240), which are used to analyze the user's responses (at 3250) and make decisions regarding the adequacy of the data that has already been collected. For example, if it is determined via the model results that there is not yet a clear classification, the interaction will be focused on collecting more data moving forward. Alternatively, if sufficient data has been collected to render a confident classification, the interaction may instead be focused on a resolution. Additionally, the interaction management will sometimes receive direct command statements/navigational commands (at 3260) from the user. These include actions such as repeating the last dialogue exchange, increasing or decreasing the volume, rephrasing a question, a request for more time, a request to skip a topic, and the like.

All this information is consumed by the action generator to determine the best course of subsequent action (at 3270). The action is selected from the question and adaptive action bank responsive to the current state (and prior history of the interaction) as well as any commands, preferences, and results already received. This may be completed using a rule based engine, in some embodiments. For example, direct navigational commands may take precedence over alternative actions, but barring a command statement by the user, the model responses may be checked against the current state to determine if the state objective has been met. If so, an action is selected from the repository that meets another objective that has not occurred in the history of the interaction. This action is also modified based on preferences, when possible. Alternatively, the action selection is based on a machine learned model (as opposed to a rule based system).

The customized action is used to manage the interaction with the client, and also is used to update the current state and historical state activity (at 3280). The process checks if the goals are met, and if the interaction should be concluded (at 3290). If not, then the entire process may be repeated for the new state and historical information, as well as any newly received response data, navigational commands, etc.

Returning to FIG. 29, during interaction (and after interaction completion when required based upon processing demands) the client response data is collected (at 2940). This data includes video/visual information as well as speech/audio information captured by the client device's camera(s) and microphone(s), respectively. Although not discussed in great depth, the collected data may likewise include biometric results via haptic interfaces or the like. The health state is then classified using this collected response data (at 2950).

Figure 33:
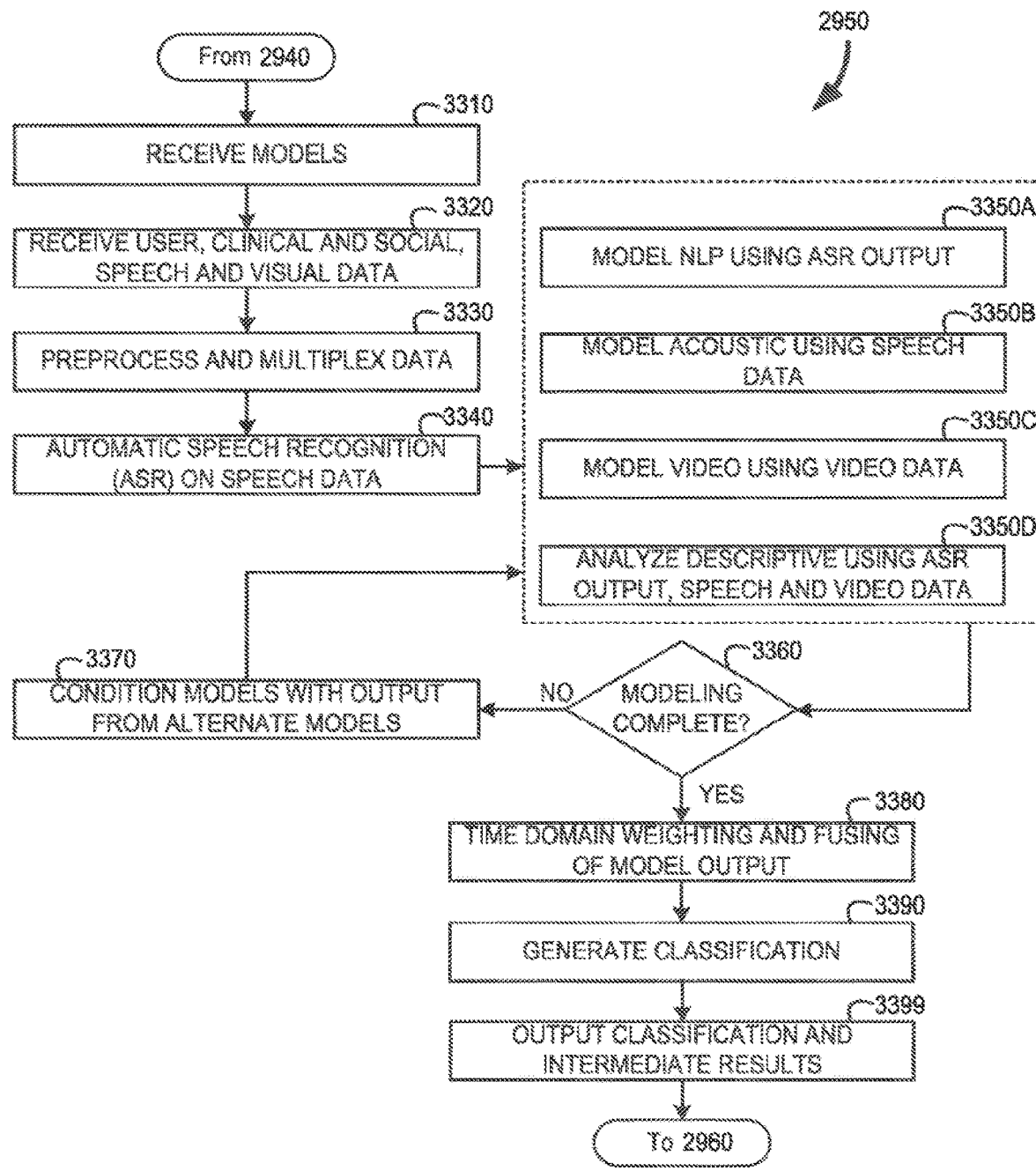
FIG. 33 is a logic flow diagram of the example process of classifying the mental state of the client, in accordance with some embodiments.

FIG. 33 provides a greater detail of the example process for classification. The models are initially retrieved (at 3310) from the model repository. The user data, social data, clinical data and speech and visual data are all provided to the runtime model server(s) for processing (at 3330). The inclusion of the clinical and/or social data sets the present screening or monitoring methodologies apart from prior screening or monitoring methods.

This data is preprocessed to remove artifacts, noise and the like. The preprocessed data is also multiplexed into (at 3330). The preprocessed and multiplexed data is supplied to the models for analysis, as well as to third party ASR systems (at 3340). The ASR output may be consolidated (when multiple ASR systems are employed in concert), and the resulting machine readable speech data is also provided to the models. The data is then processed by the NLP model (at 3350*a*), the acoustic model (at 3350*b*), the video model (at 3350*c*) and for descriptive features (at 3350*d*). Each of the models operates in parallel, with results from any given model being fed to the others to condition their operations. A determination is made if the modeling is complete (at 3360). Due to the fact that the model results are interdependent upon results of the alternative models, the process of modeling is cyclical, in some cases, whereby the models are conditioned (at 3370) with the results of the other models, and the modeling process repeats until a finalized result is determined.

Figure 34:
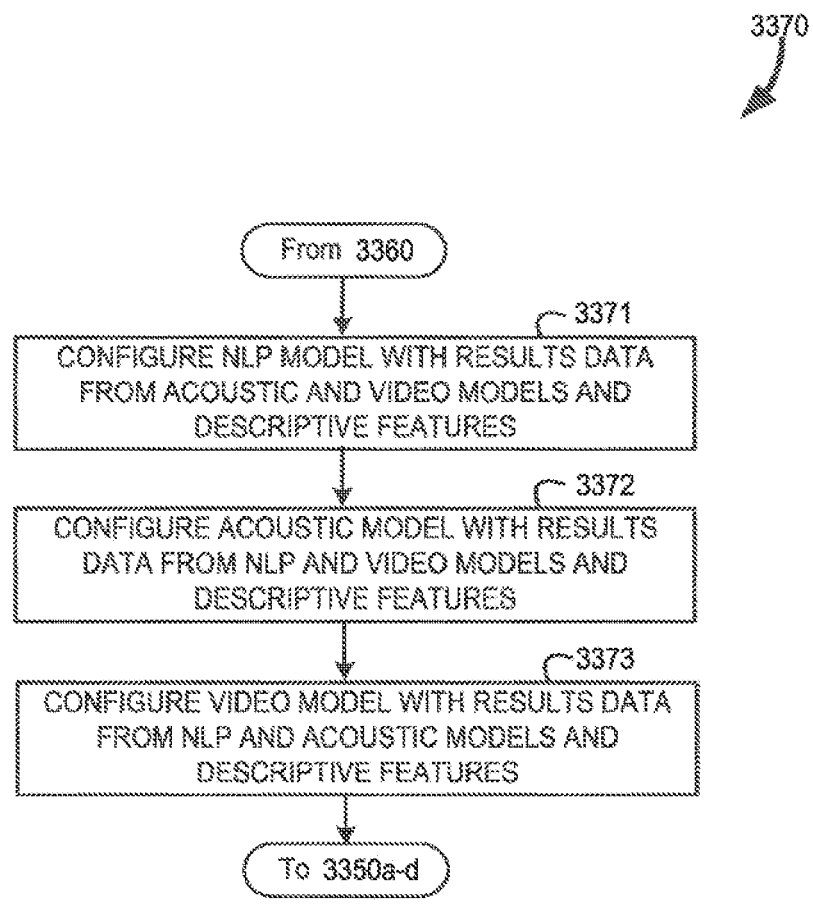
FIG. 34 is a logic flow diagram of the example process of model conditioning, in accordance with some embodiments.

FIG. 34 describes the process of model conditioning in greater detail. Model conditioning essentially includes three sub-processes operating in parallel, or otherwise interleaved. These include the configuration of the NLP model using the results of the acoustic model and video model, in addition to the descriptive features (at 3371), the configuration of the acoustic model using the results of the NLP model and video model, in addition to the descriptive features (at 3372), and configuration of the video model using the results of the acoustic model and NLP model, in addition to the descriptive features (at 3373). As previously discussed, this conditioning is not a clearly ordered process, as intermediate results from the acoustic model for example may be used to condition the NLP model, the output of which may influence the video model, which then in turn conditions the acoustic model, requiring the NLP model to be conditioned based upon updated acoustic model results. This may lead to looped computing processes, wherein each iteration the results are refined to be a little more accurate than the previous iteration. Artificial cutoffs are imposed in such computational loops to avoid infinite cycling and breakdown of the system due to resource drain. These cutoffs are based upon number of loop cycles, or upon the degree of change in a value between one loop cycle and the next. Over time, the results from one loop cycle to the next become increasingly closer to one another. At some point additional looping cycles are not desired due to the diminishing returns to the model accuracy for the processing resources spent.

One example of this kind of conditioning is when the NLP model determines that the user is not speaking. This result is used by the video model to process the individuals facial features based upon mouth bounding and eye bounding. However, when the user is speaking, the video model uses this result to alter the model for emotional recognition to rely less upon the mouth regions of the user and rather rely upon the eye regions of the user's face. This is but a single simplified example of one type of model conditioning, as is not limiting.

Returning to FIG. 33, after modeling is completed, each model is then combined (fused) by weighting the classification results by the time domains (at 3380). This sub process is described in greater detail in relation to FIG. 35. As noted before, sometimes one model is relied upon more heavily than another model due to the classification confidence, or based upon events in the response. The clearest example of this is that if there is a period of time in which the user is not speaking, then the NLP model classification for this time period should be minimized, whereas the weights for video modeling and acoustic modeling should be afforded a much larger weight. Likewise, if two models are suggesting that the third model is incorrect or false, due to dishonesty or some other dissonance, then the odd model's classification may also be weighted lower than the other models accordingly.

Figure 35:
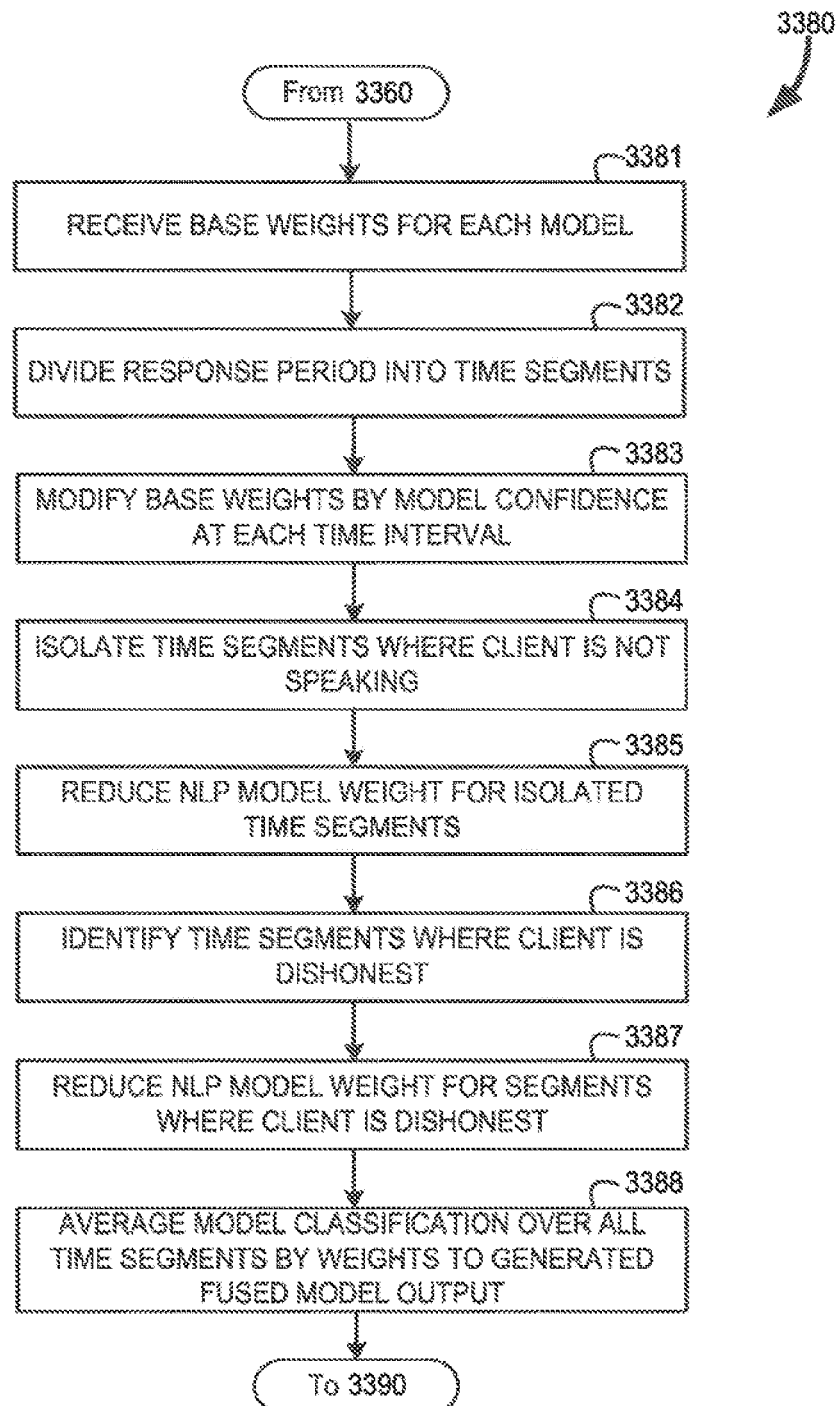
FIG. 35 is a logic flow diagram of the example process of model weighting and fusion, in accordance with some embodiments.

In FIG. 35, this weighting process involves starting with a base weight for each model (at 3381). The response is then divided up into discrete time segments (at 3382). The length of these time segments is configurable, and in one embodiment, they are set to a three second value, as most spoken concepts are formed in this length of time. The base weights for each of the models are then modified based upon model confidence levels, for each time period (at 3383). For example, if the NLP model is classified as being 96% confident during the first six seconds, but only 80% confident in the following twelve seconds, a higher weight will be applied to the first two time periods, and a lower weight for the following four time periods.

The system also determines when the user is not speaking, generally by relying upon the ASR outputs (at 3384). During these periods the NLP model is not going to be useful in determining the user's classification, and as such the NLP model weights are reduced for these time periods (at 3385). The degree of reduction may differ based upon configuration, but in some embodiments, the NLP is afforded no weight for periods when the user is not speaking.

Likewise, periods where the patient exhibits voice-based biomarkers associated with being dishonest may also be identified, based upon features and conclusions from the video and acoustic models (at 3386). Excessive fidgeting, shifting gaze, higher pitch and mumbling may all be correlated with dishonesty, and when multiple features are simultaneously present, the system flags these periods of the interaction as being suspect. During such time periods the NLP model weights is again reduced (at 3387), but only marginally. Even when a user is not being entirely honest, there is still beneficial information contained in the words they speak, especially for depression diagnosis. For example, even if a user is being dishonest about having suicidal thoughts (determined by sematic analysis) syntactical features may still be valid in determining the user's classification. As such, during periods of dishonesty, while the weight is tempered, the reduction is generally a quarter reduction in weight as opposed to a more steep weight reduction.

After all the weight adjustments have been made, the system performs a weighted average, over the entire response time period, of the models' classification results (at 3388). The final result of this condensation of the classifications over time and across the different component models results in the fused model output.

Returning to FIG. 33, this fused model output generates a final classification (at 3390) for the interaction. This classification, model results, and features are then output in aggregate or in part (at 3399). Returning to FIG. 29, these results are then presented to the client and other interested stakeholders (at 2960). This may include selecting which results any given entity should receive. For example, a client may be provided only the classification results, whereas a physician for the client will receive features relating to mood, topics of concern, indications of self-harm or suicidal thoughts, and the like. In contrast, an insurance company will receive the classification results, and potentially a sampling of the clinical data as it pertains to the individual's risk factors.

Even after reporting out classification results, the process continues by collecting new information as it becomes available, re-training models to ensure the highest levels of accuracy, and subsequent interactions and analysis of interaction results.

Figure 36:
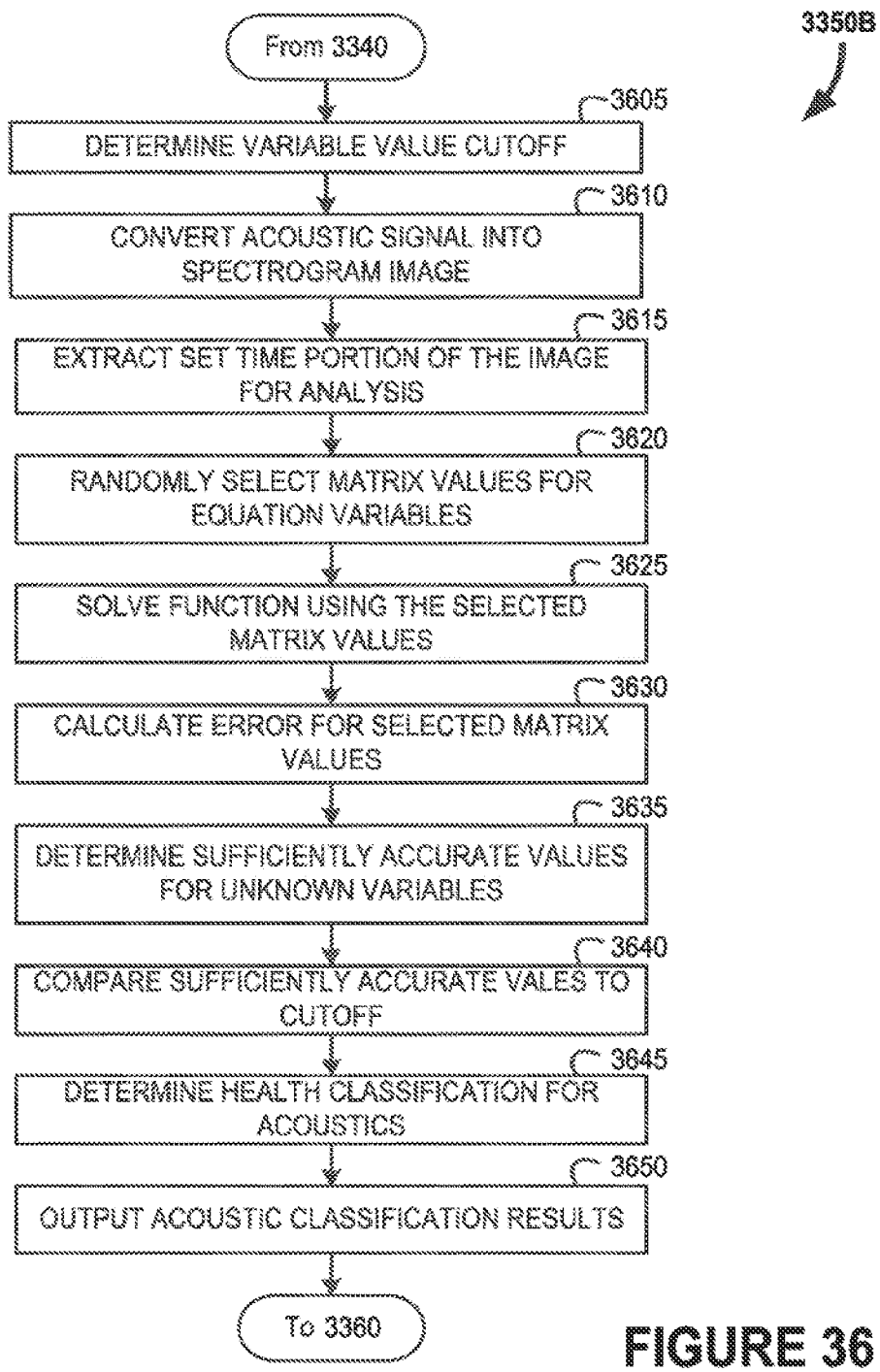
FIG. 36 is a logic flow diagram of the example simplified process of acoustic analysis, provided for illustrative purposes only.

Turning now to FIG. 36, one example substantiation of an acoustic modeling process 3350b is presented in greater detail. It should be noted, that despite the enhanced detail in this example process, this is still a significant simplification of but one of the analysis methodologies, and is intended purely as an illustrative process for the sake of clarity, and does not limit the analyses that are performed on the response data.

In this example process, a variable cutoff value is determined from the training datasets (at 3605). The acoustic signal that is received, in this particular analysis, is converted into a spectrogram image (at 3610), which provides information on the frequency of the audio signal and the amplitude at each of these frequencies. This image also tracks these over time. In this example process, a sample of the spectrogram image is taken that corresponds to a set length of time (at 3615). In some cases, this may be a ten second sample of the spectrogram data.

The image is converted into a matrix. This matrix is used in an equation to represent a higher order feature. The equation is developed from the training data utilizing machine learning techniques. The equation includes unknown variables, in addition to the input matrix of the high order feature (here the spectrogram image sample). These unknown variables are multiplied, divided, added or subtracted from the feature matrix (or any combination thereof). The solution to the equation is also known, resulting in the need to randomly select values for the unknown variables (at 3620) in an attempt to solve the equation (at 3630) and get a solution that is similar to the known solution.

The difference between the solved equation values is compared to the known solution value in order to calculate the error (at 3630). This process is repeated thousands or even millions of times until a close approximation of the correct variable values are found, as determined by a sufficiently low error calculation (at 3635). Once these sufficiently accurate values are found, they are compared against the cutoff values that were originally determined from the training data (at 3640). If the values are above or below the cutoffs, this indicates the existence or absence of the classification, based on the equation utilized. In this manner the classification for the spectrogram analysis may be determined (at 3645), which may be subsequently output (at 3650) for incorporation with the other model results.

Figure 37:
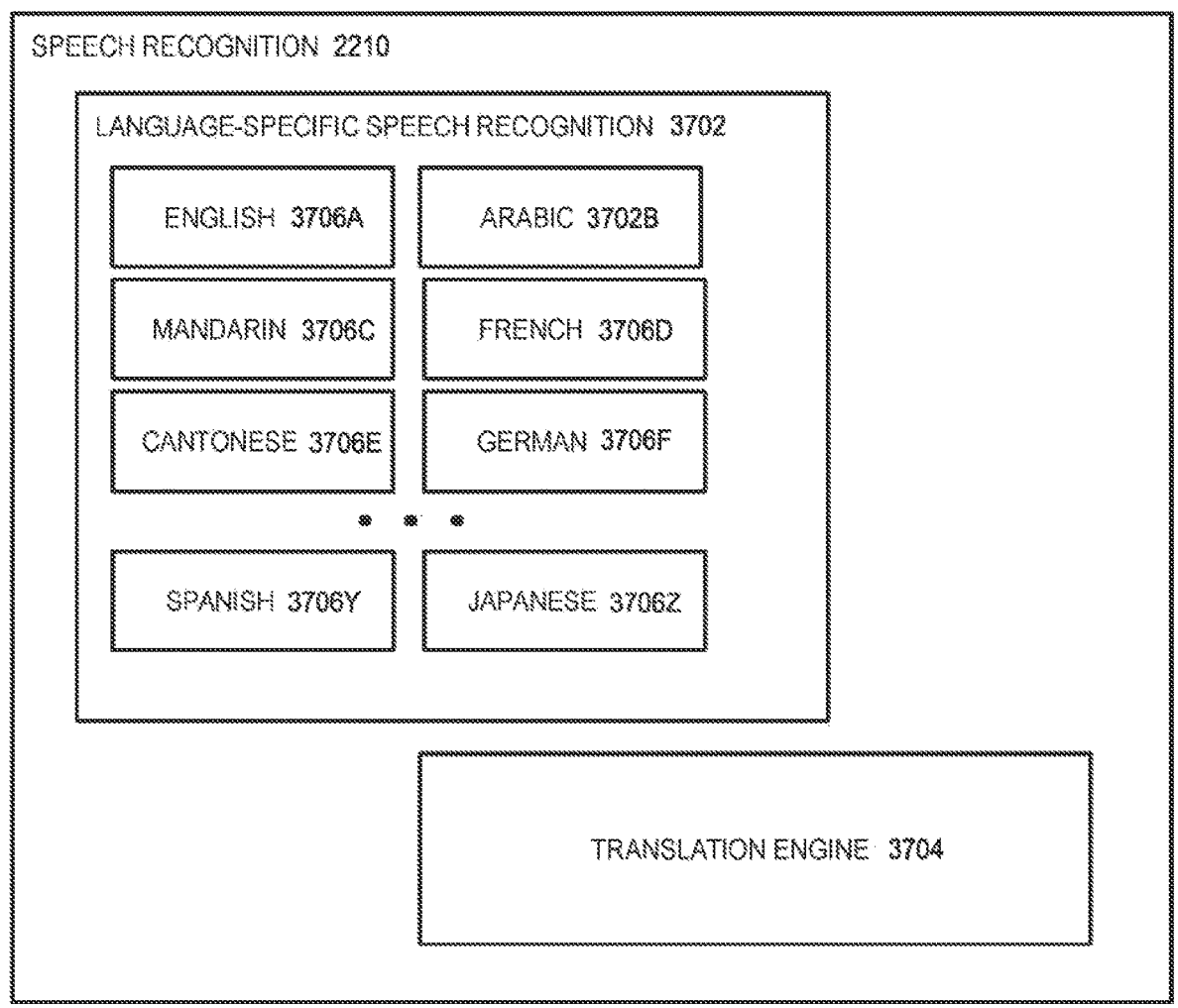
FIG. 37 is a block diagram showing speech recognition logic of the modeling computer system in greater detail.

Modeling system logic 5320 includes speech recognition 2210 (FIG. 22), which is shown in greater detail in (FIG. 37). Speech recognition is specific to the particular language of the speech. Accordingly, speech recognition 2210 includes language-specific speech recognition 3702, which in turn includes a number of language-specific speech recognition engines 3706A-Z. The particular languages of language-specific speech recognition engines 3706A-Z shown in (FIG. 14)7) are merely illustrative examples.

Speech recognition 2210 also includes a translation engine 3704. Suppose for example that the patient speaks a language that is recognized by any of language-specific speech recognition engines 3706A-Z but is not processed by language models 2214 (FIG. 22). Language-specific speech recognition 3702 (FIG. 37) produces text in the language spoken by the patient, i.e., the patient's language, from the audio signal received from the patient. To enable application of language models 2214, which cannot process text in the patient's language in this illustrative example, translation engine 3704 translates the text from the patient's language to a language that may be processed by language models 2214, e.g., English. While language models 2214 may not be as accurate when relying on translation by translation engine 3704, accuracy of language models 2214 is quite good with currently available translation techniques. In addition, the importance of language models 2214 is diluted significantly by the incorporation of acoustic models 2218, visual models 2222, and clinical data 2220 in the creation of composite model 2204. As a result, composite model 2204 is extremely accurate notwithstanding reliance on translation engine 3704.

Figure 10:
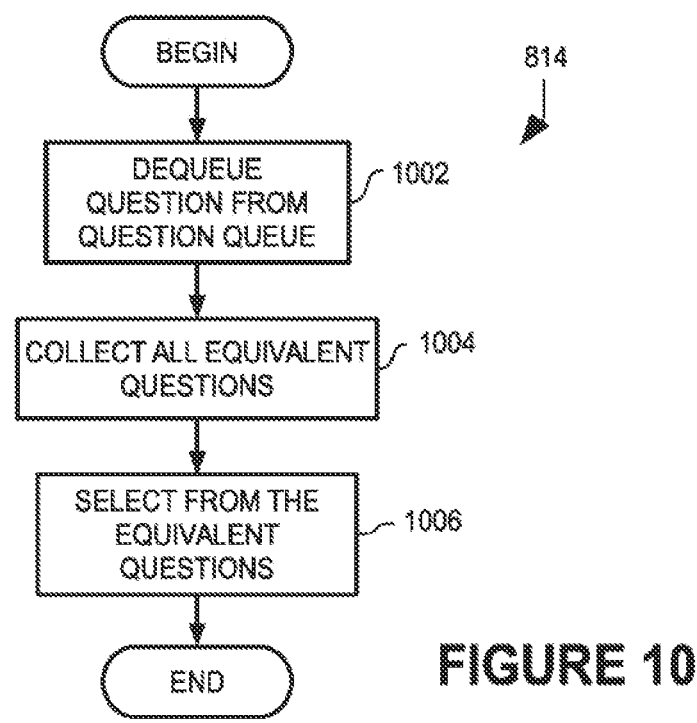
FIG. 10 is a logic flow diagram of a step of FIG. 8 in greater detail.
Figure 11:
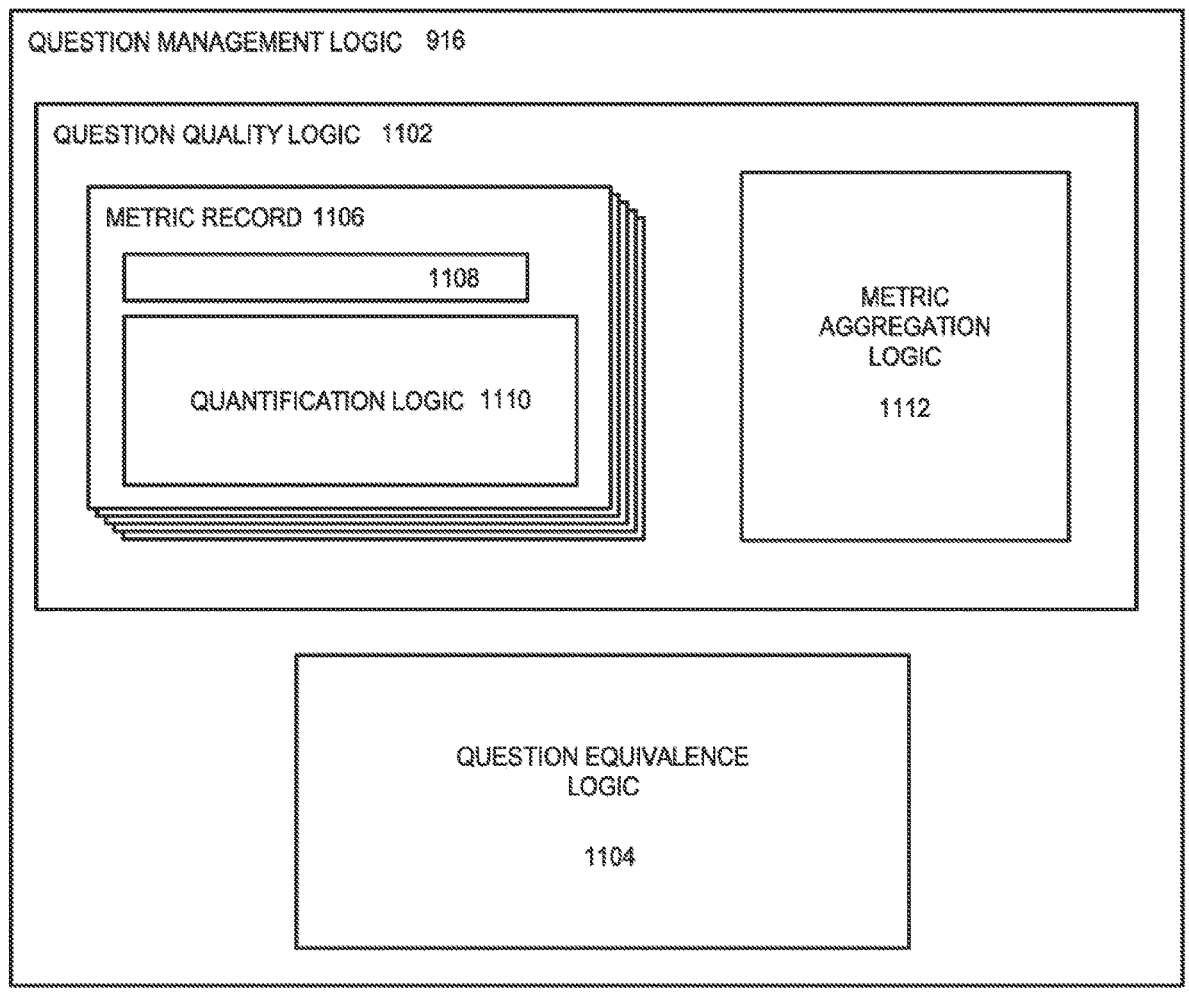
FIG. 11 is a block diagram of question management logic of the question and adaptive action bank of FIG. 9 in greater detail.
Figure 12:
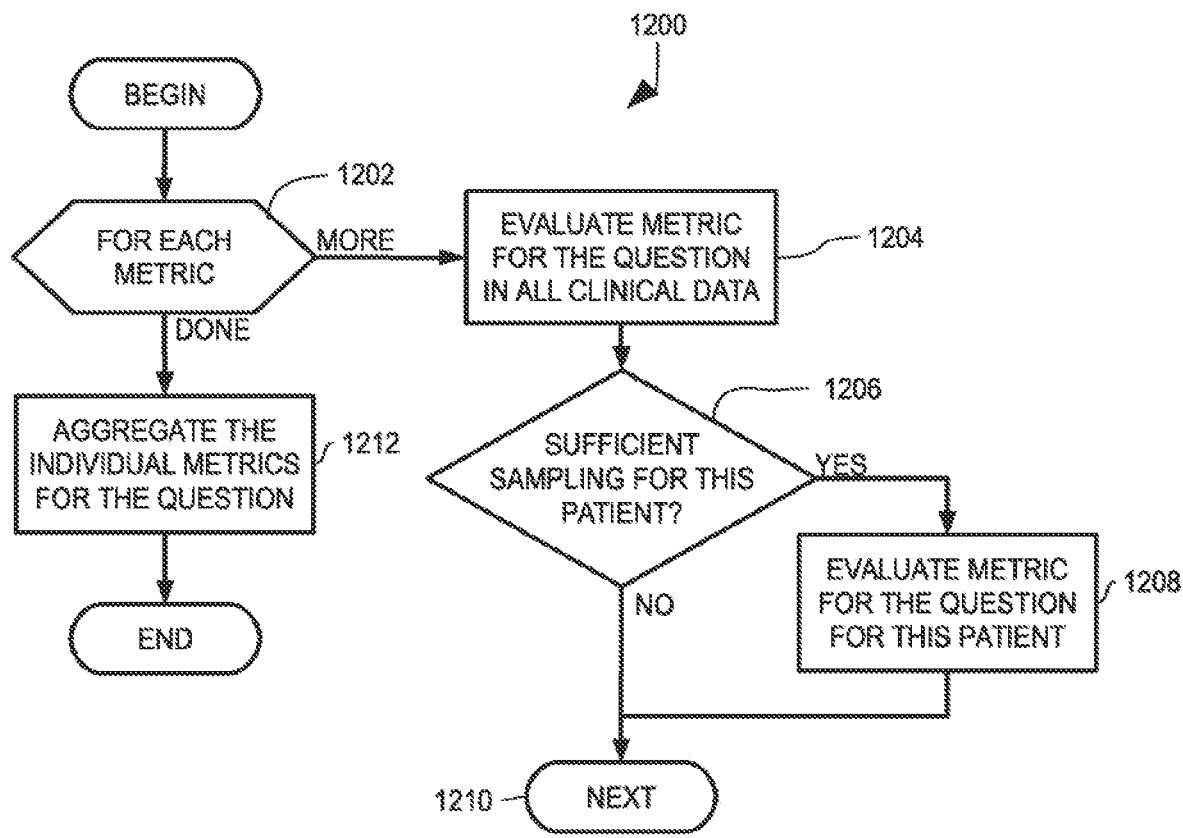
FIG. 12 is a logic flow diagram of determination of the quality of a question in accordance with the present disclosure.
Figure 38:
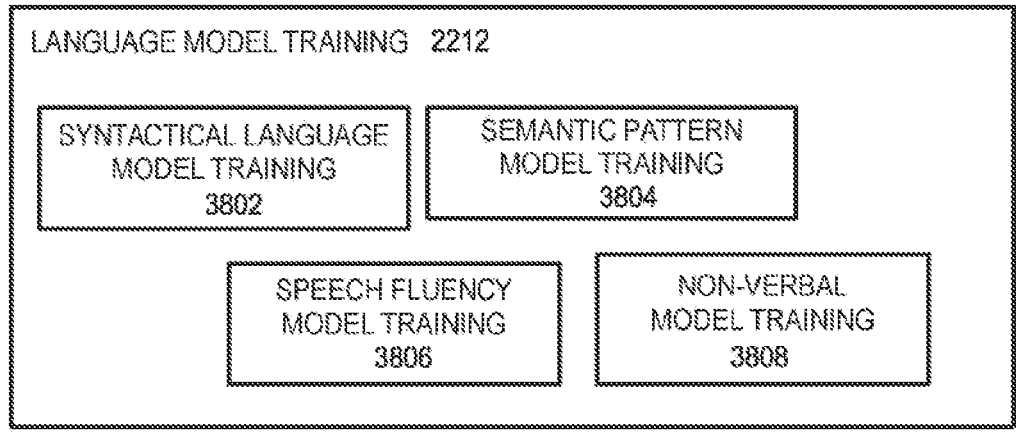
FIG. 38 is a block diagram showing language model training logic of the modeling computer system in greater detail.
Figure 39:
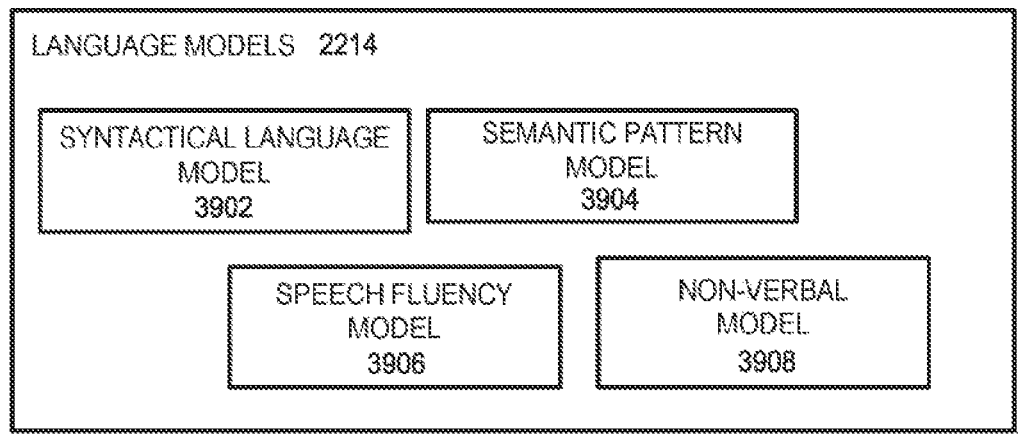
FIG. 39 is a block diagram showing language model logic of the modeling computer system in greater detail.

Modeling system logic 5320 includes language model training 2212 (FIG. 22) and language models 2214, which are shown in greater detail in FIGS. 10 and 11, respectively. Language model training 2212 (FIG. 38) includes logic for training respective models of language models 2214. For example, language model training 2212 (FIG. 38) includes syntactic language model training 3802, semantic pattern model training 3804, speech fluency model training 3806, and non-verbal model training 3808 which include logic for training syntactic language model 3902, semantic pattern model 3904, speech fluency model 3906, and non-verbal model 3908, respectively, of language models 2214.

Each of models 3902-3908 includes deep learning (also known as deep structured learning or hierarchical learning) logic that assesses the patient's depression from text received from speech recognition 2210.

Syntactic language model 3902 assesses a patient's depression from syntactic characteristics of the patient's speech. Examples of such syntactic characteristics include sentence length, sentence completion, sentence complexity, and negation. When a patient speaks in shorter sentences, fails to complete sentences, speaks in simple sentences, and/or uses relatively frequent negation (e.g., "no", "not", "couldn't", "won't", etc.), syntactic language model 3902 determines that the patient is more likely to be depressed.

Semantic pattern model 3904 assesses a patient's depression from positive and/or negative content of the patient's speech—i.e., from sentiments expressed by the patient. Some research suggests that expression of negative thoughts may indicate depression and expression of positive thoughts may counter-indicate depression. For example, "the commute here was awful" may be interpreted as an indicator for depression while "the commute here was awesome" may be interpreted as a counter-indicator for depression.

Speech fluency model 3906 assesses a patient's depression from fluency characteristics of, i.e., the flow of, the patient's speech. Fluency characteristics may include, for example, word rates, the frequency and duration of pauses in the speech, the prevalence of filler expressions such as "uh" or "umm", and packet speech patterns. Some research suggests that lower word rates, frequent and/or long pauses in speech, and high occurrence rates of filler expressions may indicate depression. Perhaps more so than others of language models 2214, speech fluency model 3906 may be specific to the individual patient. For example, rates of speech (word rates) vary widely across geographic regions. The normal rate of speech for a patient from New York City may be significantly greater than the normal rate of speech for a patient from Minnesota.

Non-verbal model 3908 assesses a patient's depression from non-verbal characteristics of the patient's speech, such as laughter, chuckles, and sighs. Some research suggests that sighs may indicate depression while laughter and chuckling (and other forms of partially repressed laughter such as giggling) may counter-indicate depression.

Figure 40:
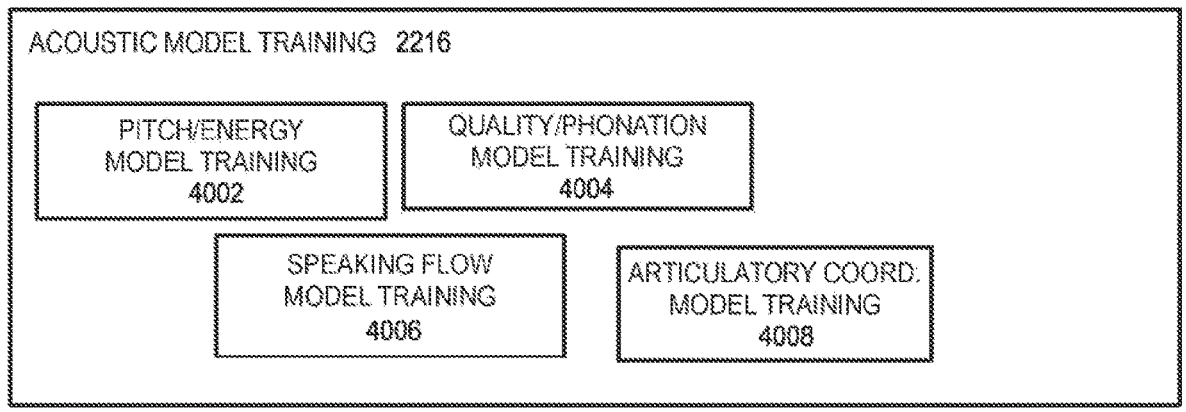
FIG. 40 is a block diagram showing acoustic model training logic of the modeling computer system in greater detail.
Figure 41:
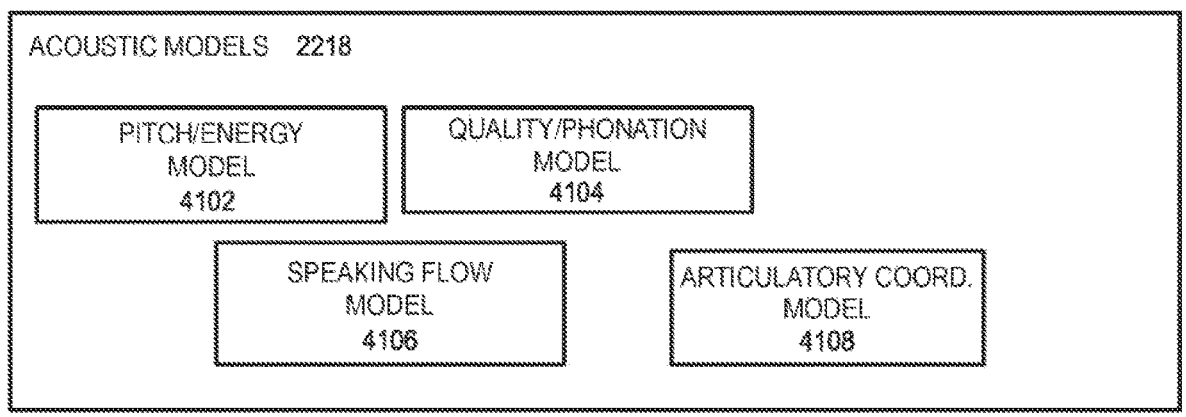
FIG. 41 is a block diagram showing acoustic model logic of the modeling computer system in greater detail.

Modeling system logic 5320 includes acoustic model training 2216 (FIG. 22) and acoustic models 2214, which are shown in greater detail in FIGS. 12 and 13, respectively. Acoustic model training 2216 (FIG. 40) includes logic for training respective models of acoustic models 2218 (FIG. 41). For example, acoustic model training 2216 (FIG. 40) includes pitch/energy model training 4002, quality/phonation model training 4004, speaking flow model training 4006, and articulatory coordination model training 4008 which include logic for training pitch/energy model 4102, quality/phonation pattern model 4104, speaking flow model 4106, and articulatory coordination model 1308, respectively, of acoustic models 2218.

Each of models 4102-4108 includes deep learning (also known as deep structured learning or hierarchical learning) logic that assesses the patient's depression from audio signals representing the patient's speech as received from collected patient data 2206 (FIG. 22) and preprocessing 2208.

Pitch/energy model 4102 assesses a patient's depression from pitch and energy of the patient's speech. Examples of energy include loudness and syllable rate, for example. When a patient speaks with a lower pitch, more softly, and/or more slowly, pitch/energy model 4102 determines that the patient is more likely to be depressed.

Quality/phonation model 4104 assesses a patient's depression from voice quality and phonation aspects of the patient's speech. Different voice source modifications may occur in depression and affect the voicing related aspects of speech, both generally and for specific speech sounds.

Speaking flow model 4106 assesses a patient's depression from the flow of the patient's speech. Speaking flow characteristics may include, for example, word rates, the frequency and duration of pauses in the speech, the prevalence of filler expressions such as "uh" or "umm", and packet speech patterns.

Articulatory coordination model 4108 assesses a patient's depression from articulatory coordination in the patient's speech. Articulatory coordination refers to micro-coordination in timing, among articulators and source characteristics. This coordination becomes worse when the patient is depressed.

Figure 42:
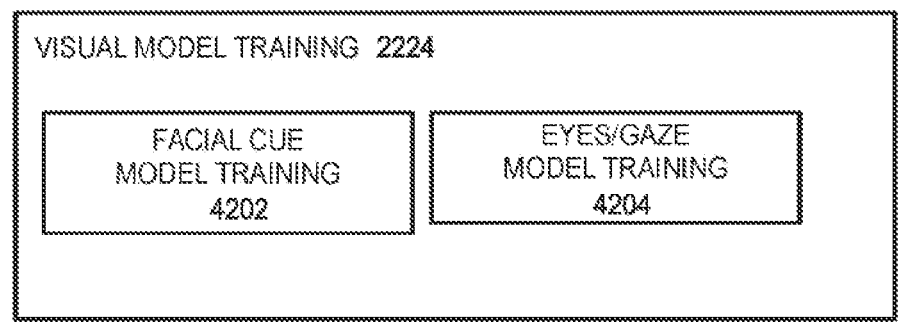
FIG. 42 is a is a block diagram showing visual model training logic of the modeling computer system in greater detail.
Figure 43:
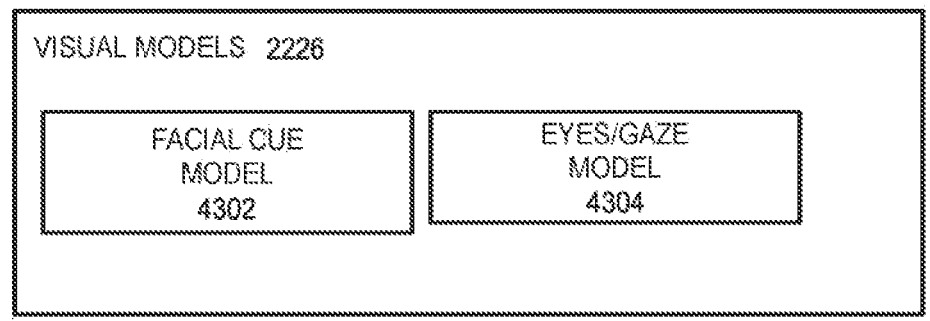
FIG. 43 is a block diagram showing visual model logic of the modeling computer system in greater detail.
Figure 53:
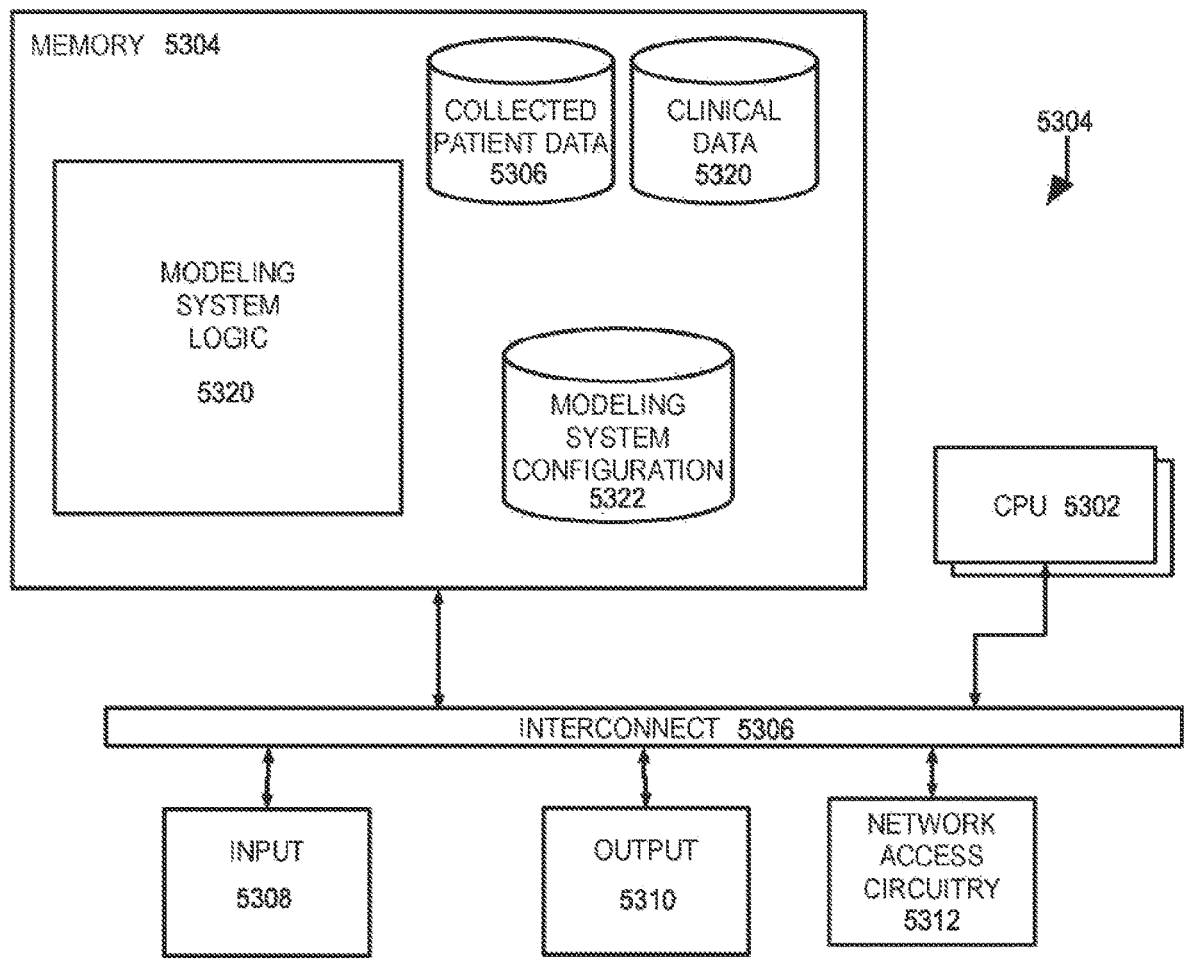
FIG. 53 is a block diagram of the modeling computer system of FIG. 3 in greater detail.

Modeling system logic 5320 (FIG. 53) includes visual model training 2224 (FIG. 22) and visual models 2226, which are shown in greater detail in FIGS. 14 and 15, respectively. Visual model training 2224 (FIG. 42) includes logic for training respective models of visual models 226 (FIG. 53). For example, visual model training 2224 (FIG. 42) includes facial cue model training 4202 and eye/gaze model training 4204 which include logic for training facial cue model 4302 and eye/gaze model 4304, respectively, of visual models 2226.

Each of models 4302-4304 includes deep learning (also known as deep structured learning or hierarchical learning) logic that assesses the patient's depression from video signals representing the patient's speech as received from collected patient data 2206 (FIG. 22) and preprocessing 2208.

Facial cue model 4302 assesses a patient's depression from facial cues recognized in the video of the patient's speech. Eye/gaze model 4304 assesses a patient's depression from observed and recognized eye movements in the video of the patient's speech.

As described above, composite model builder 2222 (FIG. 22) builds composite model 2204 by combining language models 2214, acoustic models 2218, and visual models 2226 and training the combined model using both clinical data 2220 and collected patient data 2206. As a result, composite model 2204 assesses depression in a patient using what the patient says, how the patient says it, and contemporaneous facial and eye expressions in combination. Such provides a particularly accurate and effective tool for assessing the patient's depression.

The above description is illustrative only and is not limiting. For example, while the particular mental health condition addressed by the system and methods as described herein, it should be appreciated that the techniques described herein may effectively assess and/or screen for a number of other mental health conditions such as anxiety, post-traumatic stress disorder (PTSD) and stress generally, drug and alcohol addiction, bipolar disorder, among others. In addition, while assessment test administrator 2202 is described as assessing the mental health of the human subject, who may be a patient, it is appreciated that "assessment" sometimes refers to professional assessments made by professional clinicians. As used herein, the assessment provided by assessment test administrator 2202 may be any type of assessment in the general sense, including screening or monitoring.

Scoring

The models described herein may produce scores, at various stages of an assessment. The scores produced may be scaled scores or binary scores. Scaled scores may range over a large number of values, while binary scores may be one of two discrete values. The system disclosed may interchange binary and scaled scores at various stages of the assessment, to monitor different mental states, or update particular binary scores and particular scaled scores for particular mental states over the course of an assessment.

The scores produced by the system, either binary or scaled, may be produced after each response to each query in the assessment, or may be formulated in part based on previous queries. In the latter case, each marginal score acts to fine-tune a prediction of depression, or of another mental state, as well as to make the prediction more robust. Marginal predictions may increase confidence measures for predictions of mental states in this way, after a particular number of queries and responses (correlated with a particular intermediate mental state)

For scaled scores, the refinement of the score may allow clinicians to determine, with greater precision, severities of one or more mental states the patient is experiencing. For example, the refinement of the scaled score, when observing multiple intermediate depression states, may allow a clinician to determine whether the patient has mild, moderate, or severe depression. Performing multiple scoring iterations may also assist clinicians and administrators in removing false negatives, by adding redundancy and adding robustness. For example, initial mental state predictions may be noisier, because relatively fewer speech segments are available to analyze, and NLP algorithms may not have enough information to determine semantic context for the patient's recorded speech. Even though a single marginal prediction may itself be a noisy estimate, refining the prediction by adding more measurements may reduce the overall variance in the system, yielding a more precise prediction. The predictions described herein may be more actionable than those which may be obtained by simply administering a survey, as people may have incentive to lie about their conditions. Administering a survey may yield high numbers of false positive and false negative results, enabling patients who need treatment to slip through the cracks. In addition, although trained clinicians may notice voice and face-based biomarkers, they may not be able to analyze the large amount of data the system disclosed is able to analyze.

The scaled score may be used to describe a severity of a mental state. The scaled score may be, for example, a number between 1 and 5, or between 0 and 100, with larger numbers indicating a more severe or acute form of the patient's experienced mental state. The scaled score may include integers, percentages, or decimals. Conditions for which the scaled score may express severity may include, but are not limited to depression, anxiety, stress, PTSD, phobic disorder, and panic disorder. In one example, a score of 0 on a depression-related aspect of an assessment may indicate no depression, a score of 50 may indicate moderate depression, and a score of 100 may indicate severe depression. The scaled score may be a composition of multiple scores. A mental state may be expressed as a composition of mental sub-states, and a patient's composite mental state may be a weighted average of individual scores from the mental sub-states. For example, a composition score of depression may be a weighted average of individual scores for anger, sadness, self-image, self-worth, stress, loneliness, isolation, and anxiety.

A scaled score may be produced using a model that uses a multilabel classifier. This classifier may be, for example, a decision tree classifier, a k-nearest neighbors' classifier, or a neural network-based classifier. The classifier may produce multiple labels for a particular patient at an intermediate or final stage of assessment, with the labels indicating severities or extents of a particular mental state. For example, a multilabel classifier may output multiple numbers, which may be normalized into probabilities using a softmax layer. The label with the largest probability may indicate the severity of the mental state experienced by the patient.

The scaled score may also be determined using a regression model. The regression model may determine a fit from training examples that are expressed as sums of weighted variables. The fit may be used to extrapolate a score from a patient with known weights. The weights may be based in part on features, which may be in part derived from the audiovisual signal (e.g., voice-based biomarkers) and in part derived from patient information, such as patient demographics. Weights used to predict a final score or an intermediate score may be taken from previous intermediate scores.

The scaled score may be scaled based on a confidence measure. The confidence measure may be determined based on recording quality, type of model used to analyze the patient's speech from a recording (e.g., audio, visual, semantic), temporal analysis related to which model was used most heavily during a particular period of time, and the point in time of a specific voice-based biomarker within an audiovisual sample. Multiple confidence measures may be taken to determine intermediate scores. Confidence measures during an assessment may be averaged in order to determine a weighting for a particular scaled score.

The binary score may reflect a binary outcome from the system. For example, the system may classify a user as being either depressed or not depressed. The system may use a classification algorithm to do this, such as a neural network or an ensemble method. The binary classifier may output a number between 0 and 1. If a patient's score is above a threshold (e.g., 0.5), the patient may be classified as "depressed." If the patient's score is below the threshold, the patient may be classified as "not depressed." The system may produce multiple binary scores for multiple intermediate states of the assessment. The system may weight and sum the binary scores from intermediate sates of the assessment in order to produce an overall binary score for the assessment.

The outputs of the models described herein can be converted to a calibrated score, e.g., a score with a unit range. The outputs of the models described herein can additionally or alternatively be converted to a score with a clinical value. A score with a clinical value can be a qualitative diagnosis (e.g., high risk of severe of depression). A score with a clinical value can alternatively be a normalized, qualitative score that is normalized with respect to the general population or a specific sub-population of patients. The normalized, qualitative score may indicate a risk percentage relative to the general population or to the sub-population.

The systems described herein may be able to identify a mental state of a subject (e.g., a mental disorder or a behavioral disorder) with less error (e.g., 10% less) or a higher accuracy (e.g., 10% more) than a standardized mental health questionnaire or testing tool. The error rate or accuracy may be established relative to a benchmark standard usable by an entity for identifying or assessing one or more medical conditions comprising said mental state. The entity may be a clinician, a healthcare provider, an insurance company, or a government-regulated body. The benchmark standard may be a clinical diagnosis that has been independently verified.

Confidence

The models described herein may use confidence measures. A confidence measure may be a measure of how effective the score produced by the machine learning algorithm may be in order of accurately predicting a mental state, such as depression. A confidence measure may depend on conditions under which the score was taken. A confidence measure may be expressed as a whole number, a decimal, or a percentage. Conditions may include a type of recording device, an ambient space in which signals were taken, background noise, patient speech idiosyncrasies, language fluency of a speaker, the length of responses of the patient, an evaluated truthfulness of the responses of the patient, and frequency of unintelligible words and phrases. Under conditions where the quality of the signal or speech makes it more difficult for the speech to be analyzed, the confidence measure may have a smaller value. In some embodiments, the confidence measure may be added to the score calculation, by weighting a calculated binary or scaled score with the confidence measure. In other embodiments, the confidence measure may be provided separately. For example, the system may tell a clinician that the patient has a 0.93 depression score with 75% confidence.

The confidence level may also be based on the quality of the labels of the training data used to train the models that analyze the patient's speech. For example, if the labels are based on surveys or questionnaires completed by patients rather than official clinical diagnoses, the quality of the labels may be determined to be lower, and the confidence level of the score may thus be lower. In some cases, it may be determined that the surveys or questionnaires have a certain level of untruthfulness. In such cases, the quality of the labels may be determined to be lower, and the confidence level of the score may thus be lower.

Various measures may be taken by the system in order to improve a confidence measure, especially where the confidence measure is affected by the environment in which the assessment takes place. For example, the system may employ one or more signal processing algorithms to filter out background noise, or use impulse response measurements to determine how to remove effects of reverberations caused by objects and features of the environment in which the speech sample was recorded. The system may also use semantic analysis to find context clues to determine the identities of missing or unintelligible words.

In addition, the system may use user profiles to group people based on demeanor, ethnic background, gender, age, or other categories. Because people from similar groups may have similar voice-based biomarkers, the system may be able to predict depression with higher confidence, as people who exhibit similar voice-based biomarkers may indicate depression in similar manners.

For example, depressed people from different backgrounds may be variously categorized by slower speech, monotone pitch or low pitch variability, excessive pausing, vocal timbre (gravelly or hoarse voices), incoherent speech, rambling or loss of focus, terse responses, and stream-of-consciousness narratives. These voice-based biomarkers may belong to one or more segments of patients analyzed.

Figure 44:
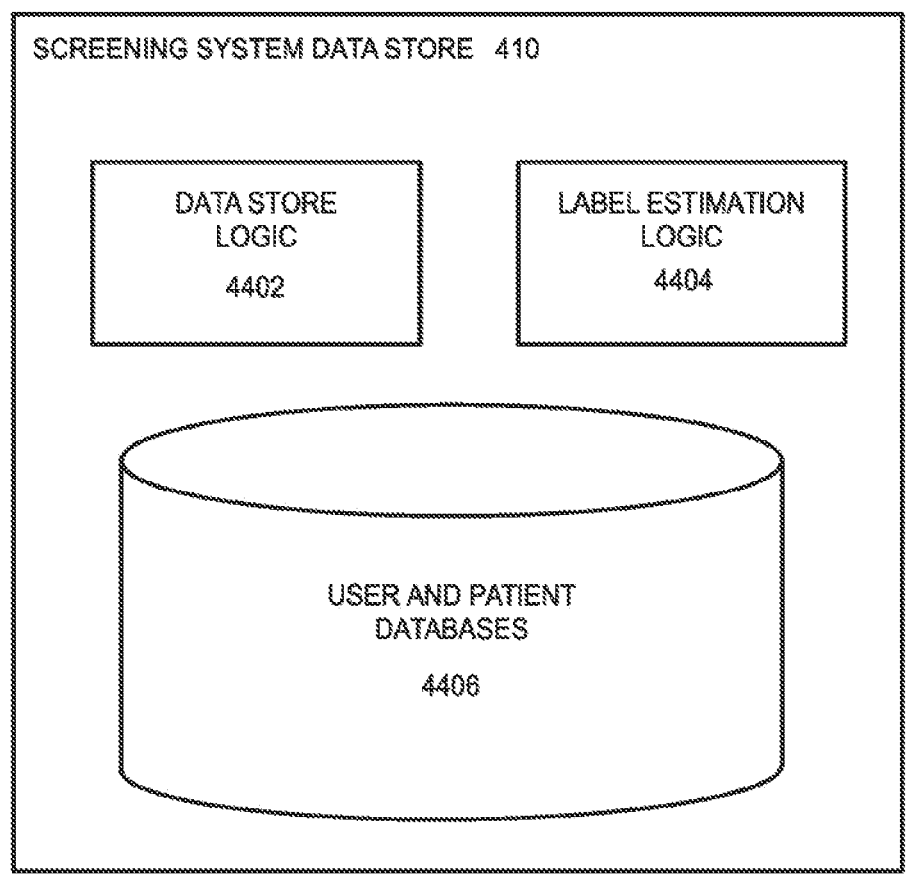
FIG. 44 is a block diagram of a screening or monitoring system data store of the interactive health screening or monitoring logic of FIG. 1A in greater detail.

Screening system data store 410 (shown in greater detail in FIG. 44) stores and maintains all user and patient data needed for, and collected by, screening or monitoring in the manner described herein. Screening system data store 410 includes data store logic 4402, label estimation logic 4404, and user and patient databases 4406. Data store logic 4402 controls access to user and patient databases 4406. For example, data store logic 4402 stores audiovisual signals of patients' responses and provides patient clinical history data upon request. If the requested patient clinical history data is not available in user and patient databases 4406, data store logic 4402 retrieves the patient clinical history data from clinical data server 106. If the requested patient social history data is not available in user and patient databases 4406, data store logic 4402 retrieves the patient social history data from social data server 108. Users who are not patients include health care service providers and payers.

Social media server 108 may include a wide variety of patient/subject data including but not limited to retail purchasing records, legal records (including criminal records), income history, as these may provide valuable insights to a person's health. In many instances, these social determinants of disease contribute more to a person's morbidity than medical care. Appendix B depicts a "Health Policy Brief: The Relative Contributions of Multiple Determinants to Health Outcomes".

Label estimation logic 4404 includes logic that specifies labels for which the various learning machines of health screening or monitoring server 102 screen. Label estimation logic 4404 includes a user interface through which human operators of health screening or monitoring server 102 may configure and tune such labels.

Label estimation logic 4404 also controls quality of model training by, inter alia, determining whether data stored in user and patient databases 4406 is of adequate quality for model training. Label estimation logic 4404 includes logic for automatically identifying or modifying labels. In particular, if model training reveals a significant data point that is not already identified as a label, label estimation logic 4404 looks for correlations between the data point and patient records, system predictions, and clinical insights to automatically assign a label to the data point.

While interactive screening or monitoring server logic 502 is described as conducting an interactive, spoken conversation with the patient to assess the health state of the patient, interactive screening or monitoring server logic 502 may also act in a passive listening mode. In this passive listening mode, interactive screening or monitoring server logic 502 passively listens to the patient speaking without directing questions to be asked of the patient.

Passive listening mode, in this illustrative embodiment, has two (2) variants. In the first, "conversational" variant, the patient is engaged in a conversation with another whose part of the conversation is not controlled by interactive screening or monitoring server logic 502. Examples of conversational passive listening include a patient speaking with a clinician and a patient speaking during a telephone call reminding the patient of an appointment with a clinician or discussing medication with a pharmacist. In the second, "fly-on-the-wall" (FOTW) or "ambient" variant, the patient is speaking alone or in a public, or semi-public, place. Examples of ambient passive listening include people speaking in a public space or a hospital emergency room and a person speaking alone, e.g., in an audio diary or leaving a telephone message. One potentially useful scenario for screening or monitoring a person speaking alone involves interactive screening or monitoring server logic 502 screening or monitoring calls to police emergency services (i.e., "9-1-1"). Analysis of emergency service callers may distinguish truly urgent callers from less urgent callers.

It should be noted that this detailed description is intended to describe what is technologically possible. Practicing the techniques described herein should comply with legal requirements and limitations that may vary from jurisdiction to jurisdiction, including federal statutes, state laws, and/or local ordinances. For example, some jurisdictions may require explicit notice and/or consent of involved person(s) prior to capturing their speech. In addition, acquisition, storage, and retrieval of clinical records should be practiced in a manner that is in compliance with applicable jurisdictional requirement(s).

Figure 45:
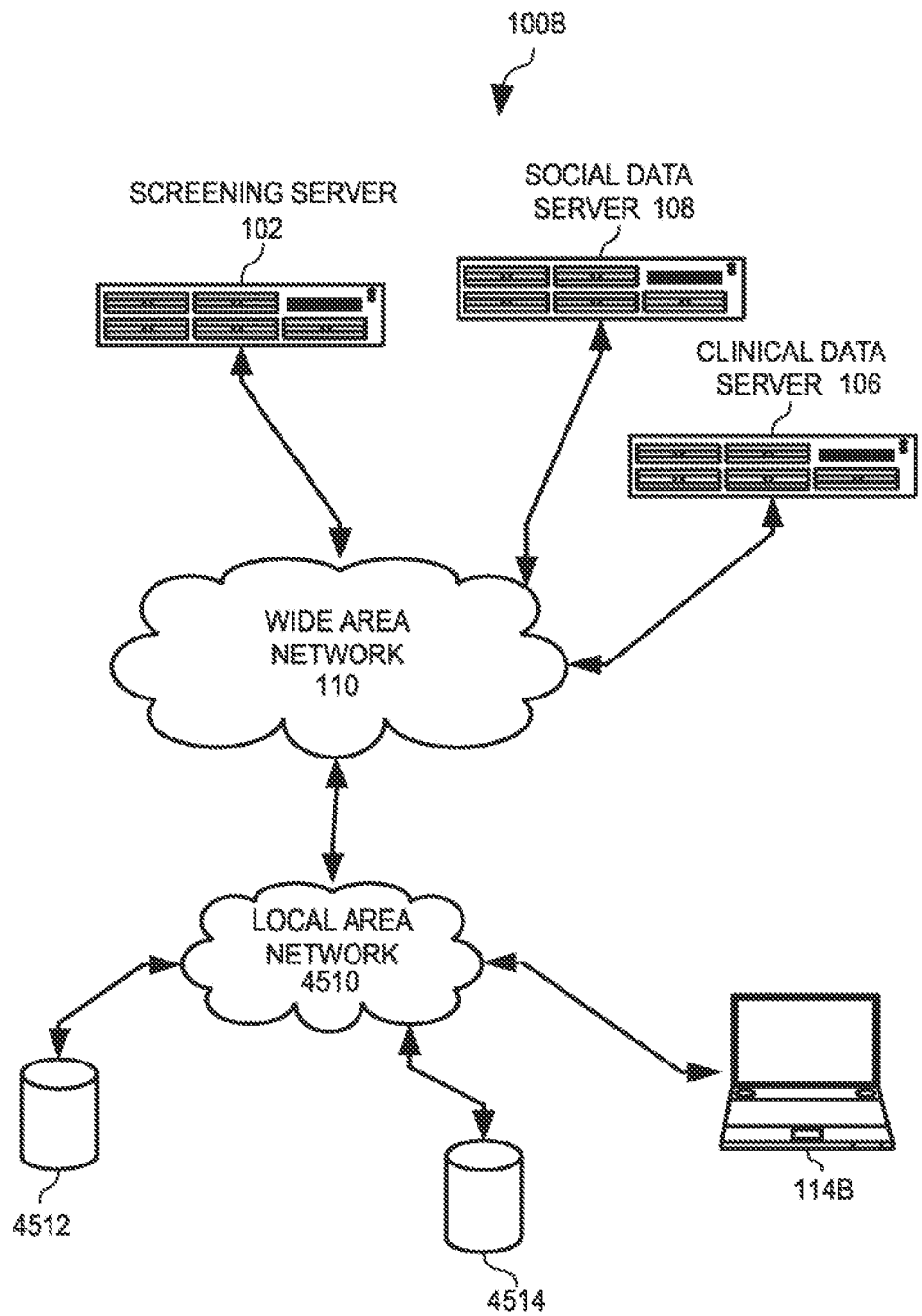
FIG. 45 shows a health screening or monitoring system in which a health screening or monitoring server estimates a health state of a patient by passively listening to ambient speech in accordance with the present disclosure.

Patient screening or monitoring system 100B (FIG. 45) illustrates a passive listening variation of patient screening or monitoring system 100 (FIG. 1). Patient screening or monitoring system 100B (FIG. 45) includes health screening or monitoring server 102, a clinical data server 106, and a social data server 108, which are as described above and, also as described above, connected to one another through WAN 110.

Since the patient and the clinician are in close physical proximity to one another in conversational passive listening, the remainder of the components of patient screening or monitoring system 110B are connected to one another and WAN 110 through a local area network (LAN) 4510.

There are a number of ways to distinguish the patient's voice from the clinician's.

A particularly convenient one is to have two (2) separate listening devices 4512 and 4514 for the patient and clinician, respectively. In this illustrative embodiment, listening devices 4512 and 4514 are smart speakers, such as the HomePod™ smart speaker available from Apple Computer of Cupertino, California, the Google Home™ smart speaker available from Google LLC of Mountain View, California, and the Amazon Echo™ available from Amazon.com, Inc. of Seattle, Washington. In other embodiments, listening devices 4512 and 4514 may be other types of listening devices such as microphones coupled to clinician device 114B, for example.

In some embodiments, a single listening device 4514 is used and screening or monitoring server 102 distinguishes between the patient and the clinician using conventional voice recognition techniques. Accuracy of such voice recognition may be improved by training screening or monitoring server 102 to recognize the clinician's voice prior to any session with a patient. While the following description refers to a clinician as speaking to the patient, it should be appreciated that the clinician may be replaced with another. For example, in a telephone call made to the patient by a health care office administrator, e.g., support staff for a clinician, the administrator takes on the clinician's role as described in the context of conversational passive listening. Similarly, in a telephone call made by a pharmacy to a patient regarding prescriptions, the person or automated machine caller calling on behalf of the pharmacy takes on this clinician role as described herein. Appendix C depicts an exemplary Question Bank for some of the embodiments in accordance with the present invention.

Figure 46:
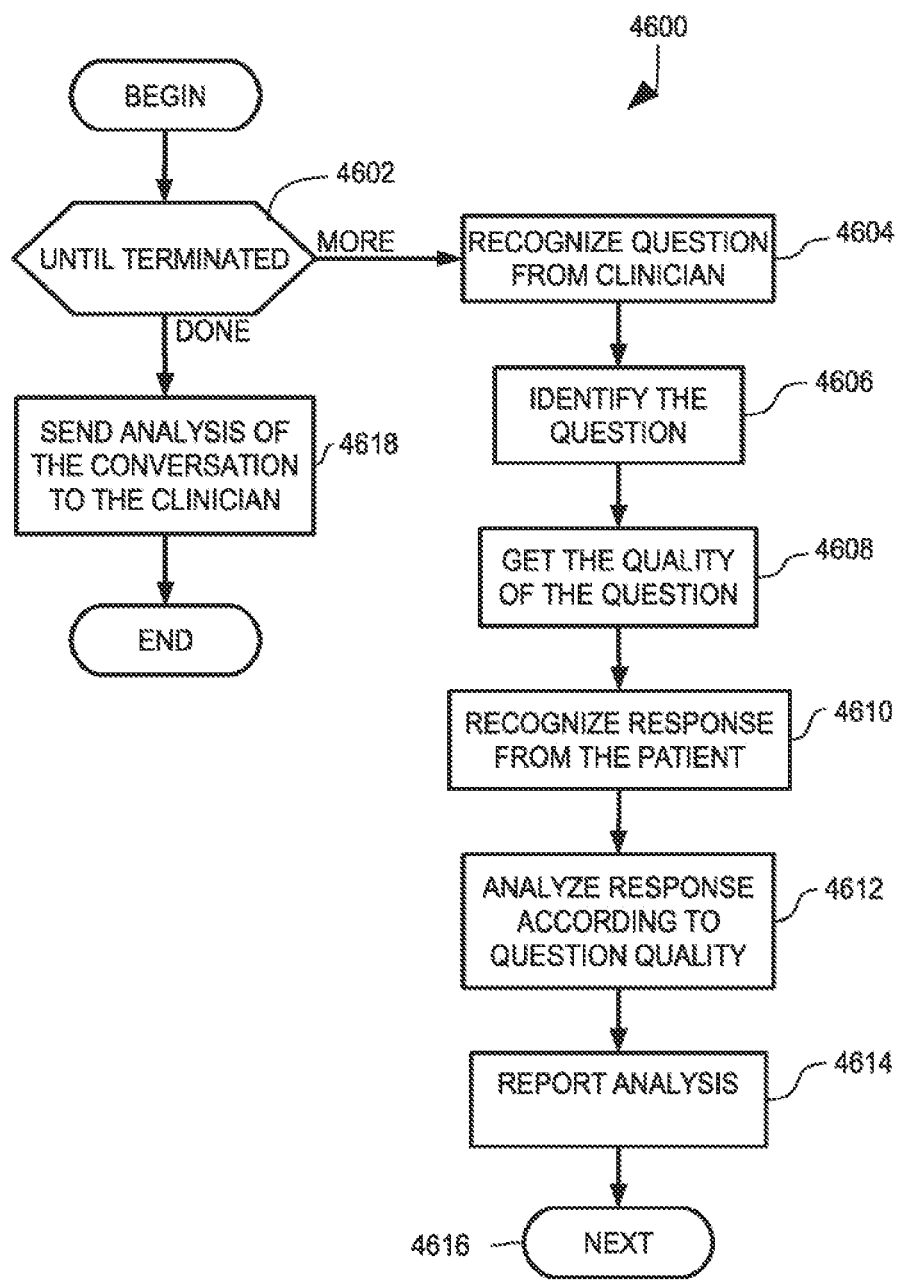
FIG. 46 is a logic flow diagram illustrating the estimation a health state of a patient by passively listening to ambient speech in accordance with the present disclosure.

Processing by interactive health screening or monitoring logic 402, particularly generalized dialogue flow logic 602 (FIG. 7), in conversational passive listening is illustrated by logic flow diagram 4600 (FIG. 46). FIG. 46 shows an instantiation of a dynamic mode, in which query content is analyzed in real-time. Loop step 4602 and next step 4616 define a loop in which generalized dialogue flow logic 602 processes audiovisual signals of the conversation between the patient and the clinician according to steps 4604-4614. While steps 4604-4614 are shown as discrete, sequential steps, they are performed concurrently with one another in an ongoing basis by generalized dialogue flow logic 602. The loop of steps 4602-4616 is initiated and terminated by the clinician using conventional user interface techniques, e.g., using clinician device 114B (FIG. 45) or listening device 4514.

In step 4604 (FIG. 46), generalized dialogue flow logic 602 recognizes a question to the patient posed by the clinician and sends the question to runtime model server logic 504 for processing and analysis. Generalized dialogue flow logic 602 receives results 1820 for the audiovisual signal of the clinician's utterance, and results 1820 (FIG. 18) include a textual representation of the clinician's utterance from ASR logic 1804 along with additional information from descriptive model and analytics 1812. This additional information includes identification of the various parts of speech of the words in the clinician's utterance.

Figure 7:
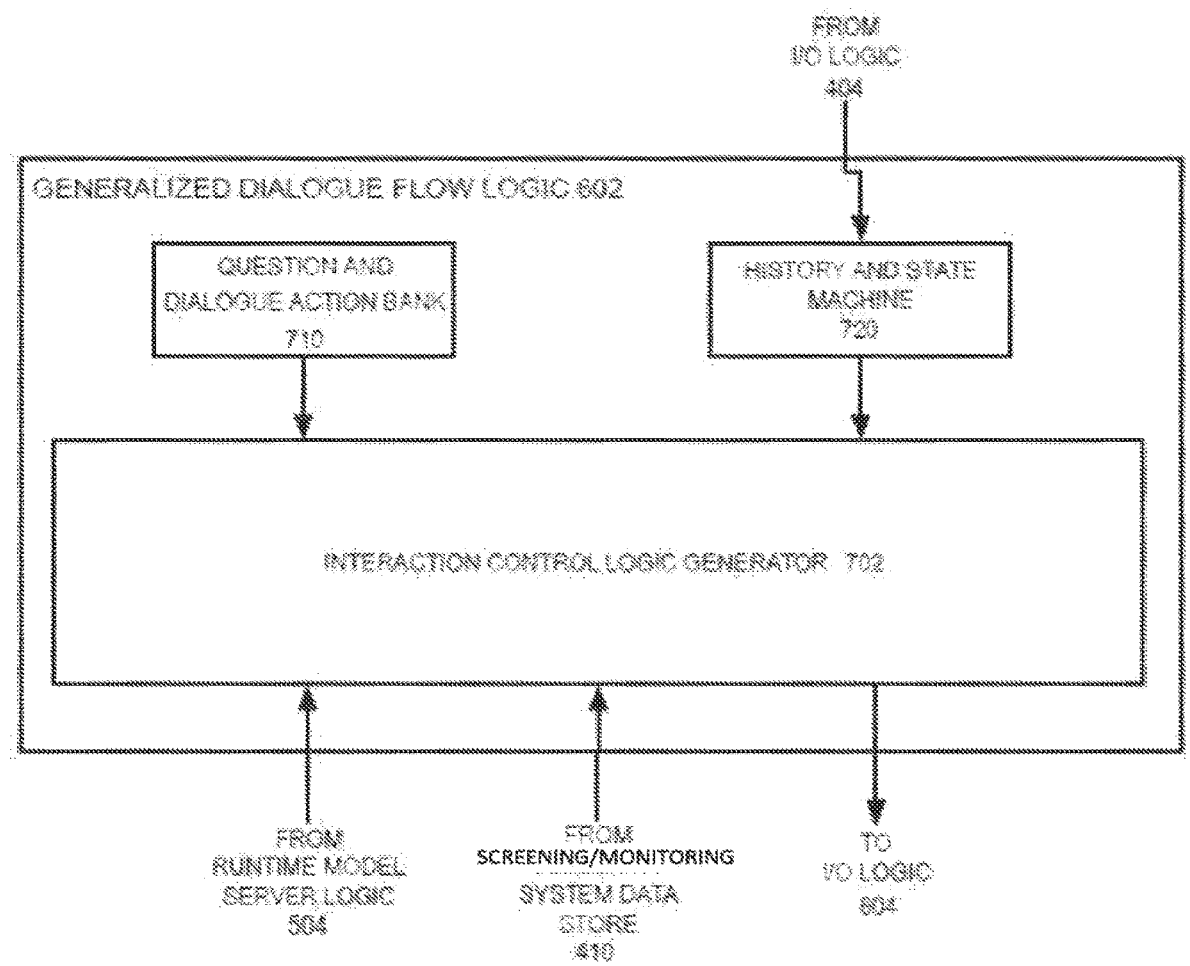
FIG. 7 is a block diagram of generalized dialogue flow logic of the interactive screening or monitoring server logic of FIG. 6 in greater detail.

In step 4606 (FIG. 46), generalized dialogue flow logic 602 identifies the most similar question in question and dialogue action bank 710 (FIG. 7). If the question recognized in step 4604 is not identical to any questions stored in question and dialogue action bank 710, generalized dialogue flow logic 602 may identify the nearest question in the manner described above with respect to question equivalence logic 1104 (FIG. 11) or may identify the question in question and dialogue action bank 710 (FIG. 7) that is most similar linguistically.

In step 4608 (FIG. 46), generalized dialogue flow logic 602 retrieves the quality of the nearest question from question and dialogue action bank 710, i.e., quality 908 (FIG. 9).

In step 4610 (FIG. 46), generalized dialogue flow logic 602 recognizes an audiovisual signal representing the patient's response to the question recognized in step 4604.

The patient's response is recognized as an utterance of the patient immediately following the recognized question. The utterance may be recognized as the patient's by (i) determining that the voice is captured more loudly by listening device 4512 than by listening device 4514 or (ii) determining that the voice is distinct from a voice previously established and recognized as the clinician's.

In step 4612, generalized dialogue flow logic 602 sends the patient's response, along with the context of the clinician's corresponding question, to runtime model server logic 504 for analysis and evaluation. The context of the clinician's question is important, particularly if the semantics of the patient's response is unclear in isolation. For example, consider that the patient's answer is simply "Yes." That response is analyzed and evaluated very differently in response to the question "Were you able to find parking?" versus in response to the question "Do you have thoughts of hurting yourself?"

In step 4614, generalized dialogue flow logic 602 reports intermediate analysis received from results 1820 to the clinician. In instances in which the clinician is using clinician device 114B during the conversation, e.g., to review electronic health records of the patient, the report may be in the form of animated gauges indicating intermediate scores related to a number of health states. Examples of animated gauges include steam gauges, i.e., round dial gauges with a moving needle, and dynamic histograms such as those seen on audio equalizers in sound systems.

Upon termination of the conversational passive listening by the clinician, processing according to the loop of steps 4602-4616 completes. In step 4618, interactive screening or monitoring server logic 502 sends final analysis of the conversation to the clinician. Generally, in the context of step 4618, the "clinician" is always a medical health professional or health records of the patient.

Thus, health screening or monitoring server 102 may screen patients for any of a number of health states passively during a conversation the patient may engage in regardless without requiring a separate, explicit screening or monitoring interview of the patient.

Figure 47:
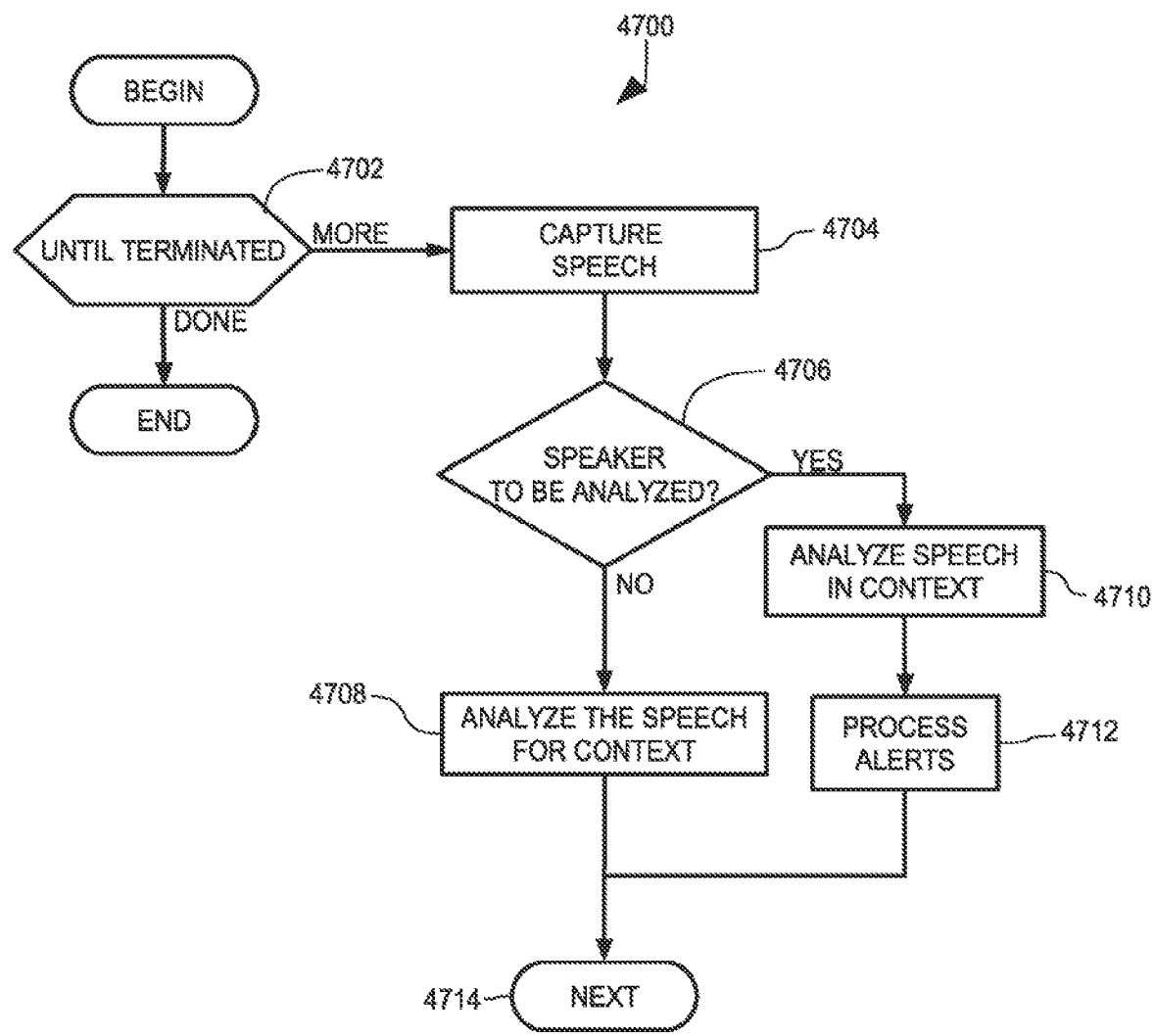
FIG. 47 is a logic flow diagram illustrating the estimation a health state of a patient by passively listening to ambient speech in accordance with the present disclosure.

In ambient passive listening, health screening or monitoring server 102 listens to and processes ambient speech according to logic flow diagram 4700 (FIG. 47). Processing by interactive health screening or monitoring logic 402, particularly generalized dialogue flow logic 602 (FIG. 7), in ambient passive listening is illustrated by logic flow diagram 4700 (FIG. 47). Loop step 4702 and next step 4714 define a loop in which generalized dialogue flow logic 602 processes audiovisual signals of ambient speech according to steps 4704-4712. While steps 4704-4714 are shown as discrete, sequential steps, they are performed concurrently with one another in an ongoing basis by generalized dialogue flow logic 602. The loop of steps 4702-4714 is initiated and terminated by a human operator of the listening device(s) involved, e.g., listening device 4514.

In step 4704 (FIG. 47), generalized dialogue flow logic 602 captures ambient speech. In test step 4708, interactive screening or monitoring server logic 502 determines whether the speech captured in step 4704 is spoken by a voice that is to be analyzed. In ambient passive listening in areas that are at least partially controlled, many people likely to speak in such areas may be registered with health screening or monitoring server 102 such that their voices may be recognized. In schools, students may have their voices registered with health screening or monitoring server 102 at admission.

In some embodiments, the people whose voices are to be analyzed are admitted students that are recognized by generalized dialogue flow logic 602. In hospitals, hospital personnel may have their voices registered with health screening or monitoring server 102 at hiring. In addition, patients in hospitals may register their voices at first contact, e.g., at an information desk or by hospital personnel in an emergency room. In some embodiments, hospital personnel are excluded from analysis when recognized as the speaker by generalized dialogue flow logic 602.

In an emergency room environment in which analysis of voices unknown to generalized dialogue flow logic 602 is important, generalized dialogue flow logic 602 may still track speaking by unknown speakers. Multiple utterances may be recognized by generalized dialogue flow logic 602 as emanating from the same individual person. Health screening or monitoring server 102 may also determine approximate positions of unknown speakers in environments with multiple listening devices, e.g., by triangulation using different relative amplitudes and/or relative timing of arrival of the captured speech at multiple listening devices.

In other embodiments of ambient passive listening in which only one person speaks, the speaker may be asked to identify herself. Alternatively, in some embodiments, the identity of the speaker may be inferred or is not especially important. In an audio diary, the speaker may be authenticated by the device or may be assumed to be used by the device's owner. In police emergency telephone call triage, the identity of the caller is not as important as the location of the speaker and qualities of the speaker's voice such as emotion, energy, and the substantive content of the speaker's speech.

In these embodiments in which only one person speaks, generalized dialogue flow logic 602 always determines that the speaker is to be analyzed.

If the speaker is not to be analyzed, generalized dialogue flow logic 602 sends the captured ambient speech to runtime model server logic 504 for processing and analysis for context. Generalized dialogue flow logic 602 receives results 1820 for the audiovisual signal of the captured speech, and results 1820 (FIG. 18) include a textual representation of the captured speech from ASR logic 1804 along with additional information from descriptive model and analytics 1812. This additional information includes identification of the various parts of speech of the words in the clinician's utterance. Generalized dialogue flow logic 602 processes results 1820 for the captured speech to establish a context.

After step 4708 (FIG. 47), processing transfers through next step 4714 to loop step 4702 and passive listening accord to the loop of steps 4702-4714 continues.

If in test step 4706, interactive screening or monitoring server logic 502 determines that the speech captured in step 4704 is spoken by a voice that is to be analyzed, processing transfers to step 4710. In step 4710, generalized dialogue flow logic 602 sends the captured speech, along with any context determined in prior yet contemporary performances of step 4708 or step 4710, to runtime model server logic 504 for analysis and evaluation.

In step 4712, generalized dialogue flow logic 602 processes any alerts triggered by the resulting analysis from runtime model server logic 504 according predetermined alert rules. These predetermined alert rules are analogous to work-flows 4810 described below. In essence, these predetermined alert rules are in the form of if-then-else logic elements that specify logical states and corresponding actions to take in such states.

The following are examples of alert rules that may be implemented by interactive screening or monitoring server logic 502. In a police emergency system call in which the caller, speaking initially to an automated triage system, whose speech is determined to be highly emotional and anxious and to semantically describe a highly urgent situation, e.g., a car accident with severe injuries, a very high priority may be assigned to the call and taken ahead of less urgent callers. In a school hallway in which interactive screening or monitoring server logic 502 recognizes frantic speech and screaming and semantic content describing the presence of weapon and/or blatant acts of violence, interactive screening or monitoring server logic 502 may trigger immediate notification of law enforcement and school personnel. In an audio diary in which a patient is detected to be at least moderately depressed, interactive screening or monitoring server logic 502 may record the analysis in the patient's clinical records such that the patient's behavioral health care provider may discuss the diary entry when the patient is next seen. In situations in which the triggering condition of the captured speech is particularly serious and urgent, interactive screening or monitoring server logic 502 may report the location of the speaker if it may be determined.

Processing according to the loop of steps 4702-4714 (FIG. 47) continues until stopped by a human operator of interactive screening or monitoring server logic 502 or of the involved listening devices.

Thus, health screening or monitoring server 102 may screen patients for any of a number of health states passively outside the confines of a one-to-one conversation with a health care professional.

As described above with respect to FIG. 4, health care management logic 408 makes expert recommendations in response to health state analysis of interactive health screening or monitoring logic 402. Health care management logic 408 is shown in greater detail in FIG. 68.

Health care management logic 408 includes manual work-flow management logic 4802, automatic work-flow generation logic 4804, work-flow execution logic 4806, and work-flow configuration 4808. Manual work-flow management logic 4802 implements a user interface through which a human administrator may create, modify, and delete work-flows 4810 of work-flow configuration 4808 by physical manipulation of one or more user input devices of a computer system used by the administrator. Automatic work-flow generation logic 4804 performs statistical analysis of patient data stored within screening or monitoring system data store 410 to identify work-flows to achieve predetermined goals. Examples of such goals include things like minimizing predicted costs for the next two (2) years of a patient's care and minimizing the cost of an initial referral while also maximizing a reduction in Hemoglobin A1C in one year.

Work-flow execution logic 4806 processes work-flows 4810 of work-flow configuration 4808, evaluating conditions and performing actions of work-flow elements 4820.

In some embodiments, work-flow execution logic 4806 processes work-flows 4810 in response to receipt of final results of any screening or monitoring according to logic flow diagram 800 (FIG. 8) using those results in processing conditions of the work-flows.

Figure 48:
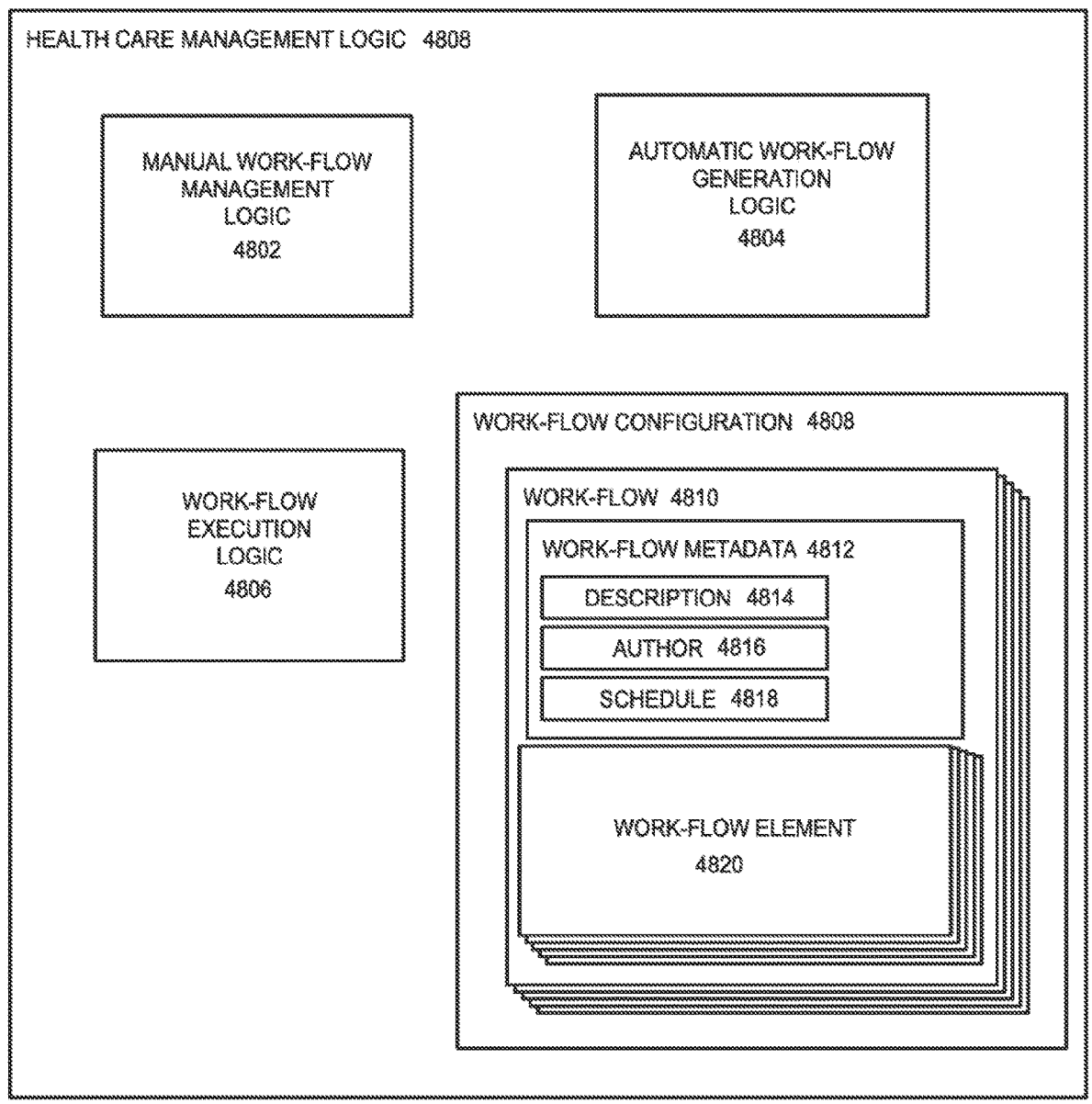
FIG. 48 is a block diagram of health care management logic of the health screening or monitoring server of FIG. 4 in greater detail.

Work-flow configuration 4808 (FIG. 48) includes data representing a number of work-flows 4810. Each work-flow 4810 includes work-flow metadata 4812 and data representing a number of work-flow elements 4820.

Work-flow metadata 4812 is metadata of work-flow 4810 and includes data representing a description 4812, an author 4816, and a schedule 4818. Description 4812 is information intended to inform any human operator of the nature of work-flow 4810. Author 4816 identifies the entity that created work-flow 4810, whether a human administrator or automatic work-flow generation logic 4804. Schedule 4818 specifies dates and times and/or conditions in which work-flow execution logic 4806 is to process work-flow 4810.

Figure 49:
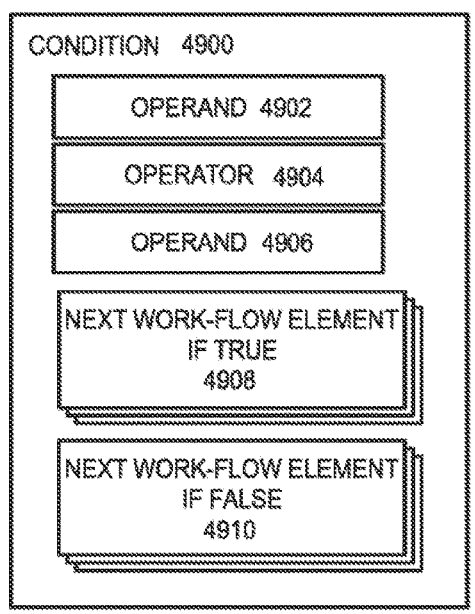
FIGS. 49 and 50 are respective block diagrams of component conditions and actions of work-flows of the health care management logic of FIG. 48.
Figure 50:
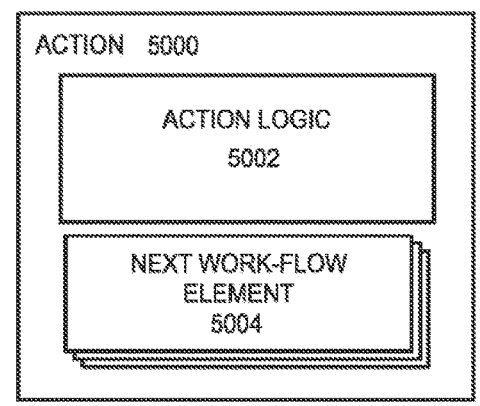

Work-flow elements 4820 collectively define the behavior of work-flow execution logic 4806 in processing the work-flow. In this illustrative embodiment, work-flow elements are each one of two types: conditions, such as condition 4900 (FIG. 49), and actions such as action 5000 (FIG. 50).

In this illustrative embodiment, condition 4900 specifies a Boolean test that includes an operand 4902, an operator 4904, and another operand 4906. In this illustrative embodiment, operator 4904 may be any of a number of Boolean test operators, such as $=, \neq, >, \geq, <$, and $\leq$, for example. Operands 4902 and 4906 may each be results 1820 (FIG. 18) or any portion thereof, a constant, or null. As a result, any results of a given screening or monitoring, e.g., results 1820, any information about a given patient stored in screening or monitoring system data store 410, and any combination thereof may be either of operands 4902 and 4906.

Next work-flow element(s) 4908 specify one or more work-flow elements to process if the test of operands 4902 and 4906 and operator 4904 evaluate to a Boolean value of true, and next work-flow element(s) 4910 specify one or more work-flow elements to process if the test of operands 4902 and 4906 and operator 4904 evaluate to a Boolean value of false.

Each of next work-flow element(s) 4908 and 4910 may be any of a condition, an action, or null. By accepting conditions such as condition 4900 in next work-flow element(s) 1908 and 4910, complex tests with AND and OR operations may be represented in work-flow elements 4820. In alternative embodiments, condition 4900 may include more operands and operators combined with AND, OR, and NOT operations.

Since each of operands 4902 and 4906 may be null, condition 4900 may test for the mere presence or absence of an occurrence in the patient's data. For example, to determine whether a patient has ever had a Hemoglobin A1C blood test, condition 4900 may determine whether the most recent Hemoglobin A1C test results to null. If equal, the patient has not had any Hemoglobin A1C blood test at all.

Action 5000 (FIG. 50) includes action logic 5002 and one or more next work-flow element(s) 5004. Action logic 5002 represents the substantive action to be taken by work-flow execution logic 4806 and typically makes or recommends a particular course of action in the care of the patient that may range from specific treatment protocols to more holistic paradigms. Examples include referring the patient to a care provider, enrolling the patient in a particular program of care, and recording recommendations to the patient's file such that the patient's clinician sees the recommendation at the next visit. Examples of referring a patient to a care provider include referring the patient to a psychiatrist, a medication management coach, physical therapist, nutritionist, fitness coach, dietitian, social worker, etc. Examples of enrolling the patient in a program include telepsychiatry programs, group therapy programs, etc.

Examples of recommendations recorded to the patient's file include recommended changes to medication, whether a change in the particular drug prescribed or merely in dosage of the drug already prescribed to the patient, and other treatments. In addition, referrals and enrollment may be effected by recommendations for referrals and enrollment in the patient's file, allowing a clinician to make the final decision regarding the patient's care.

As described above, automatic work-flow generation logic 4804 (FIG. 48) performs statistical analysis of patient data stored within screening or monitoring system data store 410 to identify work-flows to achieve predetermined goals. Examples of such goals given above include minimizing predicted costs for the next two (2) years of a patient's care and minimizing the cost of an initial referral while also maximizing a reduction in Hemoglobin A1C in one year. Automatic work-flow generation logic 4804 is described in the illustrative context of the first, namely, minimizing predicted costs for the next two (2) years of a patient's care.

Figure 51:
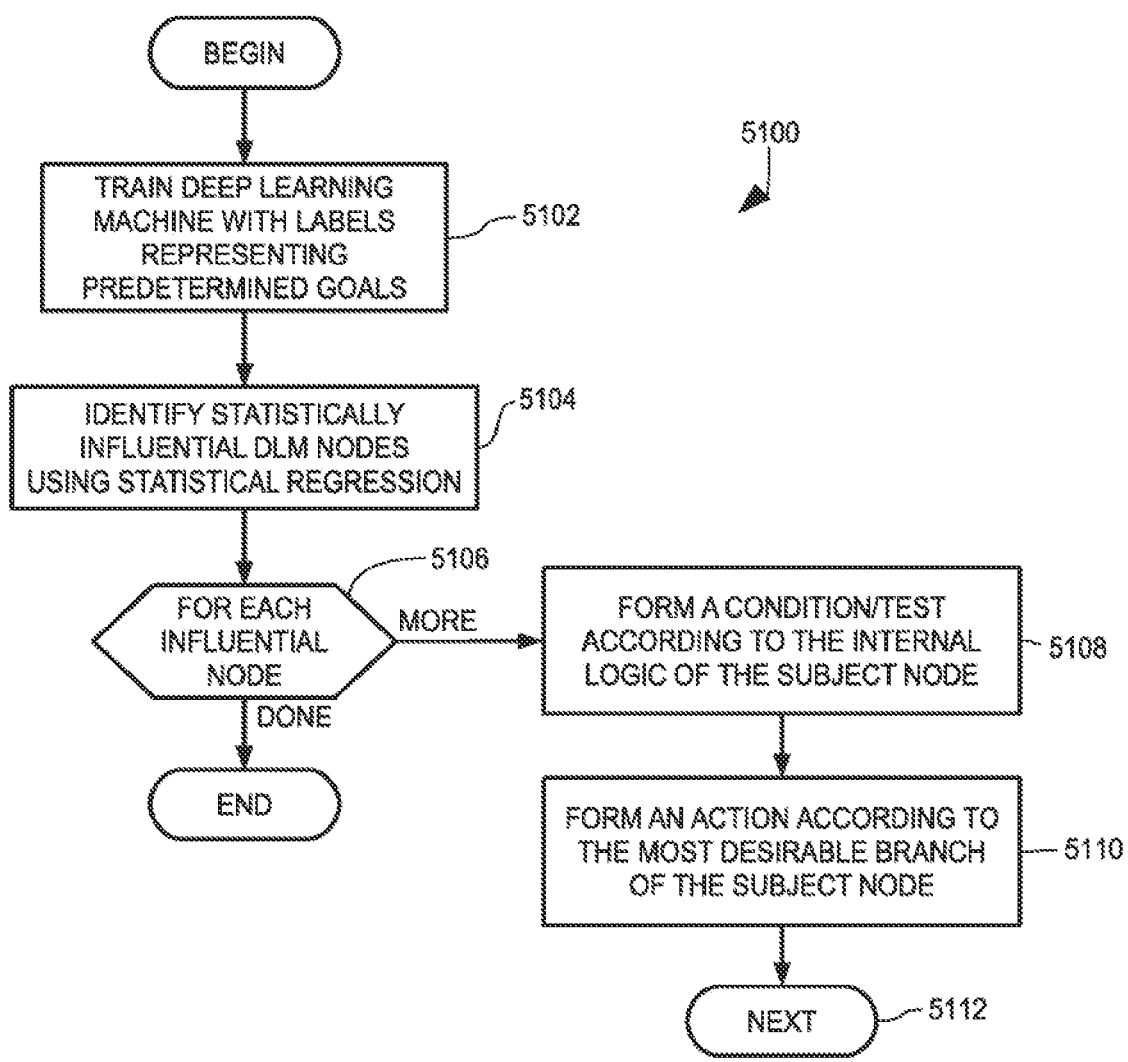
FIG. 51 is a logic flow diagram of the automatic formulation of a work-flow of the health care management logic of FIG. 48 in accordance with the present disclosure.

The manner in which automatic work-flow generation logic 4804 identifies work-flows to achieve predetermined goals is illustrated by logic flow diagram 5100 (FIG. 51).

Automatic work-flow generation logic 4804 includes deep learning machine logic. In step 5102, human computer engineers configure this deep learning machine logic of automatic work-flow generation logic 4804 to analyze patient data from screening or monitoring system data store 410 in the context of labels specified by users, e.g., labels related to costs of the care of each patient over a 2-year period in this illustrative example. Users of health screening or monitoring server 102 who are not merely patients are typically either health care providers or health care payers. In either case, information regarding events in a given patient's health care history is available and is included in automatic work-flow generation logic 4804 by the human engineers such that automatic work-flow generation logic 4804 may track costs of a patient's care from the patient's medical records.

Further in step 5102, the human engineers use all relevant data of screening or monitoring system data store 410 to train the deep learning machine logic of automatic work-flow generation logic 4804. After such training, the deep learning machine logic of automatic work-flow generation logic 4804 includes an extremely complex decision tree that predicts the costs of each patient over a 2-year period.

In step 5104, automatic work-flow generation logic 4804 determines which events in a patient's medical history have the most influence over the cost of the patient's care in a 2-year period for statistically significant portions of the patient population. In particular, automatic work-flow generation logic 4804 identifies deep learning machine (DLM) nodes of the decision tree that have the most influence over the predetermined goals, e.g., costs of the care of a patient over a 2-year period. There are several known techniques for making such a determination automatically, and automatic work-flow generation logic 4804 implements one or more of them to identify these significant nodes. Examples of techniques for identifying significantly influential events/decisions ("nodes" in machine learning parlance) in a deep learning machine include random decision forests (supervised or unsupervised), multinomial logistic regression, and naïve Bayes classifiers, for example. These techniques are known and are not described herein.

Loop step 5106 and next step 5112 define a loop in which automatic work-flow generation logic 4804 processes each of the influential nodes identified in step 5104. In a given iteration of the loop of steps 5106-5112, the particular node processed by automatic work-flow generation logic 4804 is sometimes referred to as the subject node.

In step 5108, automatic work-flow generation logic 4804 forms a condition, e.g., condition 4900 (FIG. 49), from the internal logic of the subject node. The internal logic of the subject node receives data representing one or more events in a patient's history and/or one or more phenotypes of the patient and makes a decision that represents one or more branches to other nodes. In step 5108 (FIG. 51), automatic work-flow generation logic 4804 generalizes the data received by the subject node and the internal logic of the subject node that maps the received data to a decision.

In step 5110, automatic work-flow generation logic 4804 forms an action, e.g., action 5000 (FIG. 50), according to the branch from the subject node that ultimately leads to the best outcome related to the predetermined goal, e.g., to the lowest cost over a 2-year period. The condition formed in step 5108 (FIG. 51) and the action formed in step 5110 collectively form a work-flow generated by automatic work-flow generation logic 4804.

Once all influential nodes have been processed according to the loop of steps 5106-5112, processing by automatic work-flow generation logic 4804 completes, having formed a number of work-flows.

In this illustrative embodiment, the automatically generated work-flows are subject to human ratification prior to actual deployment within health care management logic 408. In an alternative embodiment, health care management logic 408 automatically deploys work-flows generated automatically by automatic work-flow generation logic 4804 but limits actions to only recommendations to health care professionals. It's technically feasible to fully automate work-flow generation and changes to a patient's care without any human supervision. However, such may be counter to health care public policy in place today.

Clinical Scenarios

The disclosed system may also be used to evaluate mental health from primary care health interactions. For example, the system may be used to augment inferences about a patient's mental health taken by a trained health provider individual. The system may also be used to evaluate mental health from a preliminary screening or monitoring call (e.g., a call made to a health care provider organization by a prospective patient for the purpose of setting up a medical appointment with a trained mental health professional). For a primary screen, the health care professional may ask specific questions to the patient in a particular order to ascertain mental health treatment needs of the patient. A recording device may record prospective patient responses to one or more of these questions. The prospective patient's consent may be obtained before this occurs.

The system may perform an audio analysis or a semantic analysis on audio snippets it collects from the prospective patient. For example, the system may determine relative frequencies of words or phrases associated with depression. For example, the system may predict that a user has depression if the user speaks with terms associated with negative thoughts, such as phrases indicating suicidal thoughts, self-harm instincts, phrases indicating a poor body image or self-image, and feelings of anxiety, isolation, or loneliness. The system may also pick up non-lexical or non-linguistic cues for depression, such as pauses, gasps, sighs, and slurred or mumbled speech. These terms and non-lexical cues may be similar to those picked up from training examples, such as patients administered a survey (e.g., the PHQ-9).

The system may determine information about mental health by probing a user's physical health. For example, a user may feel insecure or sad about his or her physical features or physical fitness. Questions used to elicit information may have to do with vitals, such as blood pressure, resting heart rate, family history of disease, blood sugar, body mass index, body fat percentage, injuries, deformities, weight, height, eyesight, eating disorders, cardiovascular endurance, diet, or physical strength. Patients may provide speech which indicates despondence, exasperation, sadness, or defensiveness. For example, a patient may provide excuses as to why he or she has not gotten a medical procedure performed, why his or her diet is not going well, why he or she has not started an exercise program, or speak negatively about his or her height, weight, or physical features. Expression of such negativity about one's physical health may be correlated to anxiety.

The models may be continually active or passive. A passive learning model may not change the method by which it learns in response to new information. For example, a passive learner may continually use a specific condition to converge on a prediction, even as new types of feature information are added to the system. But such a model may be limited in effectiveness without a large amount of training data available. An active learning model, by contrast, may employ a human to converge more quickly. The active learner may ask targeted questions to the human in order to do this. For example, a machine learning algorithm may be employed on a large amount of unlabeled audio samples. The algorithm may be able to easily classify some as being indicative of depression, but others may be ambiguous. The algorithm may ask the patient if he or she were feeling depressed when uttering a specific speech segment. Or the algorithm may ask a clinician to classify the samples.

The system may be able to perform quality assurance of health providers using voice biomarkers. Data from the system may be provided to health care providers in order to assist the health care providers with detecting lexical and non-lexical cues that correspond to depression in patients. The health care providers may be able to use changes in pitch, vocal cadence, and vocal tics to determine how to proceed with care. The system may also allow health care providers to assess which questions elicit reactions from patients that are most predictive for depressions. Health care providers may use data from the system to train one another to search for lexical and non-lexical cues, and monitor care delivery to determine whether it is effective in screening or monitoring patients. For example, a health care provider may be able to observe a second health care provider question a subject to determine whether the second health care provider is asking questions that elicit useful information from the patient. The health care provider may be asking the questions in person or may be doing so remotely, such as from a call center. Health care providers may, using the semantic and audio information produced by the system, produce standardized methods of eliciting information from patients, based on which methods produce the most cues from patients.

The system may be used to provide a dashboard tabulating voice-based biomarkers observed in patients. For example, health care providers may be able to track the frequencies of specific biomarkers, in order to keep track of patients' conditions. They may be able to track these frequencies in real time to assess how their treatment methods are performing. They may also be able to track these frequencies over time, in order to monitor patients' performances under treatment or recovery progress. Mental health providers may be able to assess each other's performances using this collected data.

Dashboards may show real-time biomarker data as a snippet is being analyzed. They may show line graphs showing trends in measured biomarkers over time. The dashboards may show predictions taken at various time points, charting a patient's progress with respect to treatment. The dashboard may show patients' responses to treatment by different providers.

The system may be able to translate one or more of its models across different patient settings. This may be done to account for background audio information in different settings. For example, the system may employ one or more signal processing algorithms to normalize audio input across settings. This may be done by taking impulse response measurements of multiple locations and determining transfer functions of signals collected at those locations in order to normalize audio recordings. The system may also account for training in different locations. For example, a patient may feel more comfortable discussing sensitive issues at home or in a therapist's office than over the phone. Thus, voice-based biomarkers obtained in these settings may differ. The system may be trained in multiple locations, or training data may be labeled by location before it is processed by the system's machine learning algorithms.

The models may be transferred from location to location, for example, by using signal processing algorithms. They may also be transferred by modifying the questions asked of patients based on their locations. For example, it may be determined which particular questions, or sequences of questions, correspond to particular reactions within a particular location context. The questions may then be administered by the health care providers in such fashion as to provide the same reactions from the patients.

The system may be able to use standard clinical encounters to train voice biomarker models. The system may collect recordings of clinical encounters for physical complaints. The complaints may be regarding injuries, sicknesses, or chronic conditions. The system may record, with patient permission, conversation patients have with health care providers during appointments. The physical complaints may indicate patients' feelings about their health conditions. In some cases, the physical complaints may be causing patients significant distress, affecting their overall dispositions and possibly causing depression.

The data may be encrypted as it is collected or while in transit to one or more servers within the system. The data may be encrypted using a symmetric-key encryption scheme, a public-key encryption scheme, or a blockchain encryption method. Calculations performed by the one or more machine learning algorithms may be encrypted using a homomorphic encryption scheme, such as a partially homomorphic encryption scheme or a fully homomorphic encryption scheme.

The data may be analyzed locally, to protect privacy. The system may analyze data in real-time by implementing a trained machine learning algorithm to operate on speech sample data recorded at the location where the appointment is taking place.

Alternatively, the data may be stored locally. To preserve privacy, features may be extracted before being stored in the cloud for later analysis. The features may be anonymized to protect privacy. For example, patients may be given identifiers or pseudonyms to hide their true identities. The data may undergo differential privacy to ensure that patient identities are not compromised. Differential privacy may be accomplished by adding noise to a data set. For example, a data set may include 100 records corresponding to 100 usernames and added noise. If an observer has information about 99 records corresponding to 99 users and knows the remaining username, the observer will not be able to match the remaining record to the remaining username, because of the noise present in the system.

In some embodiments, a local model may be embedded on a user device. The local model may be able to perform limited machine learning or statistical analysis, subject to constraints of device computing power and storage. The model may also be able to perform digital signal processing on audio recordings from patients. The mobile device used may be a smartphone or tablet computer. The mobile device may be able to download algorithms over a network for analysis of local data. The local device may be used to ensure privacy, as data collected and analyzed may not travel over a network.

Voice-based biomarkers may be associated with lab values or physiological measurements. Voice-based biomarkers may be associated with mental health-related measurements. For example, they may be compared to the effects of psychiatric treatment, or logs taken by healthcare professionals such as therapists. They may be compared to answers to survey questions, to see if the voice-based analysis matches assessments commonly made in the field.

Voice-based biomarkers may be associated with physical health-related measurements. For example, vocal issues, such as illness, may contribute to a patient producing vocal sounds that need to be accounted for in order to produce actionable predictions. In addition, depression predictions over a time scale in which a patient is recovering from an illness or injury may be compared to the patient's health outcomes over that time scale, to see if treatment is improving the patient's depression or depression-related symptoms. Voice-based biomarkers may be compared with data relating to brain activity collected during multiple time points, in order to determine the clinical efficacy of the system.

Training of the models may be continuous, so that the model is continuously running while audio data is collected. Voice-based biomarkers may be continually added to the system and used for training during multiple epochs. Models may be updated using the data as it is collected.

The system may use a reinforcement learning mechanism, where survey questions may be altered dynamically in order to elicit voice-based biomarkers that yield high-confidence depression predictions. For example, the reinforcement learning mechanism may be able to select questions from a group. Based on a previous question or a sequence of previous questions, the reinforcement mechanism may choose a question that may yield a high-confidence prediction of depression.

The system may be able to determine which questions or sequences of questions may be able to yield particular elicitations from patients. The system may use machine learning to predict a particular elicitation, by producing, for example, a probability. The system may also use a softmax layer to produce probabilities for multiple elicitations. The system may use as features particular questions as well as at what times these questions are asked, how long into a survey they are asked, the time of day in which they are asked, and the point of time within a treatment course within which they are asked.

For example, a specific question asked at a specific time about a sensitive subject for a patient may elicit crying from a patient. This crying may be associated strongly with depression. The system may, when receiving context that it is the specific time, may recommend presentation of the question to the patient.

The system may include a method of using a voice-based biomarker to dynamically affect a course of treatment. The system may log elicitations of users over a period of time and determine, from the logged elicitations, whether or not treatment has been effective. For example, if voice-based biomarkers become less indicative of depression over a long time period, this might be evidence that the prescribed treatment is working. On the other hand, if the voice-based biomarkers become more indicative of depression over a long time period, the system may prompt health care providers to pursue a change in treatment, or to pursue the current course of treatment more aggressively.

The system may spontaneously recommend a change in treatment. In an embodiment where the system is continually processing and analyzing data, the system may detect a sudden increase in voice-based biomarkers indicating depression. This may occur over a relatively short time window in a course of treatment. The system may also be able to spontaneously recommend a change if a course of treatment has been ineffective for a particular time period (e.g., six months, a year).

The system may be able to track a probability of a particular response to a medication. For example, the system may be able to track voice based biomarkers taken before, during, and after a course of treatment, and analyze changes in scores indicative of depression.

The system may be able to track a particular patient's probability of response to medication by having been trained on similar patients. The system may use this data to predict a patient's response based on responses of patients from similar demographics. These demographics may include age, gender, weight, height, medical history, or a combination thereof.

The system may also be able to track a patient's likely adherence to a course of medicine or treatment. For example, the system may be able to predict, based on analysis of time series voice-based biomarkers, whether a treatment is having an effect on a patient. The health care provider may then ask the patient whether he or she is following the treatment.

In addition, the system may be able to tell, based on surveying the questions, if the patient is following the treatment by analyzing his or her biomarkers. For example, a patient may become defensive, take long pauses, stammer, or act in a manner that the patient is clearly lying about having adhered to a treatment plan. The patient may also express sadness, shame, or regret regarding not having followed the treatment plan.

The system may be able to predict whether a patient will adhere to a course of treatment or medication. The system may be able to use training data from voice-based biomarkers from many patients in order to make a prediction as to whether a patient will follow a course of treatment. The system may identify particular voice-based biomarkers as predicting adherence. For example, patients with voice-based biomarkers indicating dishonesty may be designated as less likely to adhere to a treatment plan.

The system may be able to establish a baseline profile for each individual patient.

An individual patient may have a particular style of speaking, with particular voice-based biomarkers indicating emotions, such as happiness, sadness, anger, and grief. For example, some people may laugh when frustrated or cry when happy. Some people may speak loudly or softly, speak clearly or mumble, have large or small vocabularies, and speak freely or more hesitantly. Some people may have extroverted personalities, while others may be more introverted.

Some people may be more hesitant to speak than others. Some people may be more guarded about expressing their feelings. Some people may have experienced trauma and abuse. Some people may be in denial about their feelings.

A person's baseline mood or mental state, and thus the person's voice-based biomarkers, may change over time. The model may be continually trained to account for this. The model may also predict depression less often. The model's predictions over time may be recorded by mental health professionals. These results may be used to show a patient's progress out of a depressive state.

The system may be able to make a particular number of profiles to account for different types of individuals. These profiles may be related to individuals' genders, ages, ethnicities, languages spoken, and occupations, for example.

Particular profiles may have similar voice-based biomarkers. For example, older people may have thinner, breathier voices than younger people. Their weaker voices may make it more difficult for microphones to pick up specific biomarkers, and they may speak more slowly than younger people. In addition, older people may stigmatize behavioral therapy, and thus, not share as much information as younger people might.

Men and women may express themselves differently, which may lead to different biomarkers. For example, men may express negative emotions more aggressively or violently, while women may be better able to articulate their emotions.

In addition, people from different cultures may have different methods of dealing with or expressing emotions, or may feel guilt and shame when expressing negative emotions. It may be necessary to segment people based on their cultural backgrounds, in order to make the system more effective with respect to picking up idiosyncratic voice-based biomarkers.

The system may account for people with different personality types by segmenting and clustering by personality type. This may be done manually, as clinicians may be familiar with personality types and how people of those types may express feelings of depression. The clinicians may develop specific survey questions to elicit specific voice-based biomarkers from people from these segmented groups.

The voice-based biomarkers may be able to be used to determine whether somebody is depressed, even if the person is holding back information or attempting to outsmart testing methods. This is because many of the voice-based biomarkers may be involuntary utterances. For example, the patient may equivocate or the patient's voice may quaver.

Particular voice-based biomarkers may correlate with particular causes of depression. For example, semantic analysis performed on many patients, in order to find specific words, phrases, or sequences thereof that indicate depression. The system may also track effects of treatment options on users, in order to determine their efficacy. Finally, the system may use reinforcement learning to determine better methods of treatment available.

Computer Figures

Figure 52:
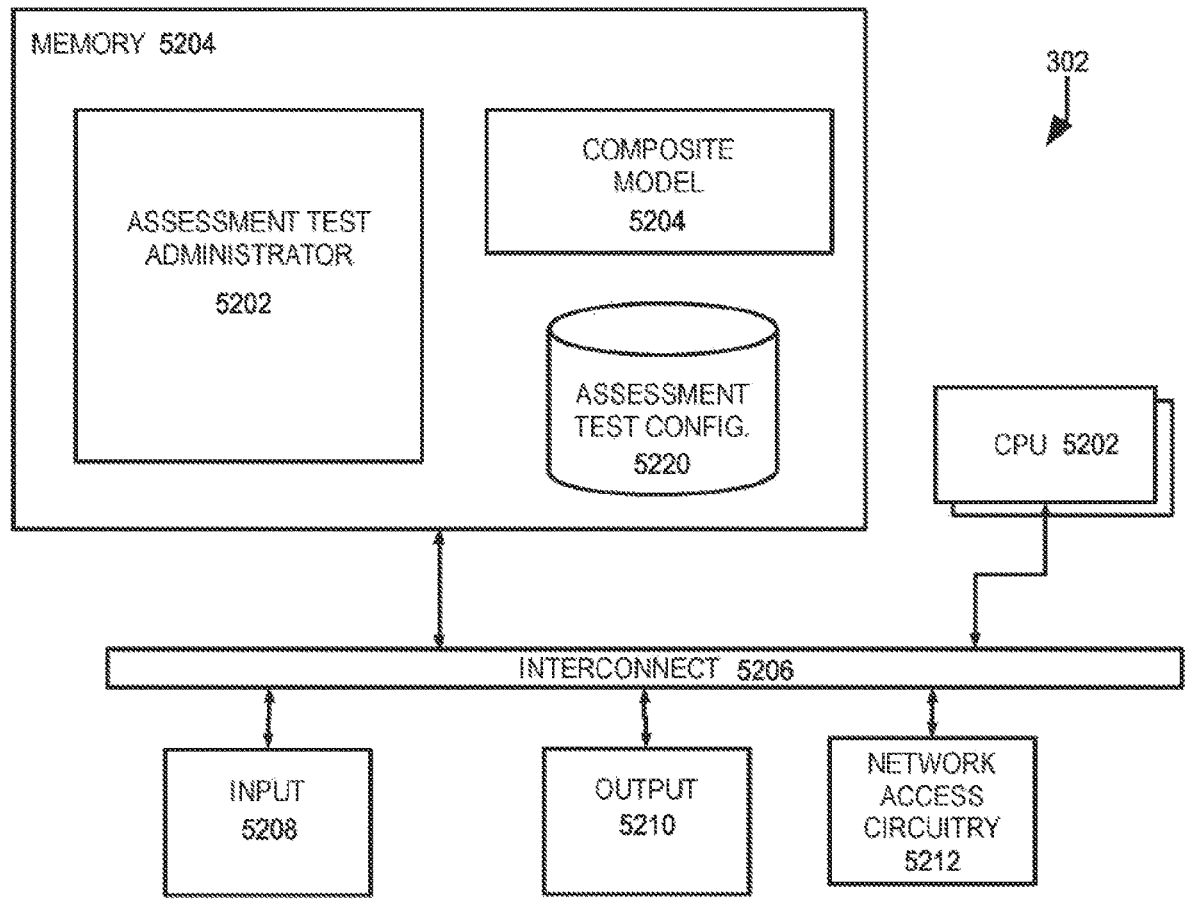
FIG. 52 is a block diagram of the real-time computer system of FIG. 3 in greater detail.

Real-time system 302 is shown in greater detail in (FIG. 52). Real-time system 302 includes one or more microprocessors 5202 (collectively referred to as CPU 5202) that retrieve data and/or instructions from memory 5204 and execute retrieved instructions in a conventional manner. Memory 5204 may include generally any computer-readable medium including, for example, persistent memory such as magnetic and/or optical disks, ROM, and PROM and volatile memory such as RAM.

CPU 5202 and memory 5204 are connected to one another through a conventional interconnect 5206, which is a bus in this illustrative embodiment and which connects CPU 5202 and memory 5204 to one or more input devices 5208, output devices 5210, and network access circuitry 5212. Input devices 5208 may include, for example, a keyboard, a keypad, a touch-sensitive screen, a mouse, a microphone, and one or more cameras. Output devices 5210 may include, for example, a display—such as a liquid crystal display (LCD)—and one or more loudspeakers. Network access circuitry 5212 sends and receives data through computer networks such as network 308 (FIG. 3). Generally speaking, server computer systems often exclude input and output devices, relying instead on human user interaction through network access circuitry. Accordingly, in some embodiments, real-time system 302 does not include input device 708 and output device 5210.

A number of components of real-time system 302 are stored in memory 5204. In particular, assessment test administrator 2202 and composite model 2204 are each all or part of one or more computer processes executing within CPU 5302 from memory 5304 in this illustrative embodiment but may also be implemented using digital logic circuitry. Assessment test administrator 2202 and composite model 2204 are both logic. As used herein, "logic" refers to (i) logic implemented as computer instructions and/or data within one or more computer processes and/or (ii) logic implemented in electronic circuitry.

Assessment test configuration 5220 is data stored persistently in memory 5304 and may each be implemented as all or part of one or more databases.

Modeling system 304 (FIG. 3) is shown in greater detail in (FIG. 53). Modeling system 304 includes one or more microprocessors 5302 (collectively referred to as CPU 5302), memory 5304, an interconnect 5306, input devices 5308, output devices 5310, and network access circuitry 5312 that are directly analogous to CPU 5202 (FIG. 52), memory 5204, interconnect 5206, input devices 5208, output devices 5210, and network access circuitry 5212, respectively. Being a server computer system, modeling system 304 may omit input devices 5308 and output devices 5310.

A number of components of modeling system 304 (FIG. 53) are stored in memory 5304.

In particular, modeling system logic 5320 is all or part of one or more computer processes executing within CPU 5302 from memory 5304 in this illustrative embodiment but may also be implemented using digital logic circuitry. Collected patient data 2206, clinical data 2220, and modeling system configuration 5322 are each data stored persistently in memory 5304 and may be implemented as all or part of one or more databases.

In this illustrative embodiment, real-time system 302, modeling system 304, and clinical data server 306 are shown, at least in the Figures, as separate, single server computers. It should be appreciated that logic and data of separate server computers described herein may be combined and implemented in a single server computer and that logic and data of a single server computer described herein may be distributed across multiple server computers. Moreover, it should be appreciated that the distinction between servers and clients is largely an arbitrary one to facilitate human understanding of purpose of a given computer. As used herein, "server" and "client" are primarily labels to assist human categorization and understanding.

Figure 54:
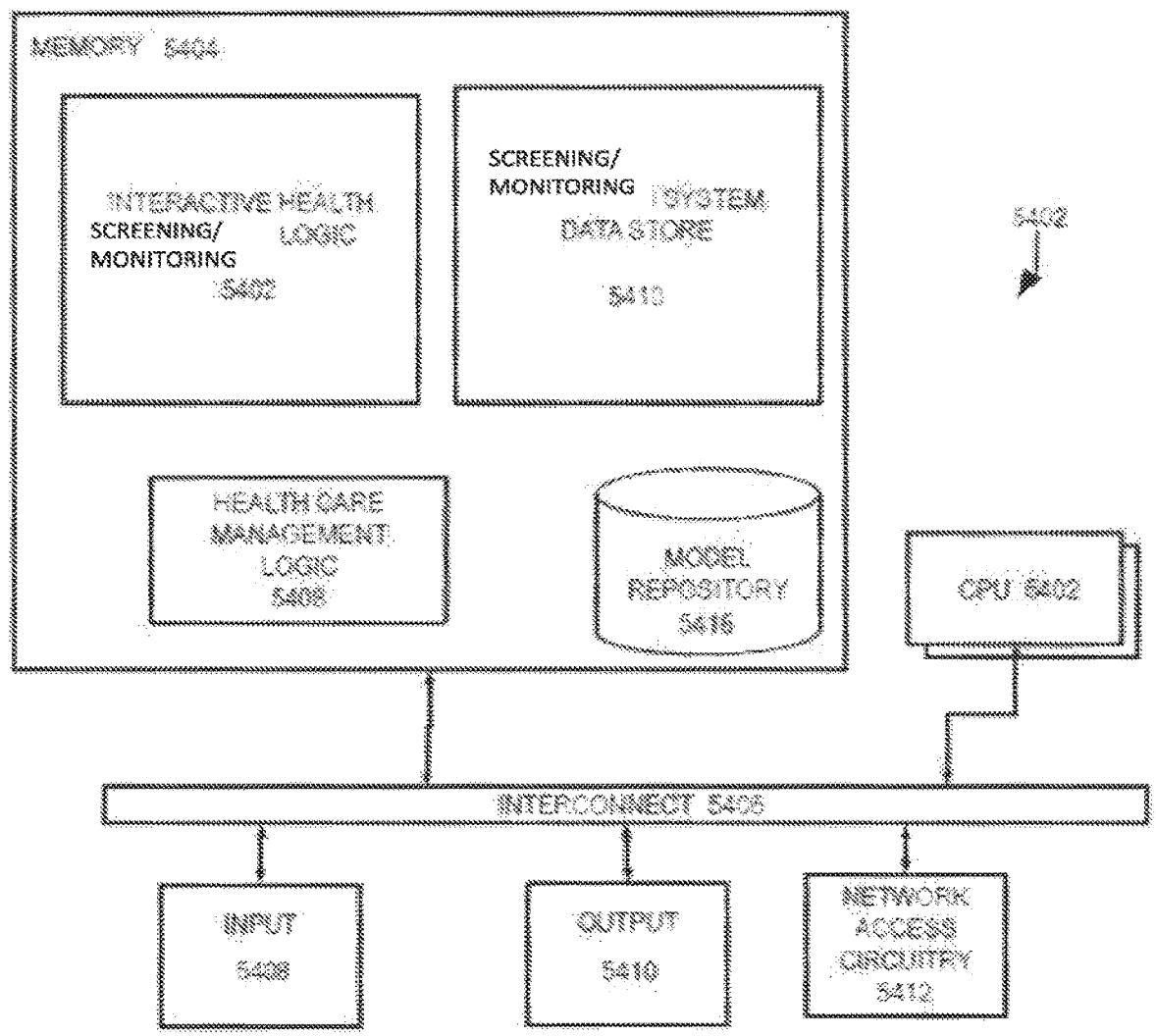
FIG. 54 is a block diagram of the health screening or monitoring server of FIG. 1A in greater detail.

Health screening or monitoring server 102 is shown in greater detail in FIG. 54. As noted above, it should be appreciated that the behavior of health screening or monitoring server 102 described herein may be distributed across multiple computer systems using conventional distributed processing techniques. Health screening or monitoring server 102 includes one or more microprocessors 5402

(collectively referred to as CPU 5402) that retrieve data and/or instructions from memory 5404 and execute retrieved instructions in a conventional manner. Memory 5404 may include generally any computer-readable medium including, for example, persistent memory such as magnetic, solid state and/or optical disks, ROM, and PROM and volatile memory such as RAM.

CPU 5402 and memory 5404 are connected to one another through a conventional interconnect 5406, which is a bus in this illustrative embodiment and which connects CPU 5402 and memory 5404 to one or more input devices 5408, output devices 5410, and network access circuitry 5412. Input devices 5408 may include, for example, a keyboard, a keypad, a touch-sensitive screen, a mouse, a microphone, and one or more cameras. Output devices 5410 may include, for example, a display—such as a liquid crystal display (LCD)—and one or more loudspeakers. Network access circuitry 5412 sends and receives data through computer networks such as WAN 110 (FIG. 1). Server computer systems often exclude input and output devices, relying instead on human user interaction through network access circuitry exclusively.

Accordingly, in some embodiments, health screening or monitoring server 102 does not include input devices 5408 and output devices 5410.

A number of components of health screening or monitoring server 102 are stored in memory 5404. In particular, interactive health screening or monitoring logic 402 and health care management logic 408 are each all or part of one or more computer processes executing within CPU 5402 from memory 5404. As used herein, "logic" refers to (i) logic implemented as computer instructions and/or data within one or more computer processes and/or (ii) logic implemented in electronic circuitry.

Screening system data store 410 and model repository 416 are each data stored persistently in memory 5404 and may be implemented as all or part of one or more databases. Screening system data store 410 also includes logic as described above.

It should be appreciated that the distinction between servers and clients is largely an arbitrary one to facilitate human understanding of purpose of a given computer. As used herein, "server" and "client" are primarily labels to assist human categorization and understanding.

The above description is illustrative only and is not limiting. For example, while much of the description above pertains to depression and anxiety, it should be appreciated that the techniques described herein may effectively estimate and/or screen for a number of other health conditions such as post-traumatic stress disorder (PTSD) and stress generally, drug and alcohol addiction, and bipolar disorder, among others. Moreover, while the majority of the health states for which health screening or monitoring server 102 screens as described herein are mental health states or behavioral health ailments, health screening or monitoring server 102 may screen for health states unrelated to mental or behavior health. Examples include Parkinson's disease, Alzheimer's disease, chronic obstructive pulmonary disease, liver failure, Crohn's disease, myasthenia gravis, amyotrophic lateral sclerosis (ALS) and decompensated heart failure.

Moreover, many modifications of and/or additions to the above described embodiment(s) are possible. For example, with patient consent, corroborative patient data for mental illness diagnostics may be extracted from one or more of the patient's biometrics including heart rate, blood pressure, respiration, perspiration, body temperature. It may also be possible to use audio without words, for privacy or for cross-language analysis. It is also possible to use acoustics modeling without visual cues.

The present invention is defined solely by the claims which follow and their full range of equivalents. It is intended that the following appended claims be interpreted as including all such alterations, modifications, permutations, and substitute equivalents as fall within the true spirit and scope of the present invention.

Figure 57:
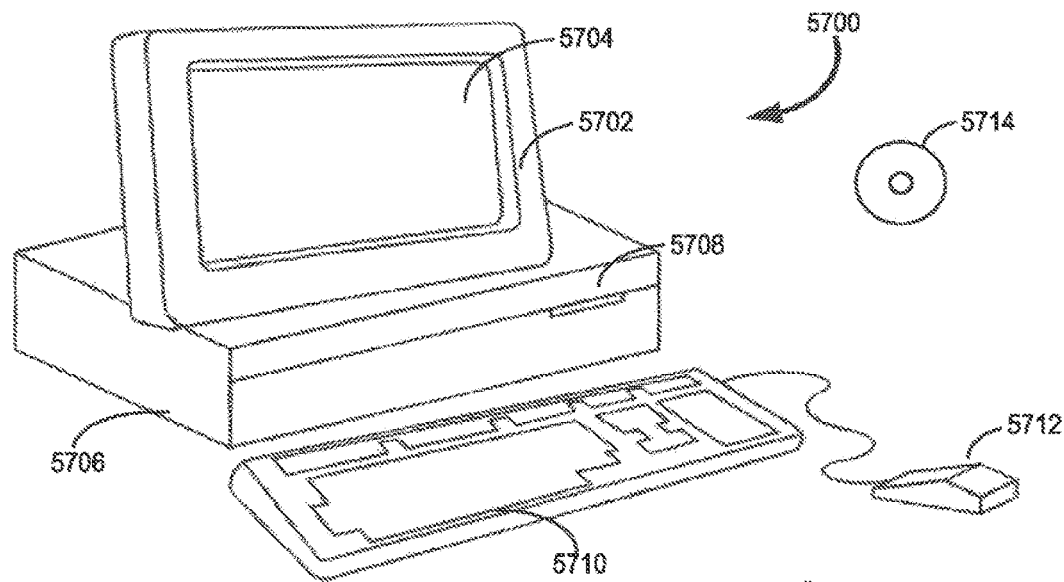
FIGS. 57 and 58 are example illustrations of a computer system capable of embodying the current disclosure.
Figure 58:
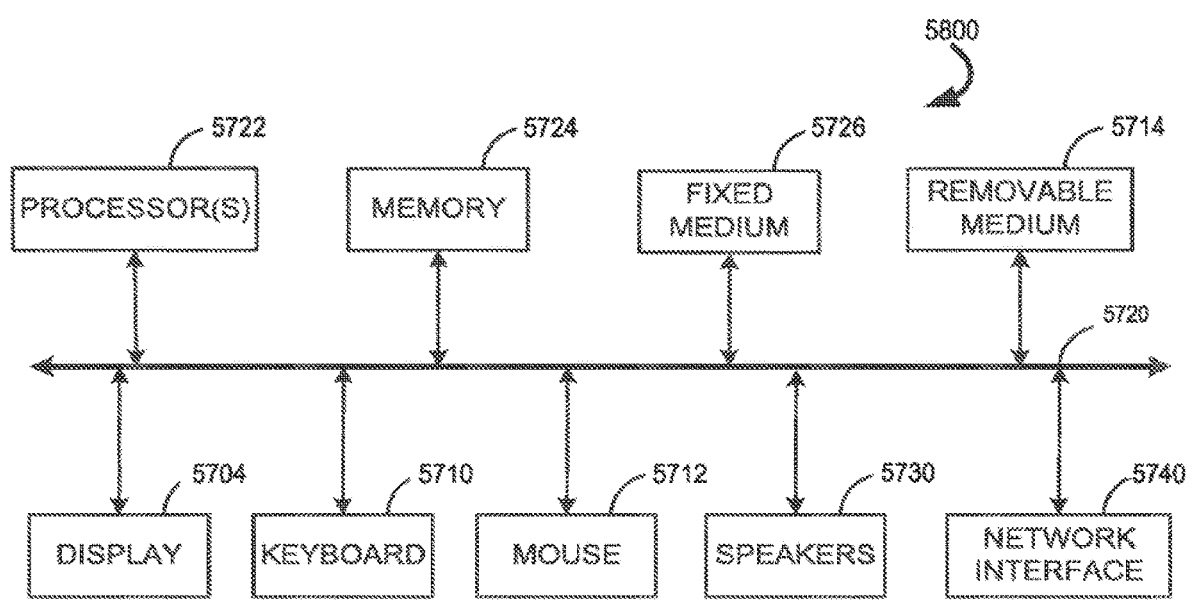

Now that the systems and methods for screening or monitoring for a health condition, namely depression in a number of the embodiments, have been described, attention shall now be focused upon examples of systems capable of executing the above functions. To facilitate this discussion, FIGS. 57 and 58 illustrate a Computer System 5700, which is suitable for implementing embodiments of the present invention. FIG. 57 shows one possible physical form of the Computer System 5700. Of course, the Computer System 5700 may have many physical forms ranging from a printed circuit board, an integrated circuit, and a small handheld device up to a huge super computer, and a collection of networked computers (or computing components operating in a distributed network). Computer system 5700 may include a Monitor 5702, a Display 5704, a Housing 5706, a Disk Drive 5708, a Keyboard 5710, and a Mouse 5712. Storage medium 5714 is a computer-readable medium used to transfer data to and from Computer System 5700.

FIG. 58 is an example of a block diagram 5800 for Computer System 5700. Attached to System Bus 5720 are a wide variety of subsystems. Processor(s) 5722 (also referred to as central processing units, or CPUs) are coupled to storage devices, including Memory 5724. Memory 5724 includes random access memory (RAM) and read-only memory (ROM). As is well known in the art, ROM acts to transfer data and instructions uni-directionally to the CPU, and RAM is used typically to transfer data and instructions in a bi-directional manner. Both of these types of memories may include any suitable of the computer-readable media described below. A Fixed medium 5726 may also be coupled bi-directionally to the Processor 5722; it provides additional data storage capacity and may also include any of the computer-readable media described below. Fixed medium 5726 may be used to store programs, data, and the like and is typically a secondary storage medium (such as a hard disk) that is slower than primary storage. It will be appreciated that the information retained within Fixed medium 5726 may, in appropriate cases, be incorporated in standard fashion as virtual memory in Memory 5724. Removable medium 5714 may take the form of any of the computer-readable media described below.

Processor 5722 is also coupled to a variety of input/output devices, such as Display 5704, Keyboard 5710, Mouse 5712 and Speakers 5730. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, motion trackers, brain wave readers, or other computers. Processor 5722 optionally may be coupled to another computer or telecommunications network using Network Interface 5740. With such a Network Interface 5740, it is contemplated that the Processor 5722 might receive information from the network or might output information to the network in the course of performing the above-described health screening or monitoring. Furthermore, method embodiments of the present invention may execute solely upon Processor 5722 or may execute over a network such as the Internet in conjunction with a remote CPU that shares a portion of the processing.

Software is typically stored in the non-volatile memory and/or the drive unit. Indeed, for large programs, it may not even be possible to store the entire program in the memory. Nevertheless, it should be understood that for software to run, if necessary, it is moved to a computer readable location appropriate for processing, and for illustrative purposes, that location is referred to as the memory in this disclosure. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

In operation, the computer system 5700 may be controlled by operating system software that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the approaches used by those skilled in the data processing arts to most effectively convey the substance of their work to others skilled in the art. An algorithm is, here and, generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general-purpose systems may be used with programs in accordance with the teachings herein, or it may prove convenient to construct more specialized apparatus to perform the methods of some embodiments. In addition, the techniques are not described with reference to any particular programming language, and various embodiments may, thus, be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a virtual machine, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure may be implemented as part of an operating system or a specific application, component, program, object, module or sequence of instructions referred to as "computer programs." The computer programs typically comprise one or more instructions set at various times in various memory and storage devices in a computer, and when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually affect the distribution.

Additional Use Cases

The systems disclosed herein may be used to augment care provided by healthcare providers. For example, one or more of the systems disclosed may be used to facilitate handoffs of patients to patient care providers. If the system, following an assessment, produces a score above a threshold for a particular mental state, the system may refer the patient to a specialist for further investigation and analysis. The patient may be referred before the assessment has been completed, for example, if the patient is receiving treatment in a telemedicine system or if the specialist is co-located with the patient. For example, the patient may be receiving treatment in a clinic with one or more specialists.

The system disclosed may be able to direct clinical processes for patients, following scoring. For example, if the patient were taking the assessment using a client device, the patient may, following completion of the assessment, be referred to cognitive behavioral therapy (CBT) services. They may also be referred to health care providers, or have appointments with health care providers made by the system. The system disclosed may suggest one or more medications.

Figure 59:
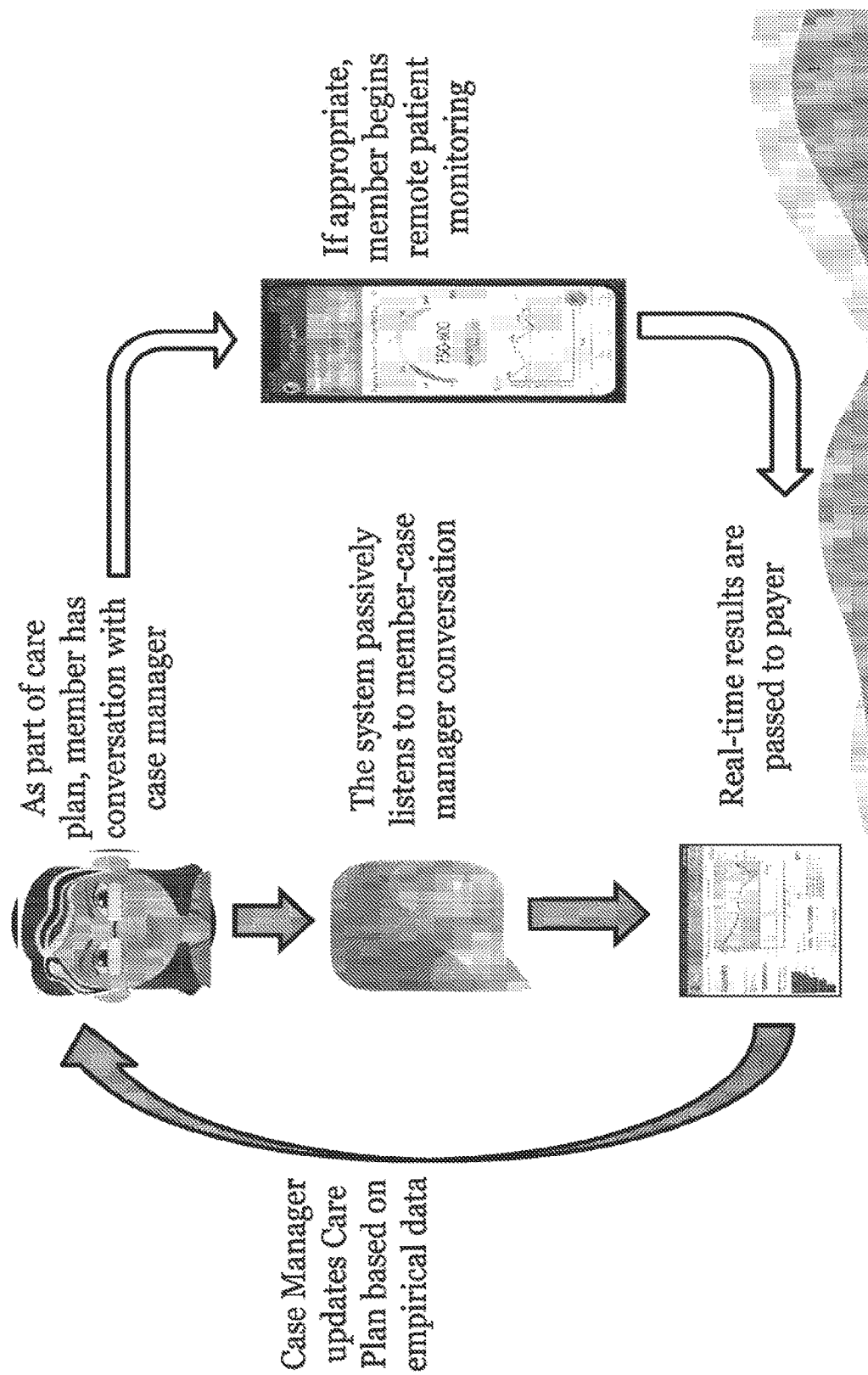
FIG. 59 shows a precision case management use case for the system.

FIG. 59 shows an instantiation of a precision case management use case for the system. In a first step, the patient has a conversation with a case manager. In a second step, one or more entities passively record the conversation, with consent of the patient. The conversation may be a face-to-face conversation. In another embodiment, the case manager may perform the conversation remotely. For example, the conversation may be a conversation using a telemedicine platform. In a third step, real time results are passed to a payer. The real time results may include a score corresponding to a mental state. In a fourth step, the case manager may update a care plan based on the real time results. For example, a particular score that exceeds a particular threshold may influence a future interaction between a care provider and a patient and may cause the provider to ask different questions of the patient. The score may even trigger the system to suggest particular questions associated with the score. The conversation may be repeated with the updated care plan.

Figure 60:
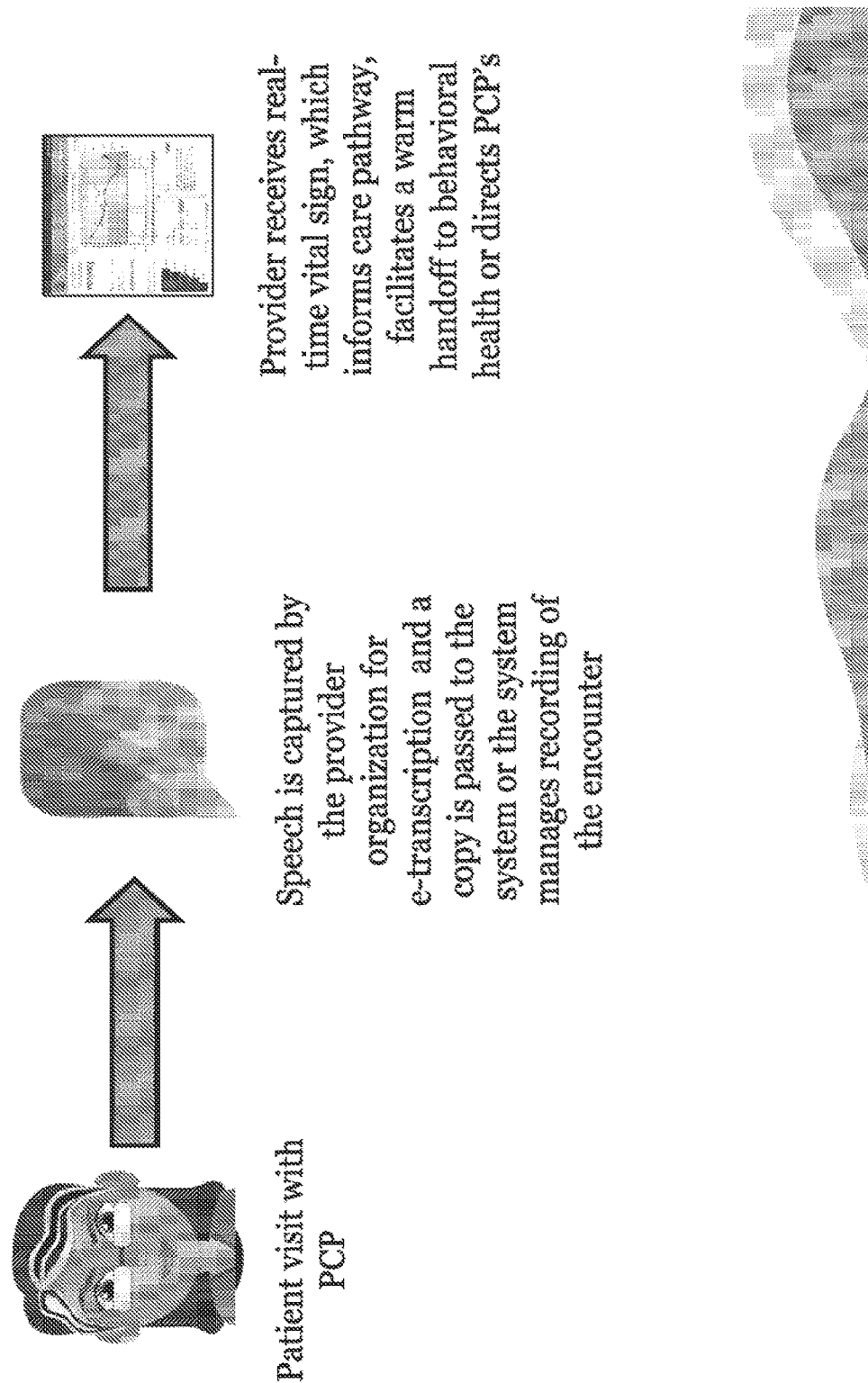
FIG. 60 shows a primary care screening or monitoring use case for the system.

FIG. 60 shows an instantiation of a primary care screening or monitoring use case for the system. In a first step, the patient visits with a primary care provider. In a second step, speech may be captured by the primary care provider's organization for e-transcription and the system may provide a copy for analysis. In a third step, the primary care provider, from the analysis, may receive a real-time vital sign informing the care pathway. This may facilitate a warm handoff to a behavioral health specialist or may be used to direct a primary care provider on a specific care pathway.

Figure 61:
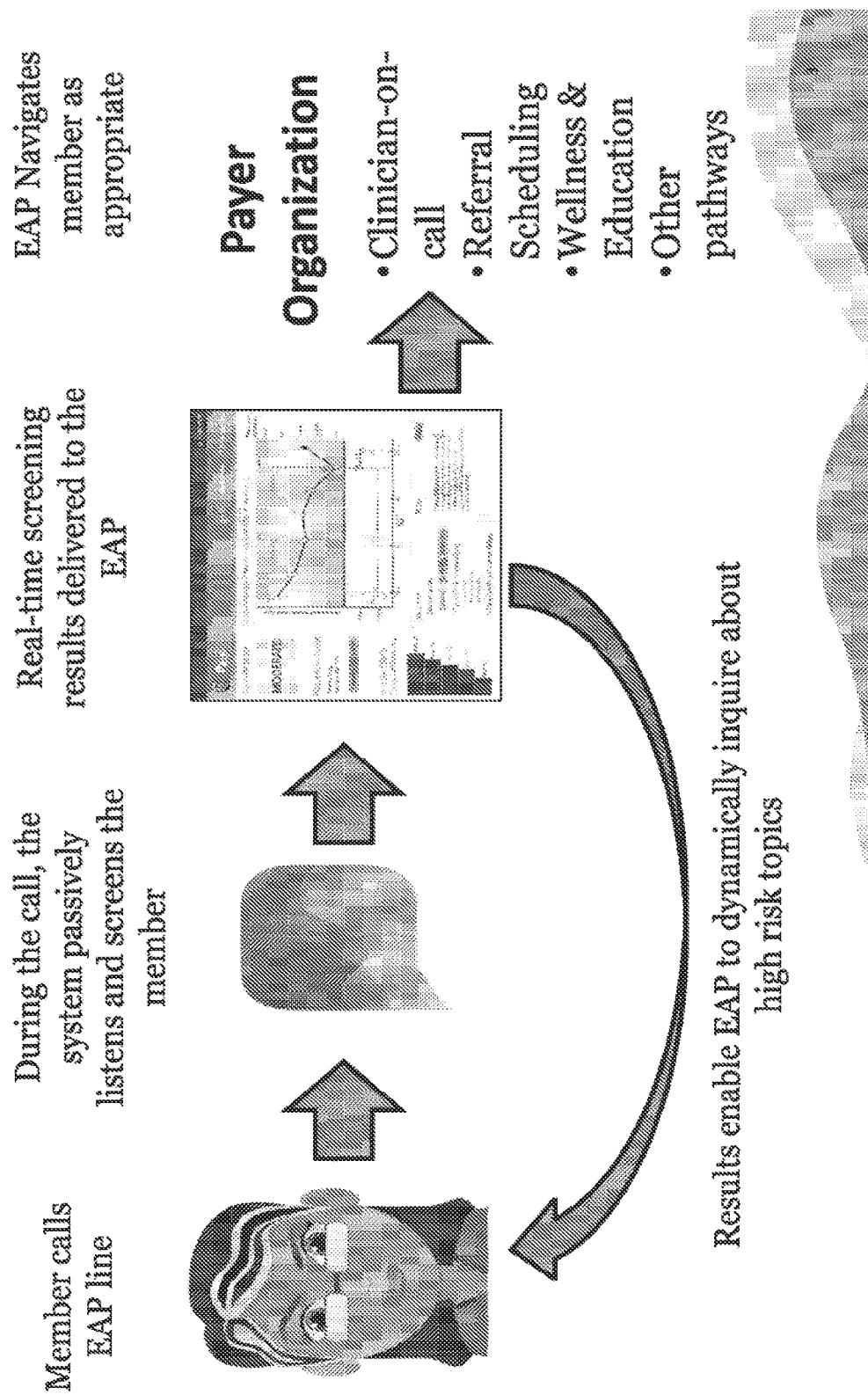
FIG. 61 shows a system for enhanced employee assistance plan (EAP) navigation and triage.

FIG. 61 shows an example system for enhanced employee assistance plan (EAP) navigation and triage. In a first step, the patient may call the EAP line. In a second step, the system may record audiovisual data and screen the patient. The real time screening or monitoring results may be delivered to the provider in real time. The provider may be able to adaptively screen the patient about high risk topics, based on the collected real-time results. The real-time screening or monitoring data may also be provided to other entities. For example, the real-time screening or monitoring data may be provided to a clinician-on-call, used to schedule referrals, used for education purposes, or for other purposes. The interaction between the patient and EAP may be in-person or may be remote. A person staffing an EAP line may be alerted in real-time that a patient has a positive screen and may be able to help direct the patient to a proper level of therapy. An EAP may also be directed to ask questions based on a result of an assessment administered to a patient, for example, a score corresponding to a patient's mental state.

Speech data as described herein may be collected and analyzed in real-time, or it may be data that is recorded and then analyzed later.

The system disclosed herein may be used to monitor interactions between unlicensed coaches and patients. The system may request consent from the patients before monitoring. The coaches may be used to administer questions. The coaches in tandem with the assessment may be able to provide an interaction with the patient that provides actionable predictions to clinicians and health care professionals, without being as costly as using the services of a clinician or health care. The assessment may be able to add rigor and robustness to judgments made by the unlicensed coaches. The assessment may also allow more people to take jobs as coaches, as it provides a method for validating coaches' methods.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

TERMS AND DEFINITIONS

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Computer Systems

Figure 62:
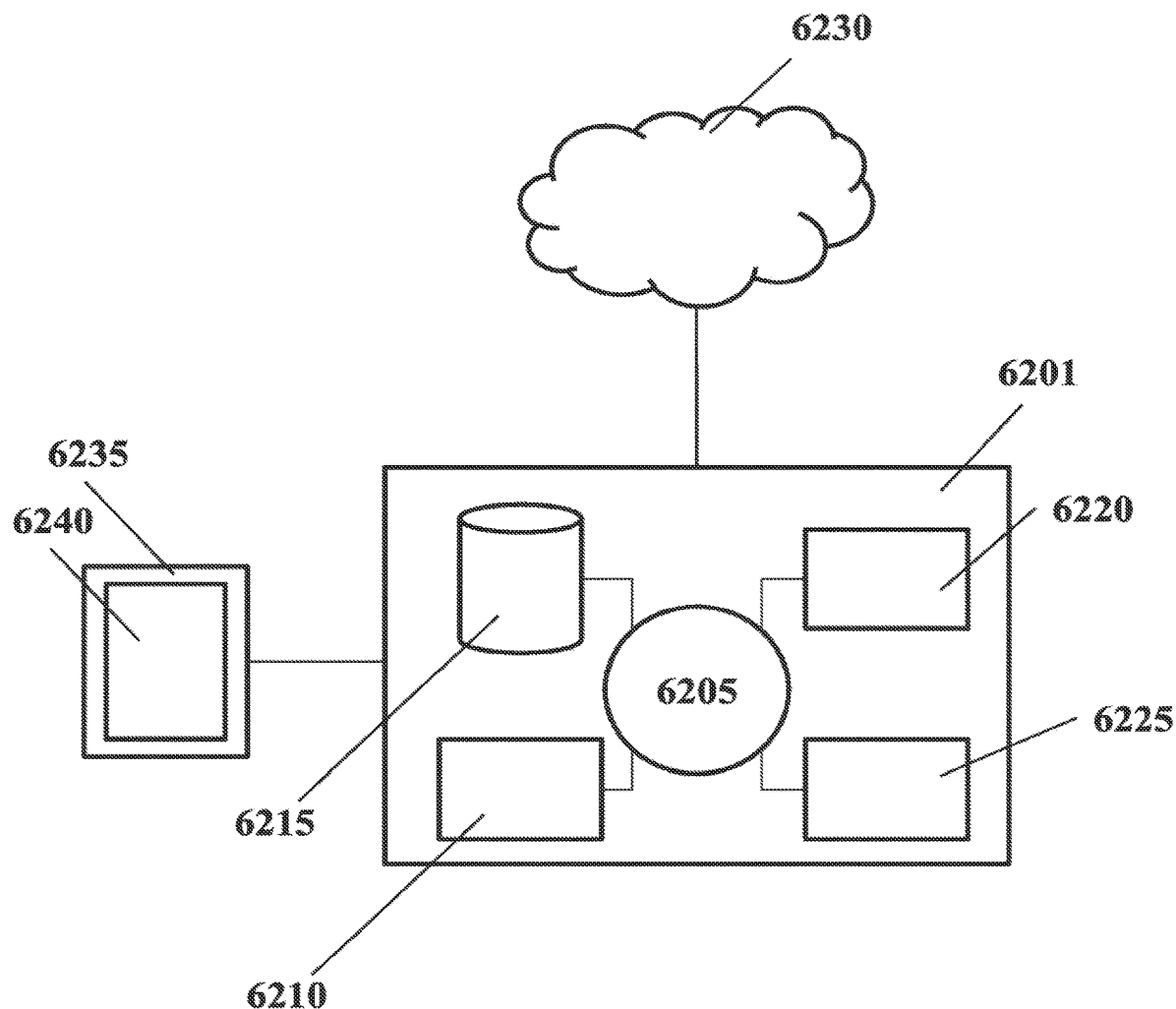
FIG. 62 shows a computer system that is programmed or otherwise configured to assess a mental state of a subject in a single session or over multiple different sessions.

The present disclosure provides computer systems that are programmed to implement methods of the disclosure. FIG. 62 shows a computer system 6201 that is programmed or otherwise configured to assess a mental state of a subject in a single session or over multiple different sessions. The computer system 6201 can regulate various aspects of assessing a mental state of a subject in a single session or over multiple different sessions of the present disclosure, such as, for example, presenting queries, retrieving data, and processing data. The computer system 6201 can be an electronic device of a user or a computer system that is remotely located with respect to the electronic device. The electronic device can be a mobile electronic device.

The computer system 6201 includes a central processing unit (CPU, also "processor" and "computer processor" herein) 6205, which can be a single core or multi core processor, or a plurality of processors for parallel processing. The computer system 6201 also includes memory or memory location 6210 (e.g., random-access memory, read-only memory, flash memory), electronic storage unit 6215 (e.g., hard disk), communication interface 6220 (e.g., network adapter) for communicating with one or more other systems, and peripheral devices 6225, such as cache, other memory, data storage and/or electronic display adapters. The memory 6210, storage unit 6215, interface 6220 and peripheral devices 6225 are in communication with the CPU 6205 through a communication bus (solid lines), such as a motherboard. The storage unit 6215 can be a data storage unit (or data repository) for storing data. The computer system 6201 can be operatively coupled to a computer network ("network") 6230 with the aid of the communication interface 6220. The network 6230 can be the Internet, an internet and/or extranet, or an intranet and/or extranet that is in communication with the Internet. The network 6230 in some cases is a telecommunication and/or data network. The network 6230 can include one or more computer servers, which can enable distributed computing, such as cloud computing. The network 6230, in some cases with the aid of the computer system 6201, can implement a peer-to-peer network, which may enable devices coupled to the computer system 6201 to behave as a client or a server.

The CPU 6205 can execute a sequence of machine-readable instructions, which can be embodied in a program or software. The instructions may be stored in a memory location, such as the memory 6210. The instructions can be directed to the CPU 6205, which can subsequently program or otherwise configure the CPU 6205 to implement methods of the present disclosure. Examples of operations performed by the CPU 6205 can include fetch, decode, execute, and writeback.

The CPU 6205 can be part of a circuit, such as an integrated circuit. One or more other components of the system 6201 can be included in the circuit. In some cases, the circuit is an application specific integrated circuit (ASIC).

The storage unit 6215 can store files, such as drivers, libraries and saved programs. The storage unit 6215 can store user data, e.g., user preferences and user programs. The computer system 6201 in some cases can include one or more additional data storage units that are external to the computer system 6201, such as located on a remote server that is in communication with the computer system 6201 through an intranet or the Internet.

The computer system 6201 can communicate with one or more remote computer systems through the network 6230. For instance, the computer system 6201 can communicate with a remote computer system of a user (e.g., the clinician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 6201 via the network 6230.

Methods as described herein can be implemented by way of machine (e.g., computer processor) executable code stored on an electronic storage location of the computer system 6201, such as, for example, on the memory 6210 or electronic storage unit 6215. The machine executable or machine readable code can be provided in the form of software. During use, the code can be executed by the processor 6205. In some cases, the code can be retrieved from the storage unit 6215 and stored on the memory 6210 for ready access by the processor 6205. In some situations, the electronic storage unit 6215 can be precluded, and machine-executable instructions are stored on memory 6210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 6201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 6201 can include or be in communication with an electronic display 6235 that comprises a user interface (UI) 6240 for providing, for example, an assessment to a patient. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 6205. The algorithm can, for example, analyze speech using natural language processing.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for identifying whether a subject is at risk of having a mental or physiological condition, comprising:
   one or more computer processors; and
   a memory comprising machine-executable instructions;
   wherein, upon execution, the instructions cause the one or more computer processors to:
   (a) obtain data from said subject, said data comprising speech data and optionally associated visual data;
   (b) process said data using a plurality of machine learning models comprising a natural language processing (NLP) model and an acoustic model to generate an NLP output and an acoustic output, wherein said plurality of machine learning models comprises a neural network trained on labeled speech data collected from one or more other subjects, wherein said labeled speech data for each of said one or more other subjects is labeled as (i) having, to some level, said mental or physiological condition or (ii) not having said mental or physiological condition;
   (c) fuse said NLP output and said acoustic output by (1) applying weights to said NLP output and said acoustic output to generate weighted outputs and (2) generating a composite output from said weighted outputs, wherein said NLP output and said acoustic output each comprise a plurality of outputs corresponding to a plurality of time segments of said speech data, and wherein said weights in (1) are temporally-based; and
   (d) output an electronic report identifying whether said subject is at risk of having said mental or physiological condition, based at least on said composite output, which risk is quantified in a form of a score having a confidence level provided in said report.

2. The system of claim 1, wherein said speech data in (a) is obtained by:
   (i) transmitting at least one query in an audio or textual format to said subject, wherein said at least one query is configured to elicit at least one verbal response from said subject; and
   (ii) receiving said speech data comprising said at least one verbal response from said subject in response to transmitting said at least one query.

3. The system of claim 2, wherein said at least one query comprises a plurality of queries and said at least one response comprises a plurality of responses, wherein said plurality of queries is transmitted in a sequential manner to said subject and configured to systematically elicit said plurality of responses from said subject.

4. The system of claim 3, wherein said plurality of queries is structured in a hierarchical manner such that each subsequent query of said plurality of queries is structured as a logical follow on to said subject's response to a preceding query, and is configured to assess or draw inferences on a plurality of aspects of said mental or physiological condition of said subject.

5. The system of claim 4, wherein the instructions further cause the one or more computer processors to:
   update said score and said confidence level based at least in part on a follow-on response from said subject to said subsequent query.

6. The system of claim 5, wherein the instructions further cause the one or more computer processors to:
   update or assign a clinical value to said updated score having said confidence level.

7. The system of claim 5, wherein the instructions further cause the one or more computer processors to:
   determine whether said confidence level meets a predetermined criterion; and
   generate one or more additional queries to assess or draw inferences on said plurality of aspects of said mental or physiological condition of said subject.

8. The system of claim 7, wherein the instructions further cause the one or more computer processors to:
   transmit said one or more additional queries to said subject to elicit one or more additional verbal responses; and
   determine whether said confidence level meets said predetermined criterion, based at least in part on said speech data comprising said one or more additional verbal responses.

9. The system of claim 8, wherein the instructions further cause the one or more computer processors to:
   continue to transmit said one or more additional queries to said subject to elicit said one or more additional verbal responses, until said confidence level is determined to meet said predetermined criterion.

10. The system of claim 2, wherein said confidence level is based at least in part on a length and/or duration measure of said at least one verbal response.

11. The system of claim 2, wherein said confidence level is based at least in part on an evaluated truthfulness of said at least one verbal response.

12. The system of claim 1, wherein said confidence level is based at least in part on a quality measure of said speech data associated with metadata of said speech data, said subject, or a context of said speech data.

13. The system of claim 1, wherein said confidence level is based at least in part on an acoustic, NLP, or speech-recognition confidence measure of said data.

14. The system of claim 3, wherein the instructions further cause the one or more computer processors to:
assign a plurality of weights to said plurality of responses.

15. The system of claim 14, wherein said plurality of weights are assigned based at least in part on a type of query configured to elicit each of said responses.

16. The system of claim 1, wherein said plurality of machine learning models are provided as (i) one or more individual models, (ii) jointly as two or more separate models, and/or (iii) a fused model comprising a composite model that is an aggregate of two or more different models.

17. The system of claim 1, wherein said processed data comprises one or more model outputs generated from said one or more models, and wherein said one or more model outputs comprise one or more of the following: an NLP output or an acoustic output.

18. The system of claim 1, wherein said weights are based at least in part on confidence measures associated with each of said NLP output and said acoustic output.

19. The system of claim 17, wherein said score is generated at least in part by fusing two or more of said model outputs.

20. The system of claim 19, wherein said two or more of said model outputs comprise at least: (1) a first model output having a first confidence measure, and (2) a second model output having a second confidence measure, and wherein said confidence level of said score is generated at least in part by fusing said first confidence measure and said second confidence measure.

21. The system of claim 20, wherein said first model output corresponds to said NLP output, and said second model output corresponds to said acoustic output.

22. The system of claim 20, wherein said two or more of said model outputs further comprise at least (3) a third model output having a third confidence measure, and wherein said confidence level of said score is generated by fusing said first confidence measure, said second confidence measure, and said third confidence measure.

23. The system of claim 22, wherein said first model output corresponds to said NLP output and said second model output corresponds to said acoustic output.

24. The system of claim 1, wherein said electronic report is usable by a user to identify whether said subject is at risk of having said mental or physiological condition.

25. The system of claim 24, wherein said score has a clinical value, wherein said user is a healthcare provider or entity, and wherein said electronic report comprising said score having said clinical value is usable by said healthcare provider or said entity to evaluate or provide care for said subject, when said subject is identified to be at risk of having said mental or physiological condition.

26. The system of claim 1, wherein at least one of said plurality of machine learning models is a deep learning model.

27. The system of claim 1, wherein applying weights to said NLP output and said acoustic output does not change a magnitude of said NLP output or said acoustic output.

* * * * *